United States Patent
Wise et al.

(10) Patent No.: US 11,147,559 B2
(45) Date of Patent: Oct. 19, 2021

(54) STAPLE HEIGHT INDICATOR FOR POWERED SURGICAL STAPLER

(71) Applicant: Ethicon LLC, Guaynabo, PR (US)

(72) Inventors: Austin E. Wise, Cincinnati, OH (US); Nicholas J. Ross, Franklin, OH (US); Shane R. Adams, Lebanon, OH (US); Douglas B. Hoffman, Harrison, OH (US); Thomas E. Adams, Loveland, OH (US)

(73) Assignee: Cilag GmbH International, Zug (CH)

( * ) Notice: Subject to any disclaimer, the term of this patent is extended or adjusted under 35 U.S.C. 154(b) by 195 days.

(21) Appl. No.: 16/583,387

(22) Filed: Sep. 26, 2019

(65) Prior Publication Data

US 2020/0281595 A1 Sep. 10, 2020

Related U.S. Application Data

(60) Provisional application No. 62/815,678, filed on Mar. 8, 2019.

(51) Int. Cl.
*A61B 17/115* (2006.01)
*A61B 90/00* (2016.01)
(Continued)

(52) U.S. Cl.
CPC ....... *A61B 17/1155* (2013.01); *A61B 17/1114* (2013.01); *A61B 90/08* (2016.02);
(Continued)

(58) Field of Classification Search
None
See application file for complete search history.

(56) References Cited

U.S. PATENT DOCUMENTS 2,737,666 A 3/1956 Elmer et al.
5,205,459 A 3/1993 Brinkerhoff et al.
(Continued)

FOREIGN PATENT DOCUMENTS

CN 102 905 489 A 1/2013
CN 105 885 481 A 8/2016
(Continued)

OTHER PUBLICATIONS

U.S. Appl. No. 16/583,376, entitled "Timer Circuit to Control Firing of Powered Surgical Stapler," filed Sep. 26, 2019.
(Continued)

*Primary Examiner* — Nathaniel C Chukwurah
(74) *Attorney, Agent, or Firm* — Frost Brown Todd LLC

(57) ABSTRACT

A surgical instrument includes a body assembly, a distally extending shaft assembly, and a distal stapling assembly configured to clamp, staple, and cut tissue. A first user feedback element is configured to visually inform a user of a first condition of the stapling assembly, and a second user feedback element is configured to visually inform the user of a second condition of the stapling assembly. A circuit board assembly includes a circuit board, a first light source configured to illuminate the first user feedback element, a second light source configured to illuminate the second user feedback element, and a light guide feature. The light guide feature is configured to direct light from the second light source toward the second user feedback element and simultaneously inhibit light emitted by the first light source from illuminating the second user feedback element.

20 Claims, 103 Drawing Sheets

(51) Int. Cl.
*A61B 17/11* (2006.01)
*A61B 17/00* (2006.01)

(52) U.S. Cl.
CPC .............. *A61B 2017/00115* (2013.01); *A61B 2017/00398* (2013.01); *A61B 2017/00734* (2013.01); *A61B 2090/0812* (2016.02)

(56) References Cited

U.S. PATENT DOCUMENTS

| | | | |
|---|---|---|---|
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A * | 8/1994 | Main .......... A61B 17/115 227/179.1 |
| 5,350,104 | A | 9/1994 | Main et al. |
| 5,533,661 | A | 7/1996 | Main et al. |
| 7,268,507 | B2 | 9/2007 | Kawamura |
| 7,794,475 | B2 | 9/2010 | Hess et al. |
| 8,408,439 | B2 | 4/2013 | Huang et al. |
| 8,453,914 | B2 | 6/2013 | Laurent et al. |
| 8,491,581 | B2 | 7/2013 | Deville et al. |
| 8,505,802 | B2 | 8/2013 | Viola et al. |
| 8,910,847 | B2 | 12/2014 | Nalagatla et al. |
| 8,931,682 | B2 | 1/2015 | Timm et al. |
| 9,161,803 | B2 | 10/2015 | Yates et al. |
| 9,283,054 | B2 | 3/2016 | Morgan et al. |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 9,629,629 | B2 | 4/2017 | Leimbeach et al. |
| 9,713,469 | B2 | 7/2017 | Leimbach et al. |
| 9,724,100 | B2 | 8/2017 | Scheib et al. |
| 9,907,552 | B2 | 3/2018 | Measamer et al. |
| 9,936,949 | B2 | 4/2018 | Measamer et al. |
| 10,092,292 | B2 | 10/2018 | Boudreaux et al. |
| 10,188,386 | B2 | 1/2019 | Measamer et al. |
| 10,194,911 | B2 | 2/2019 | Miller et al. |
| 10,226,253 | B2 | 3/2019 | DiNardo et al. |
| 10,251,224 | B2 | 4/2019 | Kim et al. |
| 10,265,066 | B2 | 4/2019 | Measamer et al. |
| 10,271,841 | B2 | 4/2019 | Overmyer et al. |
| 10,271,842 | B2 | 4/2019 | Fox et al. |
| 10,285,694 | B2 | 5/2019 | Viola et al. |
| 10,307,157 | B2 | 6/2019 | Miller et al. |
| 10,390,841 | B2 | 8/2019 | Shelton, IV et al. |
| 10,675,023 | B2 | 6/2020 | Cappola |
| 10,888,317 | B2 | 1/2021 | Measamer et al. |
| 2010/0264193 | A1 | 10/2010 | Huang et al. |
| 2011/0290856 | A1 | 12/2011 | Shelton, IV et al. |
| 2012/0116379 | A1 | 5/2012 | Yates et al. |
| 2012/0120081 | A1 | 5/2012 | Bita et al. |
| 2012/0239012 | A1 | 9/2012 | Laurent et al. |
| 2014/0144968 | A1 | 5/2014 | Shelton, IV |
| 2014/0144969 | A1 | 5/2014 | Scheib et al. |
| 2014/0151429 | A1 | 6/2014 | Scheib et al. |
| 2014/0151430 | A1 | 6/2014 | Scheib et al. |
| 2014/0158747 | A1 | 6/2014 | Measamer et al. |
| 2014/0166717 | A1 | 6/2014 | Swayze et al. |
| 2014/0166718 | A1 | 6/2014 | Swayze et al. |
| 2014/0166728 | A1 | 6/2014 | Swayze et al. |
| 2015/0083772 | A1 | 3/2015 | Miller et al. |
| 2015/0083773 | A1 | 3/2015 | Measamer et al. |
| 2015/0083774 | A1 | 3/2015 | Measamer et al. |
| 2015/0083775 | A1 | 3/2015 | Leimbach et al. |
| 2016/0374665 | A1 | 12/2016 | DiNardo et al. |
| 2016/0374666 | A1 | 12/2016 | DiNardo et al. |
| 2016/0374667 | A1 | 12/2016 | DiNardo et al. |
| 2016/0374668 | A1 | 12/2016 | Measamer et al. |
| 2016/0374669 | A1 | 12/2016 | Overmyer et al. |
| 2016/0374670 | A1 | 12/2016 | Measamer et al. |
| 2016/0374671 | A1 * | 12/2016 | Measamer .......... A61B 17/1155 227/175.1 |
| 2016/0374672 | A1 | 12/2016 | Bear et al. |
| 2016/0374673 | A1 | 12/2016 | Stager et al. |
| 2016/0374681 | A1 | 12/2016 | Miller et al. |
| 2016/0374684 | A1 | 12/2016 | DiNardo et al. |
| 2018/0132848 | A1 | 5/2018 | Miller et al. |
| 2018/0132849 | A1 | 5/2018 | Miller et al. |
| 2018/0132853 | A1 | 5/2018 | Miller et al. |
| 2018/0132854 | A1 | 5/2018 | Miller et al. |
| 2018/0310938 | A1 | 11/2018 | Kluener et al. |
| 2018/0310939 | A1 | 11/2018 | Stager et al. |

FOREIGN PATENT DOCUMENTS

| | | |
|---|---|---|
| CN | 106 286 659 A | 1/2017 |
| DE | 10 2004 017401 A1 | 10/2005 |
| EP | 3 231 379 A2 | 10/2017 |
| EP | 3 338 657 A1 | 6/2018 |
| EP | 3 395 267 A1 | 10/2018 |

OTHER PUBLICATIONS

U.S. Appl. No. 16/583,381, entitled "Power Control Circuit for Powered Surgical Stapler," filed Sep. 26, 2019.
U.S. Appl. No. 16/583,386, entitled "Electrical Potential Shifting Circuit for Powered Surgical Stapler," filed Sep. 26, 2019.
U.S. Appl. No. 16/583,690, entitled "Circular Surgical Staler," filed Sep. 26, 2019.
U.S. Appl. No. 16/583,376.
U.S. Appl. No. 16/583,381.
U.S. Appl. No. 16/583,386.
U.S. Appl. No. 16/583,690.
European Search Report, Partial, and Provisional Written Opinion dated Jun. 24, 2020 for Application No. EP 20161906.1, 14 pgs.
European Search Report, Extended, and Written Opinion dated Sep. 21, 2020 for Application No. EP 20161906.1, 17 pgs.
European Search Report, Extended, and Written Opinion dated Jun. 12, 2020 for Application No. EP 20161904.6, 8 pgs.
European Search Report, Extended, and Written Opinion dated May 28, 2020 for Application No. EP 20161910.3, 10 pgs.
European Search Report, Extended, and Written Opinion dated Jul. 17, 2020 for Application No. EP 20161916.0, 11 pgs.
European Search Report, Partial, and Written Opinion dated Jun. 3, 2020 for Application No. EP 20161915.2, 11 pgs.
European Search Report, Extended, and Written Opinion dated Oct. 26, 2020 for Application No. EP 20161915.2, 10 pgs.
International Search Report and Written Opinion dated Sep. 17, 2020 for Application No. PCT/IB2020/051649, 22 pgs.
International Search Report and Written Opinion dated Jun. 5, 2020 for Application No. PCT/IB2020/051651, 12 pgs.
International Search Report and Written Opinion dated May 27, 2020 for Application No. PCT/IB2020/051653, 17 pgs.
International Search Report and Written Opinion dated Jun. 12, 2020 for Application No. PCT/IB2020/051654, 17 pgs.
International Search Report and Written Opinion dated Sep. 21, 2020 for Application No. PCT/IB2020/051656, 13 pgs.

* cited by examiner

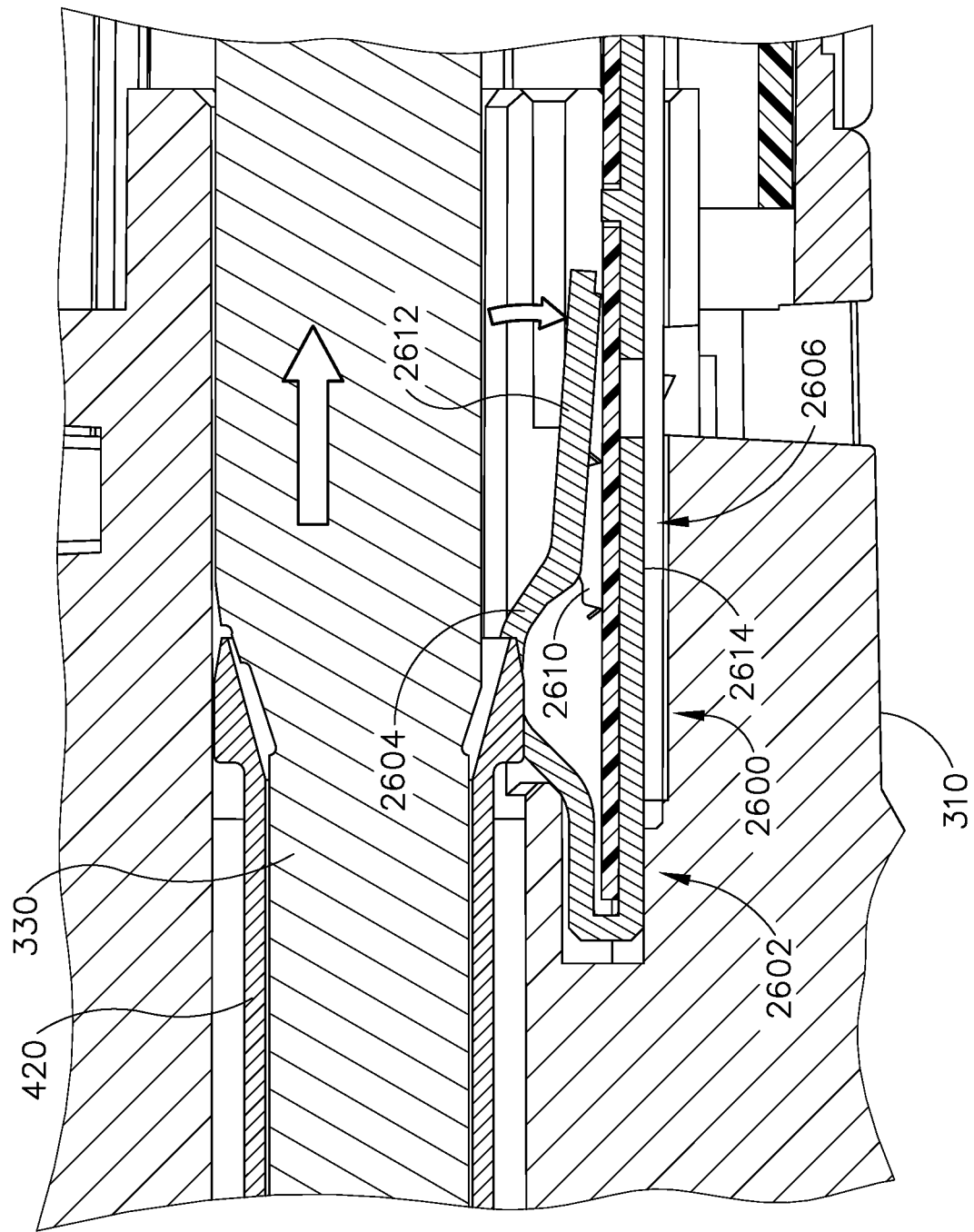

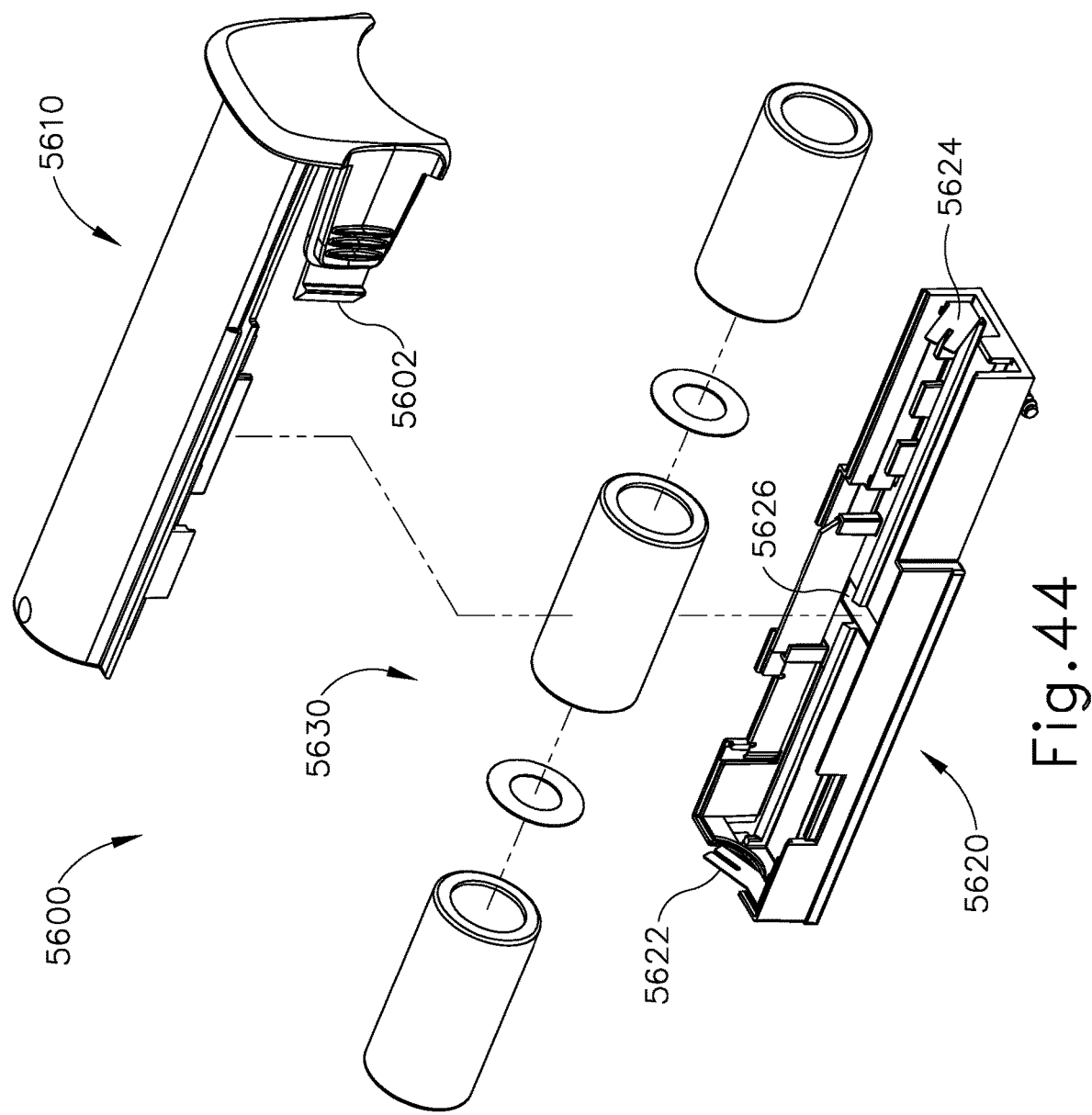

STAPLE HEIGHT INDICATOR FOR POWERED SURGICAL STAPLER

PRIORITY

This application claims priority to U.S. Provisional Pat. App. No. 62/815,678, entitled "Circular Surgical Stapler," filed Mar. 8, 2019, the disclosure of which is incorporated by reference herein.

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 16B depicts an enlarged cross-sectional side view of the contact switch of FIG. 15A moved into the closed state of FIG. 15B by proximal translation of the trocar and the anvil of the circular stapler;

FIG. 44 depicts a partially exploded perspective view of the battery pack of FIG. 42;

FIG. 95 depicts a perspective view of an exemplary alternative firing trigger having an elastically deformable paddle configured for use with the surgical instrument of FIG. 1;

Figure 1:
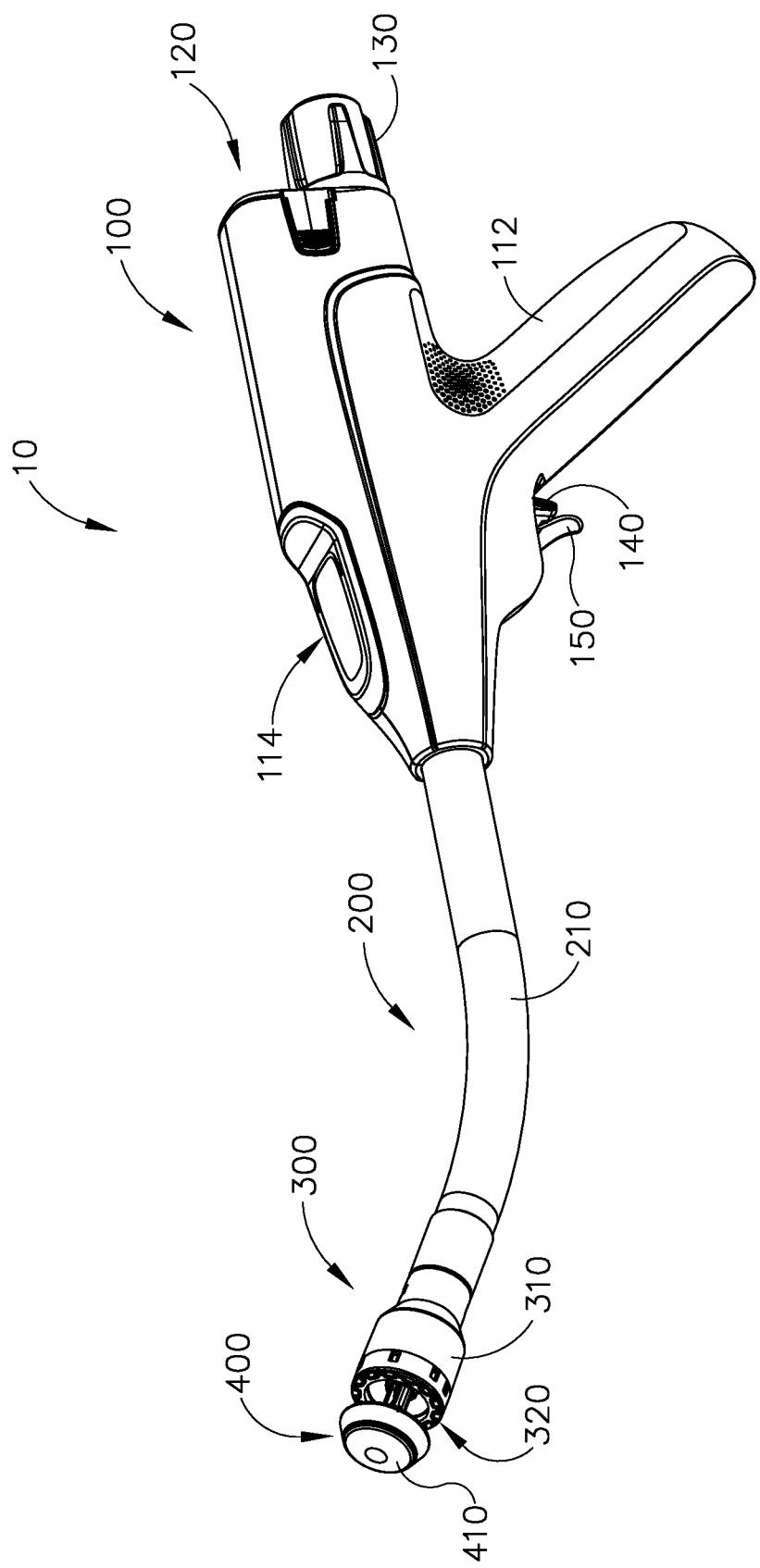
FIG. 1 depicts a perspective view of an exemplary circular stapler.
Figure 95:
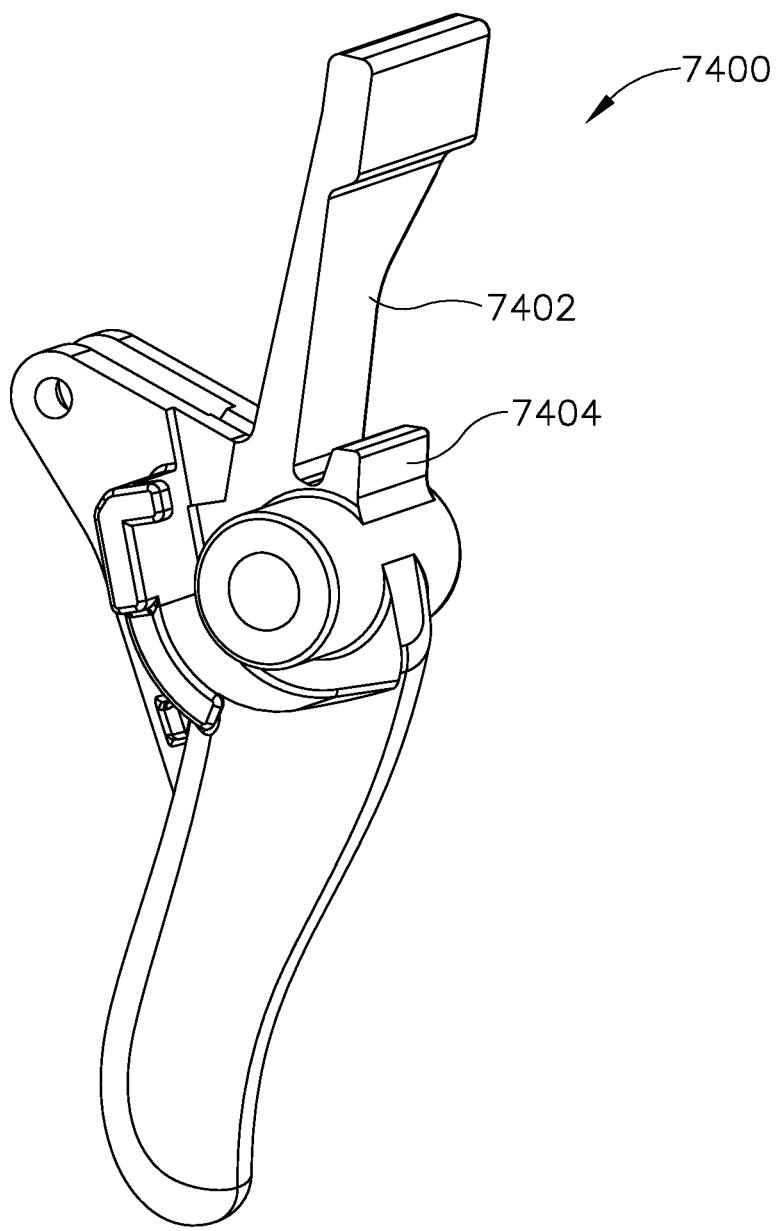
Figure 96A:
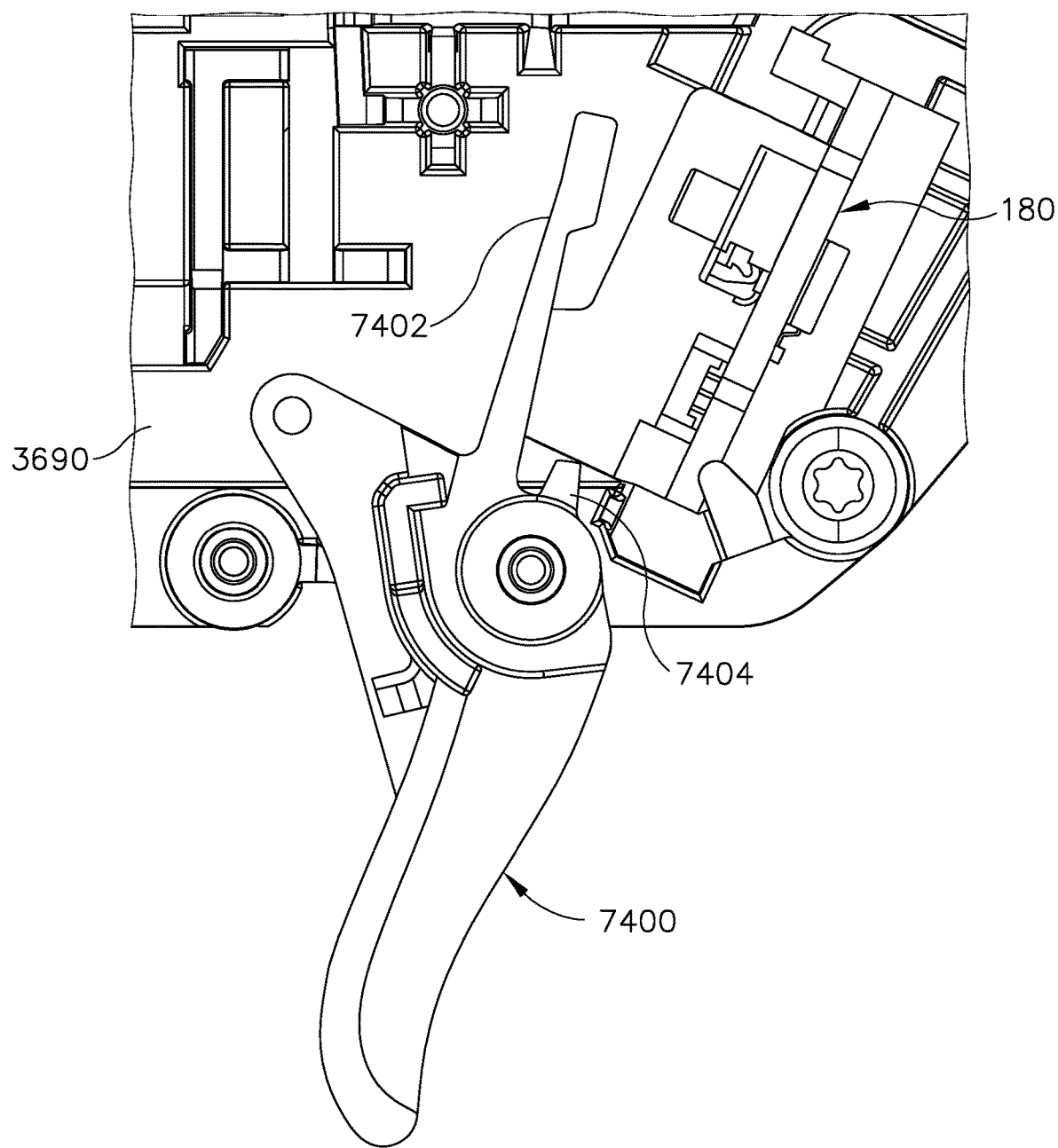
Figure 96B:
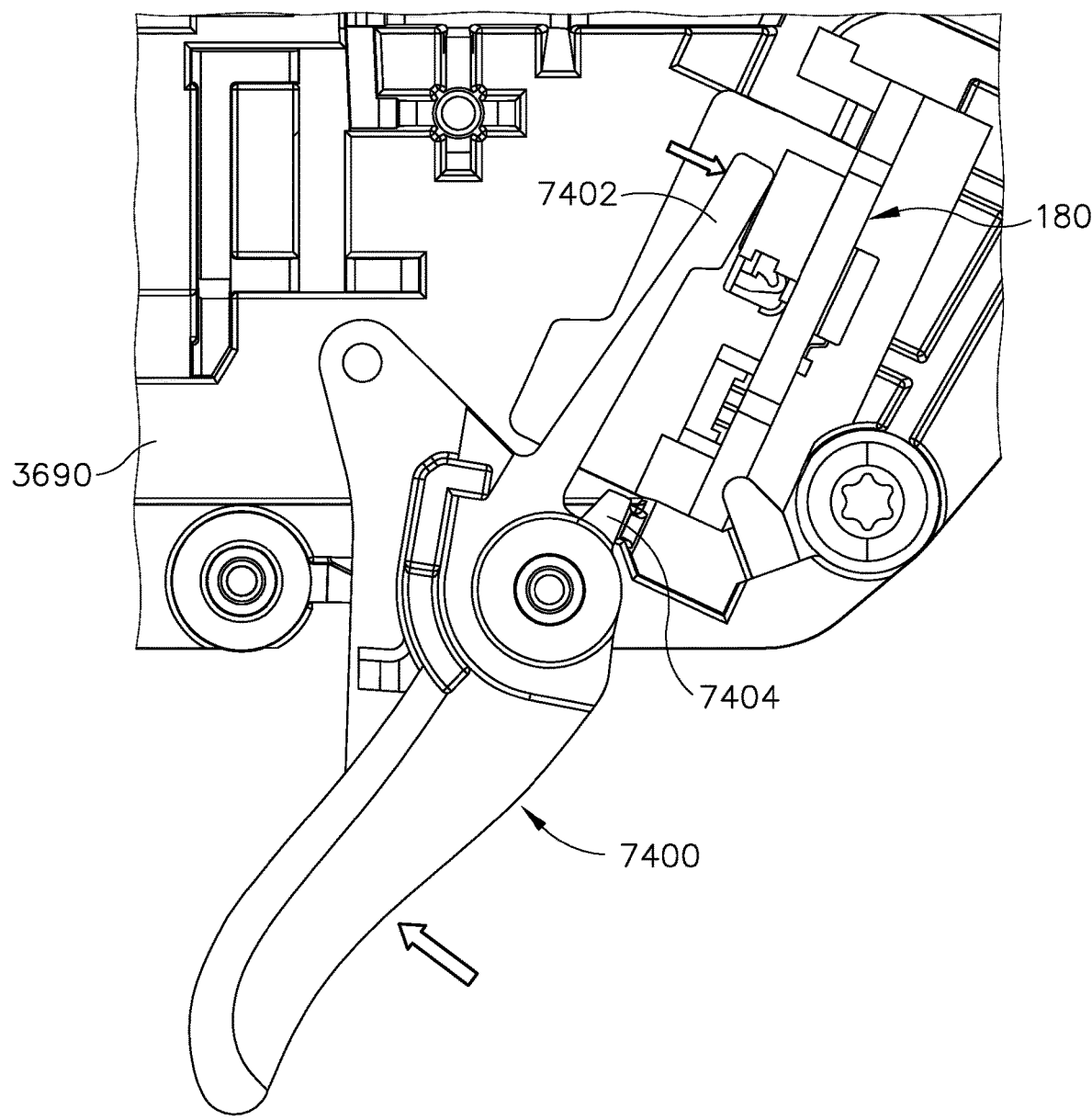

FIG. 96A depicts a side elevational view of a portion of the handle assembly of the surgical instrument of FIG. 1, with various components omitted from view, showing the firing trigger of FIG. 95 in an unactuated position; and FIG. 96B depicts a side elevational view of a portion of the handle assembly of the surgical instrument of FIG. 1, showing the firing trigger of FIG. 95 in an actuated position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

This application incorporates by reference the disclosures of U.S. Pub. No. 2015/0083772, entitled "Surgical Stapler with Rotary Cam Drive and Return," published on Mar. 26, 2015, now abandoned; U.S. Pat. No. 9,907,552, entitled "Control Features for Motorized Surgical Stapling Instrument," issued on Mar. 6, 2018; U.S. Pub. No. 2016/0374672, entitled "Method of Applying an Annular Array of Staples to Tissue," published on Dec. 29, 2016; issued as U.S. Pat. No. 10,478,189 on Nov. 19, 2019; U.S. Pub. No. 2018/0132853, entitled "Circular Stapler with Recessed Deck," published May 17, 2018; issued as U.S. Pat. No. 10,980,542 on Apr. 20, 2021; U.S. Pub. No. 2018/0132849, entitled "Staple Forming Pocket Configurations for Circular Surgical Stapler Anvil," published May 17, 2018; U.S. Pub. No. 2018/0310938, entitled "Hysteresis Removal Feature in Surgical Stapling Instrument," published Nov. 1, 2018, issued as U.S. Pat. No. 10,695,068 on Jun. 30, 2020, and U.S. Pub. No. 2018/0310939, entitled "Liquid-Immune Trigger Circuit for Surgical Instrument," published Nov. 1, 2018, issued as U.S. Pat. No. 10,729,444 on Aug. 4, 2020.

I. Overview of Exemplary Circular Stapling Surgical Instrument

Figure 2:
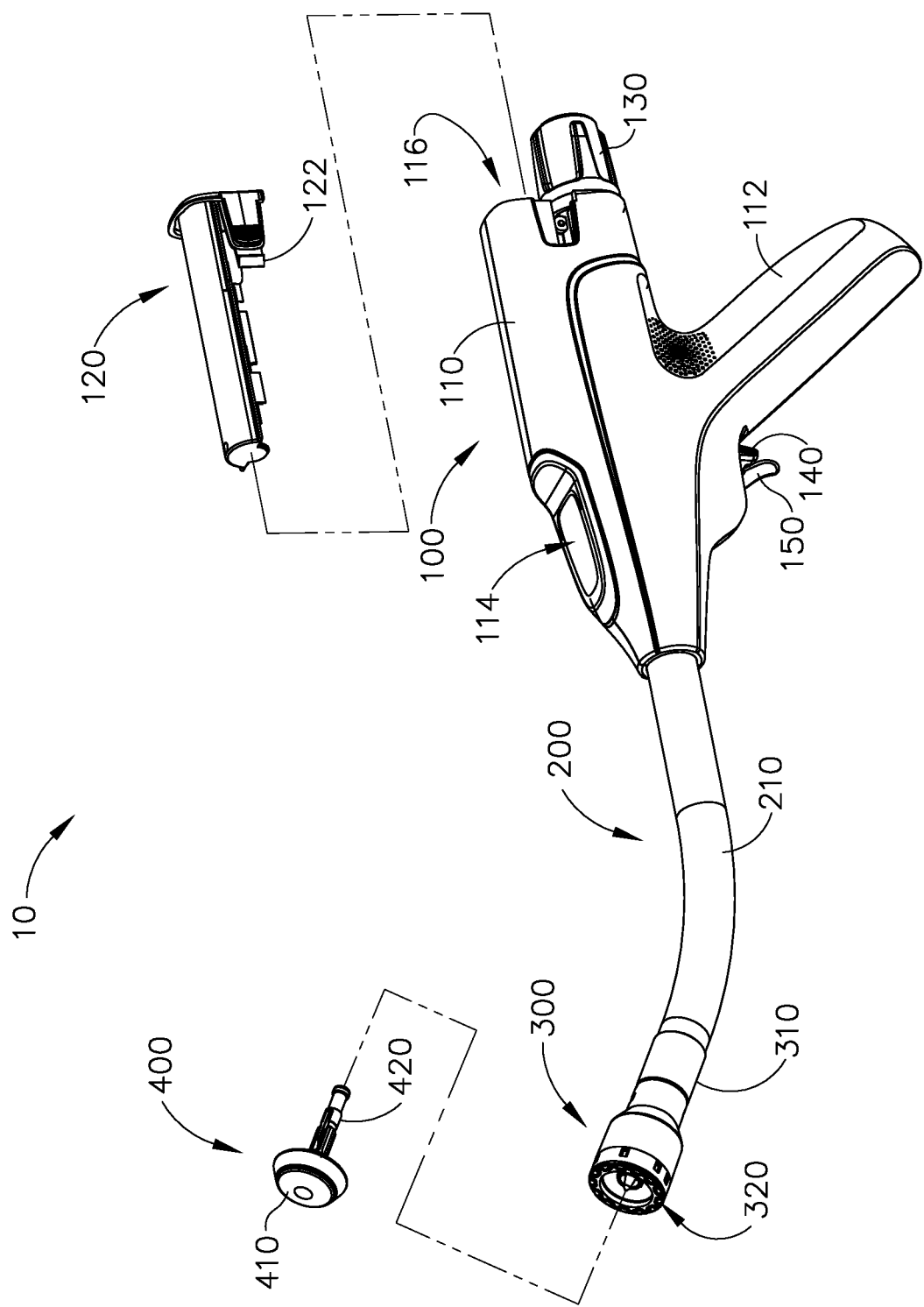
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114) that permits viewing of a movable indicator needle (1526) as will be described in greater detail below. In some versions, a series of hash marks, colored regions, and/or other fixed indicators are positioned adjacent to user feedback feature (114) in order to provide a visual context for indicator needle (1526), thereby facilitating operator evaluation of the position of needle (1526) within user feedback feature (114). Various suitable alternative features and configurations for handle assembly (100) will be apparent to those of ordinary skill in the art in view of the teachings herein.

Instrument (10) of the present example further includes a battery pack (120). Battery pack (120) is operable to provide electrical power to a motor (161) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery pack (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

II. Exemplary Anvil

A. Overview

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
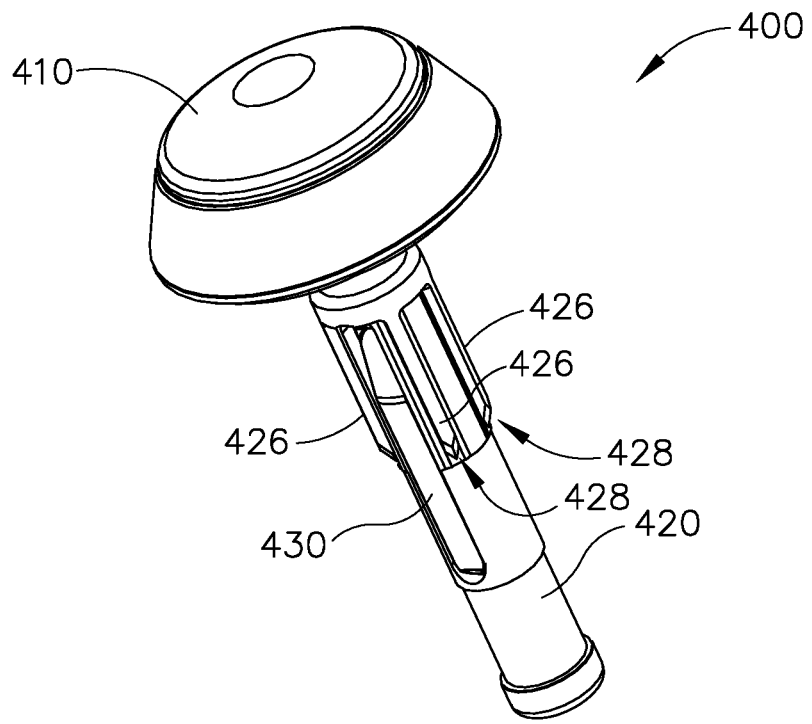
FIG. 3 depicts a perspective view of the anvil of the circular stapler of FIG. 1.
Figure 4:
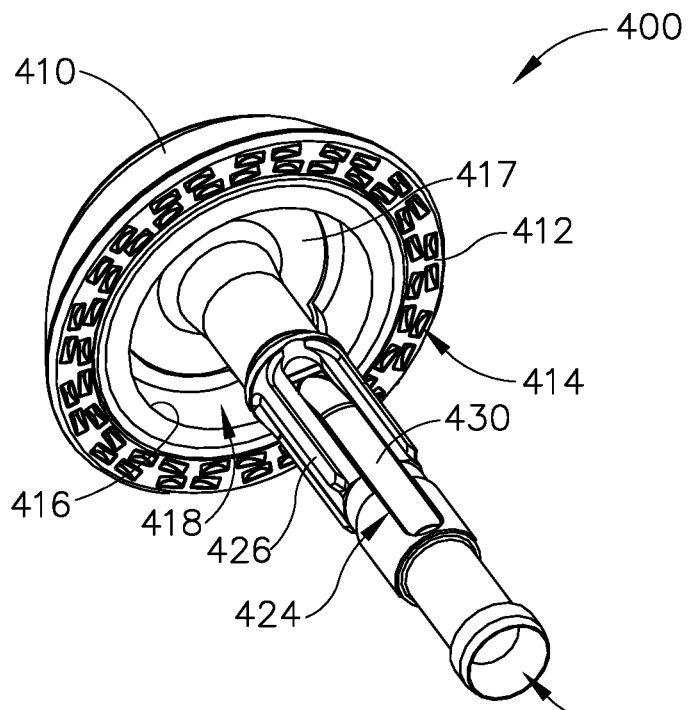
FIG. 4 depicts another perspective view of the anvil of FIG. 3.
Figure 5:
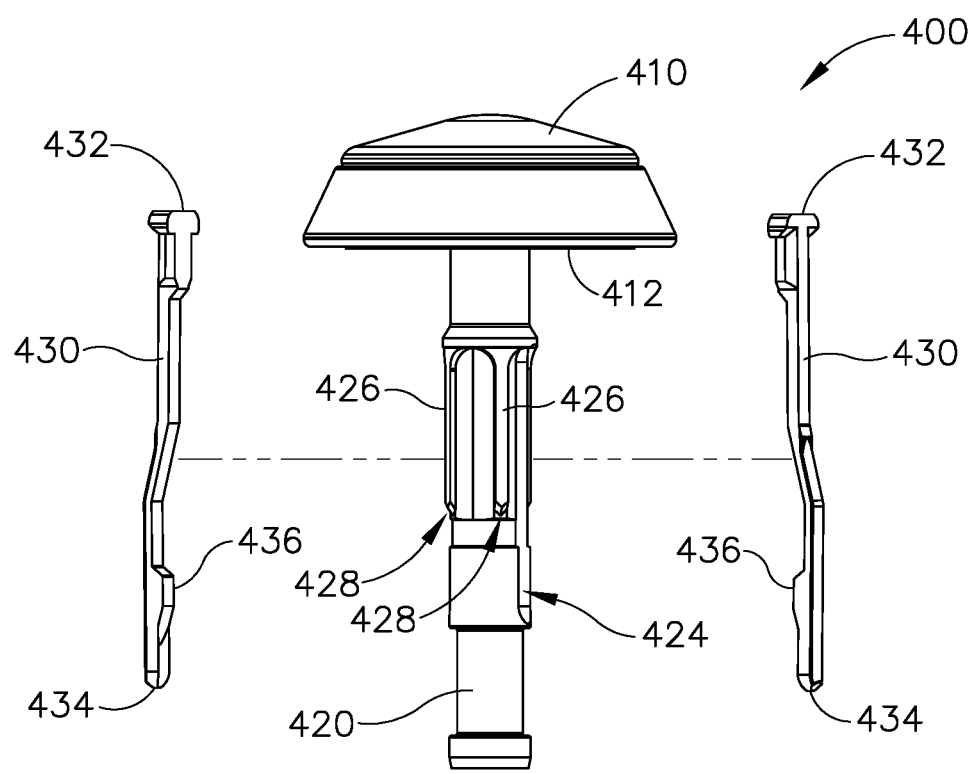
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that proximal ends (434) are positioned at the proximal ends of lateral openings (424), which are formed through the sidewall of shank (420). Lateral openings (424) thus provide clearance for proximal ends (434) and latch shelves (436) to deflect radially outwardly from the longitudinal axis defined by shank (420). However, latch members (430) are configured to resiliently bias proximal ends (434) and latch shelves (436) to pivot radially inwardly toward the longitudinal axis defined by shank (420). Latch members (430) thus act as retaining clips. This allows anvil (400) to be removably secured to a trocar (330) of stapling head assembly (300) as will be described in greater detail below. When shank (420) is secured to trocar (330) and trocar (330) is retracted proximally, the inner diameter of bore (314) in inner core member (312) of body member (310) laterally constrains latch members (430) to maintain engagement between latch shelves (436) and proximal surface (338) of head (334) of trocar (330). This engagement prevents anvil (400) from being released from trocar (330) during firing of stapling head assembly (300). It should be understood, however, that latch shelves (436) are merely optional. Anvil (400) may be removably secured to a trocar (330) using any other suitable components, features, or techniques.

As best seen in FIGS. 3-4, shank (420) of the present example includes a set of longitudinally extending splines (426) that are spaced about shank (420) in an angular array. The proximal end of each spline (426) includes a respective lead-in edge (428). As described in greater detail below, splines (426) are configured to engage corresponding splines (316) of an inner body member (310) of stapling head assembly (300) in order to consistently provide a predetermined angular alignment between anvil (400) and stapling head assembly (300). As also described below, this angular alignment may ensure that staple forming pockets (414) of anvil (400) are consistently angularly aligned appropriately with staple openings (324) of stapling head assembly (300). Thus, in the present example, splines (426) are precisely and consistently positioned in relation to staple forming pockets (414). In versions where head (410) and shank (420) are initially formed as separate pieces and then later joined together, the machine or other device that is used to join head (410) and shank (420) together may have appropriate indexing capabilities in order to reliably and consistently achieve the proper angular positioning of head (410) and shank (420) to thereby provide precise and consistent positioning of splines (426) in relation to staple forming pockets (414). Various suitable ways in which such results may be achieved will be apparent to those of ordinary skill in the art in view of the teachings herein. In some other versions, head (410) and shank (420) are formed together simultaneously, as a single unitary construction.

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90). The following description relates to several exemplary variations of anvil (400), providing staple forming pocket configurations and arrangements that differ from those of staple forming pockets (414).

It should be understood that the various alternatives to anvil (400) described below may be readily used with instrument (10), in place of anvil (400). It should also be understood that, in some instances, the configuration and arrangement of staple openings (324) in deck member (320) may need to be varied in order to complement the configuration and arrangement of the alternative staple forming pockets described below. Various suitable ways in which the alternatives to anvil (400) described below may be incorporated into instrument (10) will be apparent to those of ordinary skill in the art in view of the teachings herein.

B. Exemplary Three-Dimensional Staple Formation Features

Figure 6:
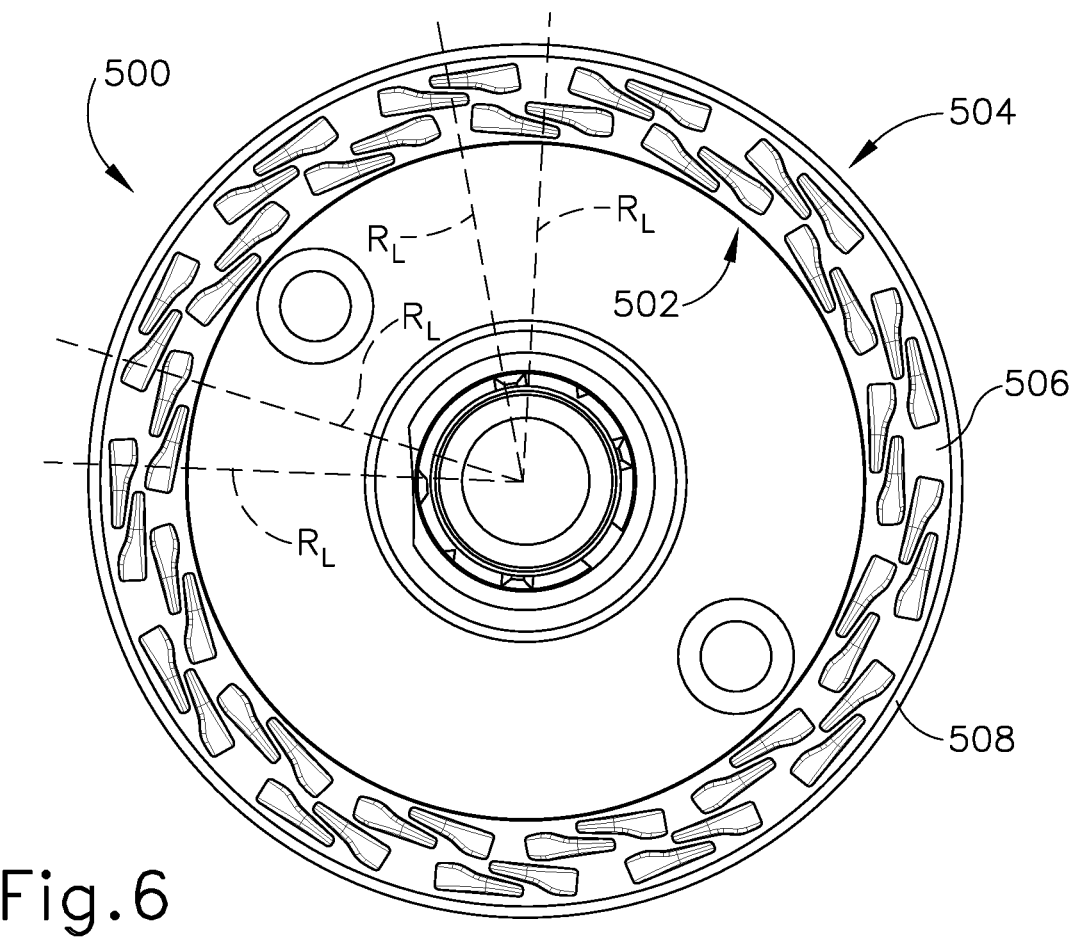
FIG. 6 depicts a bottom plan view of an exemplary alternative anvil that may be used with the circular stapler of FIG. 1 in place of the anvil of FIG. 3.
Figure 7:
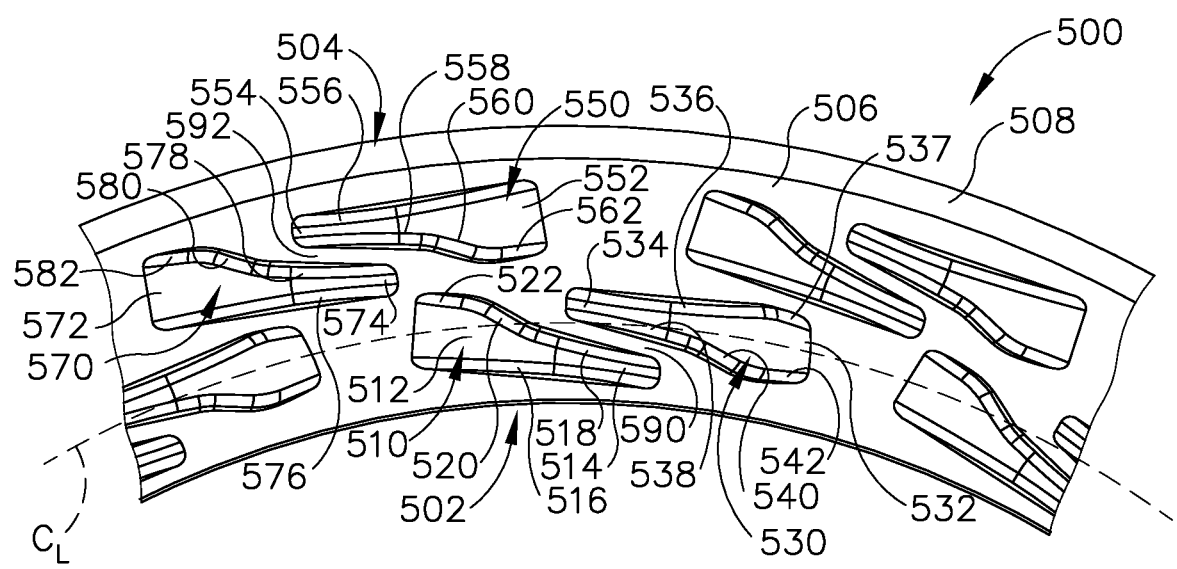
FIG. 7 depicts an enlarged bottom plan view of a portion of the anvil of FIG. 6.
Figure 8:
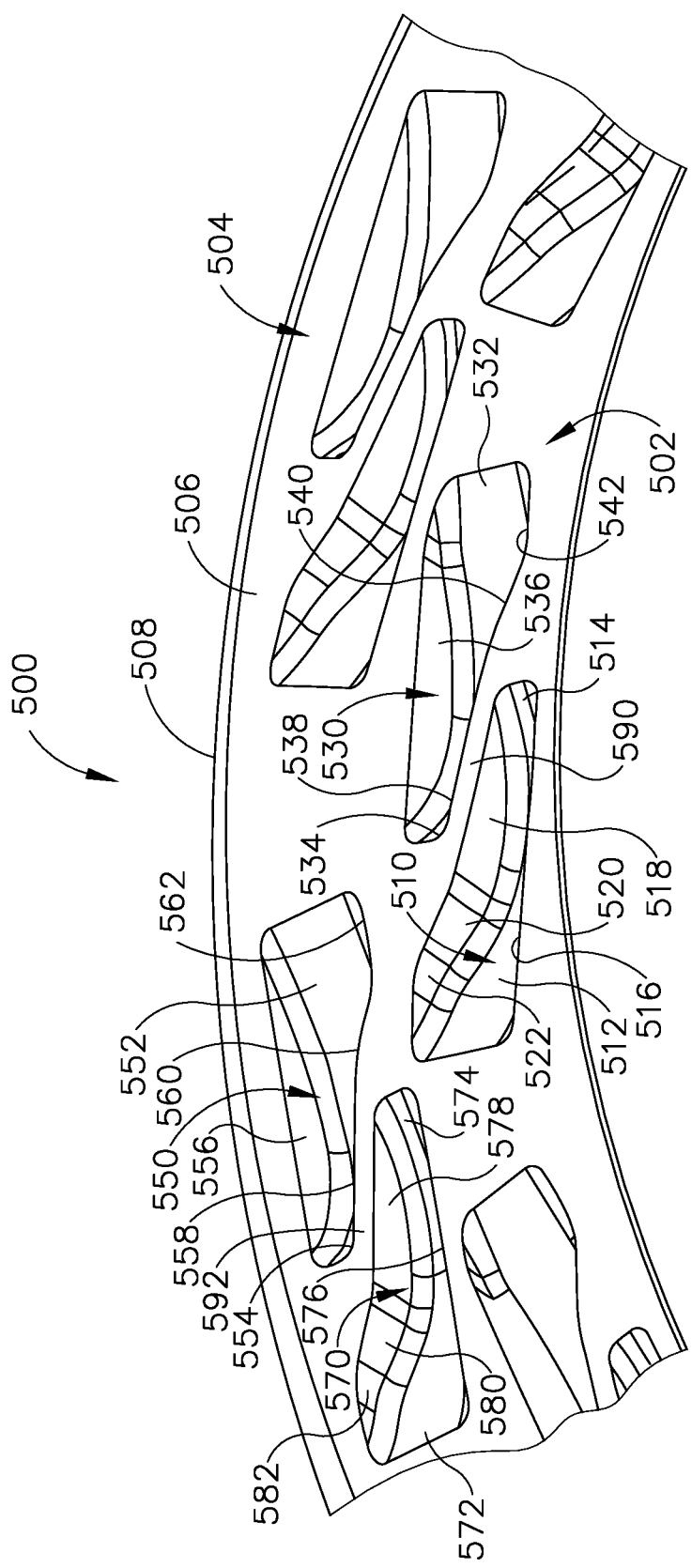
FIG. 8 depicts an enlarged perspective view of a portion of the anvil of FIG. 6.

FIGS. 6-8 show an exemplary alternative anvil (500) that may be used with a modified version of instrument (10). Anvil (500) of this example is configured and operable just like anvil (400), except for the differences described below. Anvil (500) of the present example comprises a proximal surface (506) that defines an inner annular array (502) of staple forming pockets (510, 530) and an outer annular array (504) of staple forming pockets (550, 570). A chamfered edge (508) extends about the outer perimeter of proximal surface (506). It should be understood that anvil (500) may be secured to trocar (330), that proximal surface (506) may be used to compress tissue against deck surface (322), and that staple driver (352) may drive staples (90) through tissue into staple forming pockets (510, 530, 550, 570) in order to thereby form staples (90) in the tissue.

As best seen in FIGS. 7-8, each staple forming pocket (510) comprises a staple entry surface (512) and a staple exit surface (514). Surfaces (512, 514) are contiguous with each other and define a concave recess. The concave recess formed by surfaces (512, 514) is further defined by an inner wall (516), a first outer wall (518), a second outer wall (520), and a third outer wall (522). In the present example, walls (516, 518, 520, 522) are each substantially flat. Wall (518) defines a relatively narrow, tapered gap with wall (516). Wall (522) defines a relatively wide gap with wall (516). Wall (520) is obliquely angled, providing an inwardly sloped transition from wall (522) to wall (518). Thus, walls (518, 520, 522) together provide a dogleg configuration. The edge connecting wall (516) with wall (522) is substantially straight in this example. Similarly, the edge connecting wall (516) with wall (518) is substantially straight in this example.

It should be understood that when a first leg of staple (90) is driven into staple forming pocket (510), the first leg first encounters staple entry surface (512), bends generally toward the second leg of staple (90) along a first plane that is orthogonal to the axis of the unformed first leg, and then bends proximally back generally toward the crown of staple (90). In addition, the first leg will eventually encounter wall (520), which will provide a cam surface bending the first leg along a second plane that is orthogonal to the axis of the unformed first leg. In particular, wall (520) and then wall (518) will deflect the first leg radially inwardly toward the central axis of anvil (500). Thus, staple forming pocket (510) will ultimately deflect a first leg of a staple (90) proximally and radially inwardly. Wall (516) will restrict the degree to which the first leg of staple (90) deflects radially inwardly.

Each staple forming pocket (530) comprises a staple entry surface (532) and a staple exit surface (534). Surfaces (532, 534) are contiguous with each other and define a concave recess. The concave recess formed by surfaces (532, 534) is further defined by an outer wall (536), a first inner wall (538), a second inner wall (540), and a third inner wall (542). In the present example, walls (536, 538, 540, 542) are each substantially flat. Wall (538) defines a relatively narrow, tapered gap with wall (536). Wall (542) defines a relatively wide gap with wall (536). Wall (540) is obliquely angled, providing an outwardly sloped transition from wall (542) to wall (538). Thus, walls (538, 540, 542) together provide a dogleg configuration. The edge connecting wall (536) with wall (542) is substantially straight in this example. Similarly, the edge connecting wall (536) with wall (538) is substantially straight in this example.

It should be understood that when a second leg of staple (90) is driven into staple forming pocket (530), the second leg first encounters staple entry surface (532), bends generally toward the first leg of staple (90) along a first plane that is orthogonal to the axis of the unformed second leg, and then bends proximally back generally toward the crown of staple (90). In addition, the second leg will eventually encounter wall (540), which will provide a cam surface bending the second leg along a second plane that is orthogonal to the axis of the unformed second leg. In particular, wall (540) and then wall (538) will deflect the second leg radially outwardly away from the central axis of anvil (500). Thus, staple forming pocket (530) will ultimately deflect a second leg of a staple (90) proximally and radially outwardly. Wall (536) will restrict the degree to which the second leg of staple (90) deflects radially outwardly.

Each staple forming pocket (550) comprises a staple entry surface (552) and a staple exit surface (554). Surfaces (552, 554) are contiguous with each other and define a concave recess. The concave recess formed by surfaces (552, 554) is further defined by an outer wall (556), a first inner wall (558), a second inner wall (560), and a third inner wall (562). In the present example, walls (556, 558, 560, 562) are each substantially flat. Wall (558) defines a relatively narrow, tapered gap with wall (556). Wall (562) defines a relatively wide gap with wall (556). Wall (560) is obliquely angled, providing an outwardly sloped transition from wall (562) to wall (558). Thus, walls (558, 560, 562) together provide a dogleg configuration. The edge connecting wall (556) with wall (562) is substantially straight in this example. Similarly, the edge connecting wall (556) with wall (558) is substantially straight in this example.

It should be understood that when a second leg of staple (90) is driven into staple forming pocket (550), the second leg first encounters staple entry surface (552), bends generally toward the first leg of staple (90) along a first plane that is orthogonal to the axis of the unformed second leg, and then bends proximally back generally toward the crown of staple (90). In addition, the second leg will eventually encounter wall (560), which will provide a cam surface bending the second leg along a second plane that is orthogonal to the axis of the unformed second leg. In particular, wall (560) and then wall (558) will deflect the second leg radially outwardly away from the central axis of anvil (500). Thus, staple forming pocket (550) will ultimately deflect a second leg of a staple (90) proximally and radially outwardly. Wall (556) will restrict the degree to which the second leg of staple (90) deflects radially outwardly.

Each staple forming pocket (570) comprises a staple entry surface (572) and a staple exit surface (574). Surfaces (572, 574) are contiguous with each other and define a concave recess. The concave recess formed by surfaces (572, 574) is further defined by an inner wall (576), a first outer wall (578), a second outer wall (580), and a third outer wall (582). In the present example, walls (576, 578, 580, 582) are each substantially flat. Wall (578) defines a relatively narrow, tapered gap with wall (576). Wall (582) defines a relatively wide gap with wall (576). Wall (580) is obliquely angled, providing an inwardly sloped transition from wall (582) to wall (578). Thus, walls (578, 580, 582) together provide a dogleg configuration. The edge connecting wall (576) with wall (582) is substantially straight in this example. Similarly, the edge connecting wall (576) with wall (578) is substantially straight in this example.

It should be understood that when a first leg of staple (90) is driven into staple forming pocket (570), the first leg first encounters staple entry surface (572), bends generally toward the second leg of staple (90) along a first plane that is orthogonal to the axis of the unformed first leg, and then bends proximally back generally toward the crown of staple (90). In addition, the first leg will eventually encounter wall (580), which will provide a cam surface bending the first leg along a second plane that is orthogonal to the axis of the unformed first leg. In particular, wall (580) and then wall (578) will deflect the first leg radially inwardly toward the central axis of anvil (500). Thus, staple forming pocket (570) will ultimately deflect a first leg of a staple (90) proximally and radially inwardly. Wall (576) will restrict the degree to which the first leg of staple (90) deflects radially inwardly.

As best seen in FIG. 6, staple forming pockets (510, 530, 550, 570) are arranged such that a radius line ($R_L$) extending outwardly from the center of anvil (500) passes through the region of staple entry surface (512) of staple forming pocket (510) and through the region of staple entry surface (552) of staple forming pocket (550). Thus, staple forming pockets (510, 550) overlap along a radial dimension. In addition, another radius line ($R_L$) extending outwardly from the center of anvil (500) passes through the region of staple entry surface (532) of staple forming pocket (530) and through the region of entry surface (572) of staple forming pocket (570). Thus, staple forming pockets (530, 570) overlap along a radial dimension. In addition, another radius line ($R_L$) extending outwardly from the center of anvil (500) passes through the region of exit surface (574) of staple forming pocket (570) and through the region of exit surface (554) of staple forming pocket (550). Thus, staple forming pockets (550, 570) overlap along a radial dimension. It should also be understood that staple forming pockets (550, 570) in each pair of pockets (550, 570) are interlocking in this configuration. In addition, another radius line ($R_L$) extending outwardly from the center of anvil (500) passes through the region of staple exit surface (514) of staple forming pocket (510) and through the region of exit surface (534) of staple forming pocket (530). Thus, staple forming pockets (510, 530) overlap along a radial dimension. It should also be understood that staple forming pockets (510, 530) in each pair of pockets (510, 530) are interlocking in this configuration.

In the present example, inner annular array (502) and outer annular array (504) are configured similarly, such that the inner-most pocket (510) in each pair of inner pockets (510, 530) is on the left-hand side (in the view of FIG. 7) of the pair of pockets (510, 530); and such that the inner-most pocket (570) in each pair of outer pockets (550, 570) is on the left-hand side (in the view of FIG. 7) of the pair of pockets (550, 570).

Also, in the present example, the end of wall (536) associated with staple entry surface (532) includes a bent region (537), which bends slightly inwardly toward the central region of anvil (500). It should be understood that this bent region (537) may be formed in order to maintain a minimum distance between wall (536) and wall (576), thereby maintaining a minimum distance between staple forming pocket (530) and staple forming pocket (570), which may further provide more reliable manufacturing of anvil (500). In addition, bent region (537) may provide different behavior of the second leg of the staple (90) that is formed by staple forming pocket (530). Such different behavior may relate to deflections in anvil (500) and/or a tilt that might result in the first and second legs of a given staple (90) contacting corresponding surfaces (512, 532) at different times during actuation of stapling head assembly (300).

It should also be understood that the presence of bent region (537) provides staple forming pocket (530) with a structural configuration that makes staple forming pocket (530) unique relative to the other staple forming pockets (510, 550, 570). By contrast, the structural configuration of staple forming pocket (510) is identical to the structural configuration of staple forming pocket (570); while the structural configuration of staple forming pocket (550) is the mirrored inverse of the structural configuration of staple forming pockets (510, 570).

In the present example, the spacing between pockets (510, 530) in each pair of pockets (510, 530) is equal to the spacing between pockets (550, 570) in each pair of pockets (550, 570). Thus, staples (90) formed by pockets (510, 530) will have the same crown width as staples formed by pockets (550, 570). In some other versions, however, the spacing between pockets (510, 530) in each pair of pockets (510, 530) is smaller than the spacing between pockets (550, 570) in each pair of pockets (550, 570). In such versions, pockets (550, 570) may be used to form staples (90) having a longer crown width than staples (90) that are formed using pockets (510, 530). As another merely illustrative variation, the spacing between pockets (510, 530) in each pair of pockets (510, 530) may be larger than the spacing between pockets (550, 570) in each pair of pockets (550, 570). In such versions, pockets (550, 570) may be used to form staples (90) having a shorter crown width than staples (90) that are formed using pockets (510, 530). In other words, where at least two annular arrays of staples are formed, staples (90) in one array may have a larger, smaller, or same crown width as staples (90) in another annular array.

As also seen in FIG. 7, staple forming pockets (510, 530) are arranged such that they are not fully centered along a circumferential line (CO extending along surface (506) at a constant radius from the center of anvil (500). The outermost regions of staple entry surfaces (512, 532) are radially centered along the same circumferential line (CO. However, staple forming pocket (510) is oriented substantially obliquely relative to circumferential line (CL), such that staple exit surface (514) is positioned substantially radially inwardly from circumferential line (CO. By contrast, staple exit surface (534) is positioned substantially along, with a portion position slightly radially outwardly from, circumferential line (CO. In other words, while staple forming pocket (530) is substantially aligned along circumferential line (CL), staple forming pocket (510) is substantially tilted radially inwardly relative to circumferential line (CL), with the outermost regions of staple entry surfaces (512, 532) being radially centered along a circumferential line (CO.

While the views depicted in FIGS. 7-8 only show a portion of the full circumference of anvil (500), it should be understood that the structures depicted in FIGS. 7-8 extend along the full circumference of anvil (500). The views of FIGS. 7-8 are simply being provided as an enlargement to show the structure in further detail, and are not intended to suggest that the depicted structures are only located in a limited angular range along the circumference of anvil (500).

Those of ordinary skill in the art will understand that staples formed by anvil (500) will have a three-dimensional profile, where the legs are angularly offset from a plane passing through a crown of the staple; in addition to being bent generally toward each other. By way of example only, the staples formed using anvil (500) may have an appearance similar to at least some of the staples shown and described in U.S. Pat. No. 10,092,292, entitled "Staple Forming Features for Surgical Stapling Instrument," issued Oct. 9, 2018, the disclosure of which is incorporated by reference herein. By way of further example only, the staples formed using anvil (500) may have an appearance similar to at least some of the staples shown and described in U.S. Pub. No. 2018/0132849, entitled "Staple Forming Pocket Configurations for Circular Surgical Stapler Anvil," published May 17, 2018, the disclosure of which is incorporated by reference herein.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

III. Exemplary Stapling Head Assembly

A. Overview

Figure 9:
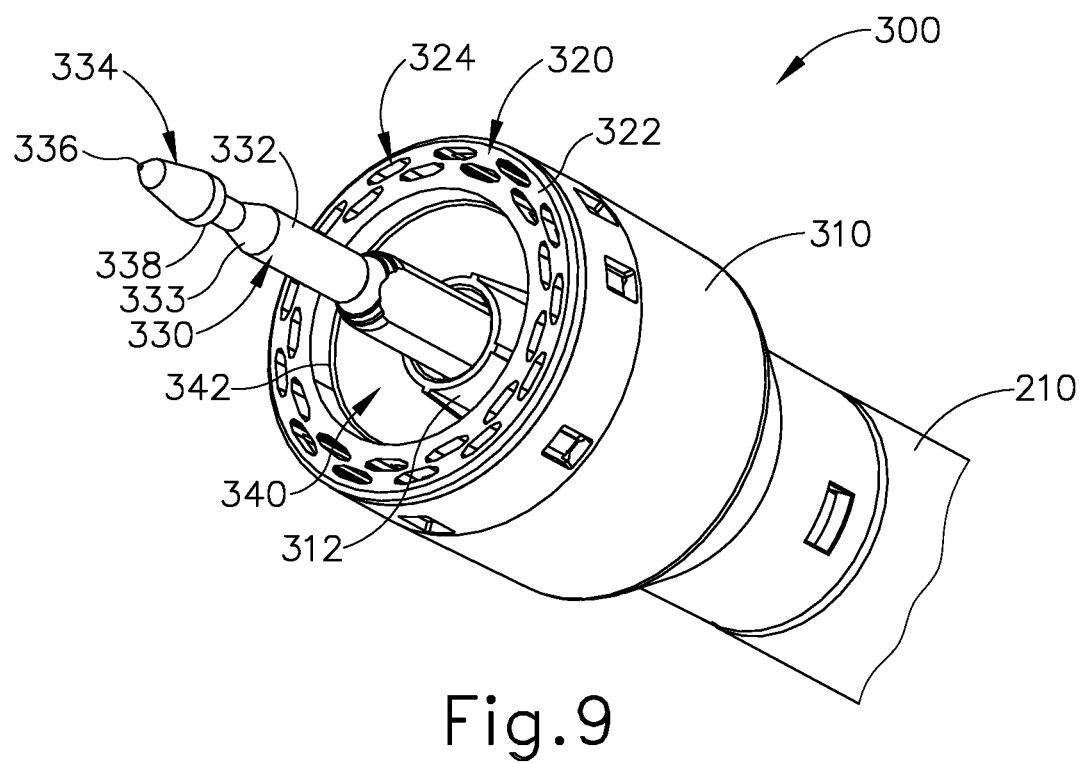
FIG. 9 depicts a perspective view of the stapling head assembly of the circular stapler of FIG. 1.
Figure 10:
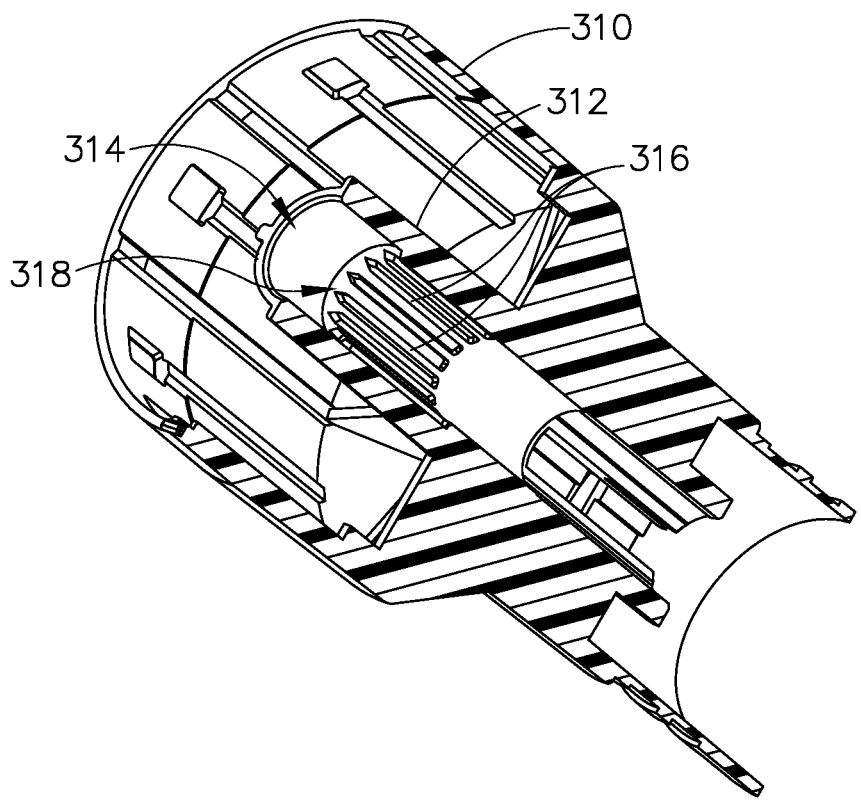
FIG. 10 depicts a perspective cross-sectional view of an inner body member of the stapling head assembly of FIG. 9.
Figure 11:
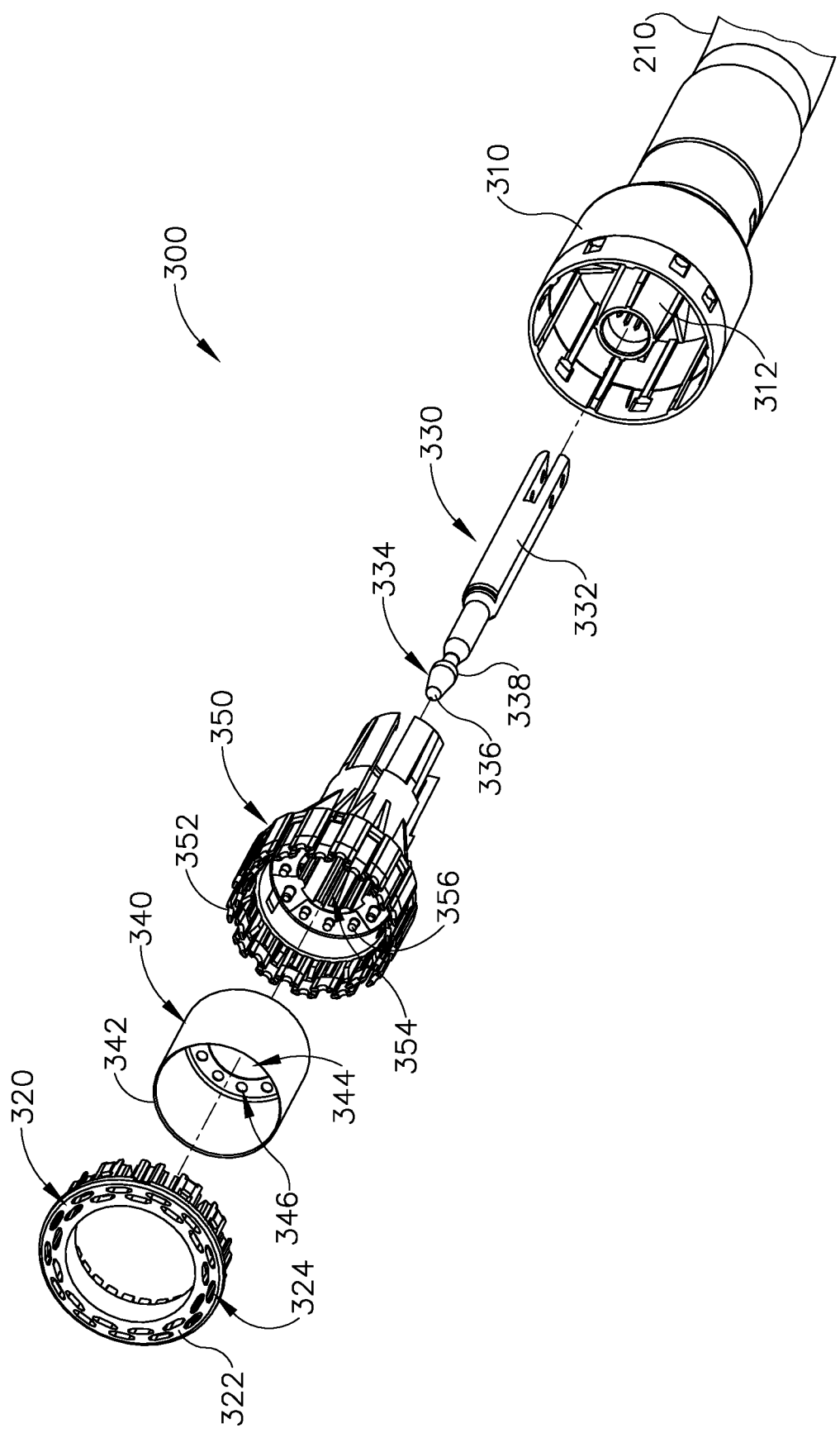
FIG. 11 depicts an exploded perspective view of the stapling head assembly of FIG. 9.

As best seen in FIGS. 9-11, stapling head assembly (300) of the present example is coupled to a distal end of shaft assembly (200) and comprises a body member (310) and a slidable staple driver member (350). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

As shown in FIG. 10, inner core member (312) of body member (310) defines a bore (314). A plurality of longitudinally extending splines (316) are equidistantly spaced in an angular array within bore (314). The distal ends of splines (316) include lead-in edges (318) that are configured to complement lead-in edges (428) of splines (426) on shank (420) of anvil (400). In particular, after shank (420) is secured to trocar (330) as described in greater detail below, and as anvil (400) is thereafter retracted proximally relative to stapling head assembly (300) as also described in greater detail below, lead-in edges (318, 428) may cooperatively engage each other to drive anvil (400) to rotate relative to trocar (330) to angularly align splines (426) of anvil (400) with the gaps between splines (316) of body member (310). The gaps between splines (316) may be configured to have a width that is substantially equal to the width of splines (426). In this manner, when splines (426) of anvil (400) are positioned within the gaps between splines (316) of body member (310), anvil (400) may achieve a predetermined angular alignment relative to stapling head assembly (300). This predetermined angular alignment may ensure that staple openings (324) of deck member (320) are precisely aligned with corresponding staple forming pockets (414, 510, 530) of anvil (400). Thus, splines (316, 426) are configured to cooperate with each other to ensure that staples ejected through staple openings (324) are accurately driven into corresponding staple forming pockets (414, 510, 530) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336)

and an inwardly extending proximal surface (338). Shaft (332) thus provides a reduced outer diameter just proximal to head (334), with proximal surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within body member (310) in response to activation of motor (161) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive inner core member (312) of body member (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive inner core member (312) of body member (310). An annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and staple driver member (350) will be apparent to those of ordinary skill in the art in view of the teachings herein.

A deck member (320) is fixedly secured to body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (324) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 9, deck member (320) defines an inner diameter that is just slightly larger than the outer diameter defined by knife member (340). Deck member (320) is thus configured to allow knife member (340) to translate distally to a point where cutting edge (342) is distal to deck surface (322).

B. Exemplary Tissue Gripping Features

Figure 12:
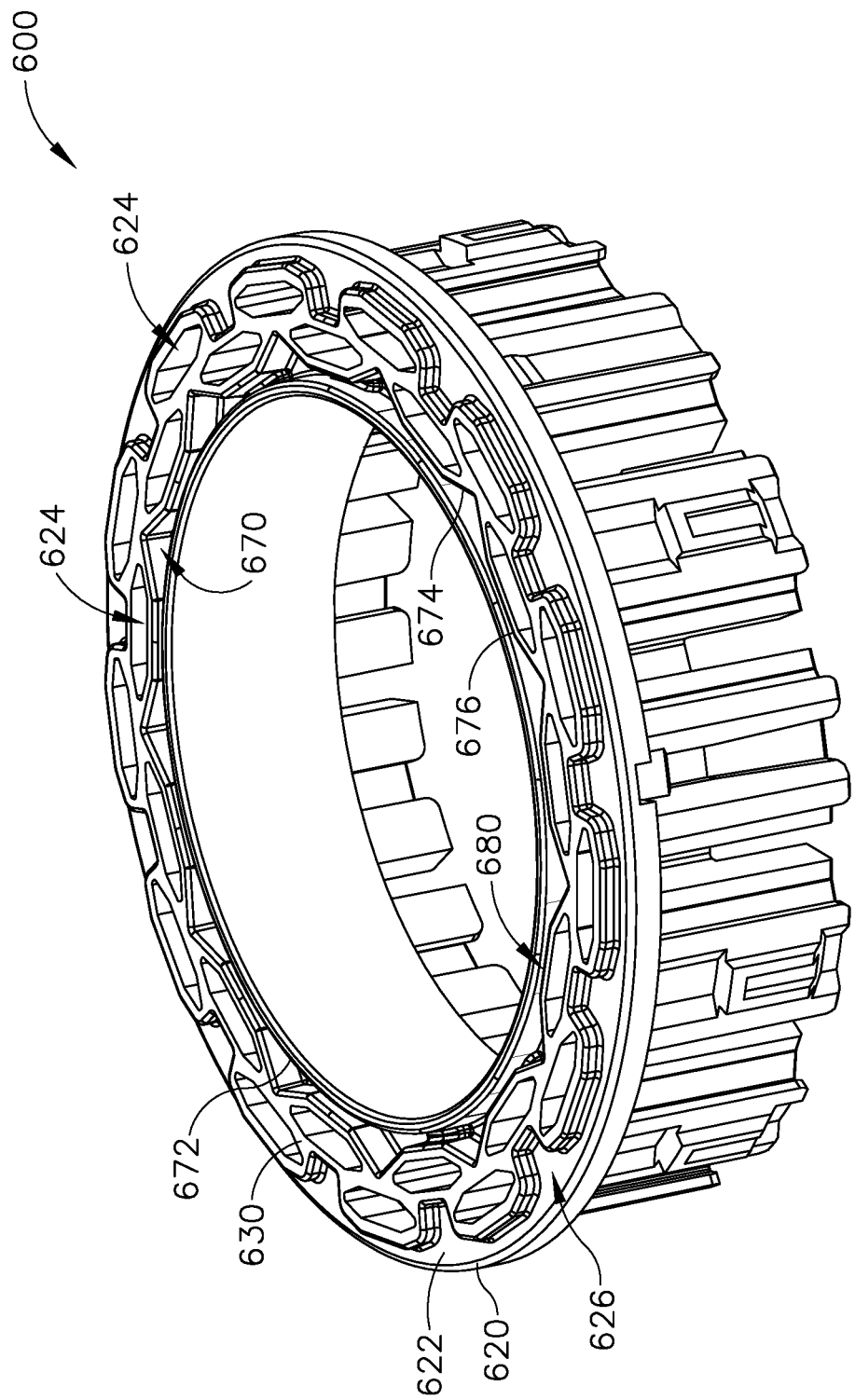
FIG. 12 depicts a perspective view of an exemplary alternative deck member that may be incorporated into the stapling head assembly of FIG. 9.
Figure 13:
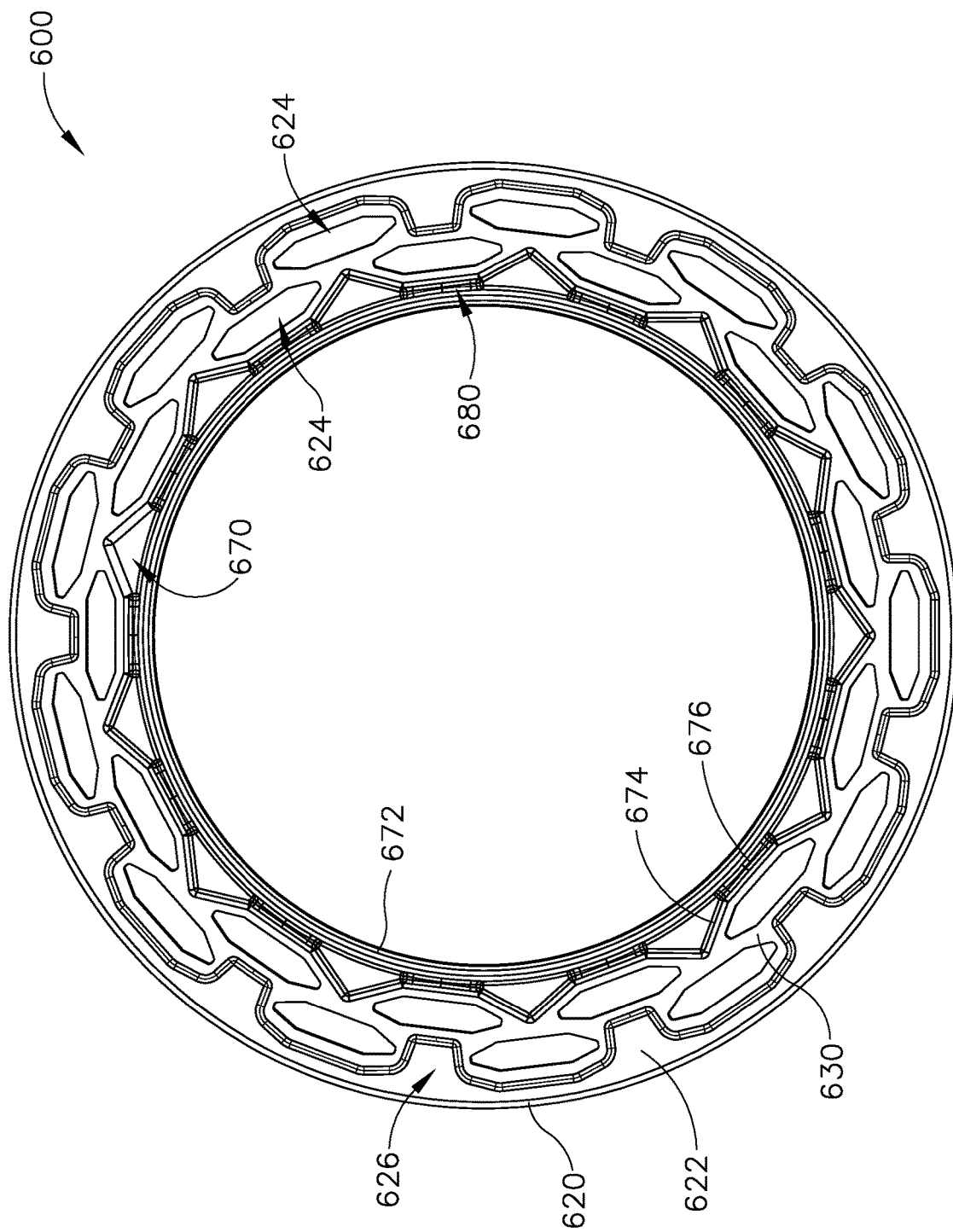
FIG. 13 depicts a top plan view of the deck member of FIG. 12.

It may be desirable to provide a version of stapling head assembly (300) that includes features that enhance gripping of tissue during actuation of stapling head assembly (300), thereby promoting successful tissue cutting and staple deployment, without increasing the risk of damaging the patient's tissue as stapling head assembly (300) slides along the tissue during positioning of stapling head assembly (300). FIGS. 12-13 show an example of a deck member (600) that provides enhanced tissue gripping effects without increasing the risk of tissue damage. Deck member (600) may be readily incorporated into stapling head assembly (300) in place of deck member (320).

Deck member (600) of this example includes a first deck surface (622), a second deck surface (630), and two concentric annular arrays of staple openings (624). Staple openings (624) are arranged to correspond with the arrangement of staple drivers (352) and staple forming pockets (414) described above. Thus, each staple opening (624) is configured to provide a path for a corresponding staple driver (352) to drive a corresponding staple through deck member (600) and into a corresponding staple forming pocket (414) when a stapling head assembly (300) incorporating deck member (600) is actuated. Deck member (600) defines an inner diameter that is just slightly larger than the outer diameter defined by knife member (340). Deck member (600) is thus configured to allow knife member (340) to translate distally to a point where cutting edge (342) is distal to the plane of second deck surface (630).

In the present example, an outer edge (620) spans around the full circumference of deck member (600) with a consistent surface geometry. In the present example, outer edge (620) is configured to prevent outer edge (620) from snagging on tissue. In some versions, outer edge (620) has a curved profile. In some other versions, outer edge (620) has a chamfered profile. Alternatively, outer edge (620) may have any other suitable kind of profile.

Second deck surface (630) is proud relative to first deck surface (622), such that first deck surface (622) is recessed relative to second deck surface (630). As shown, second deck surface (630) fully surrounds each and every staple opening (624), including the inner array of staple openings (624) and the outer array of staple openings (624). However, first deck surface (622) extends inwardly between staple openings (624) of the outer array of staple openings (624), thereby creating gaps (626) in second deck surface (630) between staple openings (624) of the outer array of staple openings (624).

A plurality of recesses (670) are spaced between the staple openings (624) of the inner annular array of staple openings (624). Recesses (670) of the present example are generally shaped like isosceles triangles, with each triangle being defined by a pair of straight walls (674) having equal length and an inner annular wall (672). The vertexes formed by walls (674) are positioned at the radially outermost points of recesses (670). In particular, these vertexes are located at radial positions corresponding to the same circumference at which the angularly outermost points of staple openings (624) are located. In other words, these vertexes of recesses (670) and corresponding points of staple openings (624) are all positioned at the same radial distance along the same circumference in this example. Alternatively, the position and configuration of recesses (670) may have any other suitable relationship with the position and configuration of staple openings (624).

Recesses (670) of the present example are joined together by channels (680) which are defined between inner annular wall (672) and respective opposing annular walls (676). Walls (672, 676) are parallel with each other and are closely positioned relative to each other, such that channels (680) are substantially small in comparison to recesses (670).

Gaps (626), recesses (670), and channels (680) are configured to receive tissue as tissue is being compressed against deck surfaces (622, 630) by anvil (400) as described above. In particular, when anvil (400) is actuated via knob (130) to compress tissue between anvil (400) and deck surfaces (622, 630), portions of the compressed tissue will enter gaps (626), recesses (670), and channels (680). By having some of the tissue enter gaps (626), recesses (670), and channels (680), this may reduce the total pressure that would otherwise be applied to the tissue if the tissue were being compressed against a consistently flat deck surface like deck surface (322). The pressure on tissue is thus concentrated only in the areas where pressure is actually needed—immediately adjacent to staple openings (624). By reducing the total pressure on the tissue, deck member (600) may reduce the risk of the tissue from becoming fractured by over-compression. In addition to reducing the total pressure on tissue, the entry of tissue portions in gaps (626), recesses (670), and channels (680) may provide a grip on the compressed tissue that is greater than the grip that could otherwise be achieved using a consistently flat deck surface like deck surface (322). The enhanced grip of tissue may promote cleaner cutting by knife member (340) and also promote more successful deployment of staples (90) in the tissue. Thus, the presence of gaps (626), recesses (670), and channels (680) may both reduce the risk of over-compression of tissue and promote greater success in cutting and stapling the tissue.

In the present example, gaps (626), recesses (670), and channels (680) all extend to substantially the same depth relative to second deck surface (630). In some other versions, gaps (626), recesses (670), and channels (680) extend to different depths relative to second deck surface (630). For instance, gaps (626) may extend to greater depths than recesses (670) relative to second deck surface (630) or vice versa. It should also be understood that gaps (626) may alternate depths relative to second deck surface (630), such that gaps (626) alternate between a relatively shallow gap (626) and a relatively deep gap (626) along at least a portion of the angular range of deck member (600). Similarly, recesses (670) may alternate depths relative to second deck surface (630), such that recesses (670) alternate between a relatively shallow recess (670) and a relatively deep recess (670) along at least a portion of the angular range of deck member (600). As yet another merely illustrative variation, the depth of a given gap (626) or recess (670) may vary within that particular gap (626) or recess (670). For instance, the radially innermost region of a given gap (626) may be deeper or shallower than the radially outermost region of that same gap (626). Similarly, the region of each recess (670) near the vertex may be deeper or shallower than the region of each recess (670) near inner annular wall (672). Other suitable variations that may be provided in the depth of gaps (626), recesses (670), and/or channels (680) relative to second deck surface (630) will be apparent to those of ordinary skill in the art in view of the teachings herein.

Inner annular wall (672) extends consistently along the full circumference of deck member (600). In particular, the height of the uppermost edge of inner annular wall (672) is consistent along the full circumference of deck member (600). The uppermost edge of inner annular wall (672) is thus configured to provide consistent pressure against the adjacent annular region of tissue as the tissue is being compressed against deck member (600) by anvil (400). This application of consistent pressure against the adjacent annular region of tissue may further assist in clean cutting of the tissue by knife member (340), particularly since knife member (340) will be severing the tissue right next to the uppermost edge of inner annular wall (672). In the present example, the uppermost edge of inner annular wall (672) is substantially flush with second deck surface (630). In some other variations, the uppermost edge of inner annular wall (672) is proud or raised relative to second deck surface (630). In still other variations, the uppermost edge of inner annular wall (672) is recessed or lower relative to second deck surface (630).

C. Exemplary Anvil Coupling Detection

In some versions of instrument (10) it may desirable to provide instrument (10) with features that are configured to indicate proper and/or improper attachment of anvil (400) to trocar (330) of stapling head assembly (300). For instance, if anvil (400) is not properly attached to trocar (330), an operator may receive audible and/or tactile feedback indicating improper attachment. Additionally, if anvil (400) is properly attached to trocar (330), an operator may receive audible, tactile, and/or visible feedback indicating proper attachment. In addition or in the alternative, features may be configured to prevent firing of stapling head assembly (300) unless anvil (400) is properly attached to trocar (330). For instance, if anvil (400) is not properly attached to trocar (330), stapling head assembly (300) may be prevented from firing. If anvil (400) is properly attached to trocar (330), firing of stapling head assembly (300) may be enabled. Various examples of such features will be described in greater detail below; while other examples will be apparent to those of ordinary skill in the art in view of the teachings herein. Moreover, the following teachings may be applied to devices that are used in various other contexts.

Figure 14B:
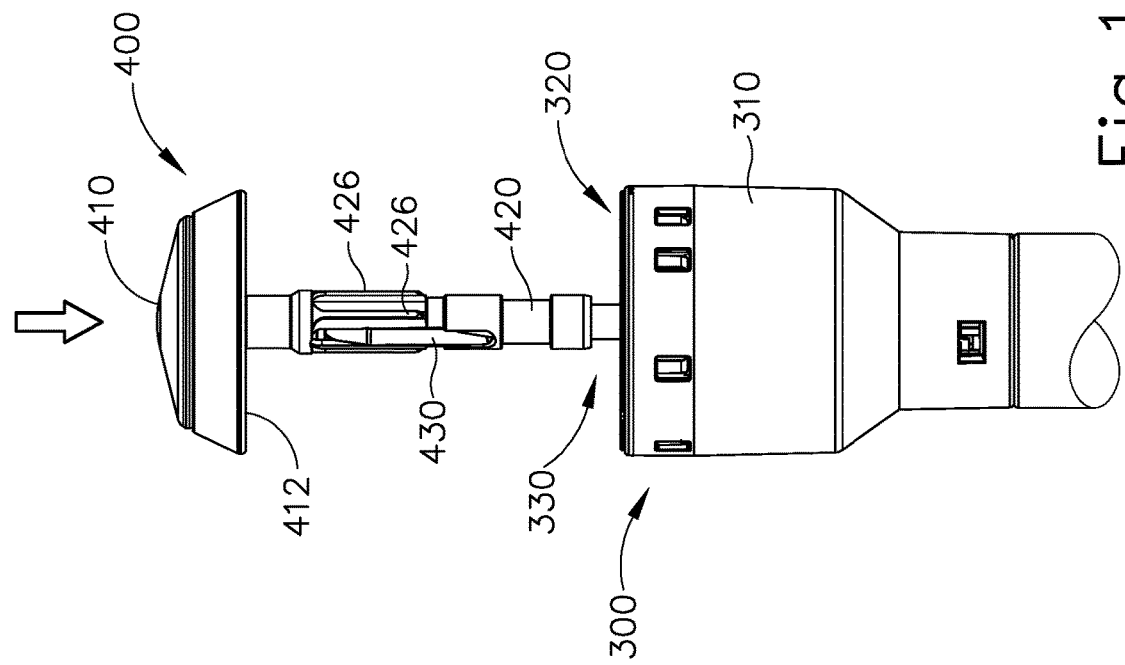
FIG. 14B shows a side elevational view of the anvil of FIG. 3 at a second longitudinal position in relation to the stapling head assembly of FIG. 9.
Figure 14A:
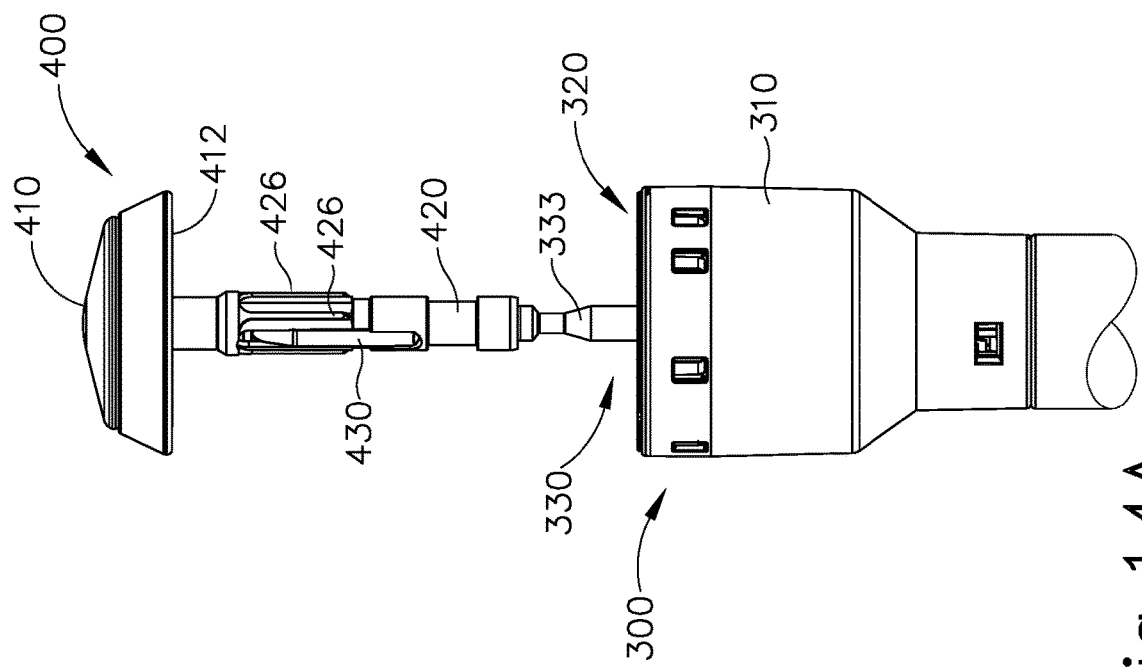
FIG. 14A shows a side elevational view of the anvil of FIG. 3 at a first longitudinal position in relation to the stapling head assembly of FIG. 9.

In the example shown in FIGS. 14A-14B, trocar (330) includes a colored region (333) that is longitudinally positioned at a location where colored region (333) is exposed before shank (420) is fully seated on trocar (330) (FIG. 14A); and covered when shank (420) is fully seated on trocar (330) (FIG. 14B). Colored region (333) may be colored using a color (e.g., orange) that is easily visible in relation to adjacent regions of trocar (330) and shank (420). When coupling shank (420) with trocar (330), the operator may observe colored region (333) to ensure that the entire colored region (333) is obscured by shank (420) before attempting to retract the combination of trocar (330) and anvil (400) relative to stapling head assembly (300). If the operator continues to see even a portion of colored region (333), the operator may continue pressing anvil (400) onto trocar (330) until colored region (333) is completely obscured by shank (420).

Even when trocar (330) includes a visual feedback feature such as colored region (333) to assist the operator with proper seating of anvil (400) on trocar (330), it may still be desirable to include a sensor feature that is operable to detect whether anvil (400) is properly seated on trocar (330). To that end, FIGS. 15A-16B depict an exemplary switch assembly (2600) that is incorporated into stapling head assembly (300) in the present example. Switch assembly (2600) includes a dome switch (2610) and a resilient actuator spring (2602). Actuator spring (2602) is secured within a cavity (2606) formed within body member (310). Dome switch (2610) is positioned between a pair of flanges (2612, 2614) of actuator spring (2602) such that movement of flange (2612) toward flange (2614) will actuate dome switch (2610).

When anvil (400) is properly secured to trocar (330) and is retracted proximally as described herein, anvil (400) causes movement of flange (2612) toward flange (2614) so as to actuate dome switch (2610). Actuation of dome switch (2610) may provide audible, tactile, and/or visible feedback to an operator indicating proper attachment. Various suitable features that may be used to provide such a response to actuation of dome switch (2610) will be apparent to those of ordinary skill in the art in view of the teachings herein. In addition, in the present example actuation of dome switch (2610) may enables firing of stapling head assembly (300). In other words, unless dome switch (2610) has been actuated, stapling head assembly (300) may not be fired in the present example.

Figure 15A:
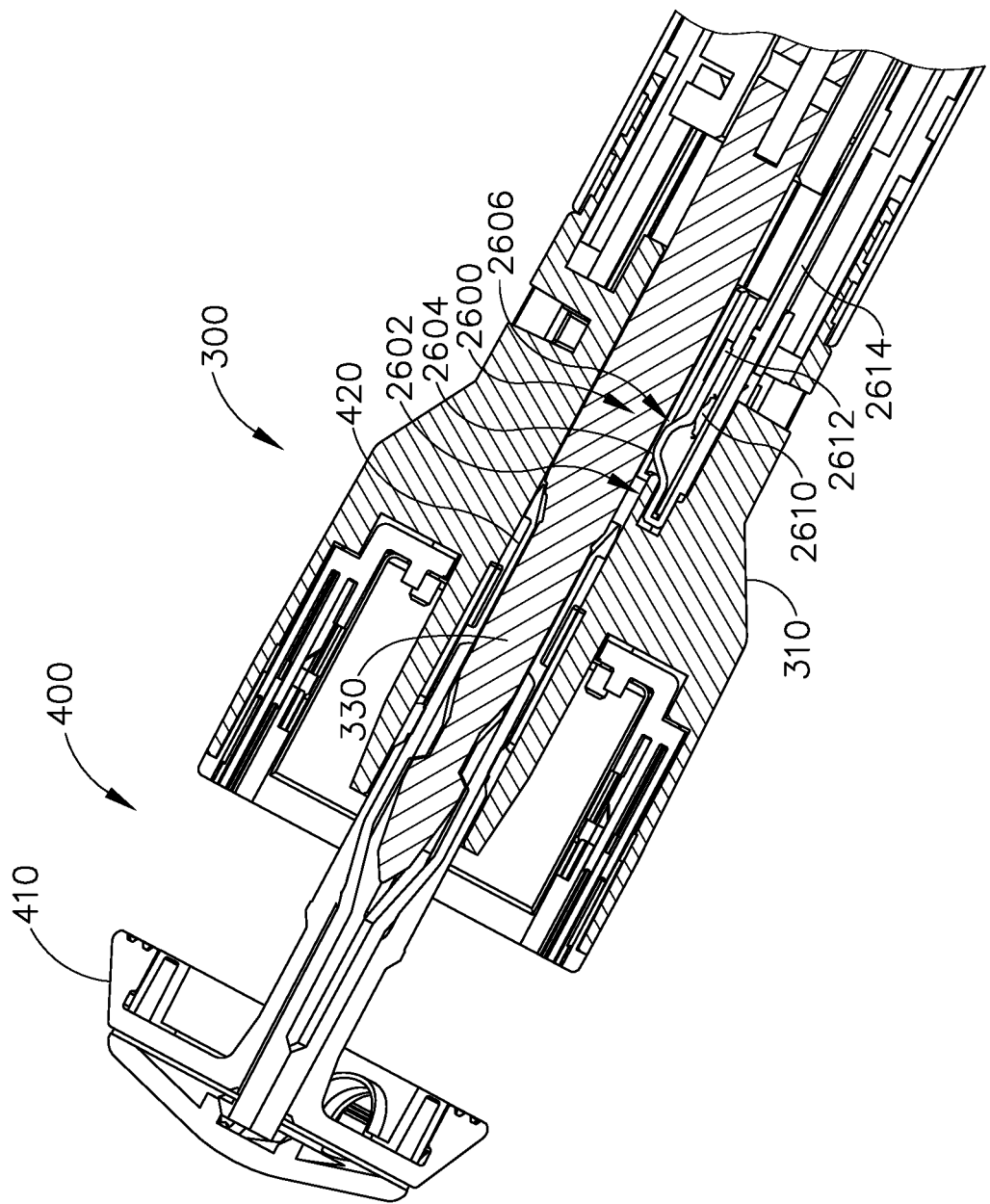
FIG. 15A depicts a cross-sectional side view of the distal end of the circular stapler of FIG. 1, with a contact switch of the circular stapler in an open state.
Figure 15B:
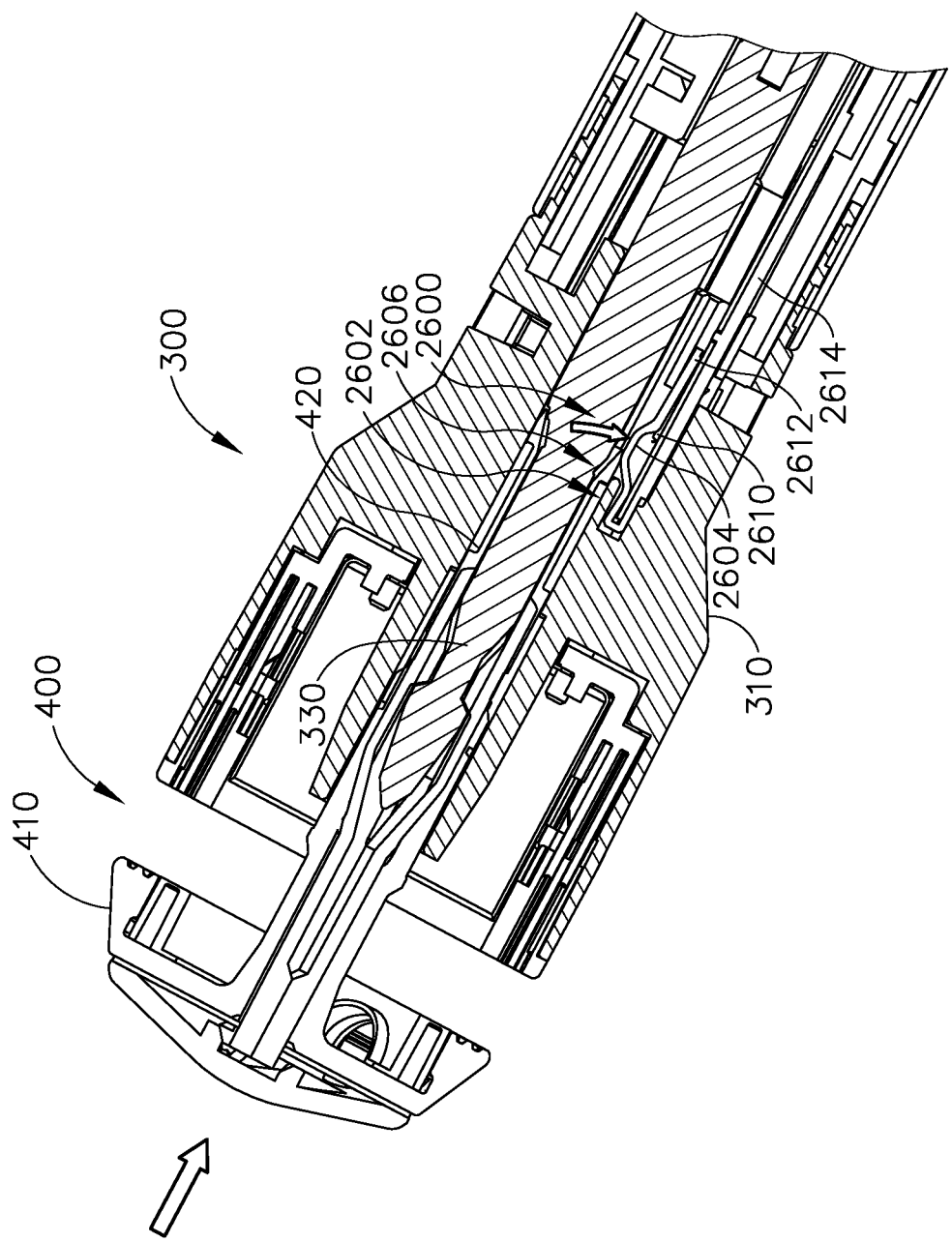
FIG. 15B depicts a cross-sectional side view of the distal end of the circular stapler of FIG. 1, with the contact switch of FIG. 15A moved into a closed state by proximal translation of a trocar and an anvil of the circular stapler.
Figure 16A:
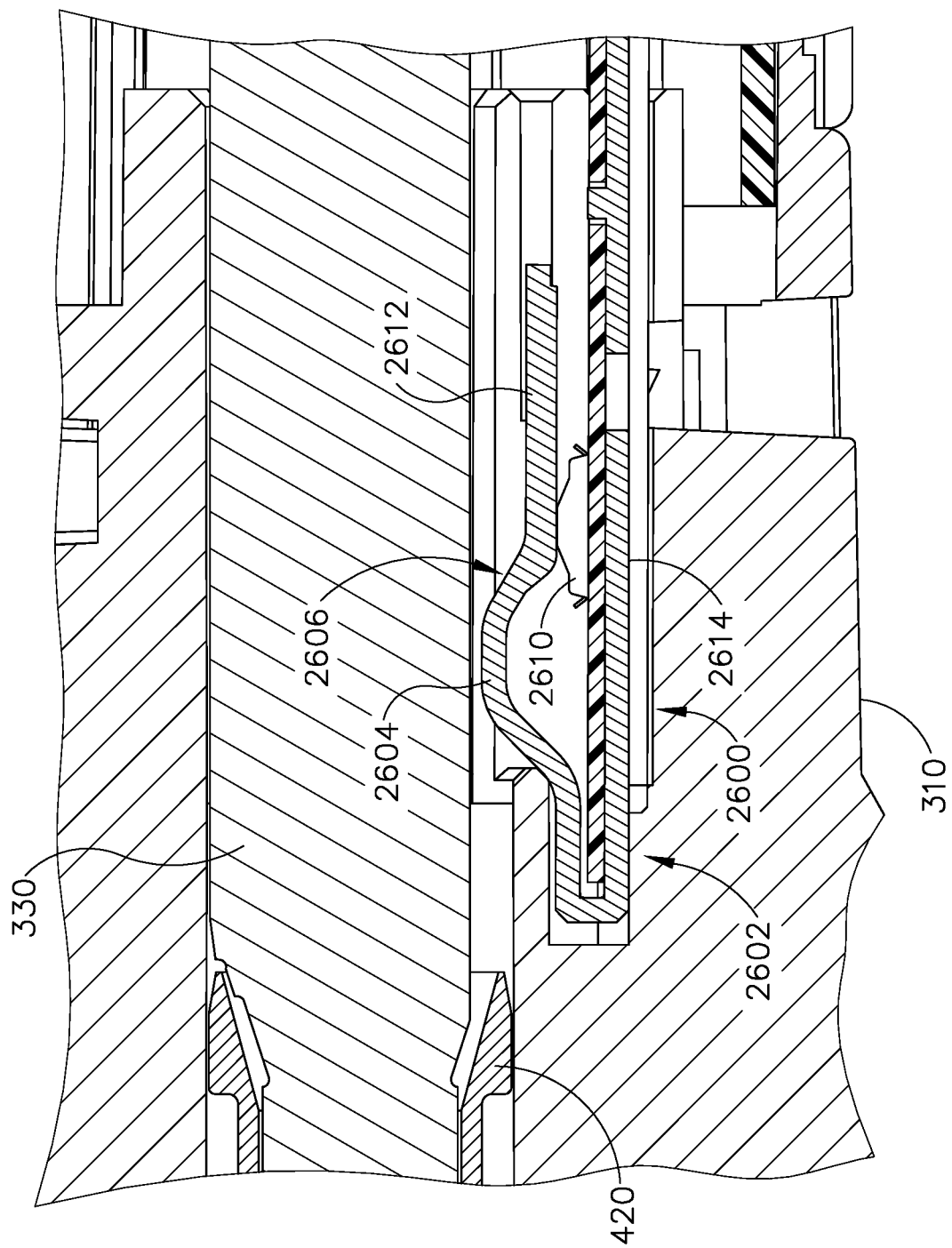
FIG. 16A depicts an enlarged cross-sectional side view of the contact switch of FIG. 15A in the open state of FIG. 15A.

After anvil (400) is secured to trocar (330), the operator then rotates knob (130) to cause trocar (330) and anvil (400) to retract proximally as described above. When trocar (330) and anvil (400) are properly secured to one another, the proximal retraction of trocar (330) and anvil (400) compresses the tissue of tubular anatomical structures (20, 40) between surfaces (412, 322) of anvil (400) and stapling head assembly (300) as described herein. When trocar (330) and anvil (400) are not properly secured to one another, trocar (330) is retracted proximally without anvil (400), such that the tissue of tubular anatomical structures (20, 40) remains uncompressed. When trocar (330) and anvil (400) are properly secured to one another, as trocar (330) and anvil (400) are retracted proximally, a proximal end of shank (420) of anvil (400) engages a raised portion (2604) of flange (2612) of actuator spring (2602) and thereby drives flange (2612) toward flange (2614), thereby actuating dome switch (2610) as shown in FIGS. 15B and 16B.

In the present example, dome switch (2610) is not actuated immediately upon proper seating of shank (420) on trocar (330). Instead, trocar (330) and anvil (400) have to be retracted proximally relative to stapling head assembly (300) by at least some distance before dome switch (2610) is actuated. In the present example, dome switch (2610) is actuated before anvil (400) reaches the "green zone" as described herein. In some other variations, dome switch (2610) is not actuated until after anvil (400) reaches the distal-most boundary of the "green zone" as described herein.

As mentioned above, the actuation of dome switch (2610) may provide audible, tactile, and/or visible feedback to an operator indicating proper attachment. Moreover, such actuation of dome switch (2610) enables firing of stapling head assembly (300). In other words, unless dome switch (2610) has been actuated, stapling head assembly (300) may not be fired. An exemplary way in which dome switch (2610) may be integrated into a control circuit (2700) will be described in greater detail below with reference to FIG. 60.

Other examples will be apparent to those of ordinary skill in the art in view of the teachings herein.

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

IV. Exemplary Drive Assemblies

Figure 17:
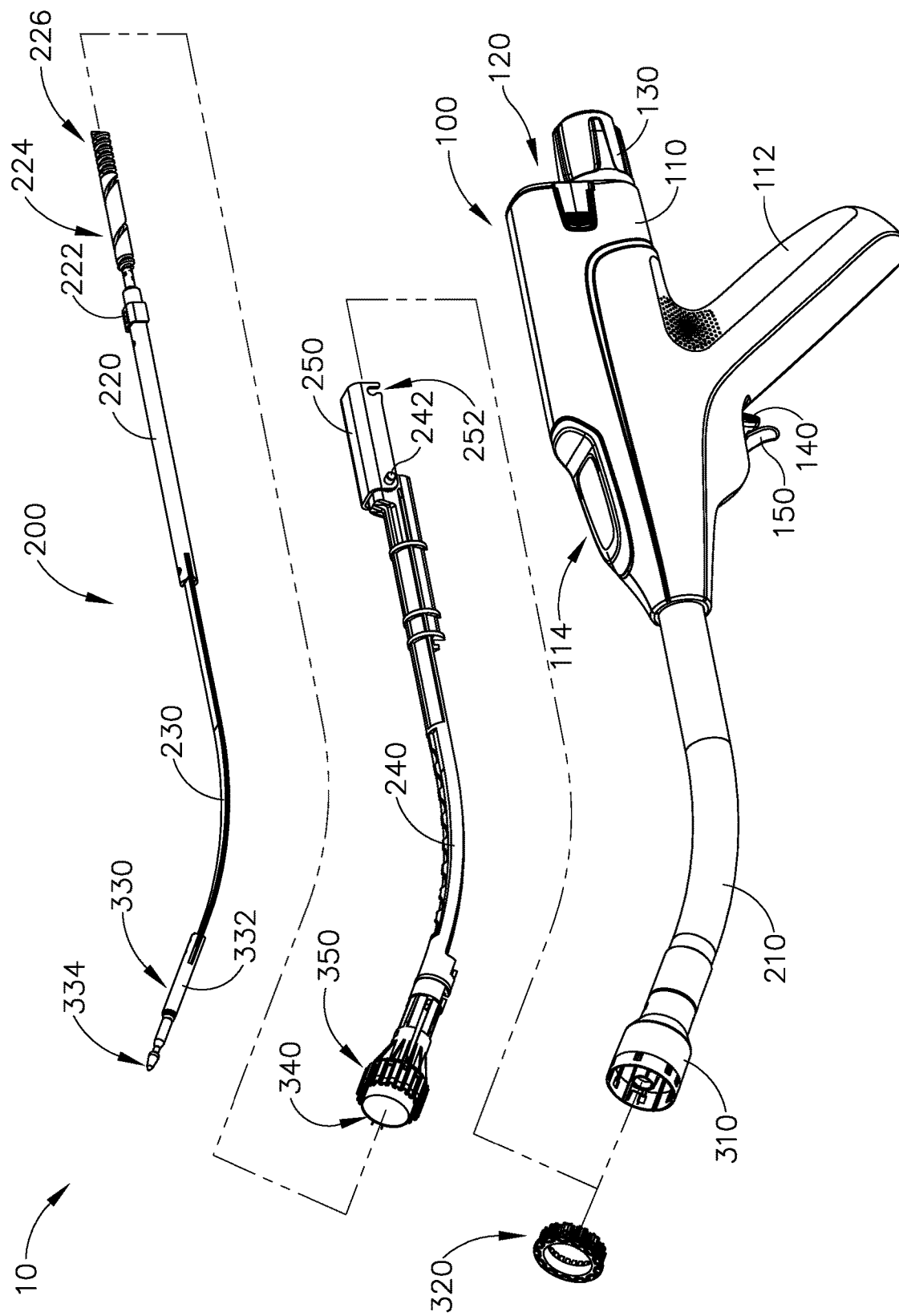
FIG. 17 depicts an exploded perspective view of the circular stapler of FIG. 1, with portions of the shaft assembly shown separately from each other.

FIG. 17 shows various components of shaft assembly (200), which couples components of stapling head assembly (300) with components of handle assembly (100). In particular, and as noted above, shaft assembly (200) includes an outer sheath (210) that extends between handle assembly (100) and body member (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of shaft (332) of trocar (330). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to shaft (332) of trocar (330). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 17, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

Figure 18:
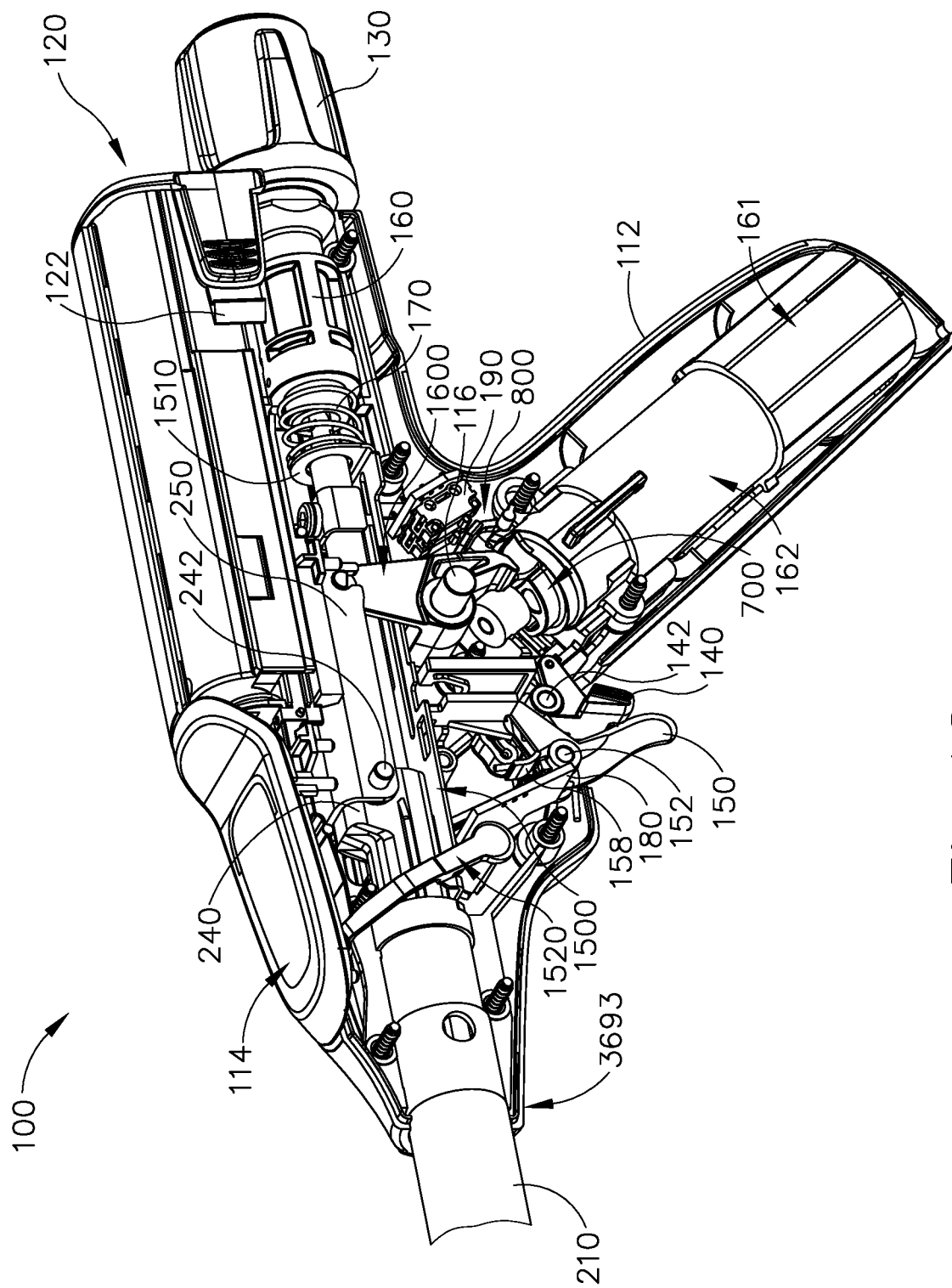
FIG. 18 depicts a perspective view of the handle assembly of the circular stapler of FIG. 1, with a housing portion omitted to reveal internal components of the handle assembly.

As shown in FIG. 18, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, firing trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

A. Exemplary Anvil Actuation Assembly

Figure 19:
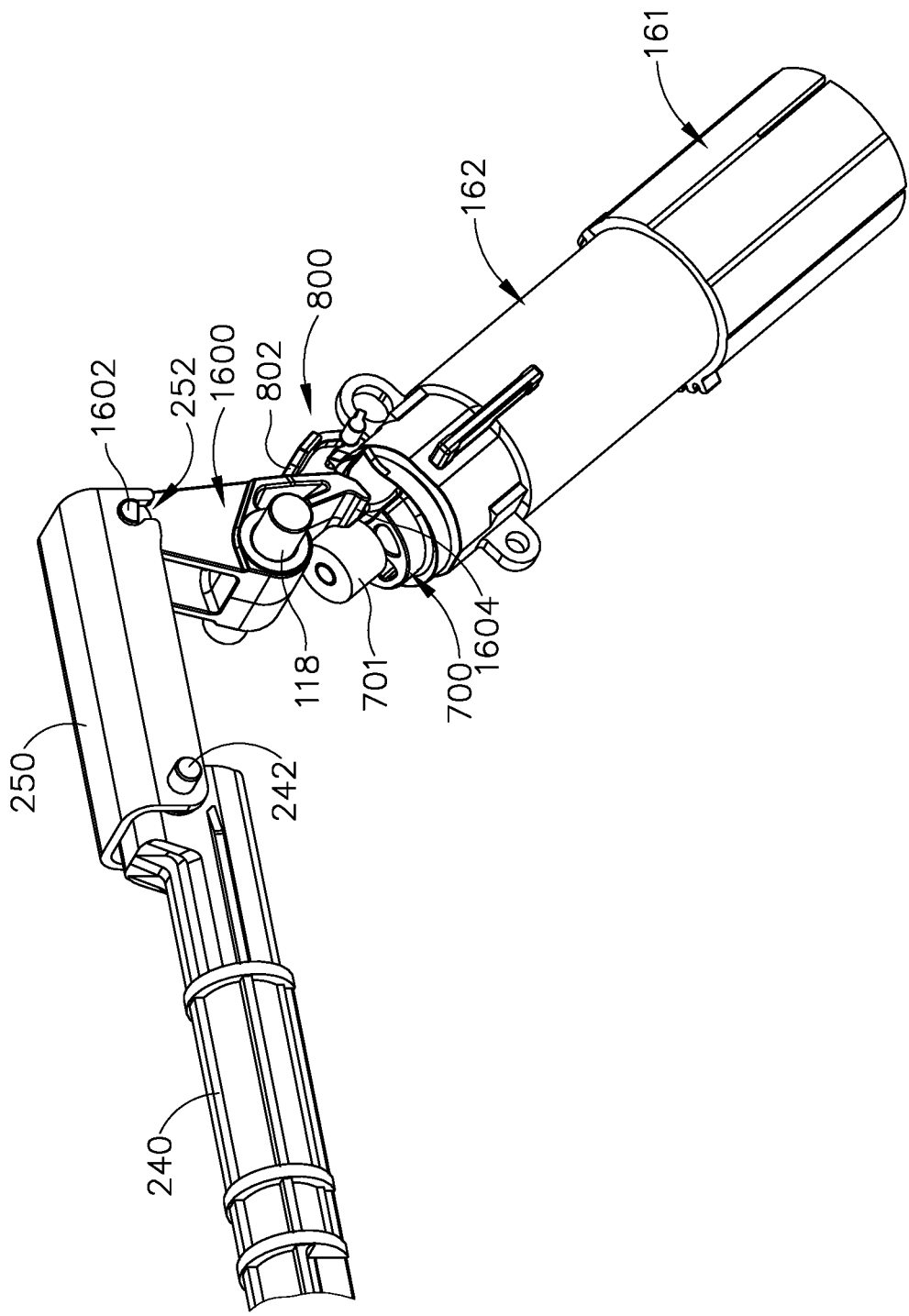
FIG. 19 depicts a perspective view of a stapling head actuation assembly of the circular stapler of FIG. 1.

Knob (130) protrudes proximally from casing (110) of handle assembly and is rotatable relative to casing (110). As shown in FIG. 19, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 27C and as described in greater detail below.

B. Exemplary Stapling Head Actuation Assembly

FIGS. 19-26D show various components that are operable to actuate stapling head assembly (300). These components include motor (161), a gearbox (162), a rotary cam member (700), a cam follower (1600), drive bracket (250) and stapling head assembly driver (240). Gearbox (162) is coupled with a drive shaft of motor (161) and is further coupled with cam member (700). Activation of motor (161) thus causes rotation of cam member (700) via gearbox (162). By way of example only, gearbox (162) may comprise a multi-stage planetary gearbox. Various suitable configurations that may be used for gearbox (162) will be apparent to those of ordinary skill in the art in view of the teachings herein. Cam member (700) is configured to interact with cam follower (1600) to pivot cam follower (1600) in two angular directions about a pin (118) as will be described in greater detail below. Pin (118) is coupled with a chassis (e.g., chassis (3690) described below that as shown includes left and right chassis portions (3691, 3693)), which is located within casing (110). A bushing (701) provides rotary support to cam member (700) relative to the chassis in casing (110).

Figure 20:
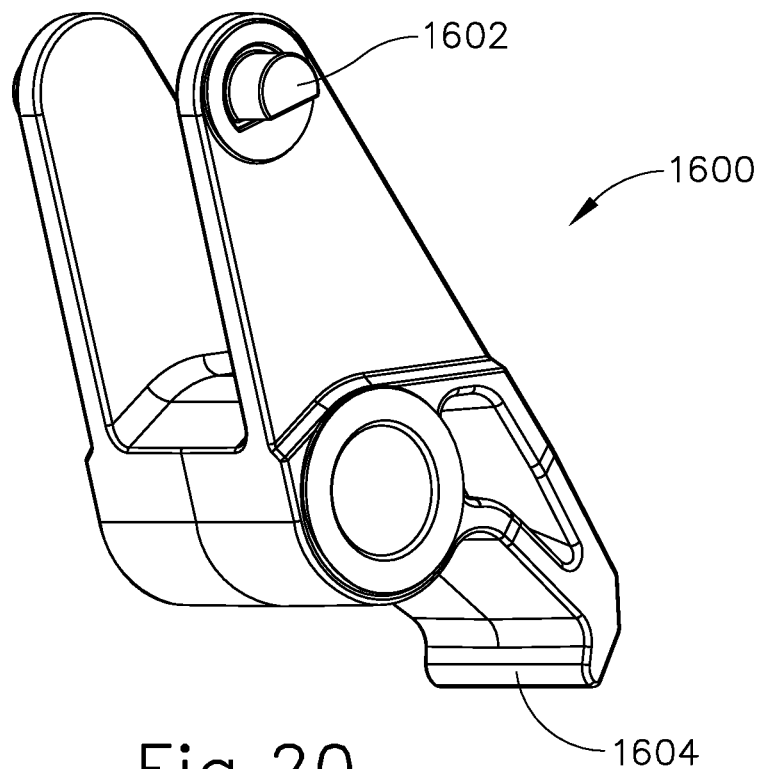
FIG. 20 depicts a perspective view of a cam follower of the stapling head actuation assembly of FIG. 19.
Figure 21:
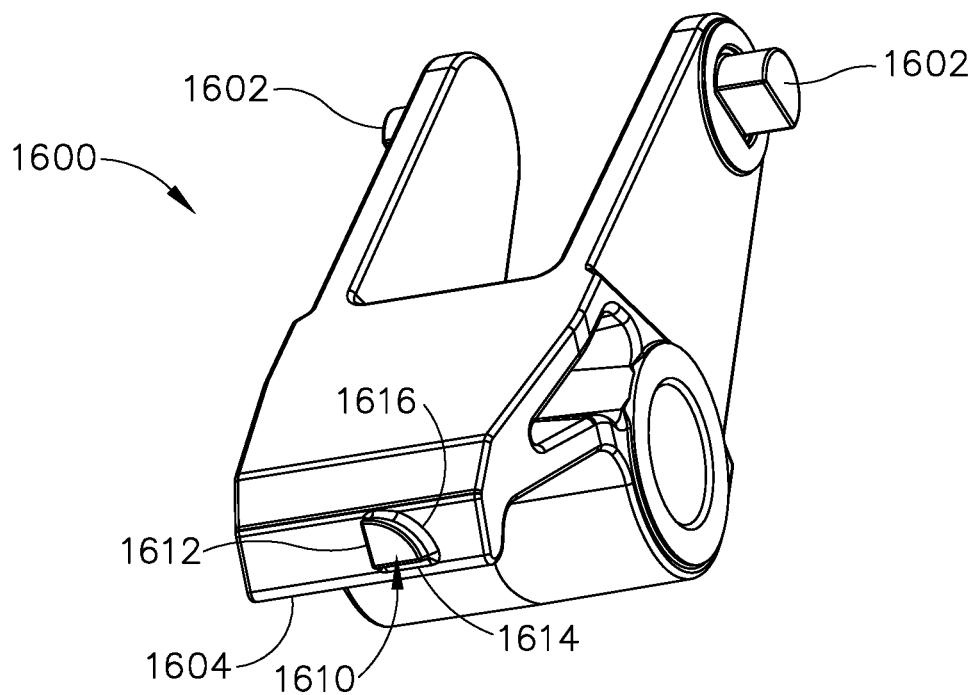
FIG. 21 depicts another perspective view of the cam follower of FIG. 20.

Cam follower (1600) is pivotably coupled with drive bracket (250) via a pair of integral pins (1602), which are received in complementary notches (252) of drive bracket (250). As shown in FIGS. 20-21, cam follower (1600) includes a first bearing feature (1604) and a second bearing feature (1610). First bearing feature (1604) consists of a rounded, horizontally extending surface. Second bearing feature (1610) is shaped like a quarter-pie defined by a straight vertical surface (1612), a horizontally extending surface (1614), and a curved surface (1616). Second bearing feature (1610) projects proximally relative to first bearing feature (1604).

Figure 22:
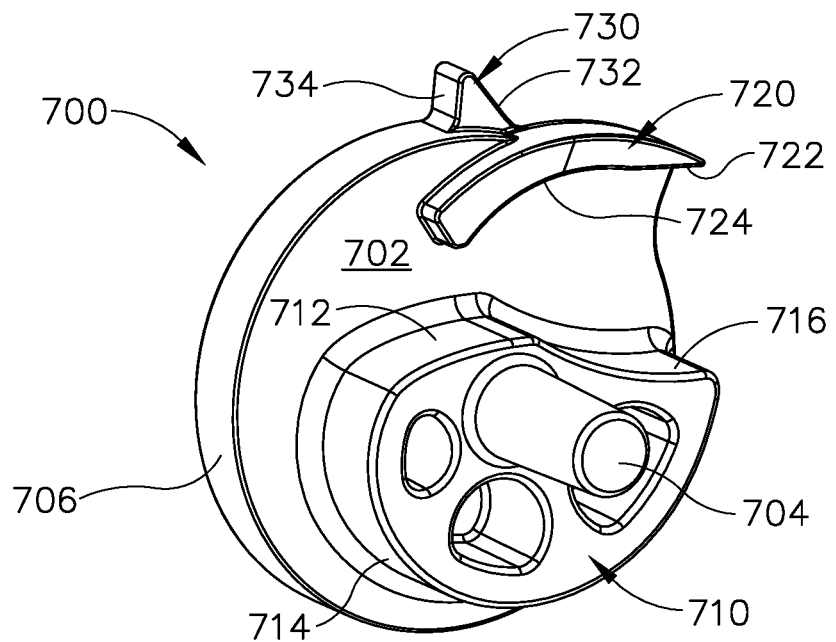
FIG. 22 depicts a perspective view of a rotary cam of the stapling head actuation assembly of FIG. 19.
Figure 23:
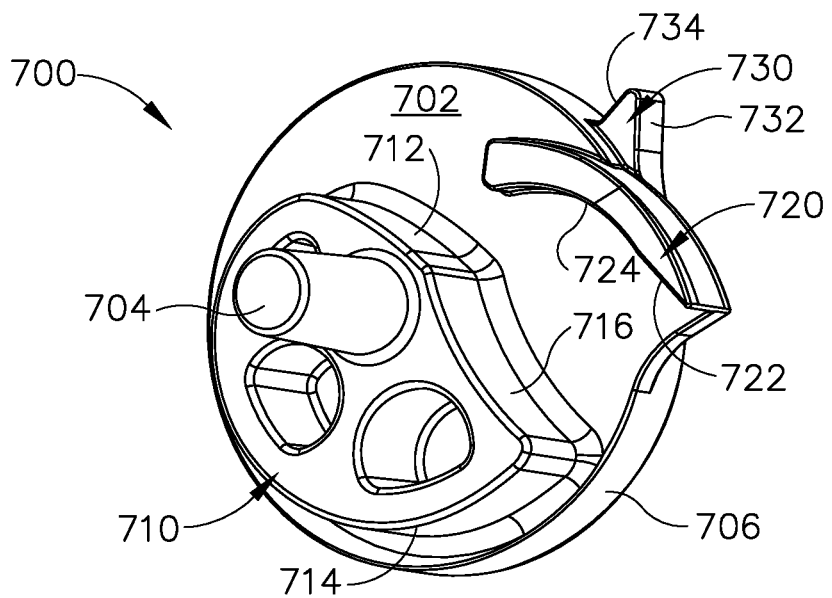
FIG. 23 depicts another perspective view of the rotary cam of FIG. 22.

FIGS. 22-23 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 24A:
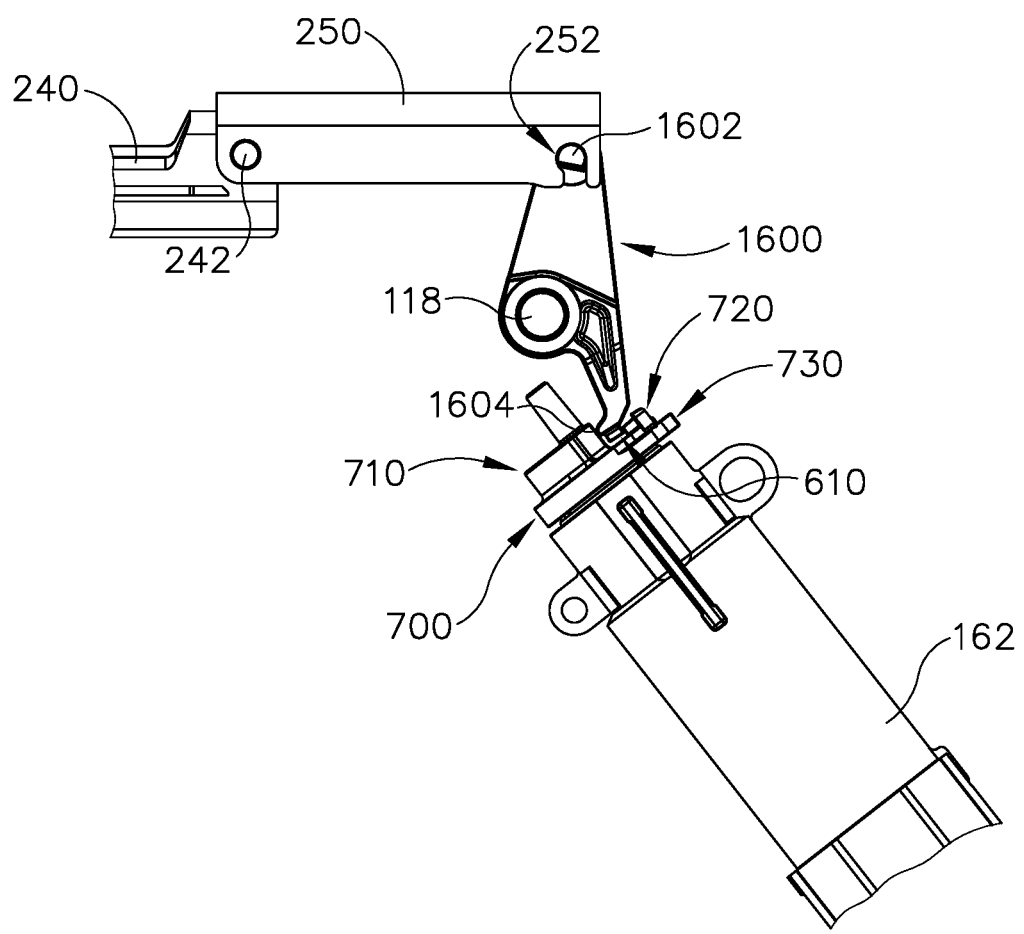
FIG. 24A depicts a side elevational view of the stapling head actuation assembly of FIG. 19, with the rotary cam in a first angular position and the cam follower in a first pivotal position.
Figure 24B:
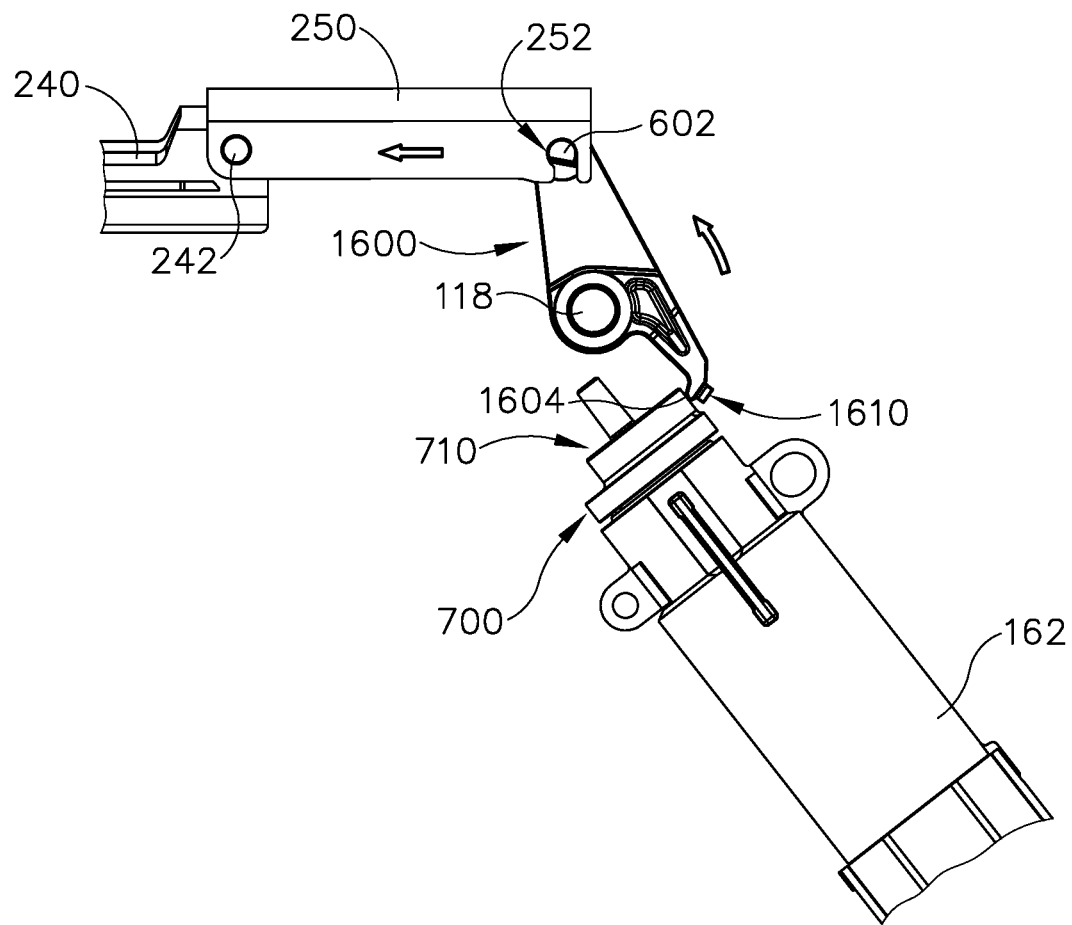
FIG. 24B depicts a side elevational view of the stapling head actuation assembly of FIG. 19, with the rotary cam in a second angular position and the cam follower in a second pivotal position.

FIGS. 24A-24B show the general interaction between cam follower (1600) and first and second cam features (710, 720), though this interaction will be described in greater detail below with reference to FIGS. 14A-14D. As cam member (700) is rotated from the position shown in FIG. 24A to the position shown in FIG. 24B, first cam feature (710) bears against first bearing feature (1604) of cam follower (1600), causing cam follower to pivot about pin (118). In the view shown in FIGS. 24A-24B, cam follower (1600) pivots counterclockwise as cam member (700) is rotated from the position shown in FIG. 24A to the position shown in FIG. 24B. As can be seen in the transition from FIG. 24A to FIG. 24B, this counterclockwise pivoting of cam follower (1600) drives drive bracket (250) and stapling head assembly driver (240) distally, thereby actuating stapling head assembly (300). As cam member (700) continues to rotate in the same direction back toward the position shown in FIG. 24A, second cam feature (720) engages and bears against second bearing feature (1610) of cam follower (1600), causing cam follower (1600) to pivot clockwise about pin (118). This clockwise pivoting of cam follower (1600) about pin (118) retracts drive bracket (250) and stapling head assembly driver (240) proximally back toward the position shown in FIG. 24A.

Referring back to FIGS. 22-23, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 13A-13B. Rocker member (800) comprises an integral pin (802), a bearing member (804), and a paddle (806). Pin (802) is pivotably coupled with the chassis in casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch buttons (192) of a motor stop module (190) as will also be described in greater detail below.

Figure 25A:
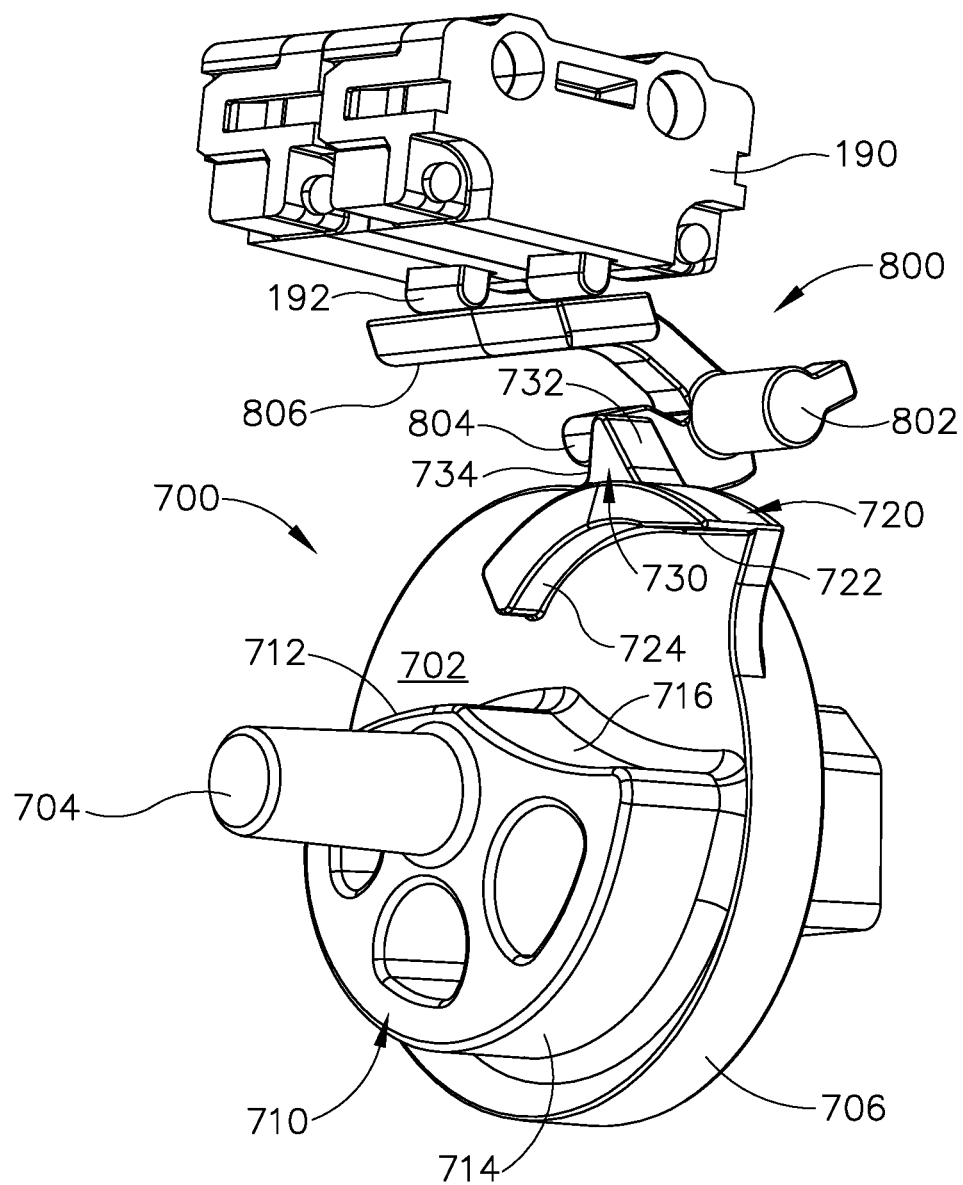
FIG. 25A depicts a perspective view of the rotary cam of FIG. 22, a rocker member, and a stop switch, with the rotary cam in a first angular position and the rocker member in a first pivotal position.
Figure 25B:
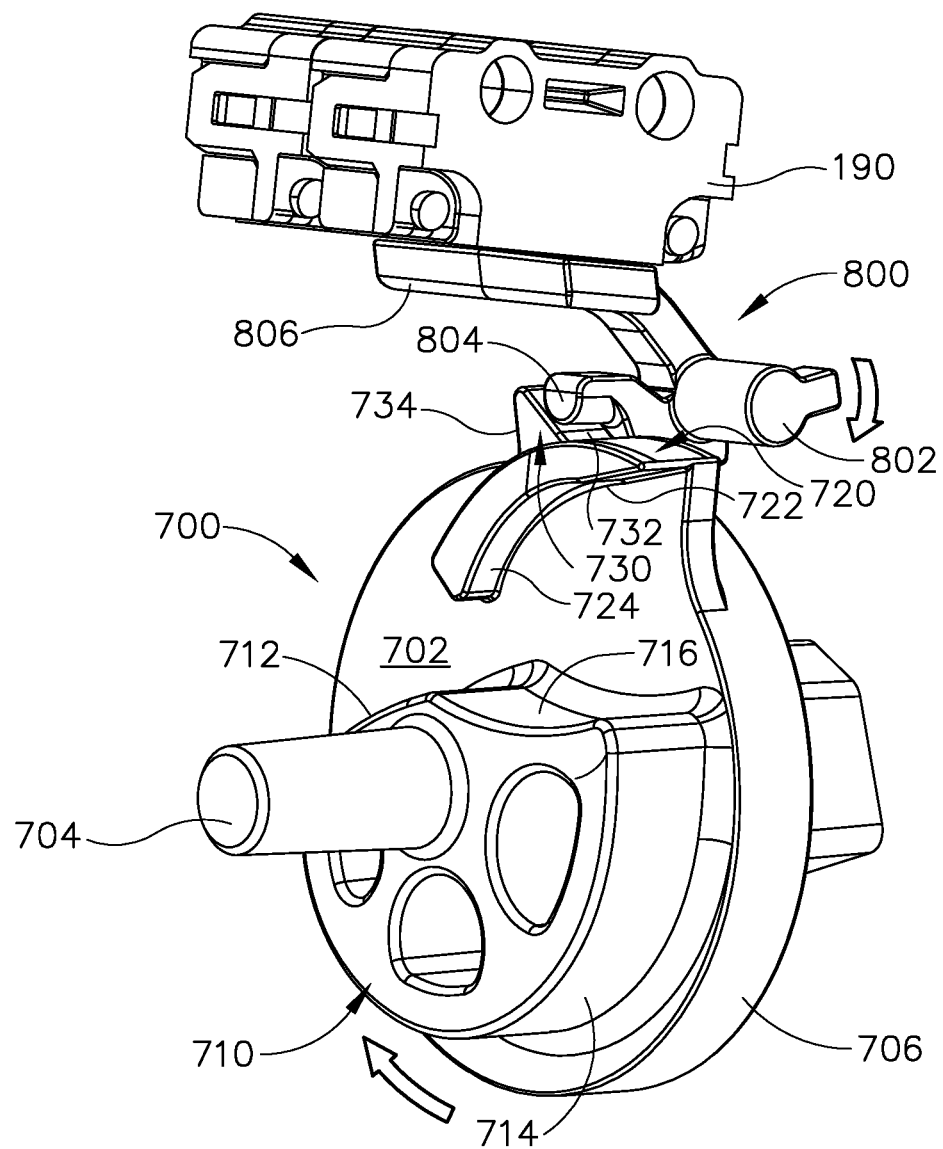
FIG. 25B depicts a perspective view of the rotary cam of FIG. 22, the rocker member of FIG. 25A, and the stop switch of FIG. 25A, with the rotary cam in a fourth angular position and the rocker member in a second pivotal position.

FIG. 25A shows cam member (700) in the same position as shown in FIG. 24A. At this stage, second surface region (734) of third cam feature (730) is adjacent to bearing member (804) of rocker member (800). FIG. 25B shows cam member (700) in a position where cam member (700) has been rotated past the position shown in FIG. 24B and back toward the position shown in FIG. 24A. However, cam member (700) has not completed a full revolution. At the stage shown in FIG. 25B, first surface region (732) has engaged and borne against bearing member (804), thereby pivoting rocker member (800) about the longitudinal axis defined by pin (802). This has caused paddle (806) to actuate switch buttons (192) of motor stop module (190). Motor stop module (190) reverses the polarity of electrical power provided to motor (161) when switch buttons (192) are actuated. This results in stopping activation of motor (161) once an actuation stroke of stapling head assembly (300) has been completed. By way of example only, motor stop module (190) may be configured and operable in accordance with at least some of the teachings of U.S. Pat. No. 9,907,552, issued Mar. 6, 2018, the disclosure of which is incorporated by reference herein. Other suitable configurations will be apparent to those of ordinary skill in the art in view of the teachings herein.

Figure 26A:
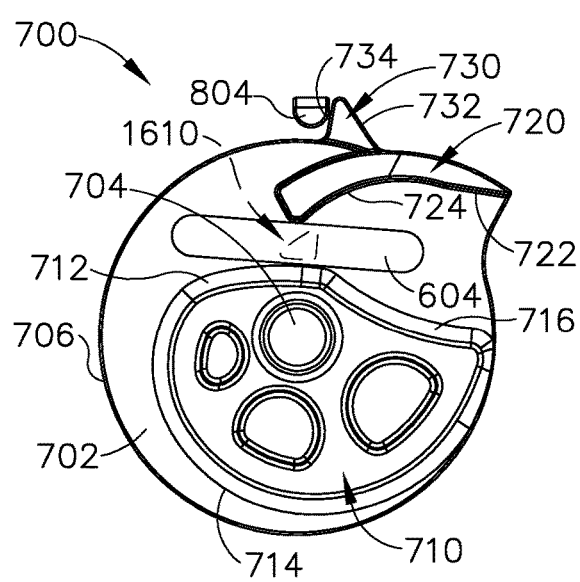
FIG. 26A depicts a schematic end view of the rotary cam of FIG. 22, the cam follower of FIG. 20, and the rocker member of FIG. 25A, with the rotary cam in the first angular position, the cam follower in the first pivotal position, and the rocker member in the first pivotal position.
Figure 26B:
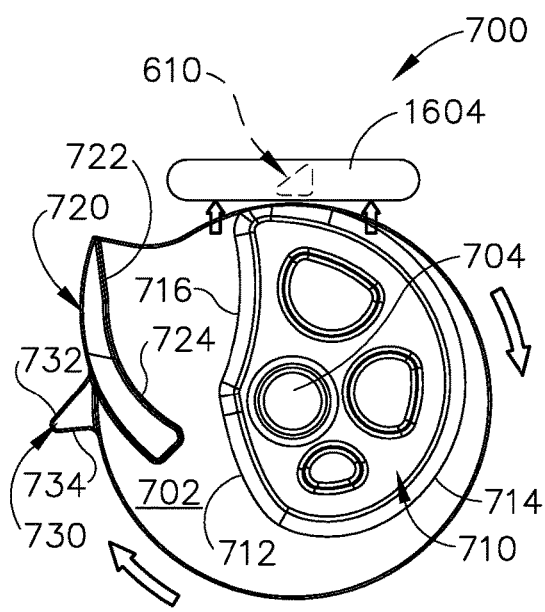
FIG. 26B depicts a schematic end view of the rotary cam of FIG. 22 and the cam follower of FIG. 20, with the rotary cam in the second angular position, the cam follower in the second pivotal position, and the rocker member of FIG. 25A in the first pivotal position.

FIGS. 26A-26D schematically depict the interaction between cam member (700), features of cam follower (1600), and features of rocker member (800) as cam member (700) rotates. It should be understood that the rotation of cam member (700) throughout the stages shown in FIGS. 26A-26D is driven by motor (161) and gearbox (162). FIG. 26A shows cam member (700) in the same position as shown in FIGS. 24A and 25A. At this stage, first bearing feature (1604) of cam follower (1600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 26B, second surface region (714) bears against bearing member (1604), thereby driving bearing member (1604) upwardly. This causes cam follower (1600) to pivot about pin (118) to the position shown in FIG. 24B. Cam follower (1600) thus drives knife member (340) and staple driver member (350) distally via drive bracket (250) and stapling head assembly driver (240). Stapling head assembly (300) is thus in an actuated state at the stage shown in FIG. 26B. In some versions, cam member (700) rotates through an angular range of approximately 270° in order to transition stapling head assembly (300) from the non-actuated state to the actuated state.

Figure 26C:
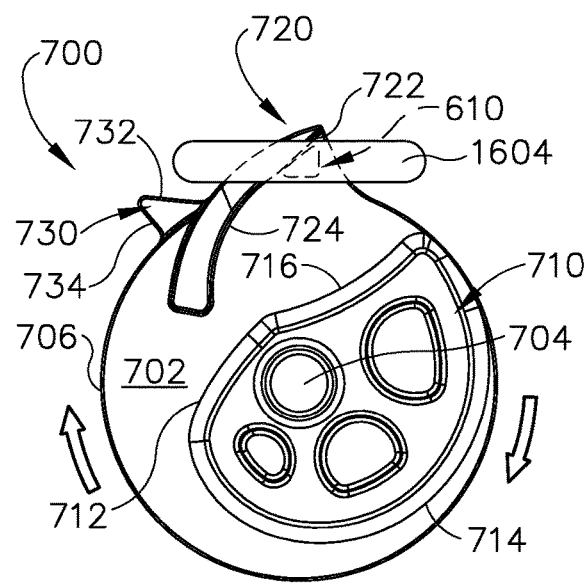
FIG. 26C depicts a schematic end view of the rotary cam of FIG. 22 and the cam follower of FIG. 20, with the rotary cam in a third angular position, the cam follower in the second pivotal position, and the rocker member of FIG. 25A in the first pivotal position.
Figure 26D:
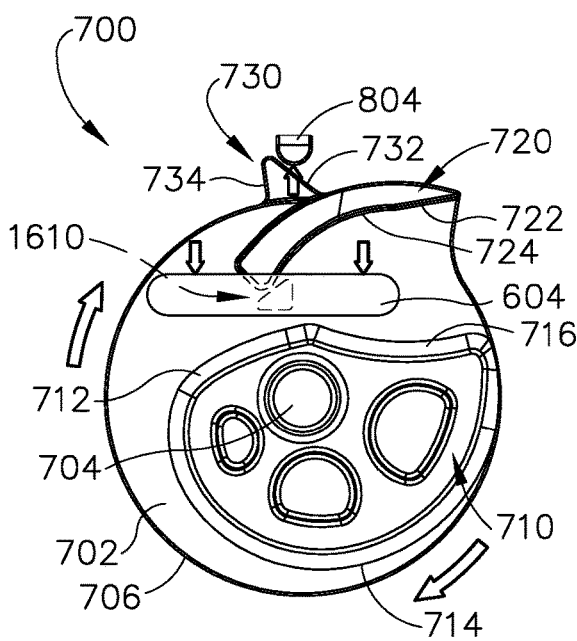
FIG. 26D depicts a schematic end view of the rotary cam of FIG. 22, the cam follower of FIG. 20, and the rocker member of FIG. 25A, with the rotary cam in a fourth angular position, the cam follower in a third pivotal position, and the rocker member in a second pivotal position.

After stapling head assembly (300) has been actuated, cam member (700) continues to rotate to the position shown in FIG. 26C. At this stage, first surface region (722) of second cam member (720) begins to engage curved surface (1616) of second bearing feature (1610) of cam follower (1600). As cam member (700) continues to rotate to the position shown in FIG. 26D, second surface region (724) engages curved surface (1616) of second bearing feature (1610), driving second bearing feature (1610) downwardly. This causes cam follower (1600) to pivot about pin (118) back from the position shown in FIG. 24B toward the position shown in FIG. 24A. Cam follower (1600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 26D. Rocker member (800) is thus in the same state in FIG. 26D as shown in FIG. 25B. Motor stop module (190) has thus been actuated at the stage shown in FIG. 26D.

It should be understood from the foregoing that cam member (700) is operable to drive knife member (340) and staple driver member (350) distally, then drive knife member (340) and staple driver member (350) proximally and actuate motor stop module (190) by rotating in a single angular direction through the range of motion shown in FIGS.

26A-26D. In the present example, cam member (700) provides the full operational sequence depicted in FIGS. 26A-26D and described above by rotating through an angular range of motion of approximately 355°. More particularly, and by way of further example only, the first 270° of rotation of cam member (700) may provide the distal movement of knife member (340) and staple driver member (350); while the remaining 85° of rotation of cam member (700) may provide the proximal movement of knife member (340) and staple driver member (350) and the actuation of motor stop module (190). Other suitable ways in which knife member (340), staple driver member (350), and motor stop module (190) may be actuated will be apparent to those of ordinary skill in the art in view of the teachings herein.

C. Exemplary Clamping and Firing Sequence

Figure 27A:
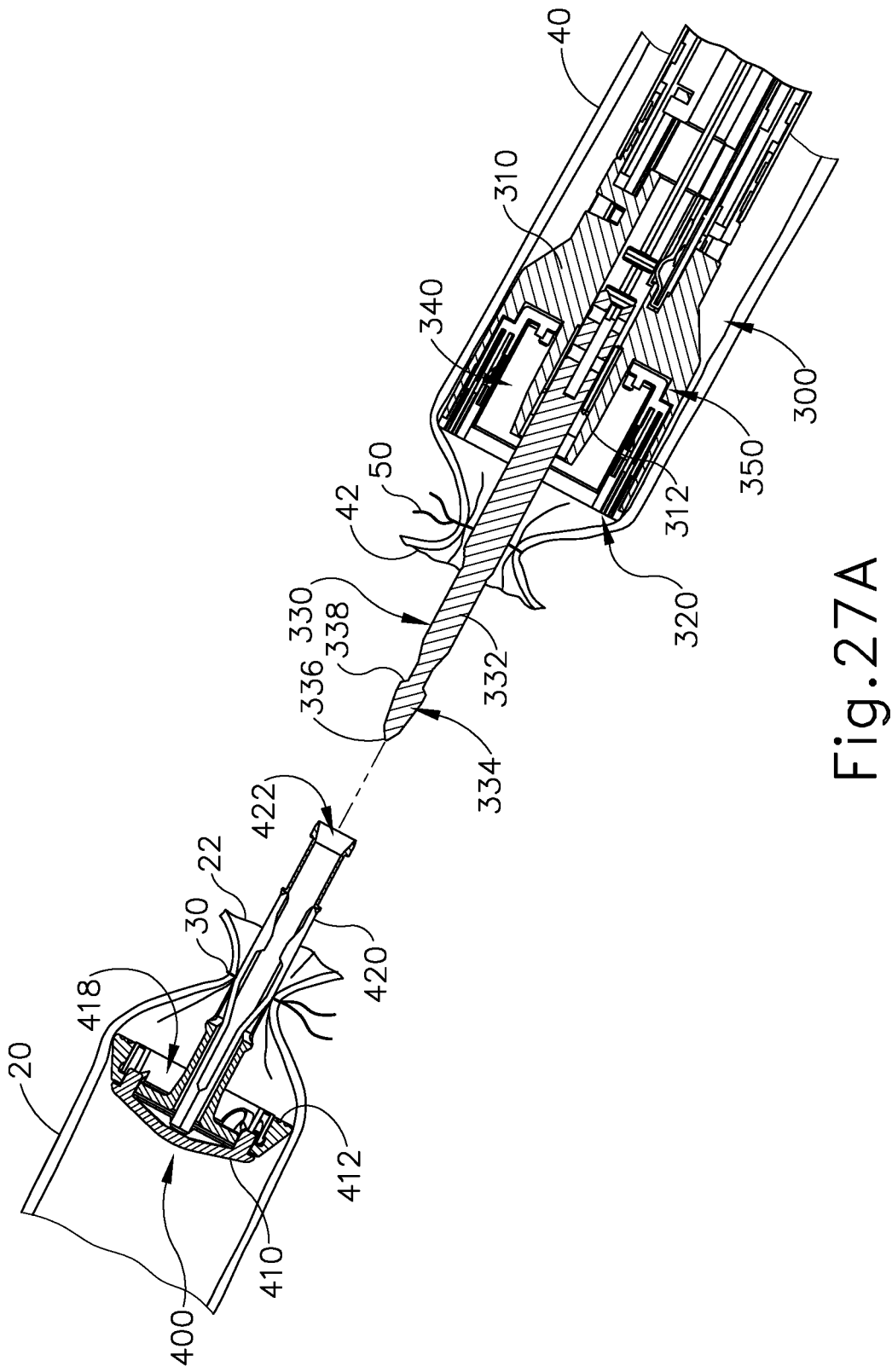
FIG. 27A depicts a cross-sectional side view of the anvil of FIG. 3 positioned within a first section of a digestive tract and the stapling head assembly of FIG. 9 positioned in a second section of the digestive tract, with the anvil separated from the stapling head assembly.
Figure 27B:
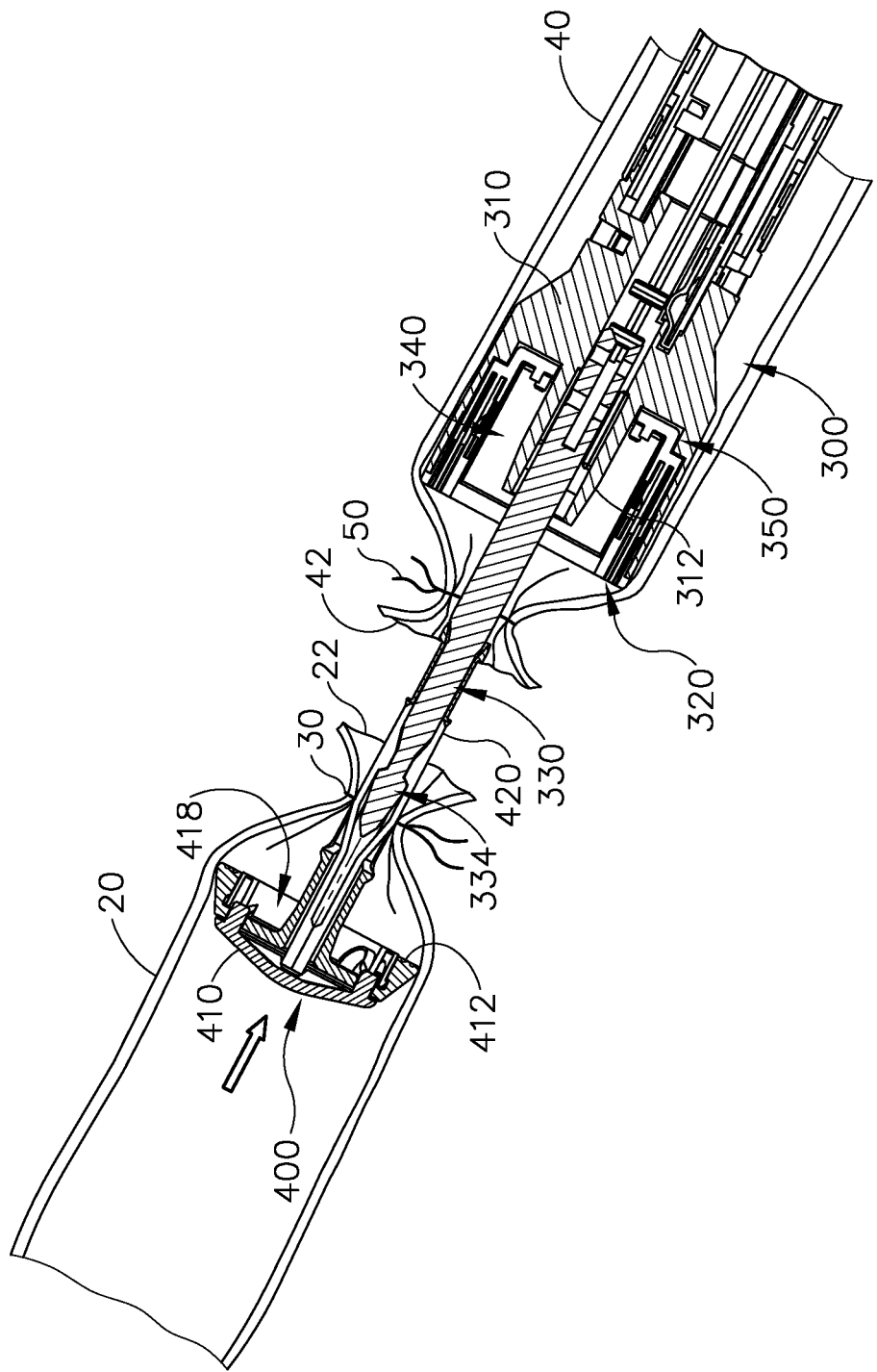
FIG. 27B depicts a cross-sectional side view of the anvil of FIG. 3 positioned within the first section of the digestive tract and the stapling head assembly of FIG. 9 positioned in the second section of the digestive tract, with the anvil secured to the stapling head assembly.
Figure 27C:
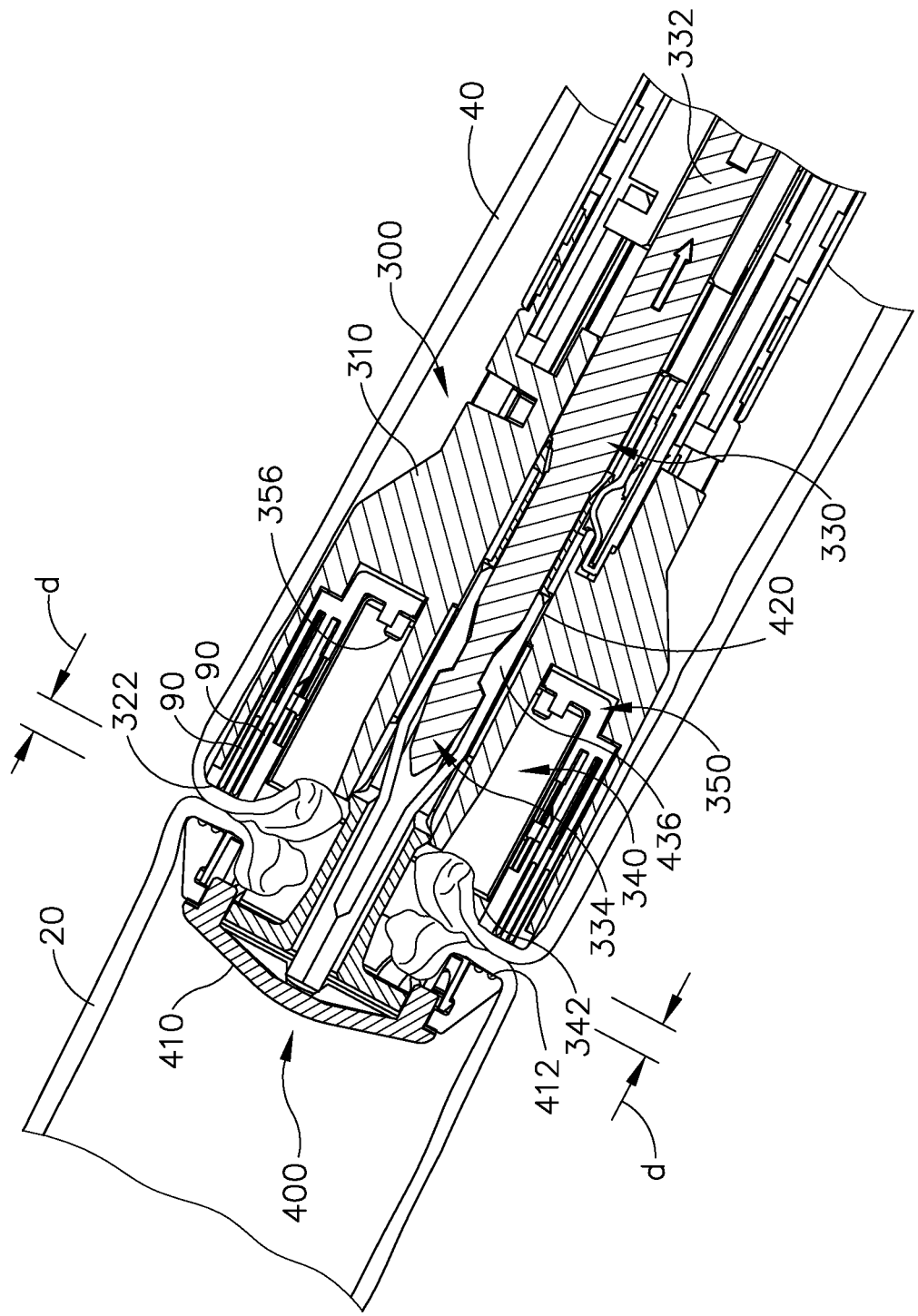
FIG. 27C depicts a cross-sectional side view of the anvil of FIG. 3 positioned within the first section of the digestive tract and the stapling head assembly of FIG. 9 positioned in the second section of the digestive tract, with the anvil retracted toward the stapling head assembly to thereby clamp tissue between the anvil and the stapling head assembly.

FIGS. 27A-27E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 27A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 27A-27E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 27A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Next, anvil (400) is secured to trocar (330) by inserting trocar (330) into bore (422) as shown in FIG. 27B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 27C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of needle (1526) within user feedback feature (114) to determine whether the gap distance (d) between opposing surfaces (412, 322) of anvil (400) and stapling head assembly (300) is appropriate; and make any necessary adjustments via knob (130).

Figure 27D:
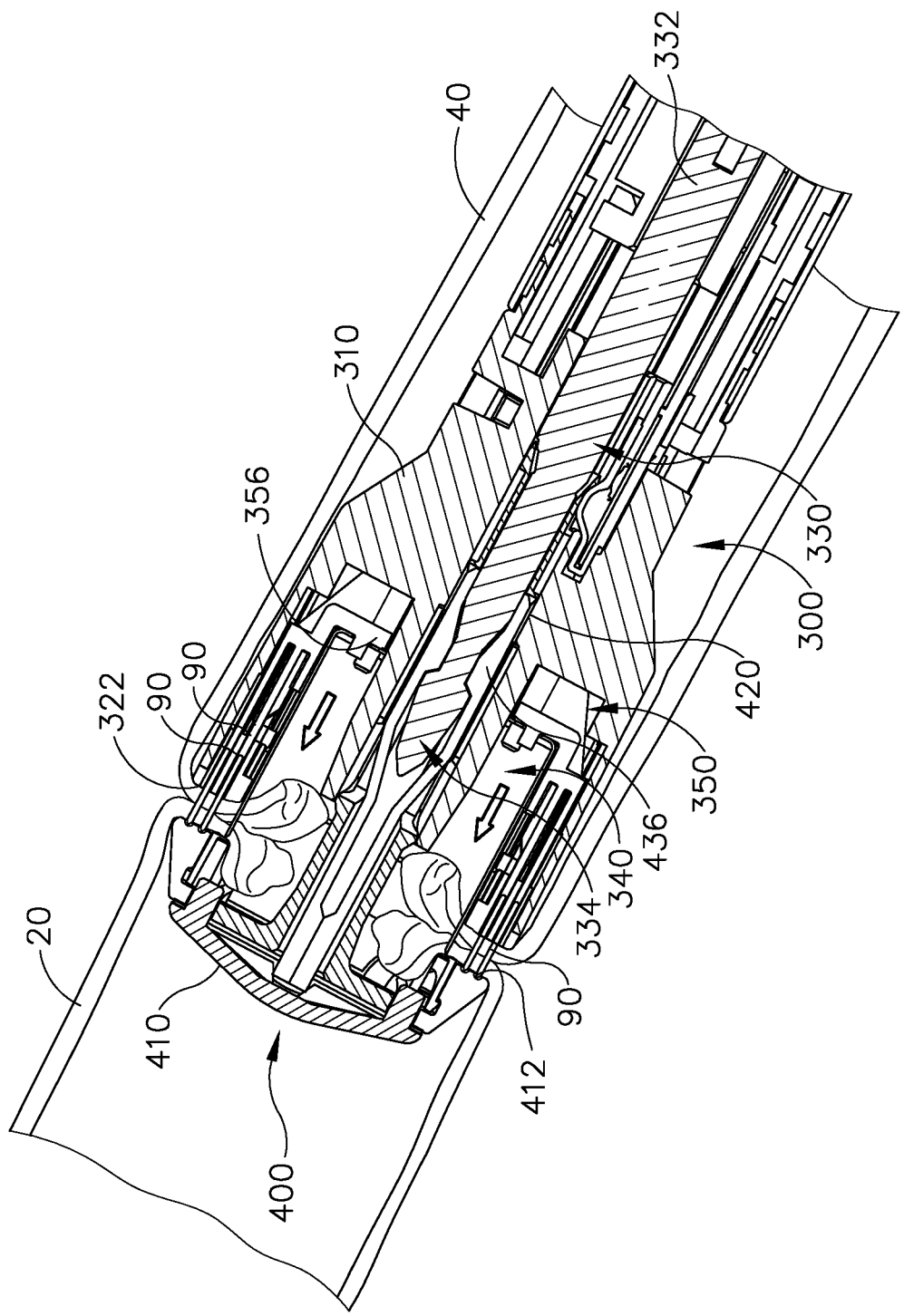
FIG. 27D depicts a cross-sectional side view of the anvil of FIG. 3 positioned within the first section of the digestive tract and the stapling head assembly of FIG. 9 positioned in the second section of the digestive tract, with the stapling head assembly actuated to sever and staple the clamped tissue.
Figure 30A:
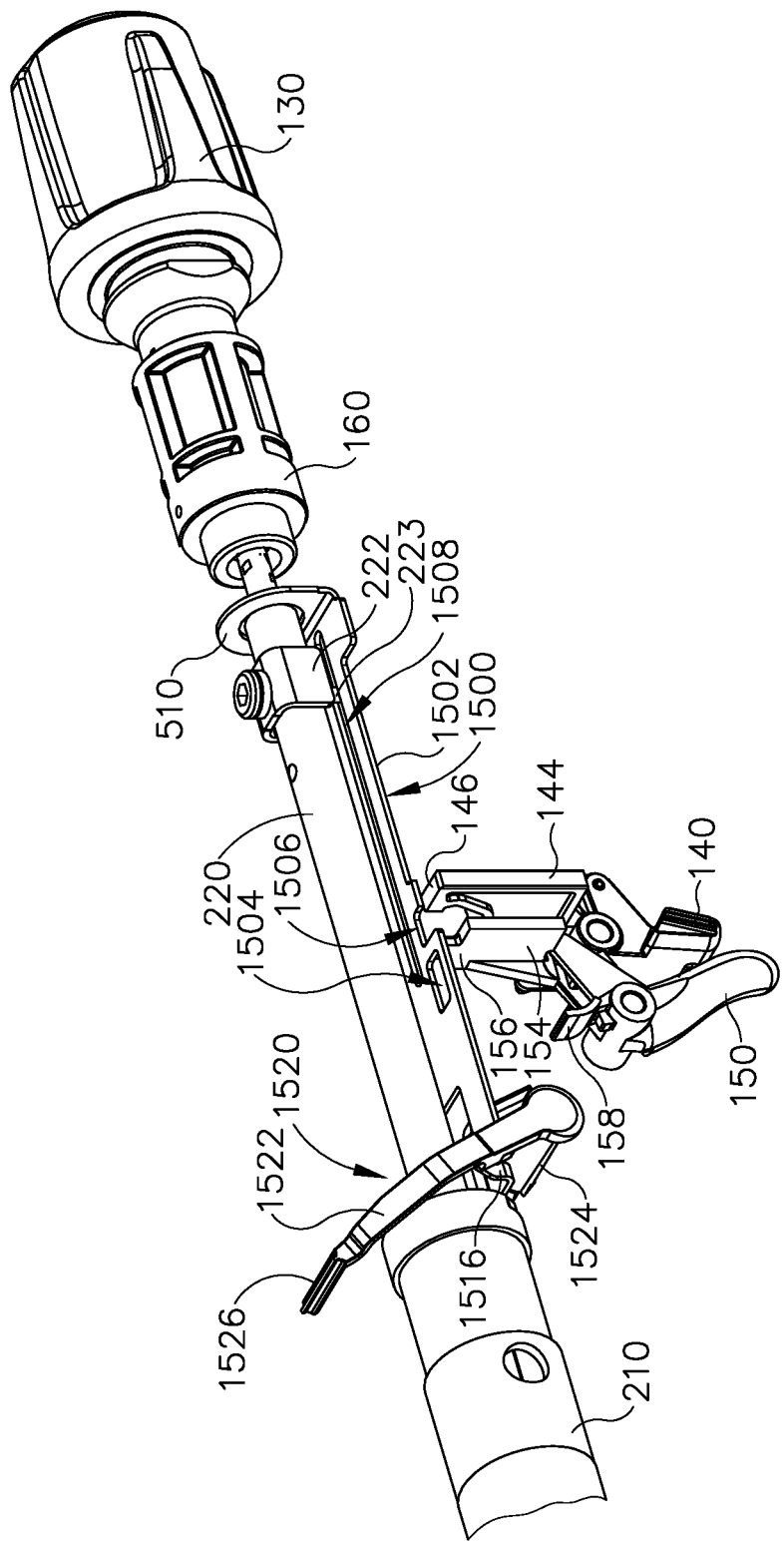
FIG. 30A depicts a perspective view of an anvil actuation assembly of the circular stapler of FIG. 1, an actuation rod in a first position.
Figure 30B:
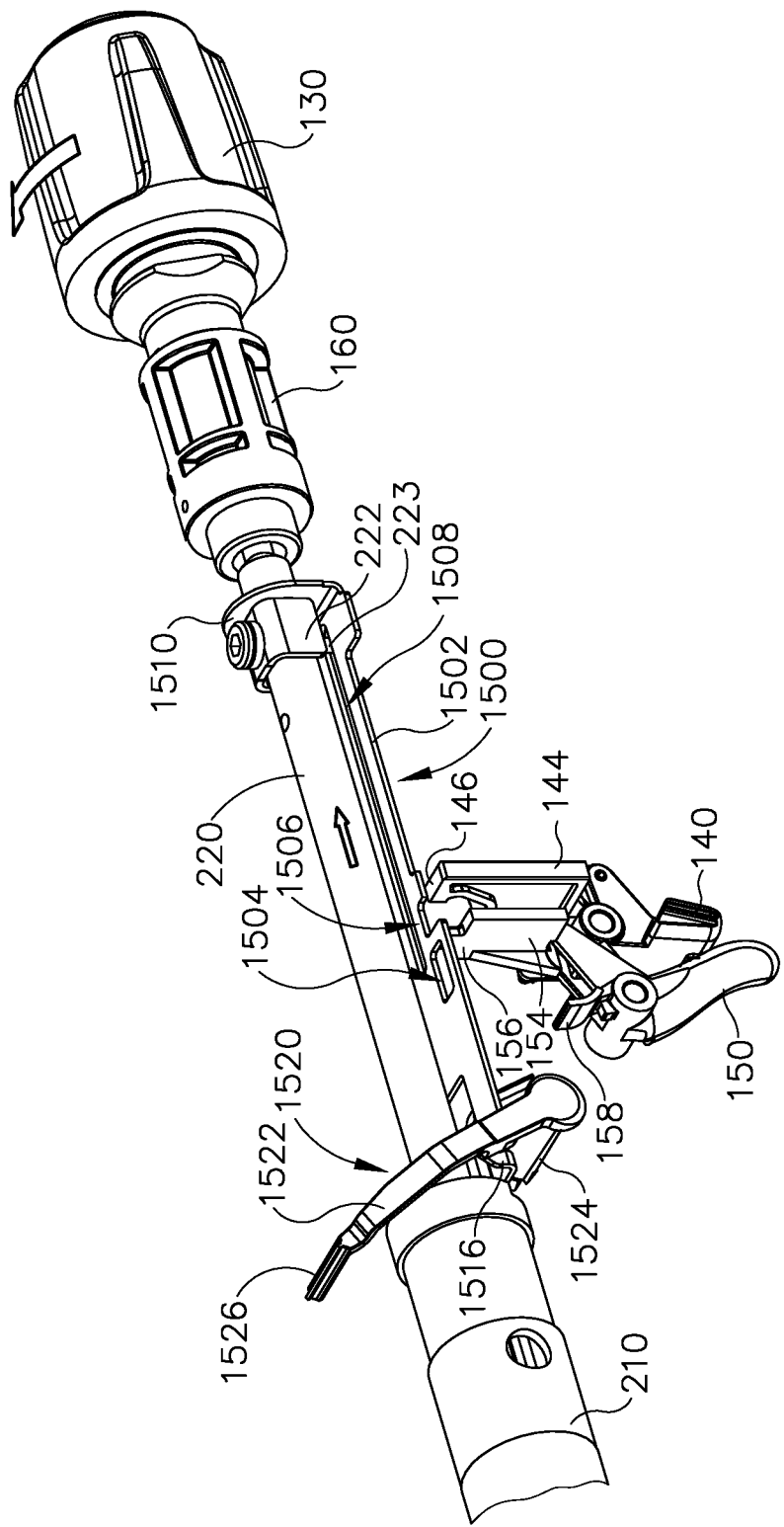
FIG. 30B depicts a perspective view of the anvil actuation assembly of FIG. 30A, with the actuation rod moved to a second position to engage the bracket of FIG. 28.
Figure 30C:
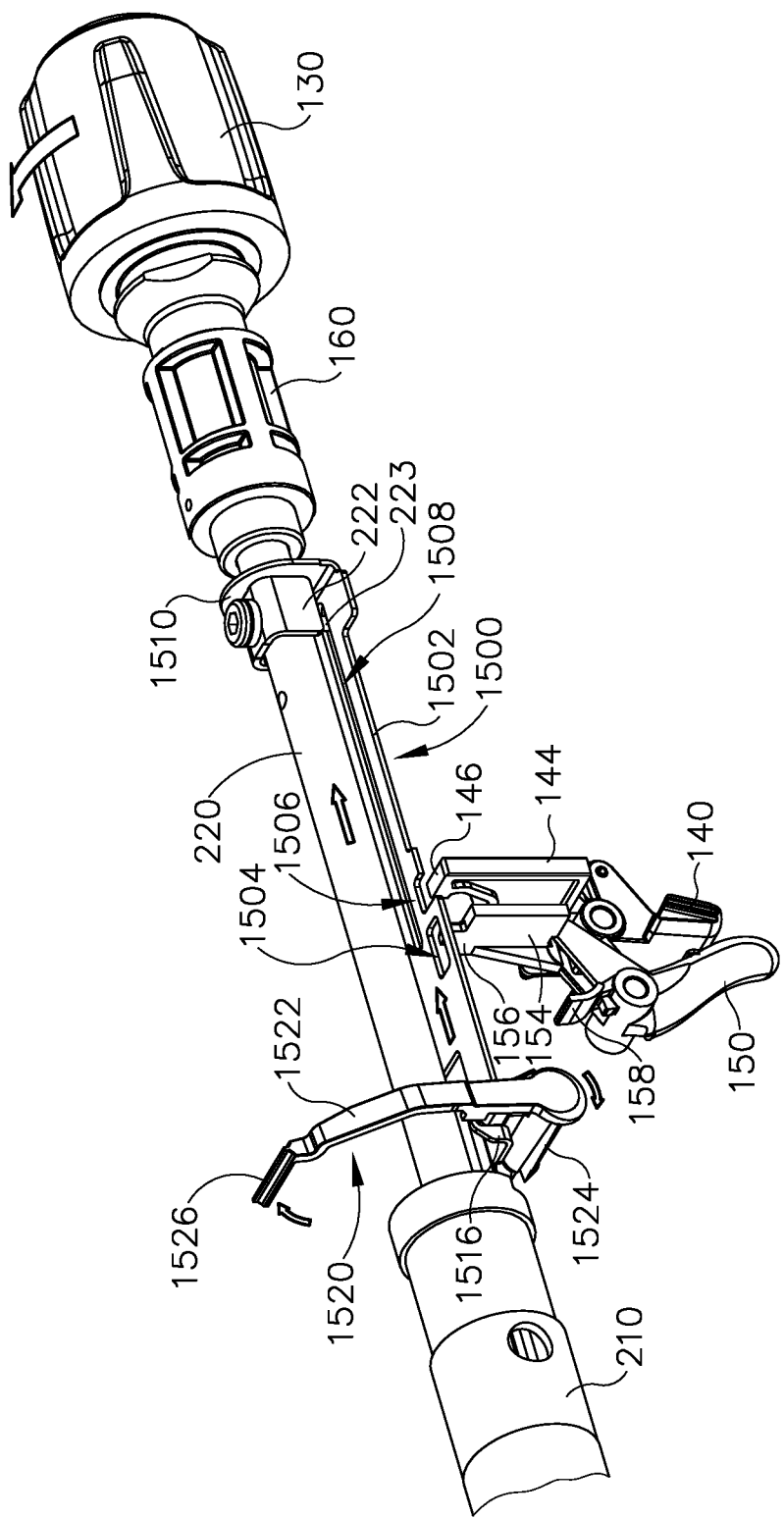
FIG. 30C depicts a perspective view of the anvil actuation assembly of FIG. 30A, with the actuation rod moved to a third position to retract the bracket of FIG. 28 proximally.
Figure 30D:
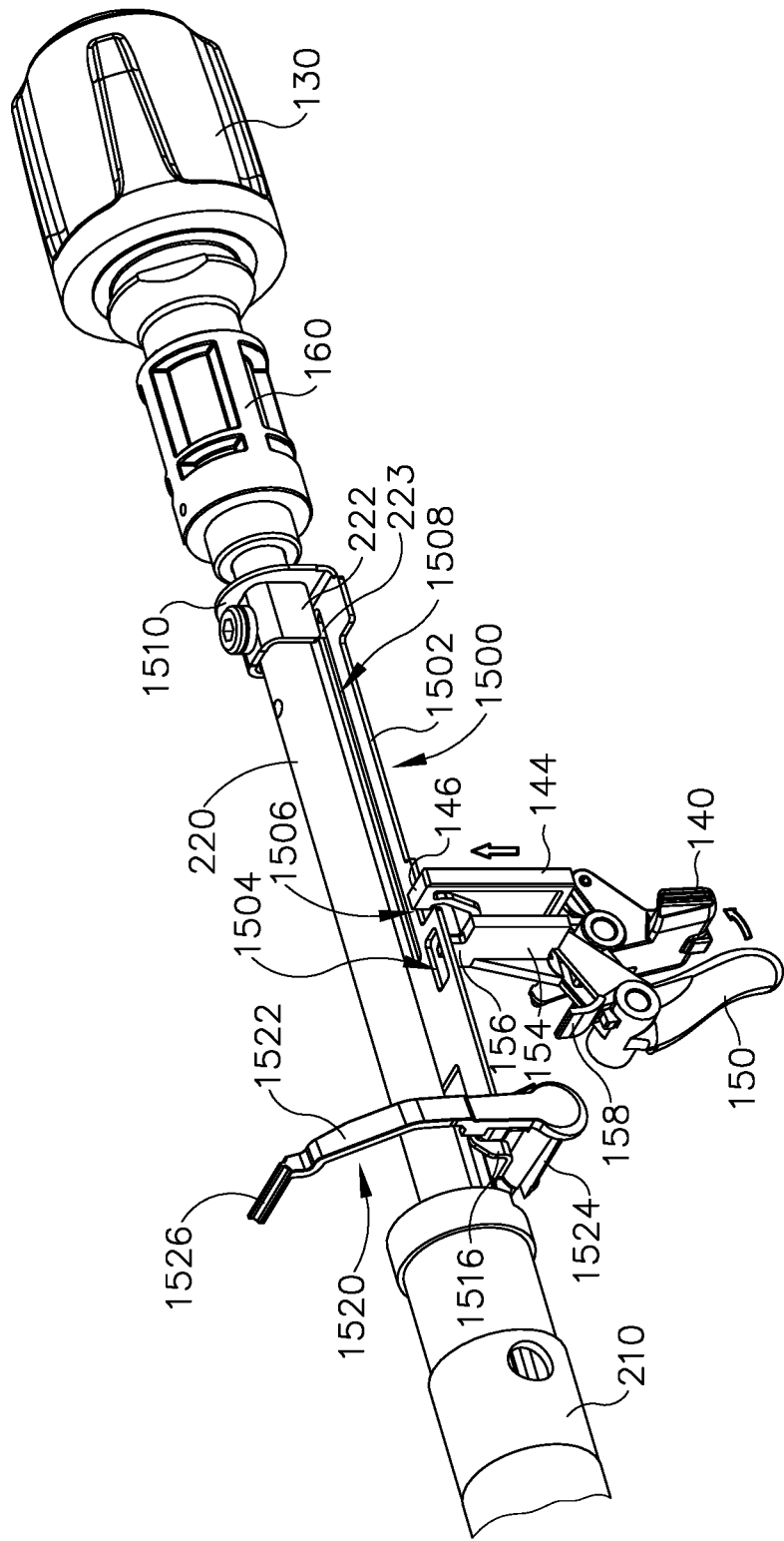
FIG. 30D depicts a perspective view of the anvil actuation assembly of FIG. 30A, with a safety trigger pivoted from a first position to a second position.
Figure 30E:
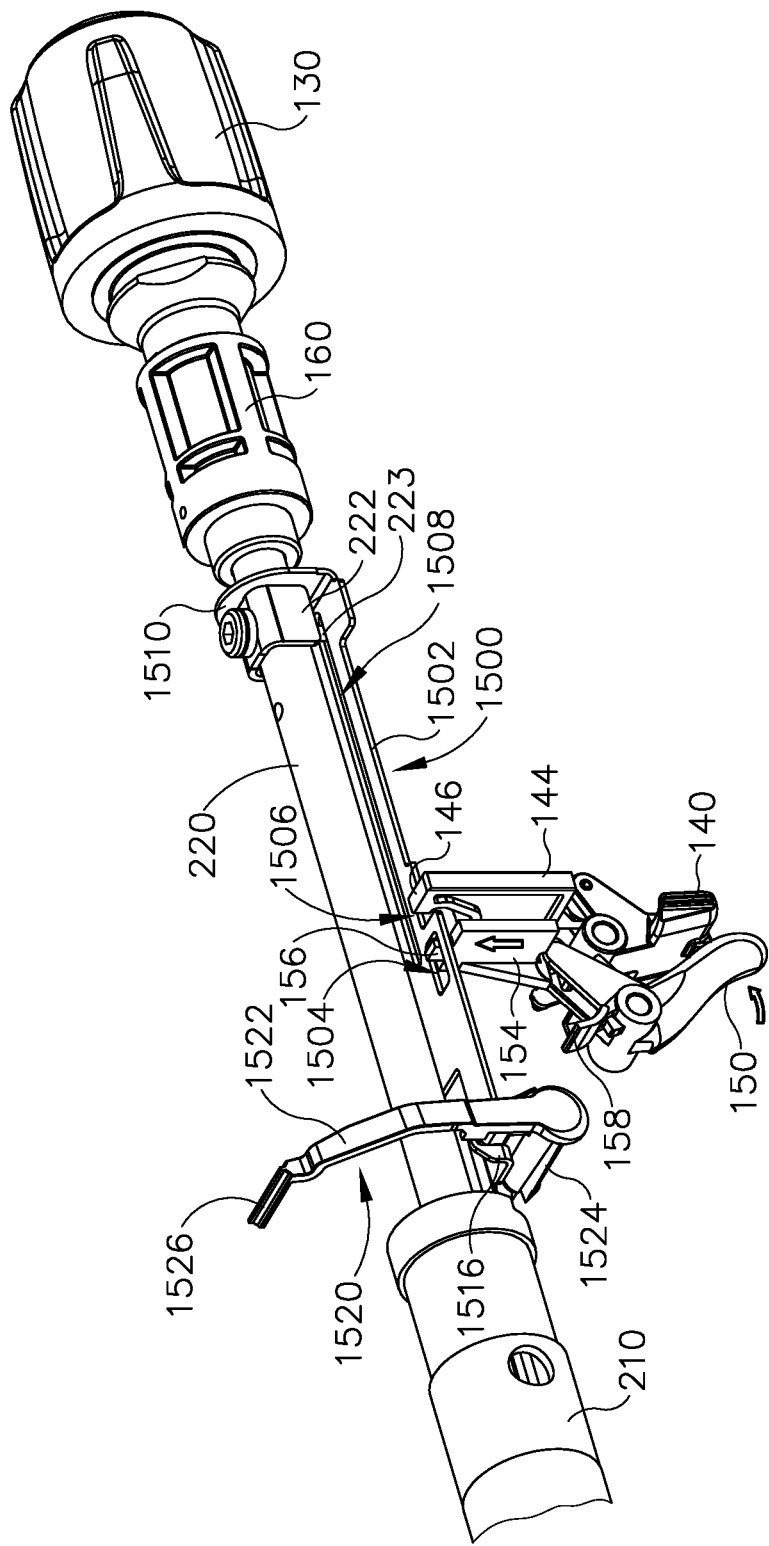
FIG. 30E depicts a perspective view of the anvil actuation assembly of FIG. 30A, with a firing trigger pivoted from a first position to a second position.

Once the operator has appropriately set the gap distance (d) via knob (130), the operator actuates safety trigger (140) (as shown in FIG. 30D) to enable actuation of firing trigger (150). The operator then actuates firing trigger (150) (as shown in FIG. 30E). This causes paddle (158) to actuate the switch of a motor activation module (180), thereby activating motor to rotate cam member (700) (as shown in FIGS. 26A-26D). This rotation of cam member (700) actuates stapling head assembly (300) by driving knife member (340) and staple driver member (350) distally as shown in FIG. 27D. As knife member (340) translates distally, cutting edge (342) of knife member (340) cuts excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 27C to the position shown in FIG. 27D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

As staple driver member (350) translates distally from the position shown in FIG. 27C to the position shown in FIG. 27D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art; or into a three-dimensional shape as described above with respect to anvil (500). In either case, the formed staples (90) secure the ends of tissue together.

Figure 27E:
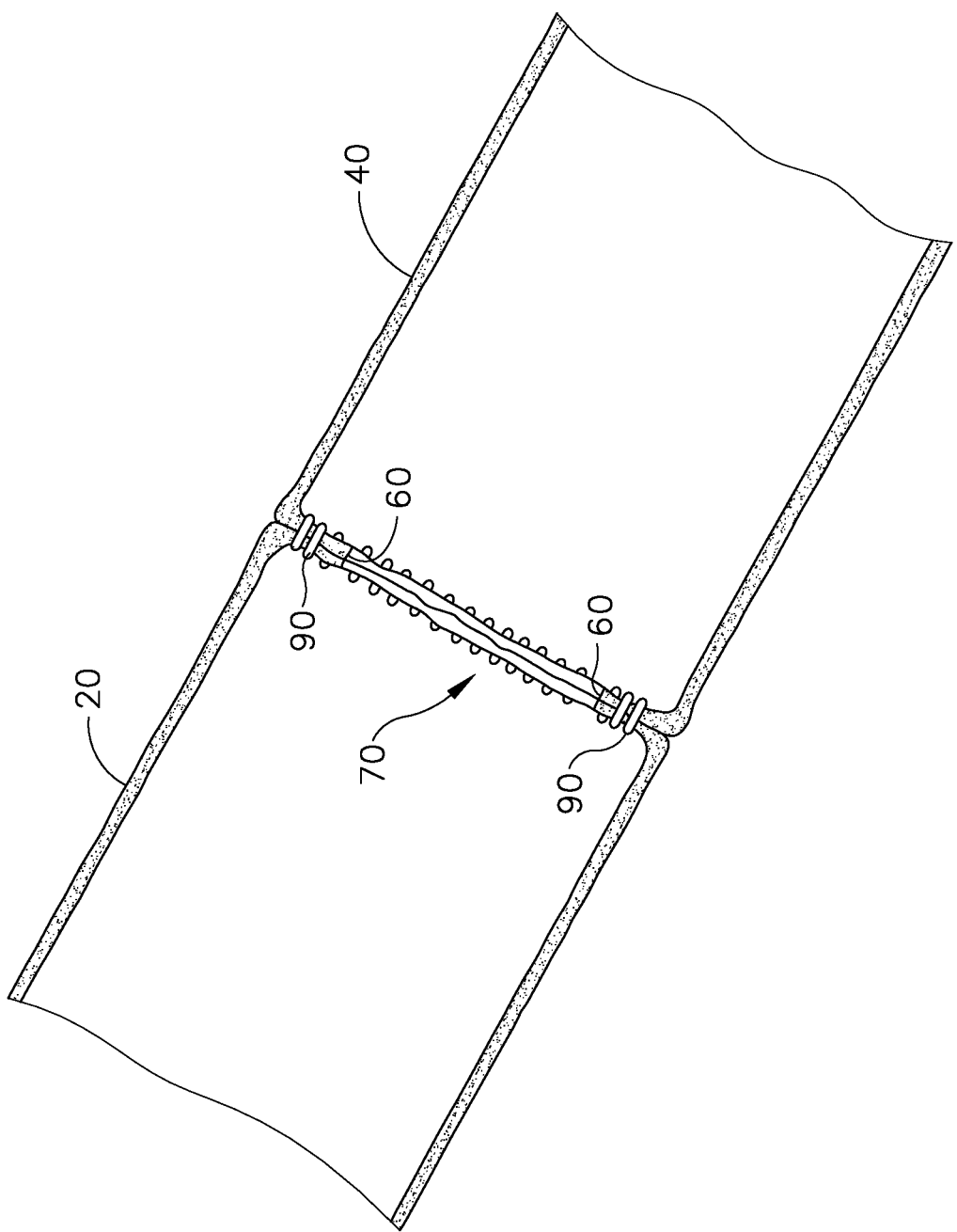
FIG. 27E depicts a cross-sectional side view of the first and second sections of the digestive tract of FIG. 27A joined together at an end-to-end anastomosis.

After the operator has actuated stapling head assembly (300) as shown in FIG. 27D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 27E. The inner diameter of the anastomosis (70) is defined by the severed edge (60) left by knife member (340).

V. Exemplary Safety Assemblies

As noted above, knob (130) may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

A. Exemplary Trigger Blocking Features and Anvil Position Indicator

Figure 28:
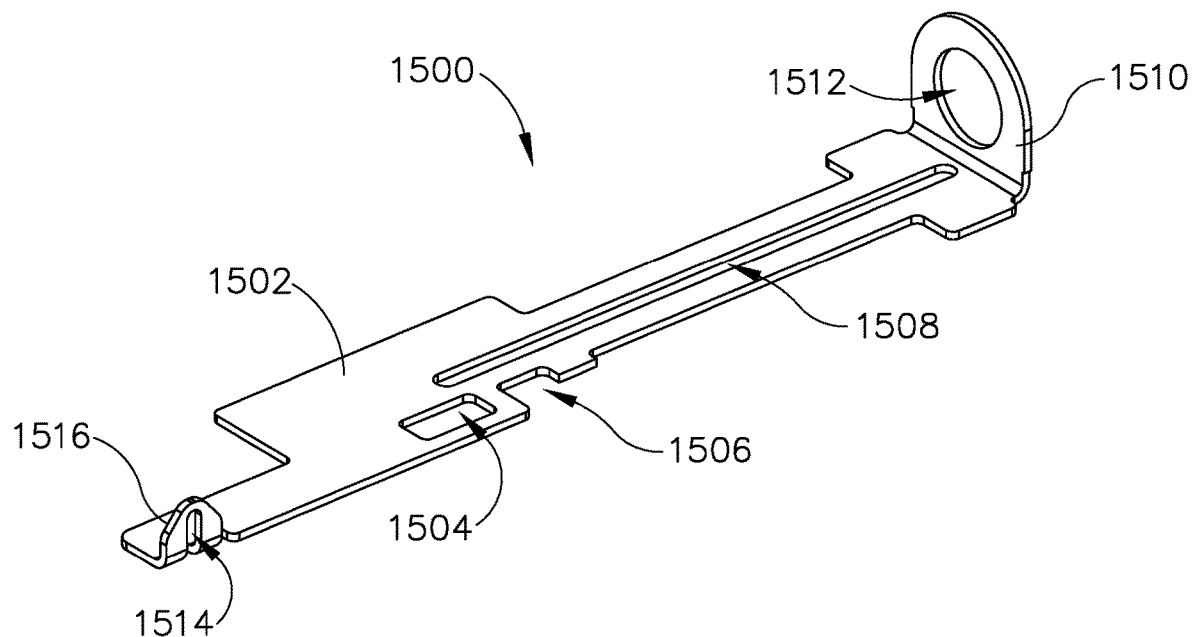
FIG. 28 depicts a perspective view of a bracket of the handle assembly of FIG. 18.

FIGS. 28-30E show components that provide feedback to the operator to indicate whether the gap distance (d) is within an appropriate range; and prevent the operator from actuating stapling head assembly (300) unless the gap distance (d) is within an appropriate range. As best seen in FIGS. 30B-30C, a bracket (1500) is configured and positioned to move in response to movement of trocar actuation rod (220). As best seen in FIG. 28, bracket (1500) includes a rigid body (1502) that defines a first slot (1504), a second slot (1506), and a third slot (1508). In some variations, third slot (1508) is omitted. An example of such a variation is described below with reference to FIG. 35.

In the present example, an upright member (1510) is positioned at the proximal end of body (1502) and defines an opening (1512). Trocar actuation rod (220) extends coaxially through opening (1512). As shown in FIG. 18, a coil spring (170) is interposed between the proximal end of upright member (1510) and a rigid bulkhead feature that is defined by a chassis (e.g., chassis (3690) described below), which is located within casing (110). The rigid bulkhead feature forms a support journal for nut (160). The bulkhead is fixed within the chassis in casing (110) and thereby provides a ground for the proximal end of coil spring (170), such that coil spring (170) resiliently imparts a distal bias to bracket (1500) via upright member (1510). Bracket (1500) further includes a laterally presented flange (1516) at the distal end of body (1502). Flange (1516) defines a slot (1514).

Figure 29:
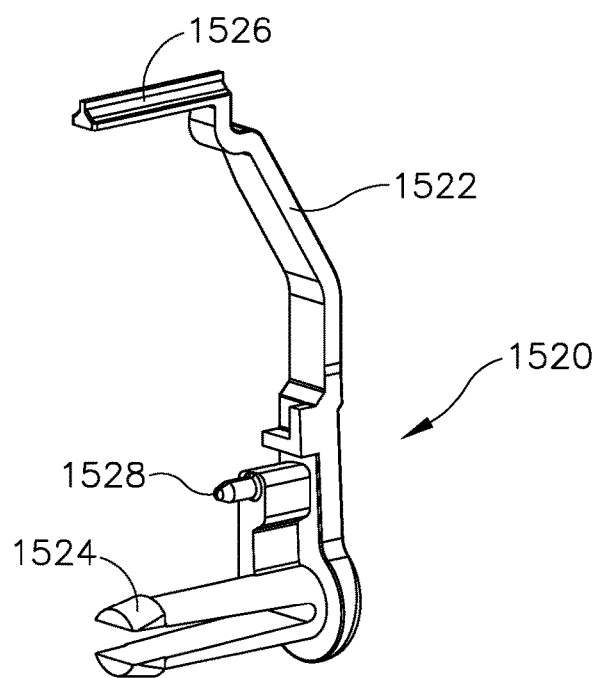
FIG. 29 depicts a perspective view of an indicator member of the handle assembly of FIG. 18.

As best seen in FIGS. 30B-30C, an indicator member (1520) is configured to pivot in response to translation of bracket (1500). As best seen in FIG. 29, indicator member (1520) comprises an upright arm (1522), a snap pin (1524) projecting laterally from a lower end of arm (1522), an indicator needle (1526) projecting laterally from an upper end of arm (1522), and a coupling pin (1528) projecting laterally from an intermediate region of arm (1522). Snap pin (1524) is configured to snap into a complementary recess provided by a chassis (e.g., left chassis portion (3691) of chassis (3690) described below), which is located within casing (110). Snap pin (1524) thereby secures indicator member (1520) to the chassis yet permits indicator member (1520) to pivot relative to the chassis about the longitudinal axis of snap pin (1524). Indicator needle (1526) is positioned to be visible through user feedback feature (114) of handle assembly (100) to thereby visually indicate the pivotal position of indicator member (1520). Coupling pin (1528) is slidably received in slot (1514) of flange (1516) of bracket (1500). This engagement between indicator member (1520), the chassis in casing (110), and bracket (1500) provides pivotal movement of indicator member (1520) in response to translation of bracket (1500).

Bracket (1500) is configured to selectively prevent and permit actuation of triggers (140, 150). In particular, slots (1504, 1506) of bracket (1500) are configured to selectively provide clearance for actuation of triggers (140, 150). As shown in FIGS. 30A-30E, safety trigger (140) is pivotably coupled with a first upright member (144). First upright member (144) is coupled with a chassis (e.g., chassis (3690) described below), which is located within casing (110), such that first upright member (144) is configured to translate upwardly in response to pivoting of safety trigger (140) toward pistol grip (112). However, body (1502) of bracket (1500) is configured to prevent this movement of first upright member (144) and safety trigger (140) by engaging the upper end (146) of first upright member (144). Body (1502) thus blocks movement of first upright member (144) and safety trigger (140) until bracket (1500) is moved to a position where slot (1506) is aligned with upper end (146) to thereby provide clearance for upward movement of first upright member (144). It should therefore be understood that safety trigger (140) cannot be pivoted toward pistol grip (112) until slot (1506) is positioned over upper end (146).

Similarly, firing trigger (150) is pivotably coupled with a second upright member (154). Second upright member (154) is coupled with a chassis (e.g., chassis (3690) described below), which is located within casing (110), such that second upright member (154) is configured to translate upwardly in response to pivoting of firing trigger (150) toward pistol grip (112). However, body (1502) of bracket (1500) is configured to prevent this movement of second upright member (154) and firing trigger (150) by engaging the upper end (156) of second upright member (154). Even if safety trigger (140) is pivoted out of the way to otherwise permit movement of firing trigger (150), body (1502) blocks movement of second upright member (154) and firing trigger (150) until bracket (1500) is moved to a position where slot (1504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (1504) is positioned over upper end (156).

Third slot (1508) is configured to receive a downwardly projecting boss (223) of clip (222), which is rigidly secured to trocar actuation rod (220). While a chassis (e.g., chassis (3690) described below), which is located within casing (110), is configured to allow bracket (1500) to translate longitudinally relative to the chassis, the chassis includes rails, channels, and/or other features that prevent bracket (1500) from rotating relative to the chassis. Thus, the positioning of boss (223) in slot (1508) prevents clip (222) and trocar actuation rod (220) from rotating relative to the chassis. Boss (223) and slot (1508) nevertheless allow bracket (1500) to translate longitudinally within casing (110) as will be described in greater detail below. As noted herein, third slot (1508) is merely optional and may be omitted in some versions.

FIGS. 30A-30E depict the above-described components at various stages of operation. In particular, in FIG. 30A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 30B. This provides proximal retraction of trocar actuation rod (220) provides retraction of trocar (330) and anvil (400). As trocar actuation rod (220) moves from the position shown in FIG. 30A to the position shown in FIG. 30B, bracket (1500) remains stationary. This is due to the fact that clip (222) is spaced apart from upright member (1510) at the stage shown in FIG. 30A and does not engage upright member (1510) until trocar actuation rod (220) reaches the position shown in FIG. 30B.

After reaching the stage shown in FIG. 30B, the operator may continue rotating knob (130) and nut (160), which causes further proximal retraction of trocar actuation rod (220) as shown in FIG. 30C. This of course causes further proximal retraction of trocar (330) and anvil (400). As trocar actuation rod (220) moves from the position shown in FIG. 30B to the position shown in FIG. 30C, clip (222) bears against bracket (1500), driving bracket (1500) proximally. This proximal movement of bracket (1500) causes indicator member (1520) to pivot from the position shown in FIG. 30B to the position shown in FIG. 30C due to the positioning of coupling pin (1528) in slot (1514) of flange (1516).

As indicator member (1520) pivots from the position shown in FIG. 30B to the position shown in FIG. 30C, the operator may observe the position of indicator needle (1526) through user feedback feature (114) of handle assembly (100). As described in greater detail below, a series of hash marks, colored regions, and/or other fixed indicators may be positioned adjacent to user feedback feature (114) in order to provide a visual context for indicator needle (1526), thereby facilitating operator evaluation of the position of needle (1526) within user feedback feature (114). It should be understood that the position of needle (1526) within user feedback feature (114) will be indicative of the longitudinal position of trocar (330) and anvil (400). The position of needle (1526) within user feedback feature (114) will thus indicate the gap distance (d) between opposing surfaces (412, 322) of anvil (400) and stapling head assembly (300). While observing the position of needle (1526) within user feedback feature (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 30C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 30B (i.e., when clip (222) first engages upright member (1510)). In some other versions, the transition from engagement by coarse helical threading (224) to fine helical threading (226) occurs sometime between the stage shown in FIG. 30B and the stage shown in FIG. 30C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 30C, slot (1506) is aligned with upper end (146) to thereby provide clearance for upward movement of first upright member (144). Similarly, slot (1504) is aligned with upper end (156) to thereby provide clearance for upward movement of second upright member (154). In the present example, slots (1504, 1506) are sized and positioned such that slots (1504, 1506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (1504, 1506) are positioned to provide clearance for upward movement of upright members (144, 154) as shown in FIG. 30C, safety trigger (140) will still block pivotal movement of firing trigger (150) about a pin (152) (FIG. 9) when safety trigger (140) is in the non-actuated position shown in FIG. 30C. Thus, in order to enable movement of firing trigger (150), the operator will need to first actuate safety trigger (140) about a pin (142) (FIG. 9) from the position shown in FIG. 30C to the position shown in FIG. 30D.

As shown in FIG. 30D, upper end (146) passes through slot (1506) as safety trigger (140) is pivoted from the position shown in FIG. 30C to the position shown in FIG. 30D. It should be understood that this movement of upper end (146) would not be possible at the stages shown in FIGS. 30A-30B (when the gap distance (d) is too great) because body (1502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (1502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (1502), knob (130), or some other feature prevents actuation when the gap distance (d) would be too small, it should be understood that instrument (10) permits actuation of safety trigger (140) only when the gap distance (d) is within the clinically acceptable range.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 30D to the position shown in FIG. 30E. As shown in FIG. 30E, upper end (156) passes through slot (1504) as firing trigger (150) is pivoted from the position shown in FIG. 30D to the position shown in FIG. 30E. It should be understood that, even in the complete absence of safety trigger (140), this movement of upper end (156) would not be possible at the stages shown in FIGS. 30A-30B (when the gap distance (d) is too great) because body (1502) would physically block upward movement of upright member (154), thereby physically blocking pivotal movement of firing trigger (150). Thus, even in the complete absence of safety trigger (140), firing trigger (150) may only be actuated when the gap distance (d) is within the clinically acceptable range.

Firing trigger (150) of the present example includes integral actuation paddle (158). Paddle (158) pivots forwardly as firing trigger (150) pivots from the position shown in FIG. 30D to the position shown in FIG. 30E. Paddle (158) is configured to actuate a switch of a motor activation module (180), which is shown in FIG. 9, when firing trigger (150) pivots from the position shown in FIG. 30D to the position shown in FIG. 30E. Motor activation module (180) is in communication with battery pack (120) and motor (161), such that motor activation module (180) is configured to provide activation of motor (161) with electrical power from battery pack (120) in response to paddle (158) actuating the switch of motor activation module (180). Thus, motor (161) will be activated when firing trigger (150) is pivoted from the position shown in FIG. 30D to the position shown in FIG. 30E. This activation of motor (161) will actuate stapling head assembly (300) as described in greater detail below.

Figure 31:
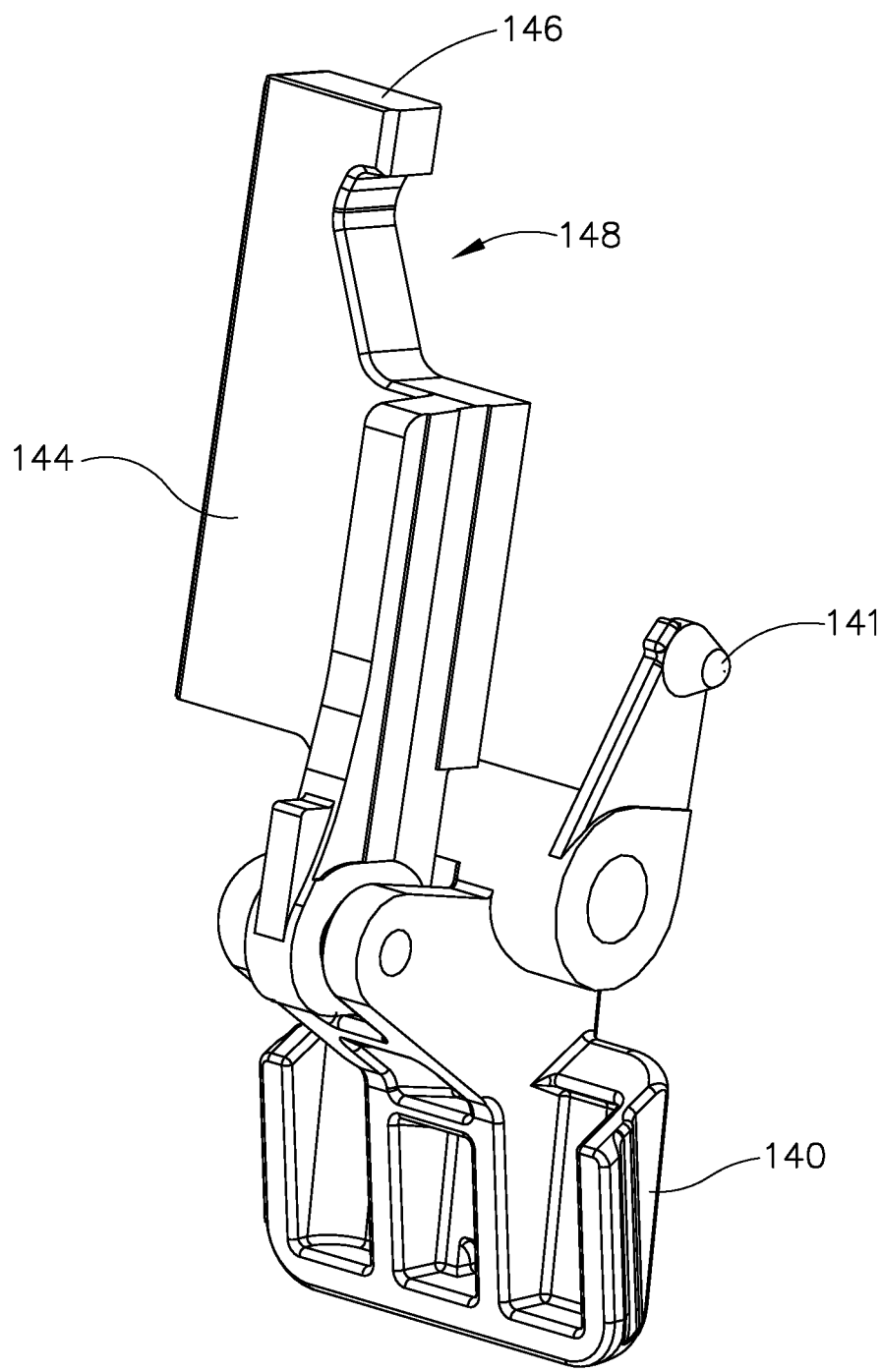
FIG. 31 depicts a perspective view of the safety trigger of FIG. 30D and an associated upright member.

As shown in FIG. 31, safety trigger (140) of the present example includes a laterally extending detent protrusion (141). Protrusion (141) is configured to cooperate with a corresponding detent recess (not shown) of a portion of a chassis (e.g., chassis (3690) described below), to selectively retain safety trigger (140) in the flipped-up position shown in FIGS. 30D-30E. In other words, protrusion (141) is configured to prevent inadvertent movement of safety trigger (140) from the flipped-up position (FIGS. 30D-30E) to the flipped-down position (FIGS. 30A-30C). Protrusion (141) nevertheless enables an operator to intentionally transition safety trigger (140) between the flipped-up position (FIGS. 30D-30E) and the flipped-down position (FIGS. 30A-30C).

As also shown in FIG. 31, first upright member (144) defines a lateral notch (148) below upper end (146) of first upright member (144). Lateral notch (148) is configured to provide clearance for longitudinal movement of bracket (1500) after safety trigger (140) is in the flipped-up position (FIGS. 30D-30E), where first upright member (144) is in an upper position. For instance, if an operator achieves a first longitudinal position of anvil (400) and trocar (330) where anvil (400) is in the "green zone" as described herein, then the operator actuates safety trigger (140) to the flipped-up position, then the operator manipulates knob (130) again to reposition anvil (400), bracket (1500) will translate during this repositioning of anvil (400). In the event that the operator repositions anvil (400) out of the "green zone," bracket (1500) will be at a longitudinal position where slot (1506) is no longer aligned with upper end (146) of first upright member (144). Thus, first upright member (144) will not be sheared or otherwise damaged in the event that the operator repositions anvil (400) out of the "green zone" after actuating safety trigger (140) to the flipped-up position. If anvil (400) is moved out of the "green zone" after safety trigger (140) is actuated to the flipped-up position, bracket (1500) will still prevent firing trigger (150) from being actuated since slot (1504) is not aligned with upper end (156) of second upright member (154) when anvil (400) is outside of the "green zone."

B. Exemplary User Interface Feature

Figure 32:
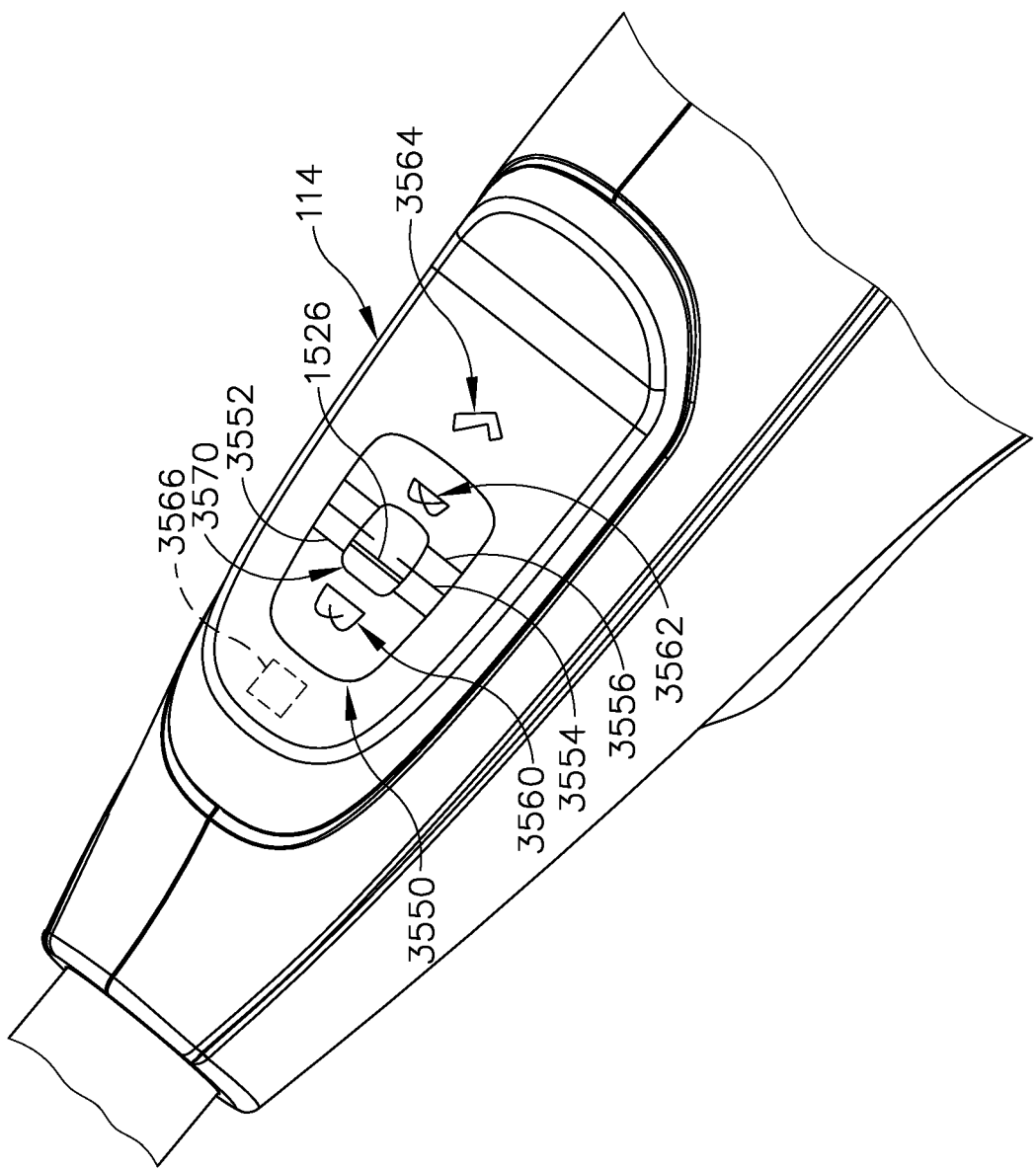
FIG. 32 depicts a perspective view of a user feedback feature of the handle assembly of FIG. 18.

As noted above, as indicator member (1520) pivots from the position shown in FIG. 30B to the position shown in FIG. 30C, the operator may observe the position of indicator needle (1526) in user feedback feature (114) of handle assembly (100). In particular, and as best seen in FIG. 32, user feedback feature (114) of the present example (also referred to herein as a "user interface") includes a graphical indicator (3550) (also referred to herein as a "lens member"), which includes fixed linear indicia (3552, 3554, 3556), graphical representations (3560, 3562) of staples, and a checkmark feature (3564). User feedback feature (114) further defines a window (3570) through which indicator needle (1526) may be viewed. In some variations, user feedback feature (114) further includes a field (3566) that may indicate a diameter associated with the size of stapling head assembly (300), the size of staples in stapling head assembly (300), the size of the gap defined between anvil (400) and stapling head assembly (300), and/or other information. By way of example only, field (3566) may indicate a stapling head assembly (300) size of 23 mm, 25 mm, 29 mm, or 31 mm.

As the operator rotates knob (130) to adjust the longitudinal position of anvil (400) relative to stapling head assembly (300), the operator may observe the position of indicator needle (1526) through window (3570), such that window (3570) and indicator needle (1526) cooperate to define a user feedback element of user feedback feature (114). Initially, indicator needle (1526) may be positioned at or near the distal end of window (3570). As anvil (400) continues to move proximally, indicator needle (1526) will eventually move proximally relative to window (3570). The operator may view the position of indicator needle (1526) in relation to fixed linear indicia (3552, 3554, 3556). The distal-most and proximal-most indicia (3552, 3556) may represent the boundaries of a "green zone," which is the acceptable range of distance between anvil (400) and stapling head assembly (300) for successful actuation of stapling head assembly (300). Thus, if indicator needle (1526) is distal to distal-most indicia (3552), the distance between anvil (400) and stapling head assembly (300) is too large; and if indicator needle (1526) is proximal to proximal-most indicia (3556), the distance between anvil (400) and stapling head assembly (300) is too small. Indicia (3554) is longitudinally positioned between indicia (3552, 3556). Graphical representation (3560) represents a relatively tall formed staple (e.g., suitable for use in relatively thick tissue); while graphical representation (3562) represents a relatively short formed staple (e.g., suitable for use in relatively thin tissue). Graphical representations (3560, 3562) may thus facilitate the operator's decision, based on tissue observations or otherwise, on whether and how to achieve a desired formed staple height by selecting an appropriate corresponding spatial relationship between indicator needle (1526) and indicia (3552, 3554, 3556).

In the present example, window (3570) is illuminated via a first light source (2702) in the form of a first light emitting diode (LED) (see FIG. 83), further facilitating viewing of indicator needle (1526) in window (3570). In addition, checkmark feature (3564) is illuminated via a second light source (2704) in the form of a second LED (see FIG. 83) when stapling head assembly (300) completes a stapling and cutting cycle. Thus, the operator may further rely on illumination of checkmark feature (3564) to confirm that the stapling and cutting cycle is complete, to thereby verify that it is safe to advance anvil (400) distally away from the anastomosis (70) and remove instrument (10) from the patient. In this capacity, checkmark feature (3564) functions as another user feedback element of user feedback feature (114). By way of example only, LED (2702) associated with window (3570) may be configured to emit white visible light while LED (2704) associated with checkmark feature (3564) may be configured to emit green visible light. In some versions, control circuit (2700) is configured to provide illumination of the LED (2702) associated with window (3570) as soon as battery pack (120) is inserted into casing (110). It will be appreciated that in other versions of instrument (10), one or both of first and second light sources (2702, 2704) may take various other suitable forms other than an LED.

C. Exemplary Hysteresis Avoidance Features

As noted above, indicator member (1520) and user feedback feature (114) cooperate to provide the operator with visual feedback indicating the longitudinal position of anvil (400) relative to stapling head assembly (300). Those of ordinary skill in the art will recognize that the precision of this positioning may be critical to the successful formation of an anastomosis (70). Thus, the real-time accuracy of the feedback provided by indicator member (1520) and user feedback feature (114) may be critical to the successful formation of an anastomosis (70).

Some versions of bracket (1500) and indicator member (1520) may provide some degree of hysteresis, such that there is a slight lag time between the adjustment of the longitudinal position of anvil (400) relative to stapling head assembly (300) and the position of indicator member (1520) in user feedback feature (114). This hysteresis may be attributable to manufacturing tolerances and/or other factors. This hysteresis may compromise the real-time accuracy of the feedback provided by indicator member (1520) and user feedback feature (114), which may in turn compromise the success of the anastomosis (70). It may therefore be desirable to configure bracket (1500), indicator member (1520), and associated features to eliminate or at least minimize such hysteresis, to thereby promote greater real-time accuracy of the feedback provided by indicator member (1520) and user feedback feature (114), to in turn thereby promote a greater chance of success in the formation of an anastomosis (70).

Figure 33:
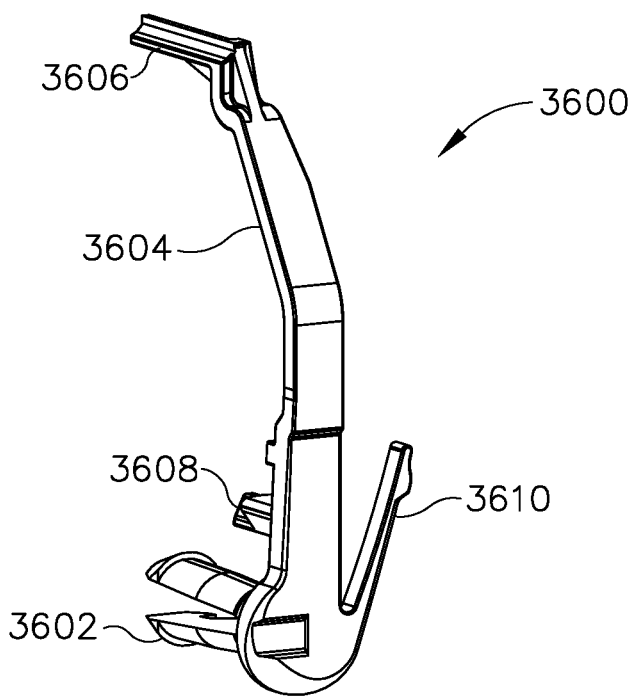
FIG. 33 depicts a perspective view of an exemplary alternative indicator member that may be incorporated into the instrument of FIG. 1.
Figure 34:
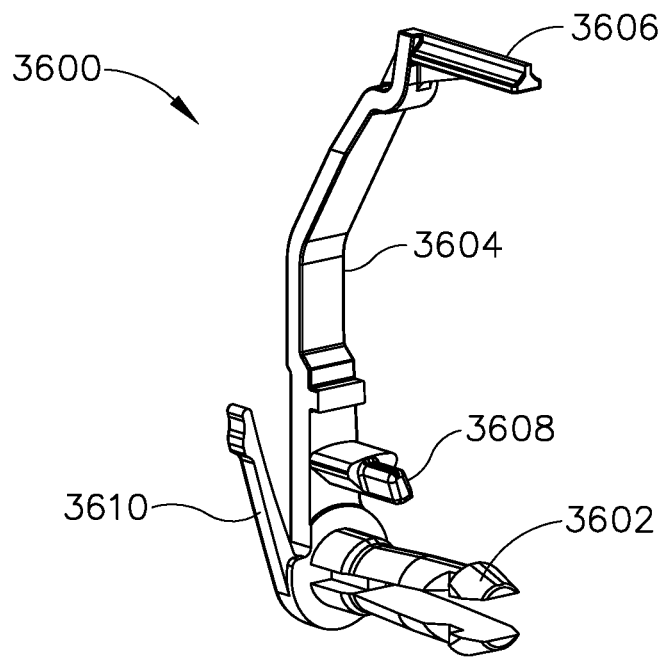
FIG. 34 depicts another perspective view of the indicator member of FIG. 33.
Figure 35:
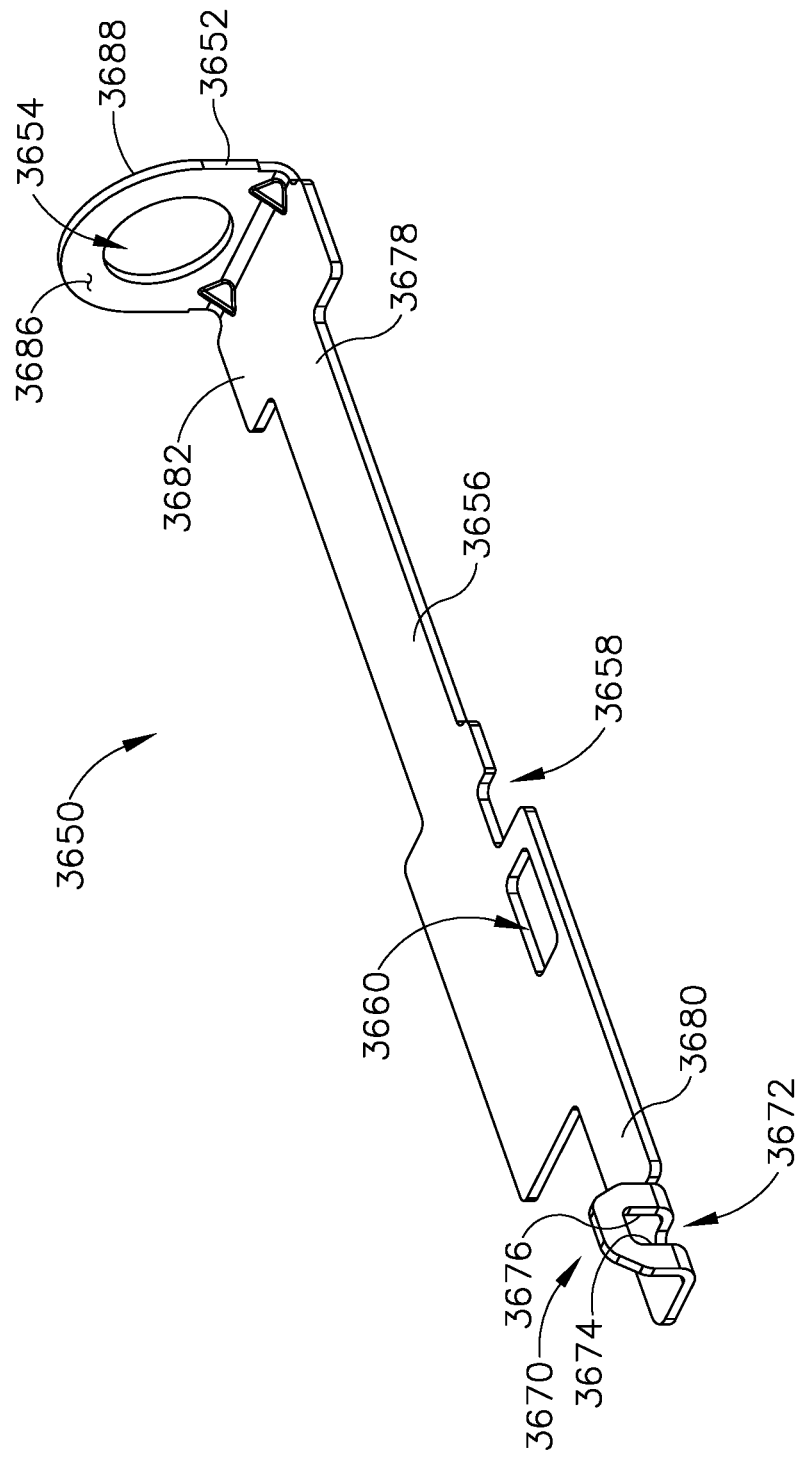
FIG. 35 depicts a perspective view of an exemplary alternative bracket that may be incorporated into the instrument of FIG. 1.

FIGS. 33-39D show exemplary alternative features that may be incorporated into instrument (10) to promote greater real-time accuracy of visual feedback indicating the longitudinal position of trocar (330) and anvil (400) relative to stapling head assembly. In particular, FIGS. 33-34 show an exemplary alternative indicator member (3600) that may be used in place of indicator member (1520); while FIG. 35 shows an exemplary alternative bracket (3650) that may be used in place of bracket (1500).

As shown in FIGS. 33-34, indicator member (3600) of this example comprises an upright arm (3604), a snap pin (3602) projecting laterally from a lower end of arm (3604), an indicator needle (3606) projecting laterally from an upper end of arm (3604), and a coupling pin (3608) projecting laterally from an intermediate region of arm (3604). Snap pin (3602) is configured to snap into a complementary recess provided by a portion of a chassis (3690) as described below. Indicator needle (3606) is positioned to be visible in user feedback feature (114) of handle assembly (100), as described above with respect to indicator needle (1526), to thereby visually indicate the pivotal position of indicator member (3600), which will indicate the longitudinal position of anvil (400) relative to stapling head assembly (300). Coupling pin (3608) is configured to fit in an opening (3672) of a flange (3670) of bracket (3650), as described below. As also described below, this engagement between indicator member (3600), chassis (3690), and bracket (3650) provides pivotal movement of indicator member (3600) in response to translation of bracket (3650). Unlike indicator member (1520) described above, indicator member (3600) of the present example comprises a resilient arm (3610), which projects upwardly and is resiliently biased to define an oblique angle relative to upright arm (3604). As described in greater detail below, resilient arm (3610) is configured to interact with chassis (3690) to provide a resilient angular bias to indicator member (3600).

Figure 36:
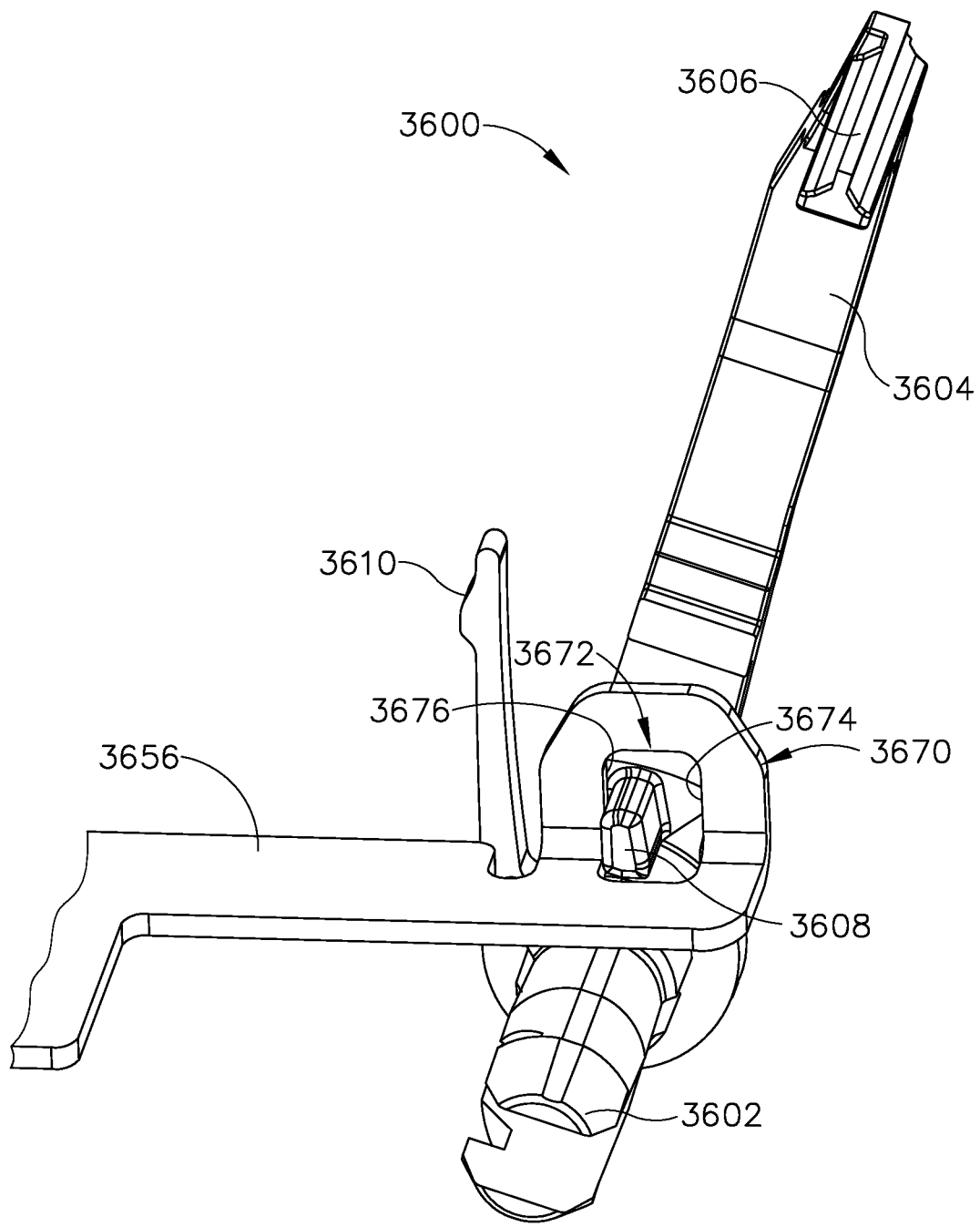
FIG. 36 depicts a perspective view of the indicator member of FIG. 33 in combination with the bracket of FIG. 35.

As shown in FIG. 35, bracket (3650) of this example comprises a rigid body (3656) that defines a first slot (3660) (which is analogous to first slot (1504), described above) and a second slot (3658) (which is analogous to second slot (1506), described above). An upright member (3652) (which is analogous to upright member (1510), described above) is positioned at the proximal end of body (3656) and defines an opening (7204) (which is analogous to opening (1512), described above). Opening (7204) is sized to receive trocar actuation rod (220); and upright member (3652) is configured to engage coil spring (170), just like the analogous features of bracket (1500) described above. Bracket (3650) further includes a laterally presented flange (3670), which defines an opening (3672). Opening (3672) extends between a distal edge (3674) and a proximal edge (3676). Bracket (3650) includes a proximal portion and a distal portion As shown in FIG. 36, and as noted above, pin (3608) is configured to fit in opening (3672) of flange (3670). The width of opening (3672) is larger than the width of pin (3608), such that pin (3608) cannot contact both edges (3674, 3676) simultaneously. This structural relationship between the width of opening (3672) and the width of pin (3608) provides some degree of lost motion between bracket (3650) and indicator member (3600), as described below with reference to FIGS. 39A-39D.

Figure 37:
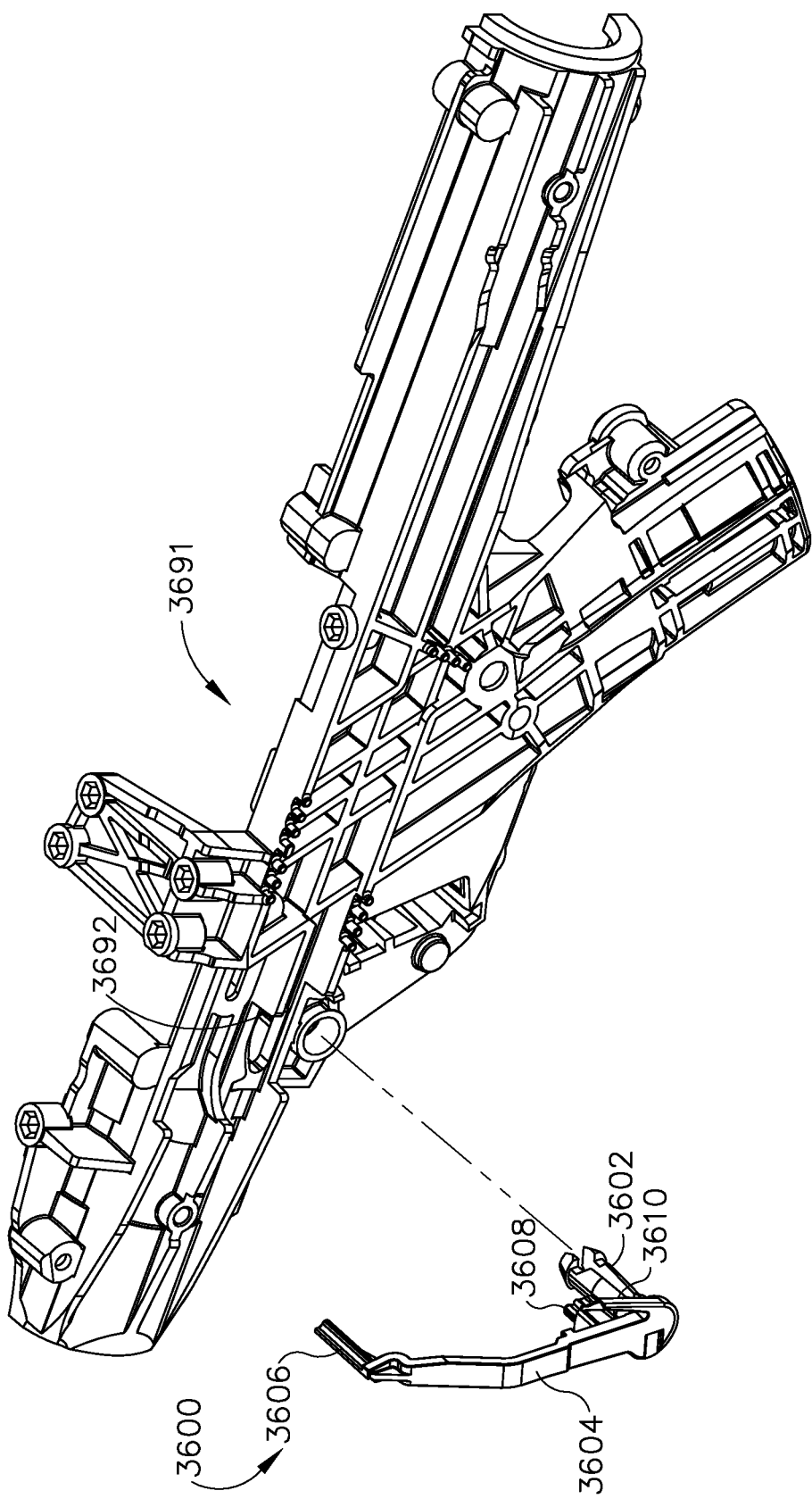
FIG. 37 depicts an exploded perspective view of the indicator member of FIG. 33 with an exemplary alternative chassis that may be incorporated into the instrument of FIG. 1.

FIG. 37 shows an exemplary left chassis portion (3691) of chassis (3690) that may be incorporated into handle assembly (100). Chassis (3690) is configured to provide a mechanical ground relative to movable components of handle assembly (100). Left chassis portion (3691) of chassis (3690) of this example comprises a distally presented ridge (3692) that is positioned for engagement with resilient arm (3610) of indicator member (3600). As shown in FIG. 37, snap pin (3602) is configured to be inserted into chassis (3690). Snap pin (3602) thereby secures indicator member (3600) to chassis (3690) yet permits indicator member (3600) to pivot relative to chassis (3690) about the longitudinal axis of snap pin (3602).

Figure 38A:
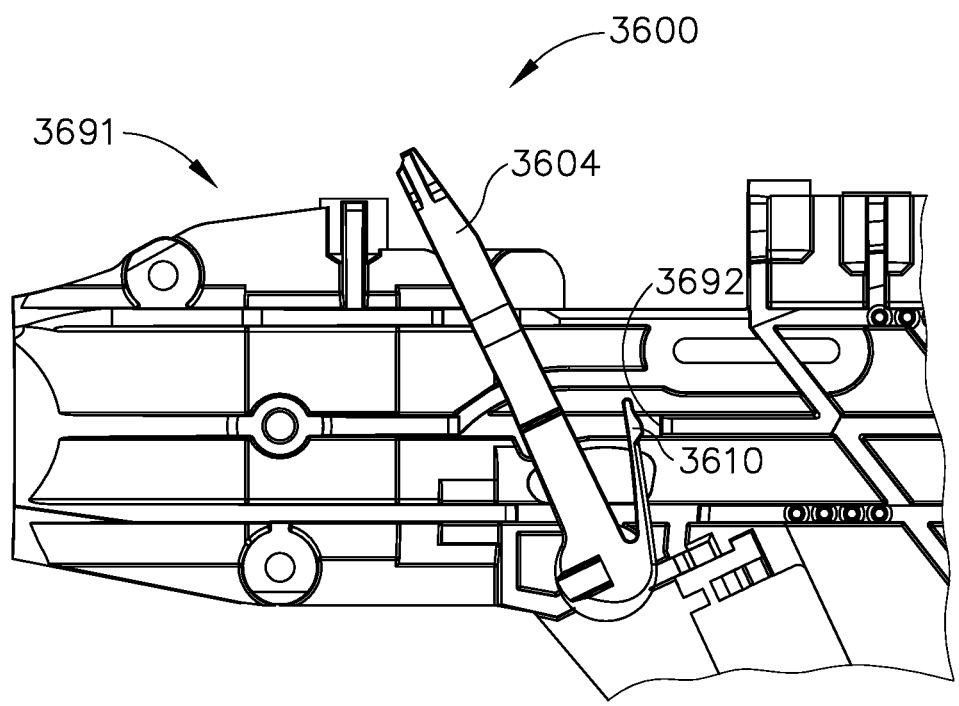
FIG. 38A depicts a side elevational view of the indicator member of FIG. 33 coupled with the chassis of FIG. 37, with the indicator member in a first angular position.

FIGS. 38A-38D show various angular positions of indicator member (3600) relative to chassis (3690) as trocar (330) and anvil (400) are retracted proximally relative to stapling head assembly (300). In particular, FIG. 38A shows indicator member (3600) at a first angular orientation. This first angular orientation would be associated with trocar (330) and anvil (400) being at a furthest distal position relative to stapling head assembly (300). For instance, this orientation may be associated with the operational states depicted in FIGS. 30A and 27B. With indicator member (3600) at this first angular orientation, resilient arm (3610) is not in contact with ridge (3692) of chassis (3690), such that a gap is defined between resilient arm (3610) and ridge (3692).

Figure 38B:
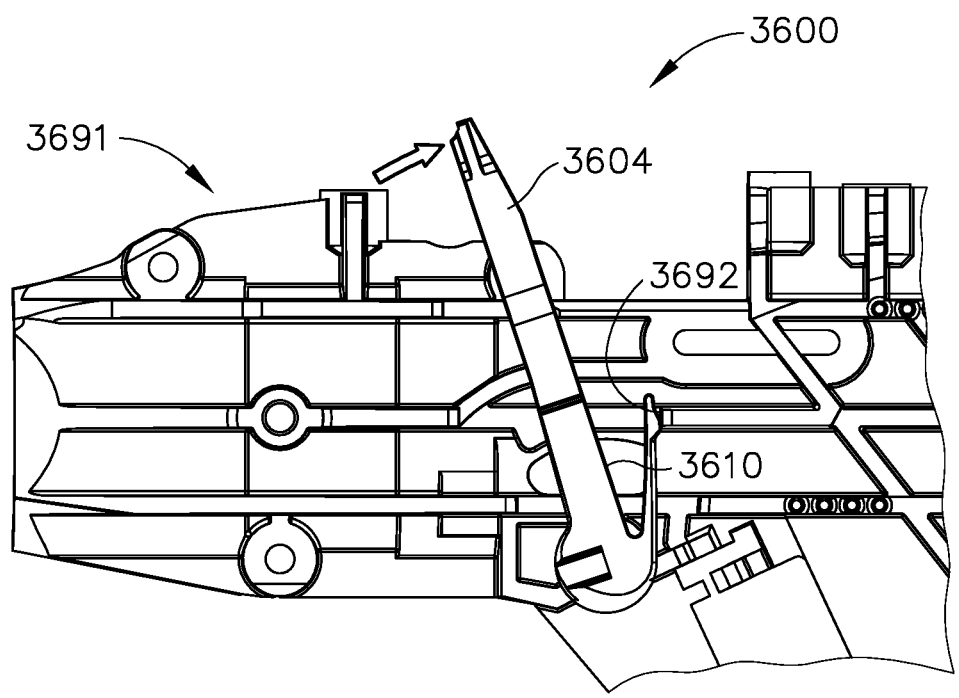
FIG. 38B depicts a side elevational view of the indicator member of FIG. 33 coupled with the chassis of FIG. 37, with the indicator member in a second angular position.
Figure 38C:
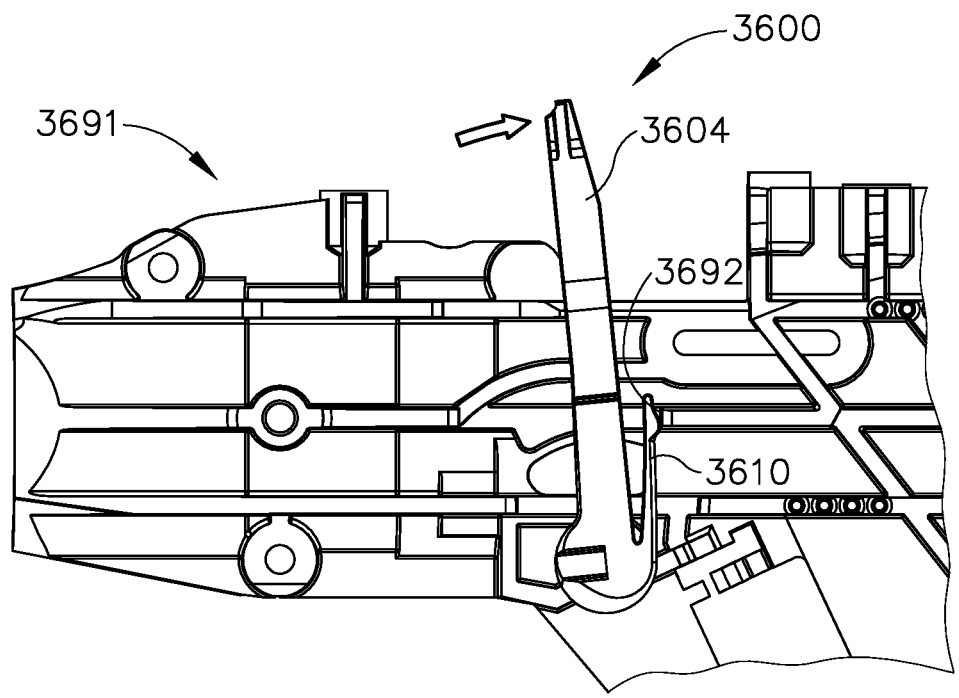
FIG. 38C depicts a side elevational view of the indicator member of FIG. 33 coupled with the chassis of FIG. 37, with the indicator member in a third angular position.
Figure 38D:
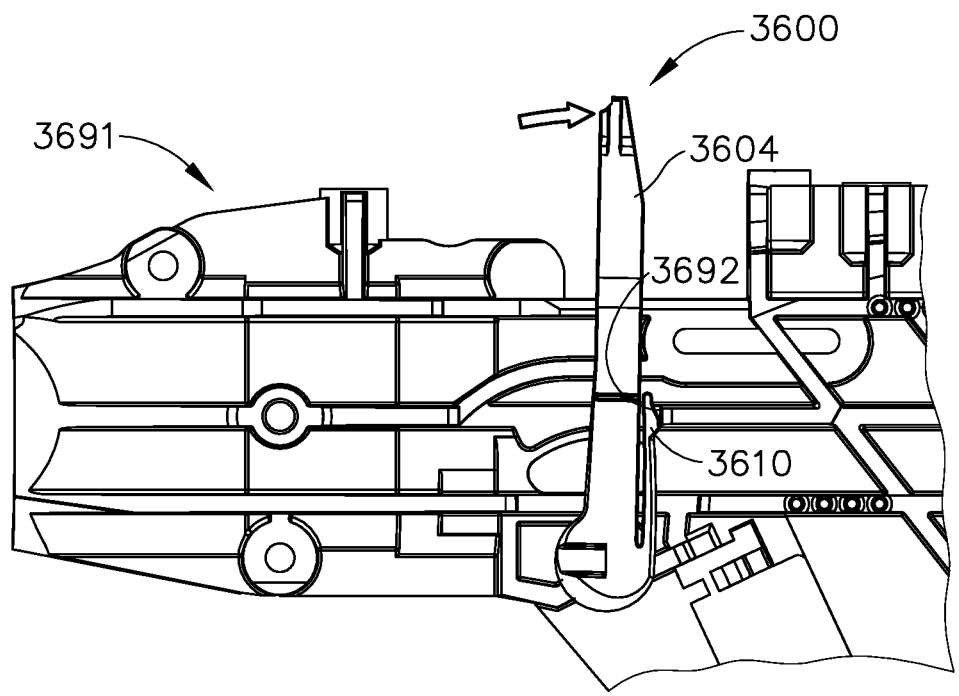
FIG. 38D depicts a side elevational view of the indicator member of FIG. 33 coupled with the chassis of FIG. 37, with the indicator member in a fourth angular position

As the operator rotates knob (130) to retract trocar (330) and anvil (400) proximally relative to stapling head assembly (300), bracket (3650) eventually pulls pin (3608) proximally, thereby causing indicator member (3600) to pivot clockwise (in the view shown in FIGS. 38A-38D) relative to chassis (3690). During this clockwise pivotal movement, resilient arm (3610) eventually contacts ridge (3692) of chassis (3690), as shown in FIG. 38B. During the stages shown in FIGS. 38A and 38B, resilient arm (3610) is in a non-stressed state. However, as the operator continues to rotate knob (130) to retract trocar (330) and anvil (400) further proximally relative to stapling head assembly (300), bracket (3650) continues to pull pin (3608) proximally, thereby causing indicator member (3600) to pivot clockwise further relative to chassis (3690). This results in deformation of resilient arm (3610), as shown in FIG. 38C. In the present example, resilient arm (3610) contacts ridge (3692) and starts deforming before anvil (400) reaches the "green zone" referred to above.

With resilient arm (3610) deformed as shown in FIG. 38C, resilient arm (3610) is in a stressed state, such that indicator member (3600) is resiliently biased in the counterclockwise (in the view shown in FIGS. 38A-38D) direction. Despite the stressed state of resilient arm (3610), the operator may continue to rotate knob (130) to retract trocar (330) and anvil (400) further proximally relative to stapling head assembly (300), thereby causing indicator member (3600) to pivot clockwise further relative to chassis (3690), eventually reaching the state shown in FIG. 38D. At this stage, resilient arm (3610) may engage upright arm (3604), such that resilient arm (3610) may not deform further. In some versions, bracket (3650) may not be enabled to translate proximally far enough for resilient arm (3610) to ground out against upright arm (3604). When the operator reverses rotation of knob (130) to thereby advance anvil (400) distally while resilient arm (3610) is in a stressed state, resilient arm (3610) will drive indicator member (3600) to rotate counterclockwise.

Figure 39A:
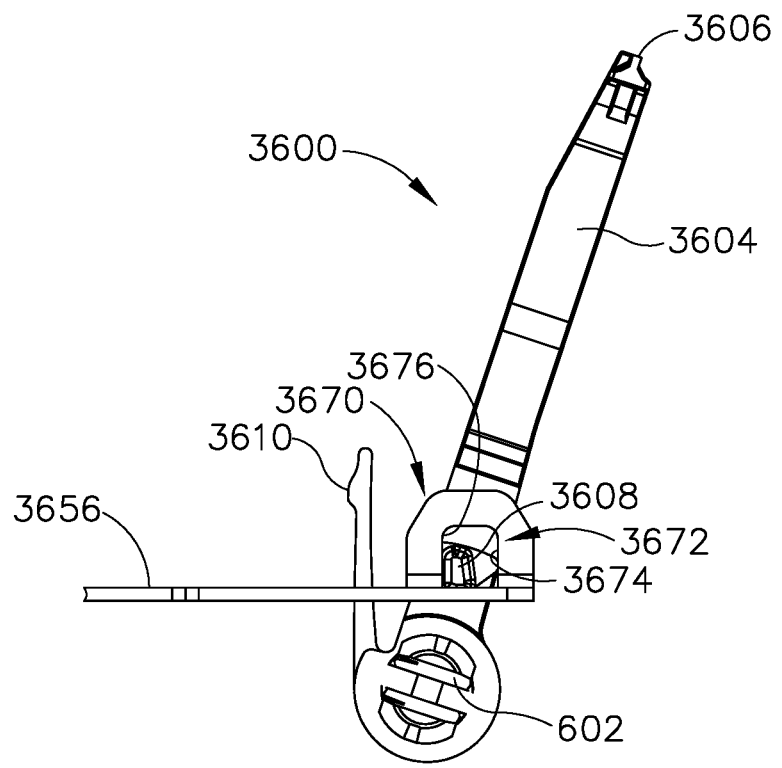
FIG. 39A depicts a side elevational view of the indicator member of FIG. 33 and the bracket of FIG. 35, with the bracket in a first longitudinal position and the indicator member in a first angular position.
Figure 39B:
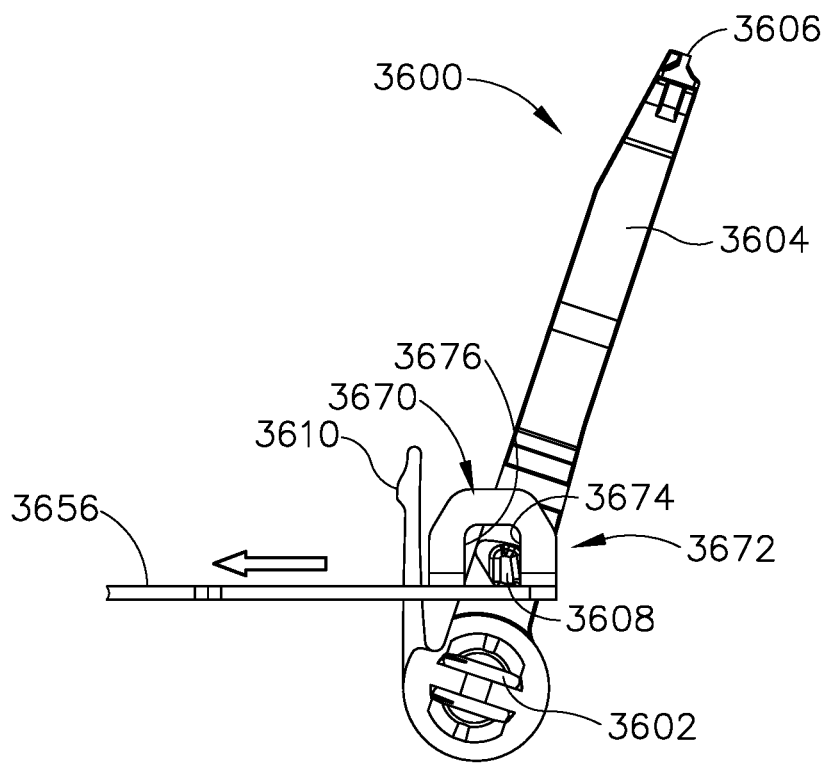
FIG. 39B depicts a side elevational view of the indicator member of FIG. 33 and the bracket of FIG. 35, with the bracket in a second longitudinal position and the indicator member in the first angular position.

As noted above, the structural relationship between the width of opening (3672) and the width of pin (3608) provides some degree of lost motion between bracket (3650) and indicator member (3600). This lost motion is shown in FIGS. 39A-39B. FIG. 39A shows bracket (3650) in a distal-most position. This operational state corresponds with the operational state shown in FIG. 38A. At this stage, proximal edge (3676) of opening (3672) is engaged with pin (3608); and pin (3608) is spaced apart from distal edge (3674) of opening (3672).

As bracket (3650) translates proximally with trocar (330) and anvil (400), bracket (3650) eventually reaches the longitudinal position shown in FIG. 39B. At this stage, distal edge (3674) of opening (3672) is engaged with pin (3608); and pin (3608) is spaced apart from proximal edge (3676) of opening (3672). However, during the transition from the stage shown in FIG. 39A to the stage shown in FIG. 39B, indicator member (3600) has not pivoted. Indicator member (3600) has thus remained stationary while bracket (3650) has translated from the position shown in FIG. 39A to the position shown in FIG. 39B. In the context of the stages shown in FIGS. 38A-38D, indicator member (3600) would remain in the position shown in FIG. 38A during the stage shown in FIG. 39A and the stage shown in FIG. 39B. In the present example, opening (3672) is sized and configured such that pin (3608) will engage distal edge (3674) of opening (3672) as shown in FIG. 39B before anvil (400) has reached a distance associated with the "green zone" as described above. Moreover, resilient arm (3610) will contact ridge (3692) before anvil (400) has reached a distance associated with the "green zone" as described above. Thus, indicator needle (3606) will not be positioned proximal to distal-most indicia (3552) in user feedback feature (114) until after indicator member (3600) has reached the position shown in FIG. 38B, which will not occur until after bracket (3650) has reached the position shown in FIG. 39B.

Figure 39C:
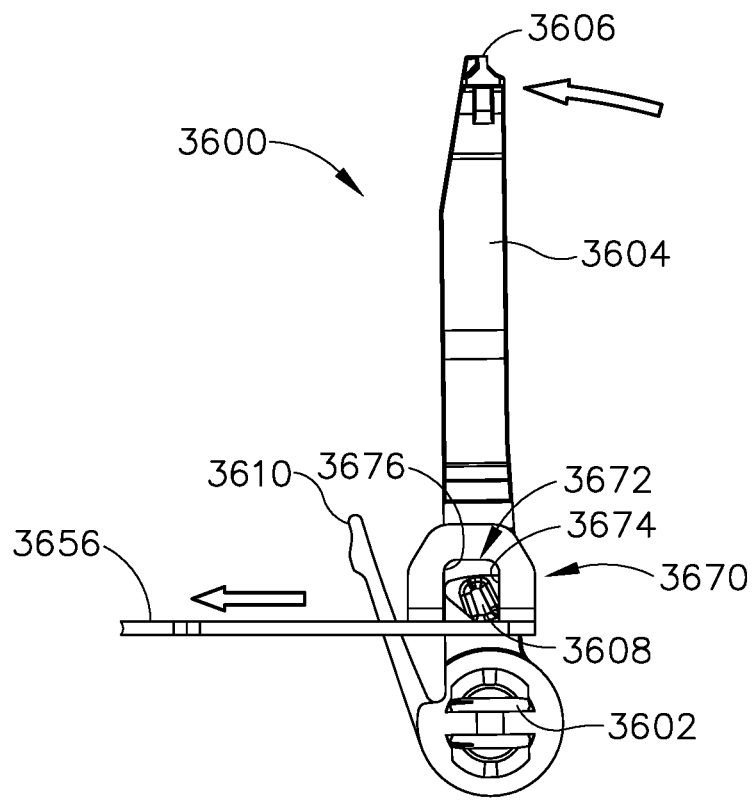
FIG. 39C depicts a side elevational view of the indicator member of FIG. 33 and the bracket of FIG. 35, with the bracket in a third longitudinal position and the indicator member in a second angular position.
Figure 39D:
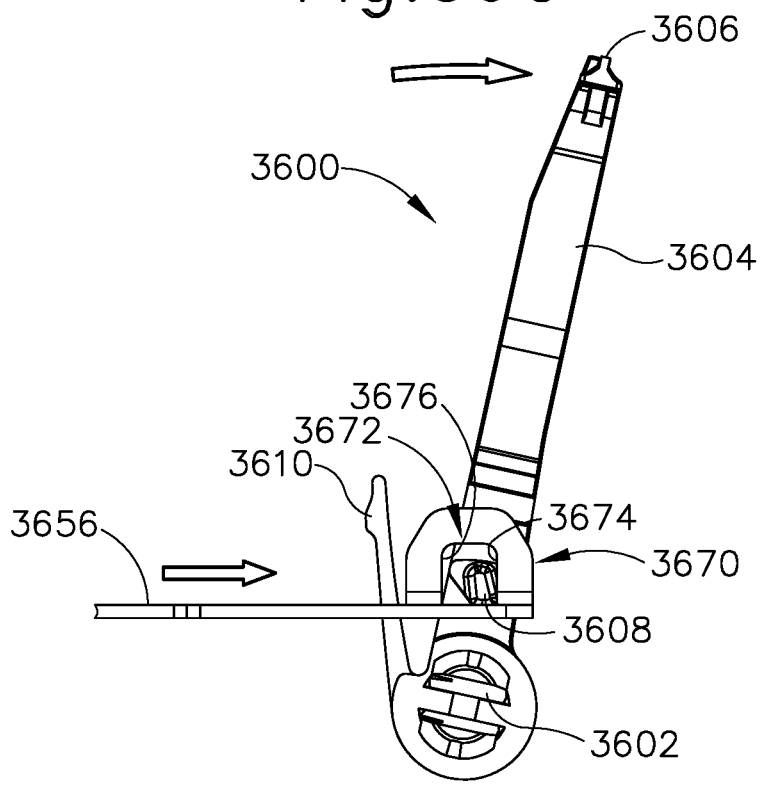
FIG. 39D depicts a side elevational view of the indicator member of FIG. 33 and the bracket of FIG. 35, with the bracket in a fourth longitudinal position and the indicator member in a third angular position.

As bracket (3650) continues to translate proximally with trocar (330) and anvil (400), bracket (3650) eventually reaches the longitudinal position shown in FIG. 39C. During the range of movement between the stage shown in FIG. 39B and the stage shown in FIG. 39C, At this stage, distal edge (3674) of flange (3670) bears against pin (3608) to drive pin (3608) proximally, thereby indicator member (3600) to the position shown in FIG. 39C. While chassis (3690) is omitted from FIGS. 39A-39D, those of ordinary skill in the art will recognize that resilient arm (3610) will be deformed (and thereby stressed) due to engagement between resilient arm (3610) and ridge (3692) during the transition from the stage shown in FIG. 39B and the stage shown in FIG. 39C. Those of ordinary skill in the art will also recognize that the relationship between bracket (3650) and indicator member (3600) shown in FIG. 39C will be provided throughout the range of motion associated with transitioning among the stages shown in FIGS. 38B-38D.

As noted above, after anastomosis (70) has been formed, or while the operator is adjusting the gap distance (d) between anvil (400) and stapling head assembly (300), the operator may drive trocar (330) and anvil (400) distally. When this occurs, bracket (3650) will also translate distally. This will result in movement shown in FIG. 39D. Since bracket (3650) is already in a proximal position (e.g., the position shown in FIG. 39C) before such distal movement is initiated, resilient arm (3610) is in a stressed state, thereby urging indicator member (3600) to pivot distally. Due to this resilient bias, pin (3608) remains engaged with distal edge (3674) of opening (3672) as bracket (3650) moves distally. As the operator continues to rotate knob (130) to drive trocar (330) and anvil (400) distally, the distally translating bracket (3650) allows resilient arm (3610) to drive indicator member (3600) back toward the pivotal position shown in FIGS. 39A-39B. After indicator member (3600) reaches the pivotal position shown in FIGS. 39A-39B, distal edge (3674) disengages pin (3608) and bracket (3650) may continue to translate distally through a certain range of motion before reaching the longitudinal position shown in FIG. 39A.

In the present example, the lost motion between bracket (3650) and indicator (3600) between the stage shown in FIG. 39A and the stage shown in FIG. 39B, and the lost motion between resilient arm (3610) and ridge (3692) between the stage shown in FIG. 38A and the stage shown in FIG. 38B, remove hysteresis from movement of indicator arm (3600) as trocar (330) and anvil (400) are retracted proximally toward stapling head assembly (300). Likewise, the lost motion between bracket (3650) and indicator (3600) between the stage shown in FIG. 39B and the stage shown in FIG. 39A, and the lost motion between resilient arm (3610) and ridge (3692) between the stage shown in FIG. 38B and the stage shown in FIG. 38A, remove hysteresis from movement of indicator arm (3600) as trocar (330) and anvil (400) are advanced distally away from stapling head assembly (300). During advancement and retraction, this lost motion will occur when anvil (400) is outside of the "green zone" referred to above. Thus, the lost motion will reduce the likelihood that the operator is misled into thinking that anvil (400) is in the "green zone" due to hysteresis that might otherwise keep indicator needle (3606) between indicia (3552, 3556) when anvil (400) is in fact outside of the "green zone."

VI. Exemplary Operational Routines

Figure 40A:
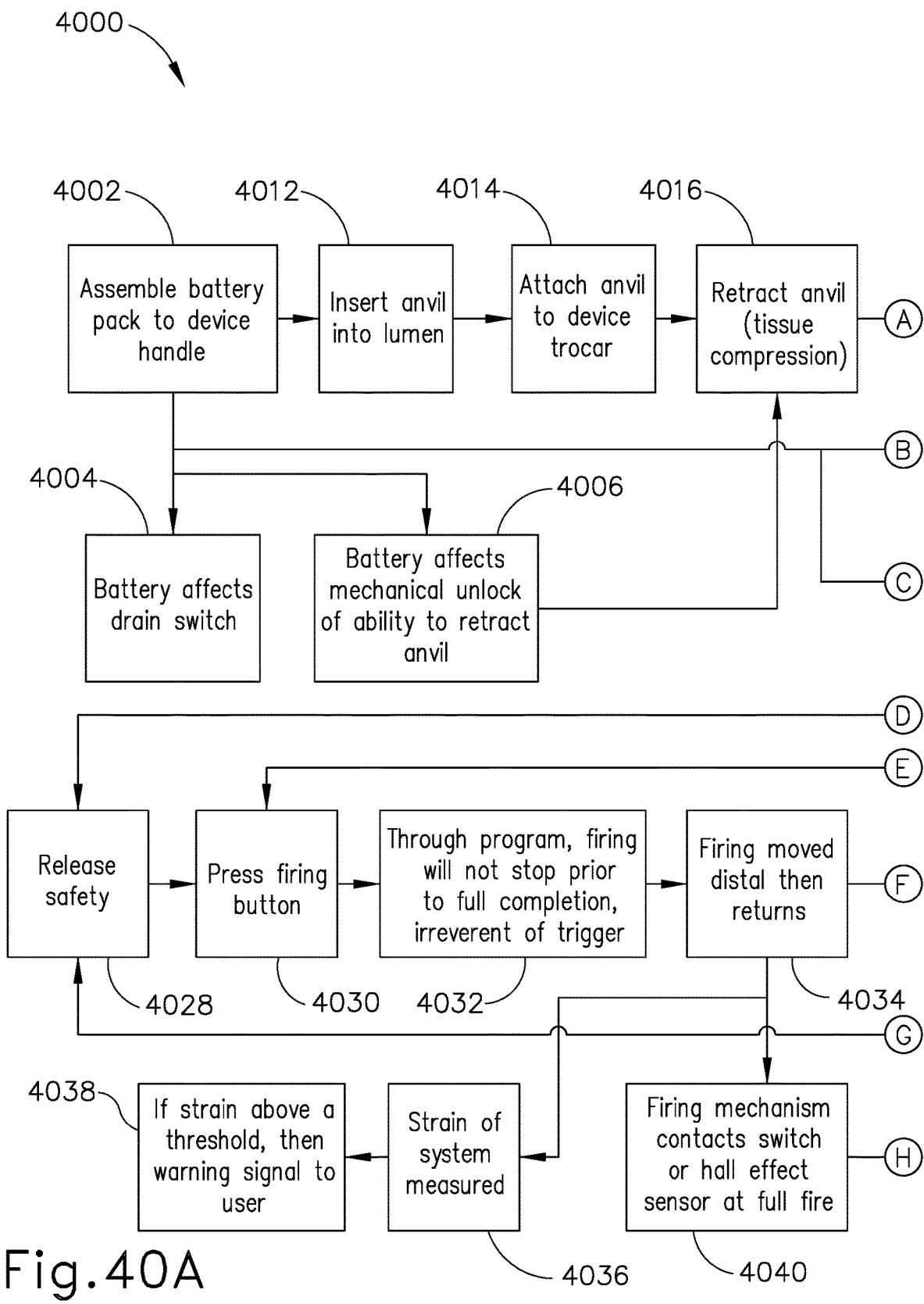
FIGS. 40A-40B depict a flow chart showing exemplary steps of operating the circular stapler of FIG. 1.
Figure 40B:
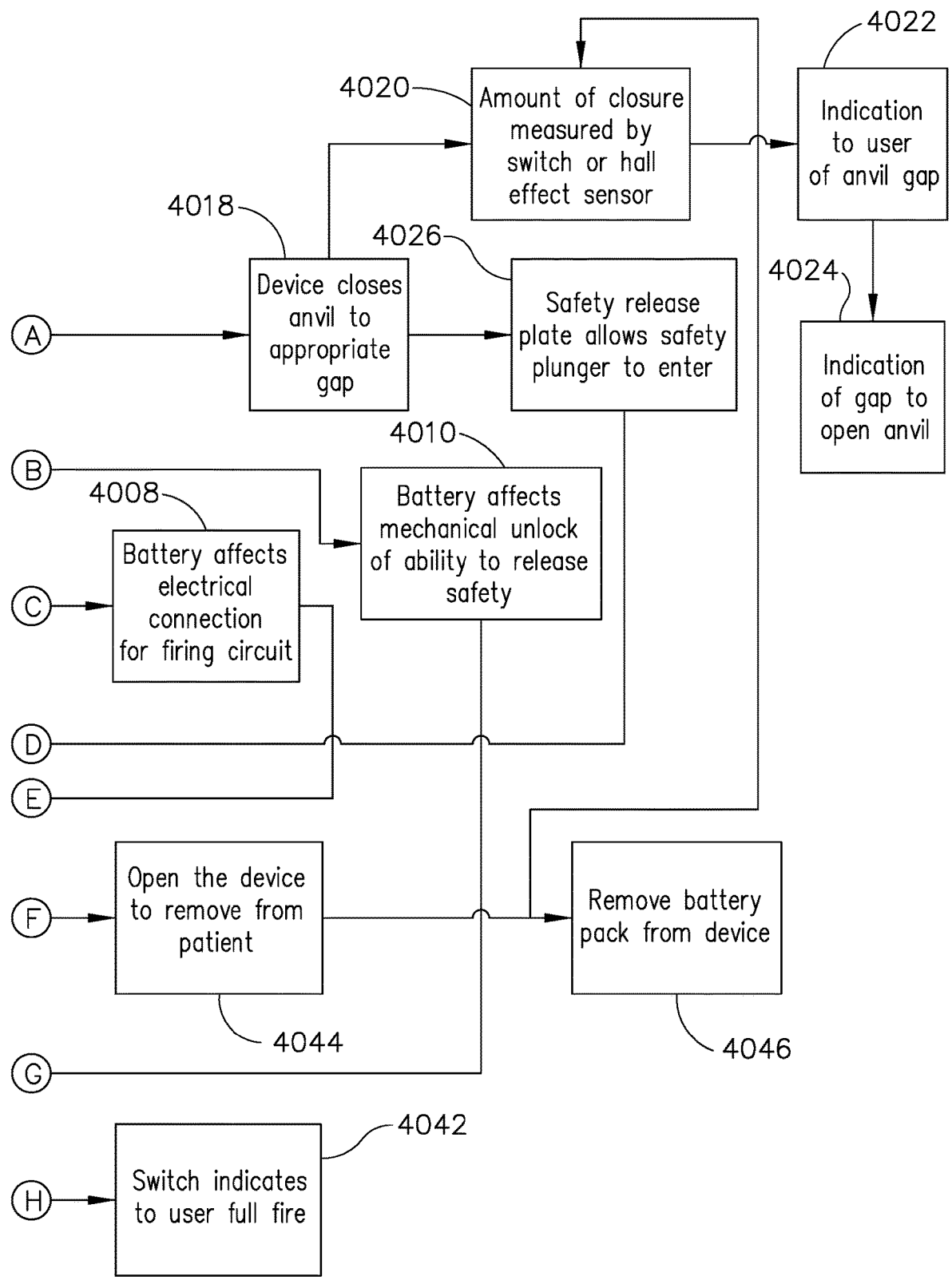
Figure 41:
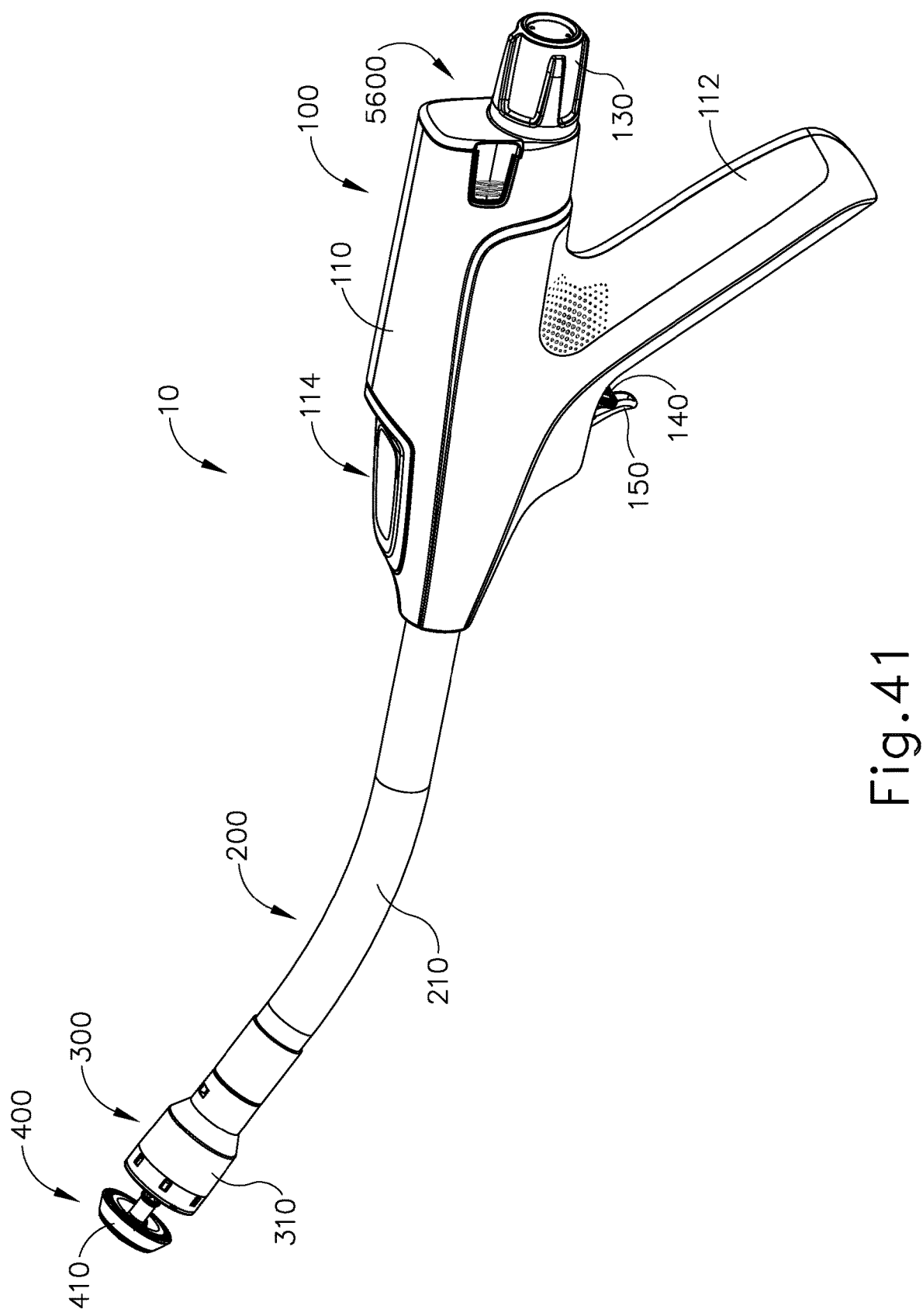
FIG. 41 depicts a perspective view of yet another exemplary alternative circular stapler.
Figure 42:
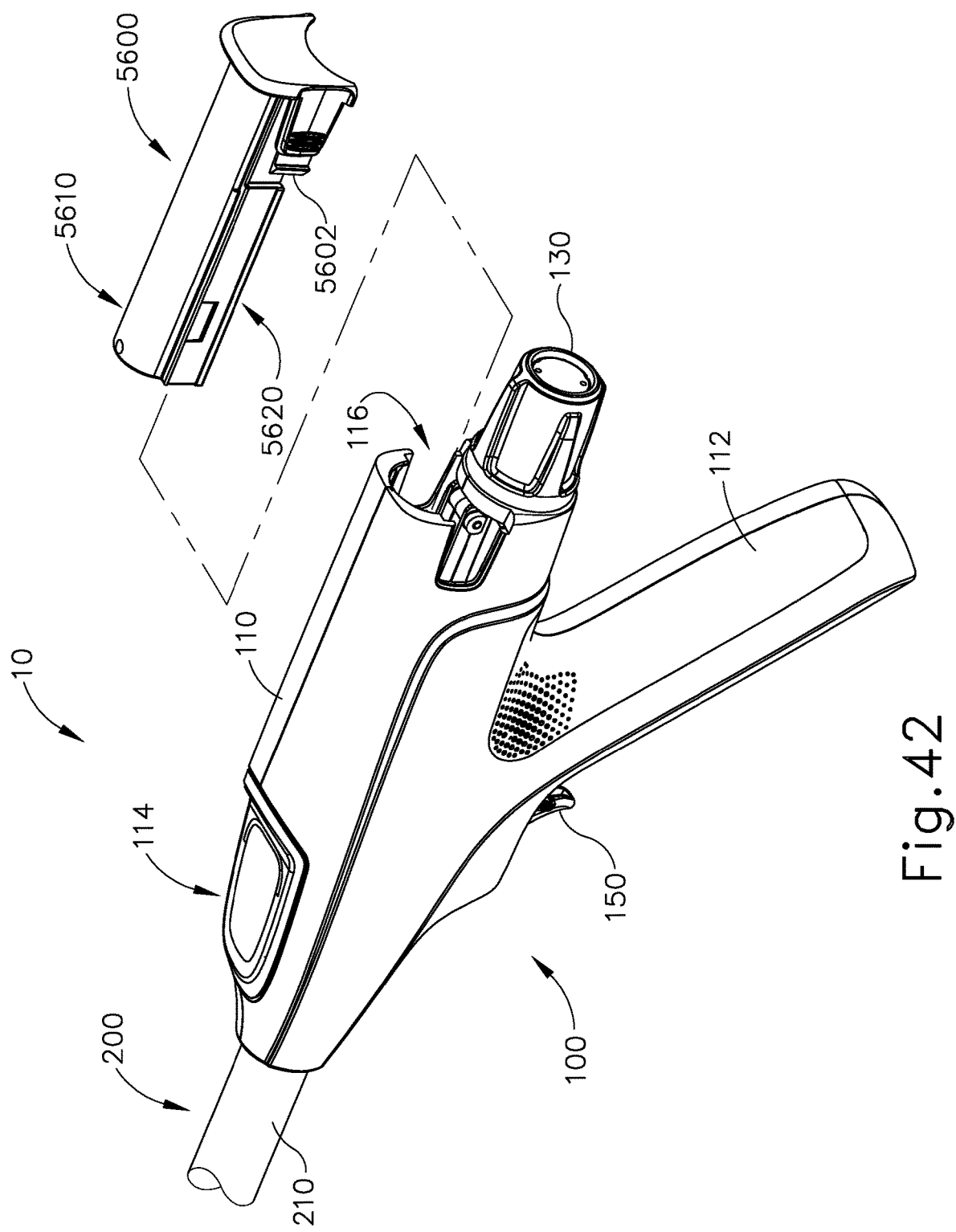
FIG. 42 depicts a perspective view of the circular stapler of FIG. 41, with a battery pack removed from a handle assembly of the circular stapler.

While the sequence described above with reference to FIGS. 27A-27E relates to how instrument (10) may be used by an operator in a surgical procedure, it should be understood that there are various routines that may be performed within instrument (10) before, during, and after the procedure depicted in FIGS. 27A-27E. FIGS. 40A-40B show various steps in an exemplary process (4000) that may be carried out through instrument (10) before, during, and after the procedure depicted in FIGS. 27A-27E. It should be understood that various steps of process (4000) are merely optional and may be omitted if desired.

In the present example, process (4000) begins with an operator inserting battery pack (120) into socket (116) of handle assembly (100), as shown in block (4002). In some versions, the insertion of battery pack (120) into socket (116) will automatically trigger one or more additional steps in process (4000). For instance, as shown in block (4004), the insertion of battery pack (120) into socket (116) may automatically activate a drain switch that begins to drain power from battery pack (120) once battery pack (120) is removed from casing (110). By way of example only, such automatic drainage of power from battery pack (120) may be provided in accordance with at least some of the other teachings herein. In addition or in the alternative, automatic drainage of power from battery pack (120) may be provided in accordance with at least some of the teachings below. Other suitable ways in which power may be automatically drained from battery pack (120) upon insertion of battery pack (120) into socket (116) will be apparent to those of ordinary skill in the art in view of the teachings herein. Alternatively, in some versions the step shown in block (4004) is simply omitted.

In addition to or as an alternative to automatically initiating drainage of power from battery pack (120), the insertion of battery pack (120) into socket (116) may also mechanically unlock the ability to retract trocar (330) and anvil (400) proximally, as shown in block (4006). By way of example only, such unlocking of the ability to retract trocar (330) and anvil (400) proximally may be provided in accordance with at least some of the other teachings herein. Other suitable ways in which the ability to retract trocar (330) and anvil (400) proximally may be automatically unlocked upon insertion of battery pack (120) into socket (116) will be apparent to those of ordinary skill in the art in view of the teachings herein. Alternatively, in some versions the step shown in block (4006) is simply omitted.

It should also be understood that the insertion of battery pack (120) into socket (116) may provide a necessary electrical connection within the circuit that actuates stapling head assembly (300), as shown in block (4008). In other words, in the absence of battery pack (120), the circuit that actuates stapling head assembly will lack a necessary electrical connection. In some other versions, instrument (10) is capable of receiving electrical power from some other source, such that battery pack (120) need not necessarily be inserted into socket (116) in order to complete a circuit that is operable to actuate stapling head assembly (300).

In some versions, the insertion of battery pack (120) into socket (116) may also mechanically unlock the ability to actuate safety trigger (140), as shown in block (4010). Various suitable ways in which the insertion of battery pack (120) into socket (116) may mechanically unlock the ability to actuate safety trigger (140) will be apparent to those of ordinary skill in the art in view of the teachings herein. Alternatively, in some versions the step shown in block (4010) is simply omitted.

Regardless of whether (or the extent to which) the steps shown in blocks (4004, 4006, 4008, 4010) are ultimately included in process (4000), process (4000) may proceed with insertion of anvil (400) into anatomical structure (20), as shown in block (4012). This step is also shown in FIG. 27A as discussed above. Continuing on with process (4000) as shown in FIGS. 40A-40B, anvil (400) is then secured to trocar (330) as shown in block (4014). This step is also shown in FIG. 27B as discussed above. Continuing on with process (4000) as shown in FIGS. 40A-40B, anvil (400) and trocar (330) are then retracted proximally to compress the tissue of anatomical structures (20, 40), as shown in block (4016). This step is also shown in FIG. 27C as discussed above. The operator rotates knob (130) in order to achieve an appropriate gap distance (d), as shown in block (4018). This step is also shown in FIGS. 30B-30C and 27C as discussed above.

In some instances, instrument (10) includes electromechanical features that monitor the gap distance (d) and provide feedback to the operator relating to the gap distance (d). By way of example only, such features may be provided in accordance with at least some of the other teachings herein. Other suitable ways in which an instrument (10) may monitor the gap distance (d) and provide feedback to the operator relating to the gap distance (d) will be apparent to those of ordinary skill in the art in view of the teachings herein. For those versions of instrument (10) that do have this capability, process (4000) includes such monitoring of the gap distance (d) as shown in block (4020). In some other versions, the step shown in block (4020) is omitted. Instrument (10) may provide audible, visual, and or tactile feedback relating to the gap distance (d) as shown in block (4022). In the event that the gap distance (d) falls below the clinically acceptable range (i.e., anvil (400) is getting too close to stapling head assembly (300)), instrument (10) may provide an indication to the operator to indicate that anvil (400) needs to be advanced distally to increase the gap distance (d), as shown in block (4024). In some other versions, the step shown in block (4024) is omitted. Thus, some versions may lack electromechanical features that monitor the gap distance (d) and provide feedback to the operator relating to the gap distance (d). In some such versions, purely mechanical features (e.g., indicator needle (3606), etc.) may be used to monitor the gap distance (d) and provide feedback to the operator relating to the gap distance (d).

Regardless of whether instrument (10) includes electromechanical features that monitor the gap distance (d) and provide feedback to the operator relating to the gap distance (d), bracket (1500) will move to a position where it unblocks actuation of safety trigger (140) when the gap distance (d) reaches the clinically acceptable range, as shown in block (4026). Such positioning of bracket (1500) is also shown in FIG. 30C as described above. The operator may actuate safety trigger (140) once bracket (1500) has moved into the unblocking position, as shown in block (4028). Such actuation of safety trigger (140) is also shown in FIG. 30D as described above. Once safety trigger (140) has been actuated, the operator may then actuate firing trigger (150), as shown in block (4030). Such actuation of firing trigger (150) is also shown in FIG. 30E as described above.

Once the operator actuates firing trigger (150), instrument (10) will complete an actuation stroke of stapling head assembly (300), regardless of what the operator does next with firing trigger (150), as shown in block (4032). In other words, the assembly that actuates stapling head assembly (300) (i.e., motor (161) and the rest of the components that couple motor (161) with stapling head assembly (300)) will effectively be fully committed to actuating stapling head assembly (300) once the operator further actuates firing trigger (150), even if the operator further manipulates firing trigger (150). By way of example only, instrument (10) may include components that provide full commitment to the actuation of stapling head assembly (300) in response to actuation of firing trigger (150) in accordance with at least some of the teachings of U.S. Pat. No. 9,907,552, entitled "Control Features for Motorized Surgical Stapling Instrument," issued Mar. 6, 2018, the disclosure of which is incorporated by reference herein. Alternatively, instrument (10) may include components that provide full commitment to the actuation of stapling head assembly (300) in response to actuation of firing trigger (150) in accordance with the teachings below.

The actuation stroke of stapling head assembly (300) includes the distal and proximal motion of various components, as shown in block (4034). This alternating motion is shown in FIGS. 24A-24B and in FIGS. 26A-26D as described above. The distal motion is also shown in FIG. 27D as described above.

In some versions of instrument (10), while the firing mechanism completes the actuation stroke of stapling head assembly (300), instrument (10) may include features that detect strain within the firing mechanism as shown in block (4036). By way of example only, such sensing may be provided in accordance with at least some of the other teachings herein. Other suitable ways in which instrument (10) may incorporate features that sense strain in the firing system be apparent to those of ordinary skill in the art in view of the teachings herein. Alternatively, such features may be omitted such that the step shown in block (4036) is omitted. In the event that such features are included, instrument (10) may provide an audible, visual, and/or tactile indication in the event that the sensing feature(s) detected that the strain has exceeded a threshold, as shown in block (4038). Of course, the step shown in block (4038) may be omitted in some versions.

In addition to or as an alternative to features that detect strain in the firing mechanism during the actuation stroke of stapling head assembly (300), some versions of instrument (10) may include a switch or other kind of sensor that detects whether a portion of the firing mechanism has traveled to an expected distance during the actuation stroke, as indicated in block (4040). By way of example only, such sensing may be provided in accordance with at least some of the other teachings herein. Other suitable ways in which instrument (10) may incorporate features that sense whether the firing mechanism has completed sufficient travel will be apparent to those of ordinary skill in the art in view of the teachings herein. Alternatively, such features may be omitted such that the step shown in block (4040) is omitted. In the event that such features are included, instrument (10) may provide an audible, visual, and/or tactile indication in the event that the sensing feature(s) detected that the actuation stroke of stapling head assembly (300) was successfully completed, as shown in block (4042).

Once stapling head assembly (300) has been successfully actuated, anvil (400) may be advanced distally from stapling head assembly (300) and instrument (10) may be withdrawn from the patient, as shown in block (4044). After instrument (10) has been withdrawn from the patient, the operator may remove battery pack (120) from handle assembly (100), as shown in block (4046).

As noted above, the above-described steps of process (4000) are merely illustrative examples. Instrument (10) may be used in various other ways as will be apparent to those of ordinary skill in the art in view of the teachings herein. In addition, instrument (10) may have various other functionalities as will be apparent to those of ordinary skill in the art in view of the teachings herein. It should be understood that some variations of instrument (10) may be incapable of performing some of the steps of process (4000). Moreover, some versions of instruments (10) may be capable of performing steps that are not included in process (4000).

As noted above with reference to block (4032), it may be desirable to ensure that the firing mechanism for stapling head assembly (300) completes a full actuation stroke in response to actuation of firing trigger (150). In other words, it may be desirable to prevent subsequent manipulation of firing trigger (150) from having any effect on the firing mechanism completing the actuation stroke of stapling head assembly (300). In some instances, instrument (10) may incorporate mechanical features that ensure completion of a full actuation stroke of stapling head assembly (300) in response to actuation of firing trigger (150), regardless of subsequent manipulation of firing trigger (150). Examples of such mechanical features are described in U.S. Pat. No. 9,907,552, entitled "Control Features for Motorized Surgical Stapling Instrument," issued Mar. 6, 2018, the disclosure of which is incorporated by reference herein. In addition to or as an alternative to using such mechanical features, instrument (10) may include electronic components that ensure completion of a full actuation stroke of stapling head assembly (300) in response to actuation of firing trigger (150), regardless of subsequent manipulation of firing trigger (150). Several examples of such electrical features are described in greater detail below, while further examples will be apparent to those of ordinary skill in the art in view of the teachings herein.

VII. Exemplary Battery Pack with Self-Draining Feature

FIGS. 41-57 depict instrument (10) including an exemplary battery pack (5600) that is configured to operate substantially similar to battery pack (120) discussed above except for any difference discussed below. For instance, battery pack (5600) is operable to provide electrical power to a motor (161) in pistol grip (112) as discussed above with reference to battery pack (120). Battery pack (5600) is removable from handle assembly (100). In particular, as shown in FIGS. 41-42 and 45A-45B, battery pack (5600) may be inserted into socket (116) defined by casing (110). Once battery pack (5600) is fully inserted in socket (116), latches (5602) of battery pack (5600) may resiliently engage interior features of casing (110) to provide a snap fit. To remove battery pack (5600), the operator may press latches (5602) inwardly to disengage latches (5602) from the interior features of casing (110) then pull battery pack (5600) proximally from socket (116). It should be understood that battery pack (5600) and handle assembly (100) may have complementary electrical contacts, pins and sockets, and/or other features that provide paths for electrical communication from battery pack (5600) to electrically powered components in handle assembly (100) when battery pack (5600) is inserted in socket (116).

Figure 43:
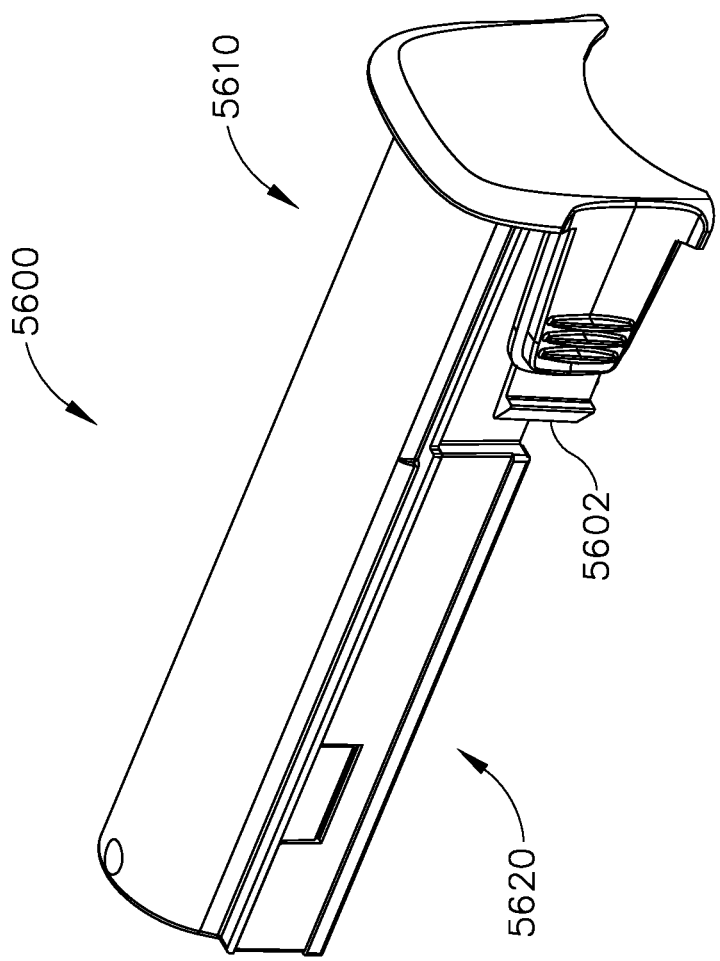
FIG. 43 depicts a perspective view of the battery pack of FIG. 42.
Figure 45A:
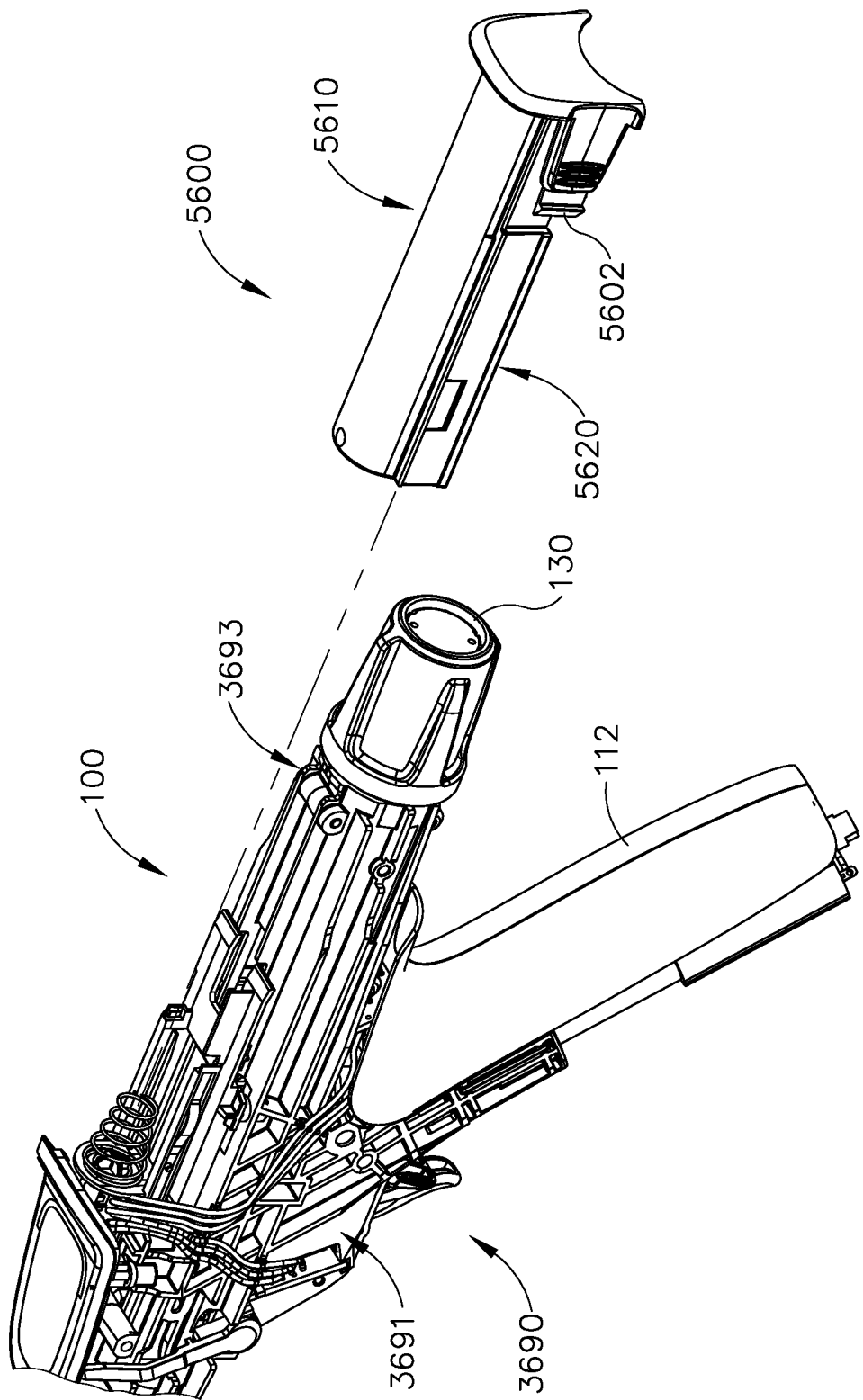
FIG. 45A depicts a perspective view of the handle assembly of FIG. 42, with a casing removed from the handle assembly, and with the battery pack of FIG. 42 spaced apart from the handle assembly.
Figure 45B:
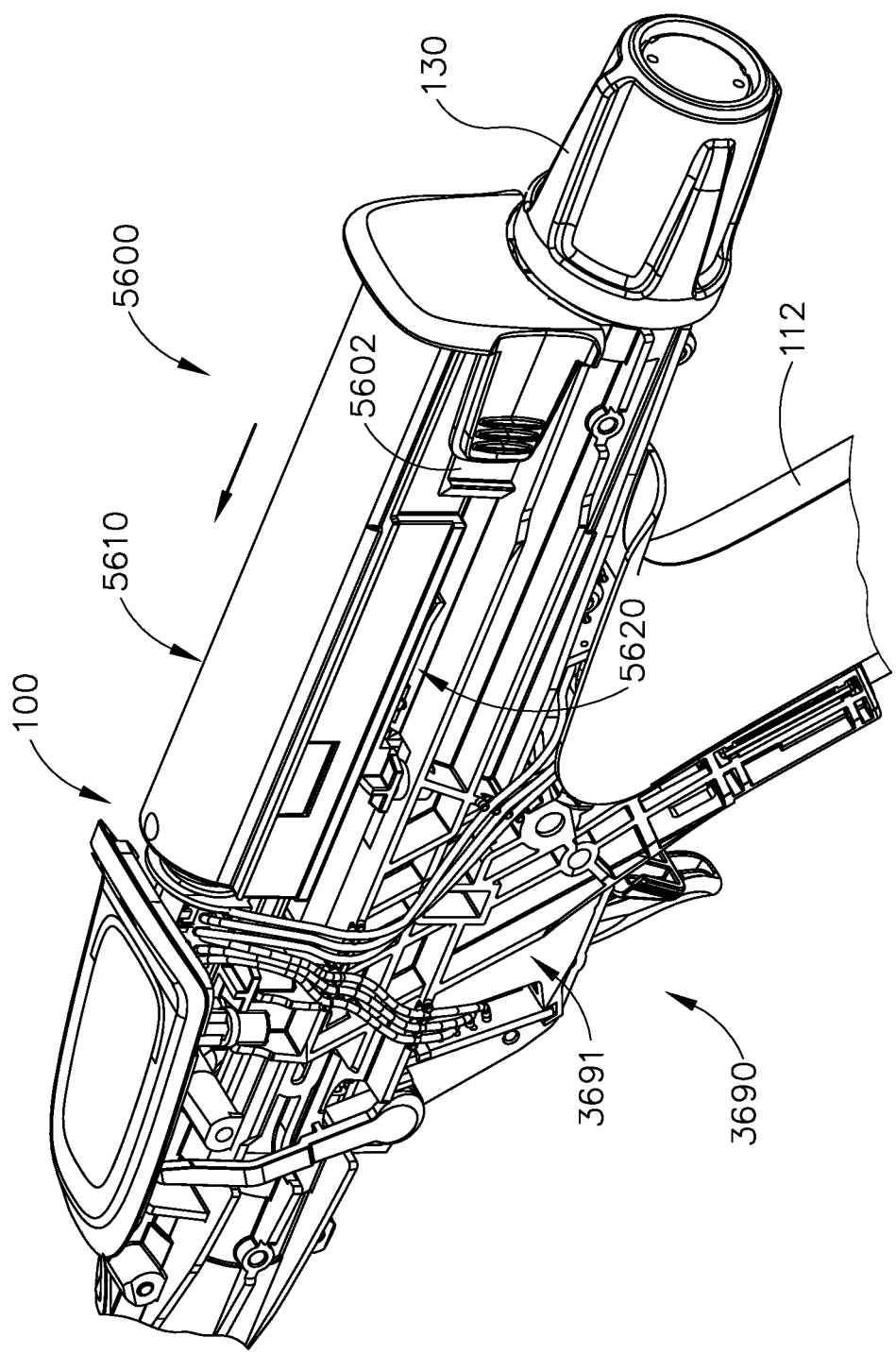
FIG. 45B depicts a perspective view of the handle assembly of FIG. 42, with a casing removed from the handle assembly, and with the battery pack of FIG. 42 coupled with the handle assembly.

As best seen in FIG. 43, battery pack (5600) includes an upper battery housing (5610) and a lower battery housing (5620). Upper battery housing (5610) and lower battery housing (5620) are configured to be secured to one another via ultrasonic welding (or using any other suitable technique) so as to provide a rigid casing that encloses a plurality of batteries (5630). Lower battery housing (5620) includes a positive battery contact (5622) configured to connect with a positive terminal of batteries (5630) and a negative battery contact (5624) configured to connect with a negative terminal of batteries (5630). Lower battery housing (5620) further includes a drain contact (5626). A proximal end of positive battery contact (5622) is biased toward drain contact (5626). As will be discussed in more detail below, contact between positive battery contact (5622) and drain contact (5626) is configured to drain batteries (5630) of power. It should be understood that casing (110) of instrument (10) and upper battery housing (5610) and batteries (5630) of battery pack (5600) have been omitted from FIGS. 46-57 to assist in understanding operation of battery pack (5600).

Figure 46:
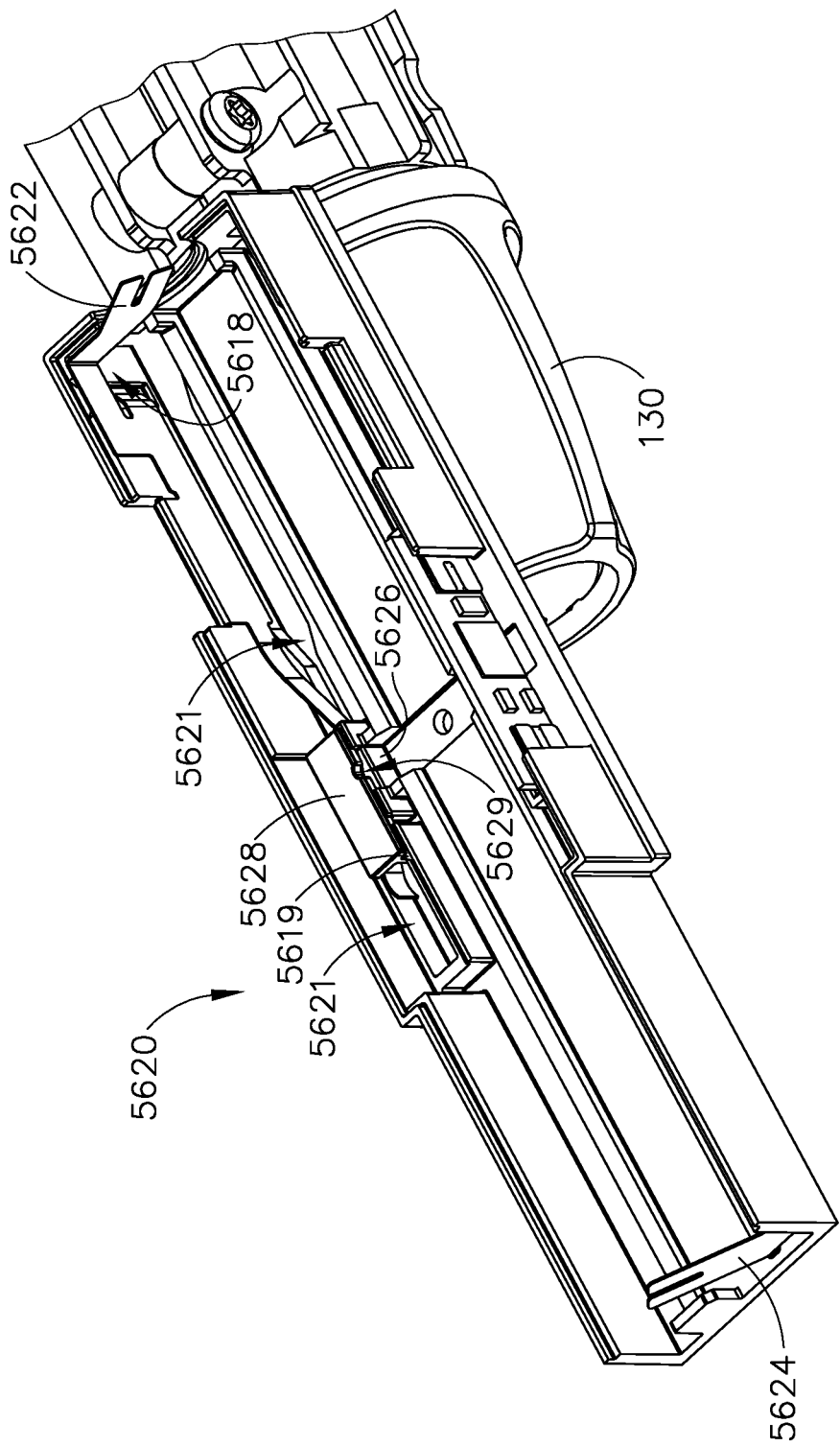
FIG. 46 depicts a perspective view of the handle assembly of FIG. 42, with a casing removed from the handle assembly, and with a lower battery housing of the battery pack of FIG. 42 in a first position relative to the handle assembly.
Figure 47:
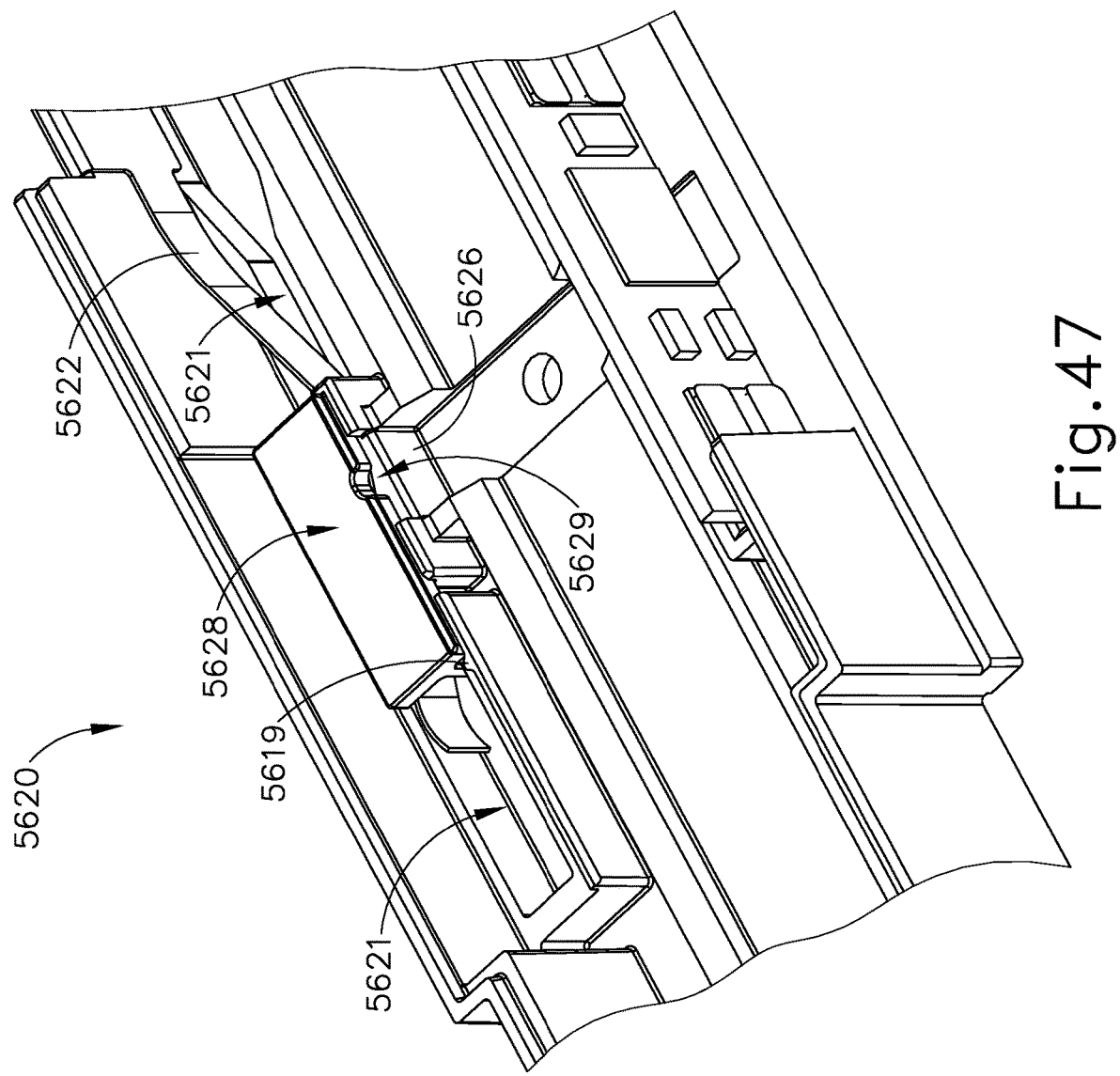
FIG. 47 depicts a detailed perspective view of the lower battery housing of FIG. 46 in the first position of FIG. 46, with a battery drain sled of the lower battery housing in a first position relative to a body of the lower battery housing.
Figure 48:
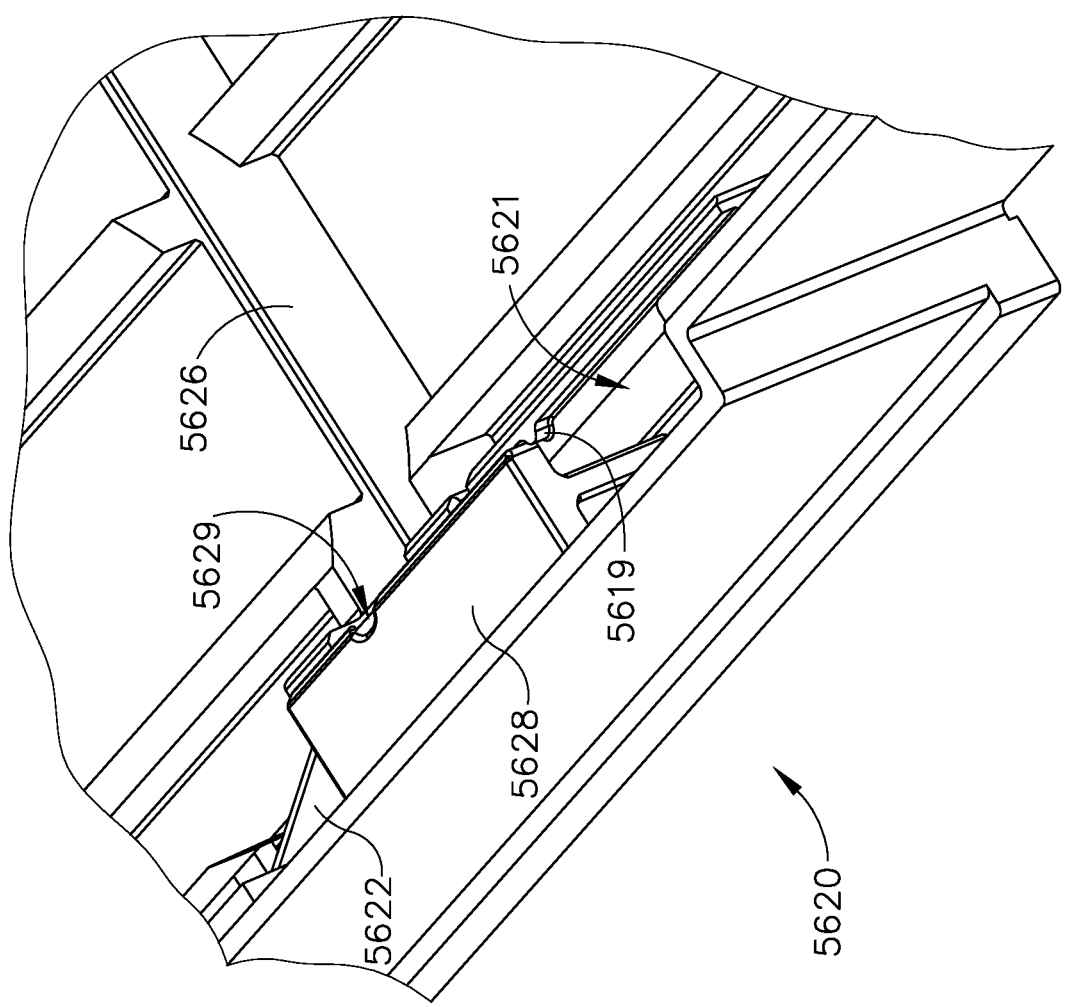
FIG. 48 depicts another detailed perspective view of the lower battery housing of FIG. 46, with the battery drain sled of FIG. 47 in the first position of FIG. 47.

Lower battery housing (5620) includes a battery drain sled (5628) that is slidably disposed within a channel (5621) formed within lower battery housing (5620) such that battery drain sled (5628) is configured to translate longitudinally within channel (5621) relative to lower battery housing (5620). As shown in FIGS. 46-48, in an initial position, battery drain sled (5628) positioned within channel (5621) between drain contact (5626) and the proximal end of positive battery contact (5622) so as to prevent contact between drain contact (5626) and positive battery contact (5622).

Figure 49:
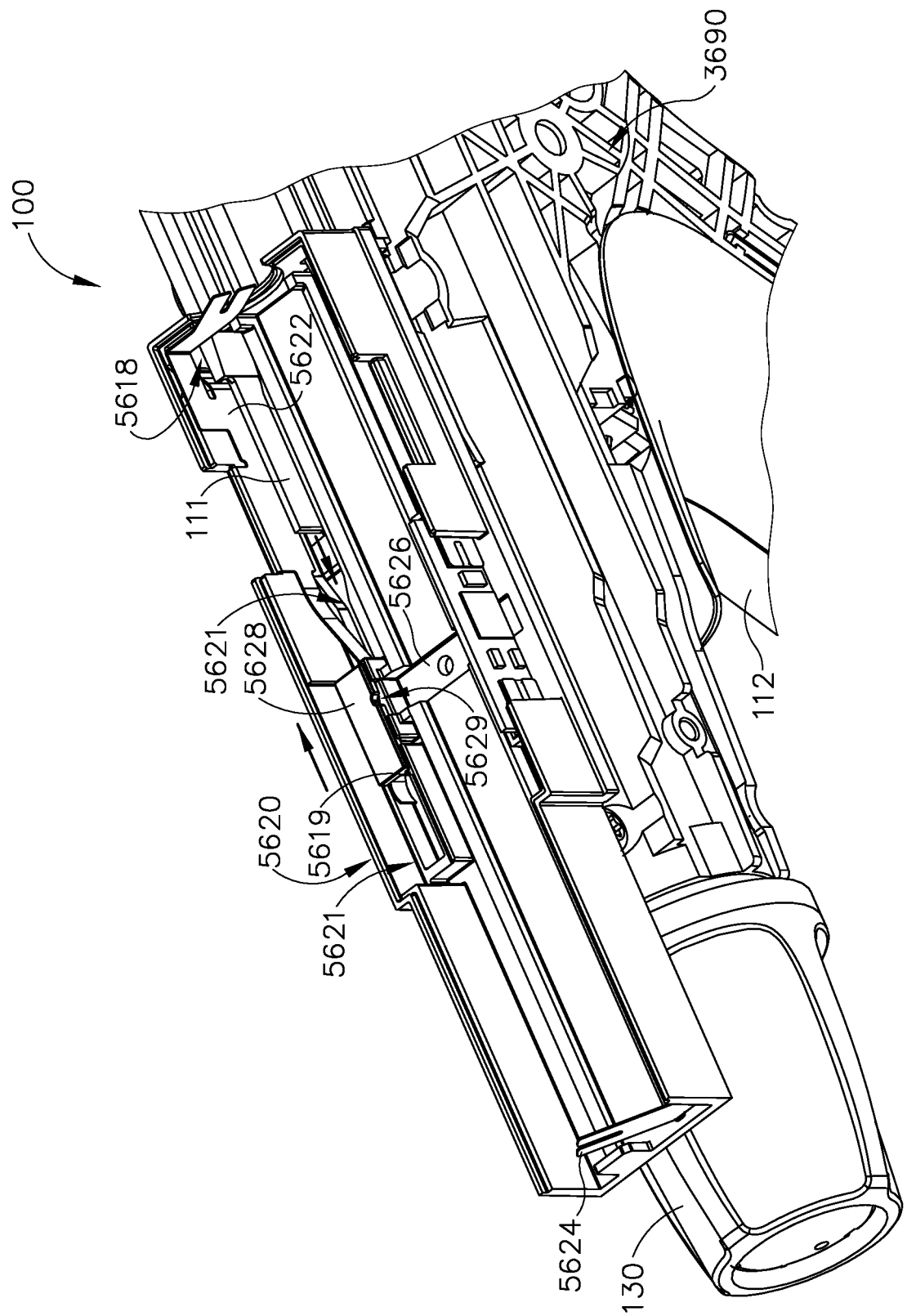
FIG. 49 depicts a perspective view of the handle assembly of FIG. 42, with a casing removed from the handle assembly, and with the lower battery housing of FIG. 46 moved distally to a second position relative to the handle assembly, and with a drain activation rail of the handle assembly received within the lower battery housing in a first position.
Figure 50:
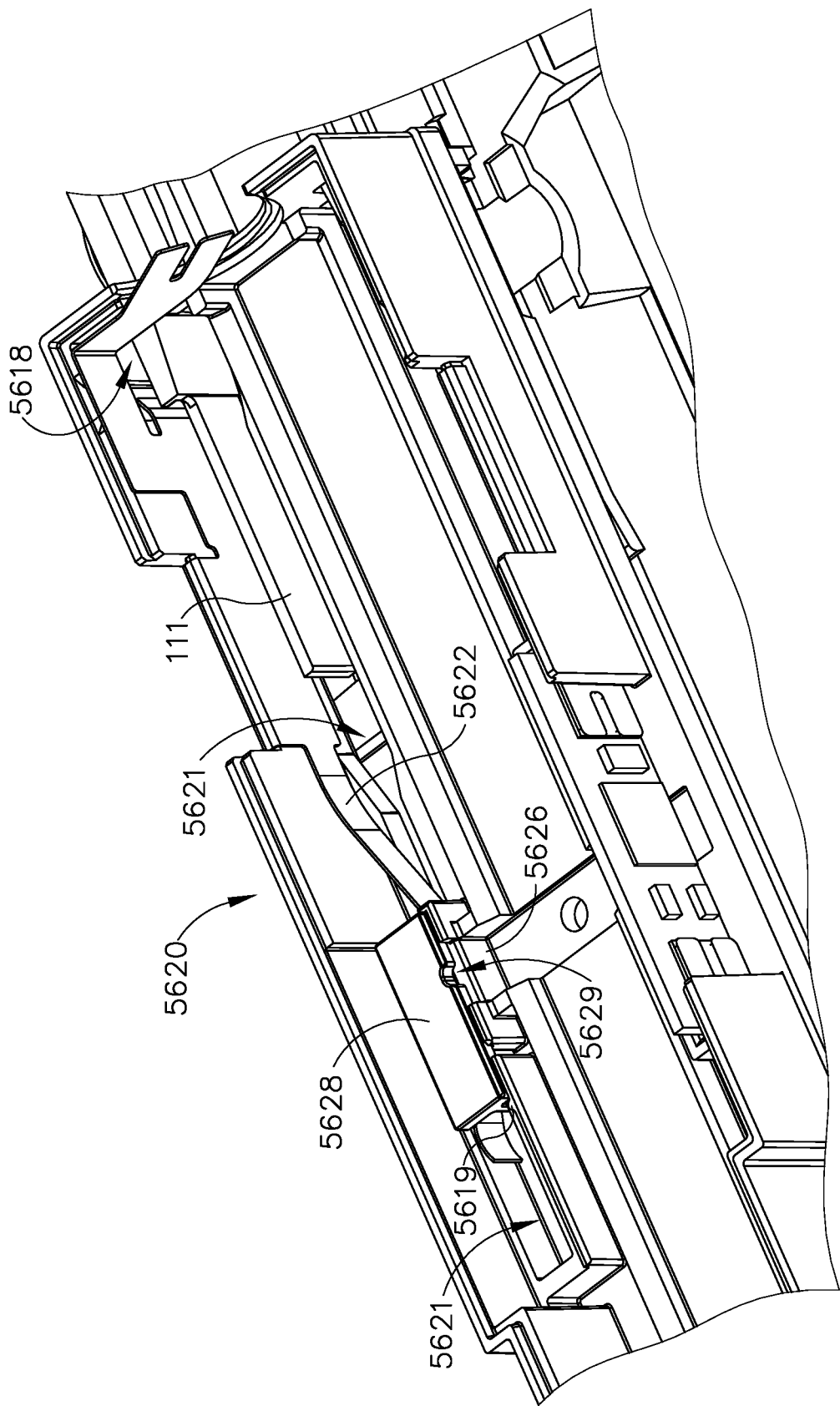
FIG. 50 depicts a detailed perspective view of the lower battery housing of FIG. 46 in the second position of FIG. 49, with the battery drain sled of FIG. 47 remaining in the first position of FIG. 47, and with the drain activation rail of FIG. 49 received within the lower battery housing in the first position of FIG. 49.

As shown in FIGS. 49-50, as battery pack (5600) is inserted into socket (116) of casing (110), a flange (111) of right chassis portion (3693) of chassis (3690) passes through an opening (5618) formed in a distal end of lower battery housing (5620) toward channel (5621) of lower battery housing (5620).

Figure 51:
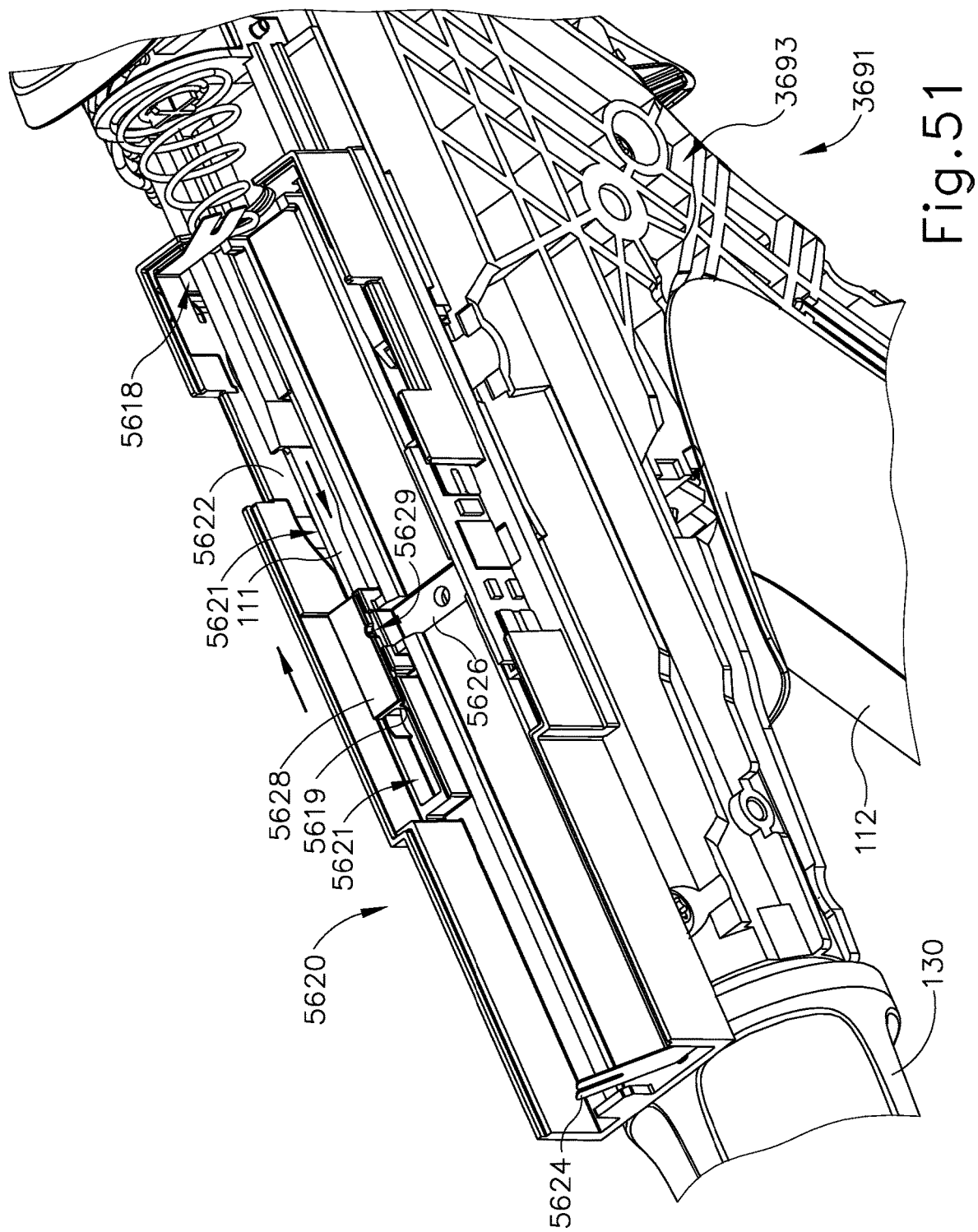
FIG. 51 depicts a perspective view of the handle assembly of FIG. 42, with a casing removed from the handle assembly, with the lower battery housing of FIG. 46 moved distally to a third position relative to the handle assembly such that the drain activation rail of FIG. 50 is moved to a second position such that the drain activation rail engages the battery drain sled of FIG. 47.
Figure 52:
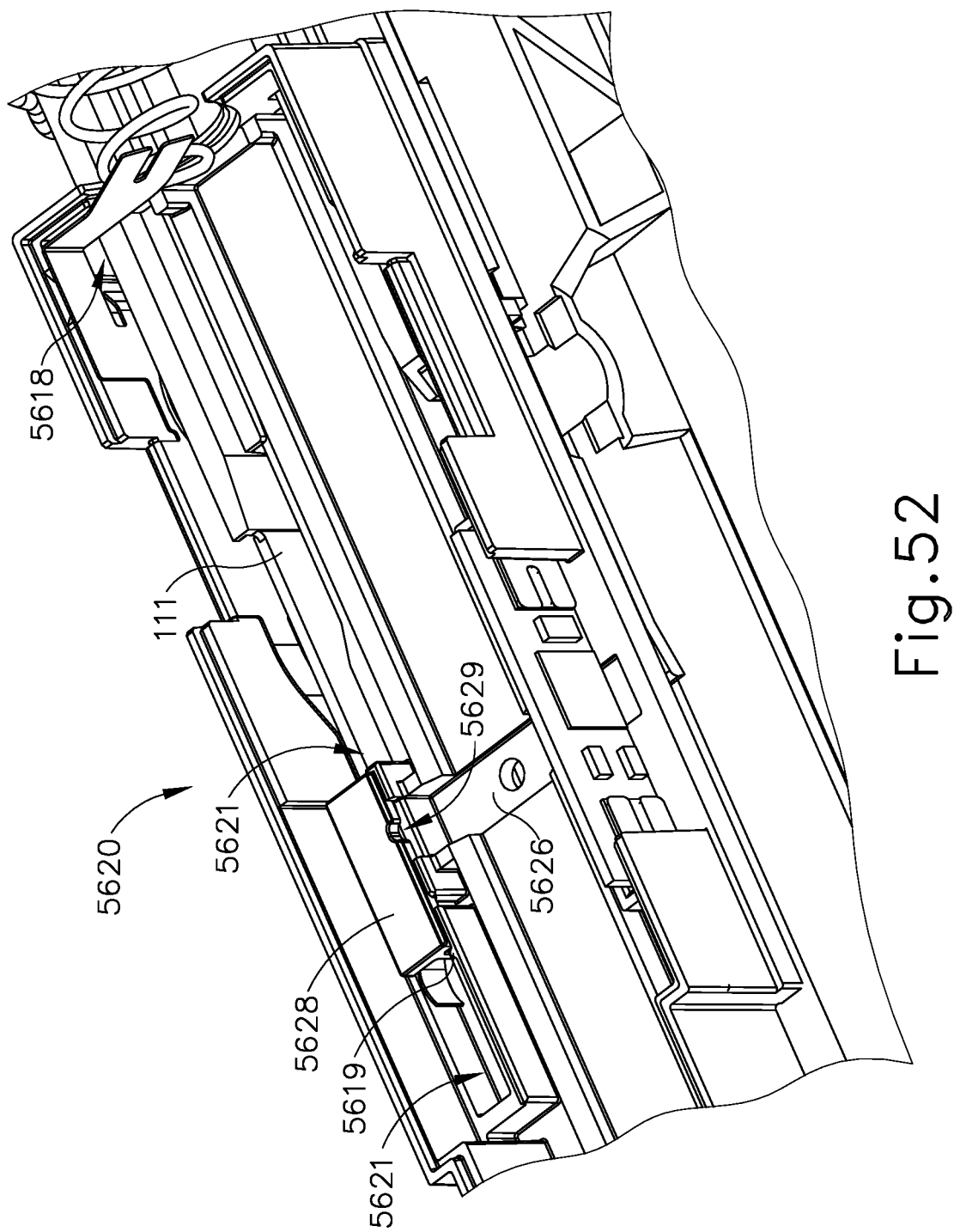
FIG. 52 depicts a detailed perspective view of the lower battery housing of FIG. 46 in the third position of FIG. 51, with the battery drain sled of FIG. 47 remaining in the first position of FIG. 47, and with the drain activation rail of FIG. 49 received within the lower battery housing in the second position of FIG. 51 such that the drain activation rail engages the battery drain sled.

As shown in FIGS. 51-52, as battery pack (5600) is further inserted into socket (116) of casing (110), flange (111) passes further through opening (5618) and into channel (5621) such that a proximal end of flange (111) comes into contact with a distal end of battery drain sled (5628).

Figure 53:
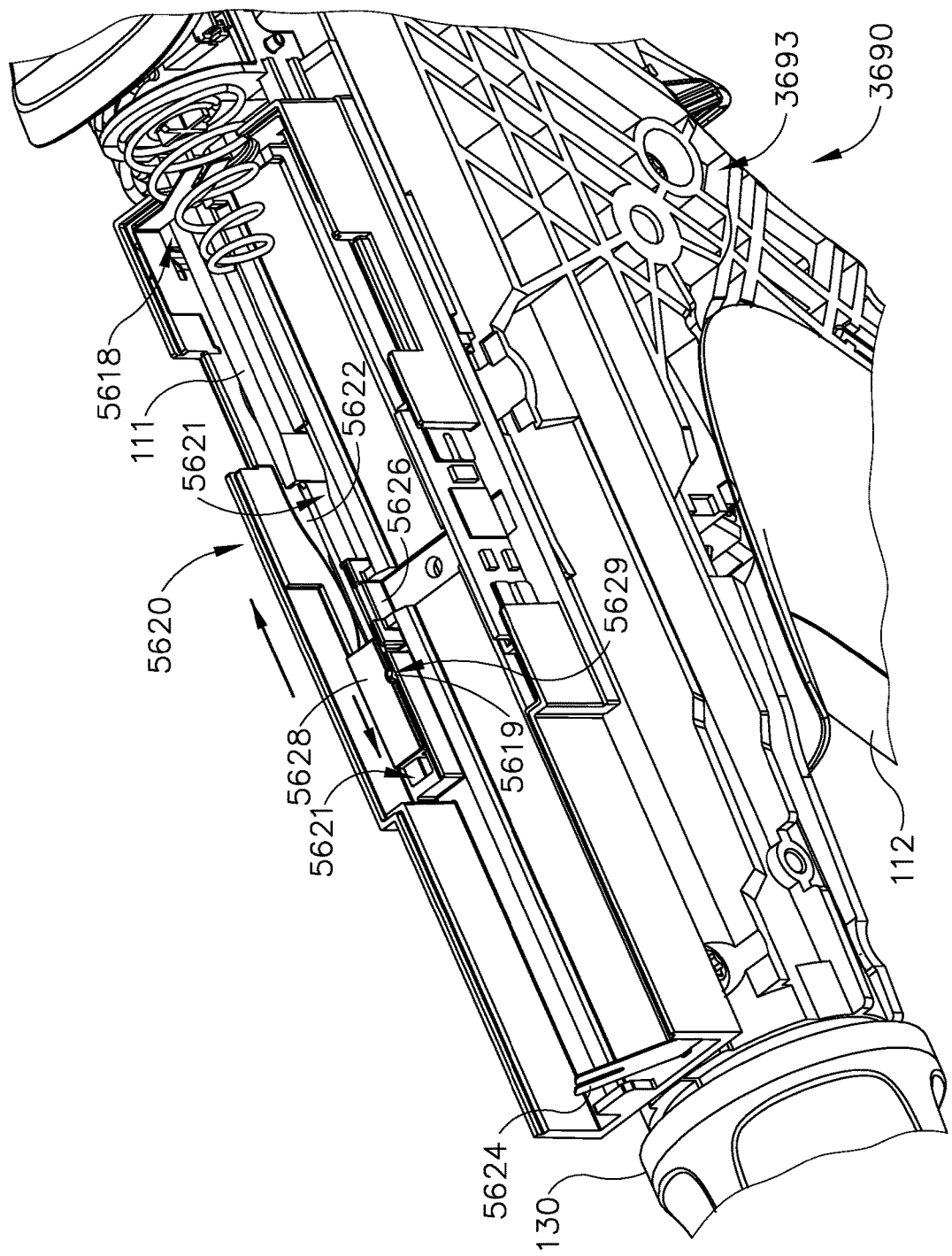
FIG. 53 depicts a perspective view of the handle assembly of FIG. 42, with a casing removed from the handle assembly, with the lower battery housing of FIG. 46 moved distally to a fourth position relative to the handle assembly such that the drain activation rail of FIG. 50 is moved to a third position such that the drain activation rail drives the battery drain sled of FIG. 47 proximally to a second position.
Figure 54:
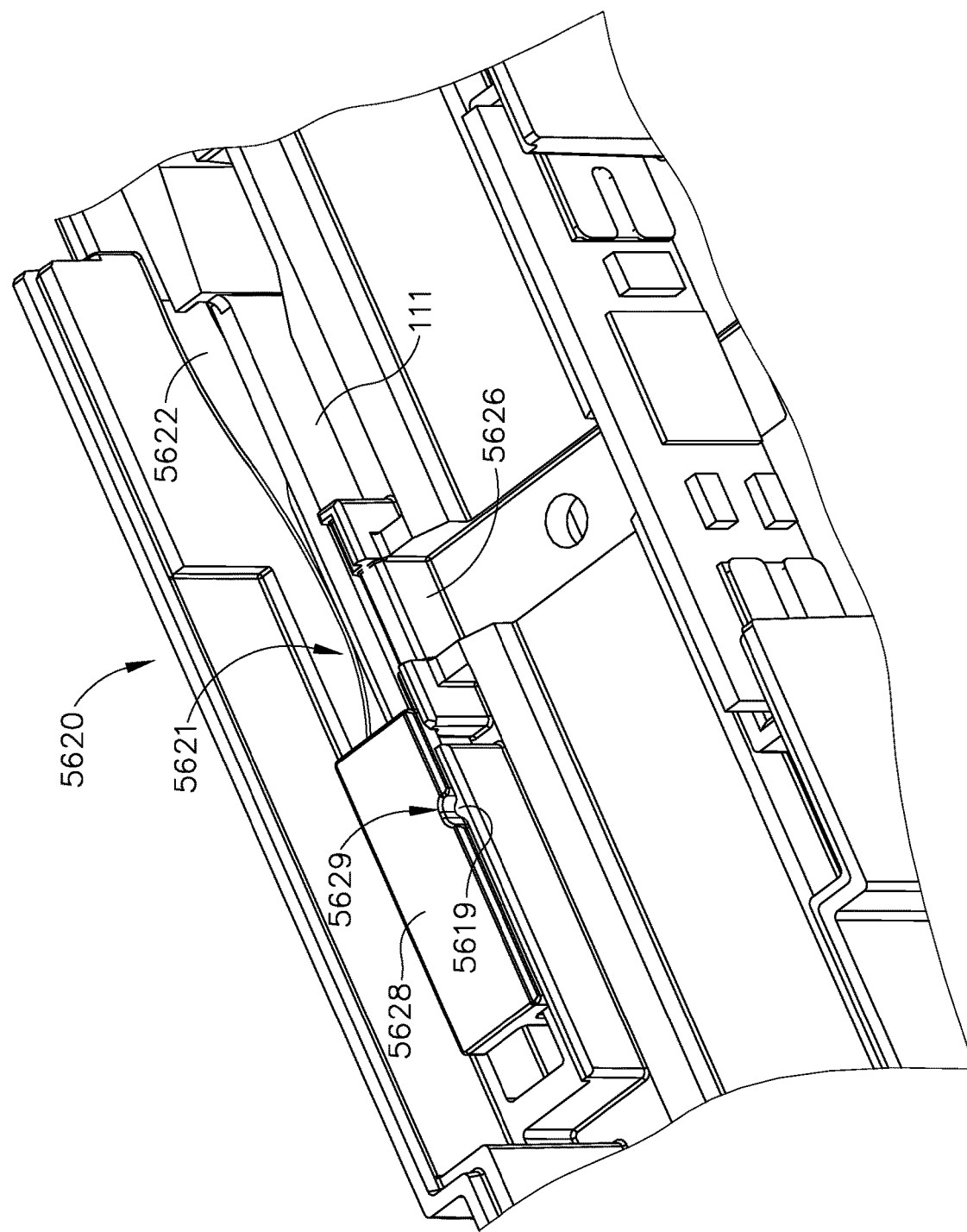
FIG. 54 depicts a detailed perspective view of the lower battery housing of FIG. 46 in the fourth position of FIG. 53, with the drain activation rail of FIG. 49 received within the lower battery housing in the third position of FIG. 53 such that the drain activation rail drives the battery drain sled of FIG. 47 moved into the second position of FIG. 53.

As shown in FIGS. 53-54, as battery pack (5600) is further inserted into socket (116) of casing (110) to a point where battery pack (5600) is fully seated within socket (116), flange (111) passes further through opening (5618) and into channel (5621) such that flange (111) drives battery drain sled (5628) proximally within channel (5621). In this position, battery drain sled (5628) is no longer between positive battery contact (5622) and drain contact (5626). However, flange (111) is now positioned between positive battery contact (5622) and drain contact (5626). Thus, it should be understood that as battery pack (5600) is passed into socket (116), battery drain sled (5628) and flange (111) cooperate to prevent contact between positive battery contact (5622) and drain contact (5626).

Figure 55:
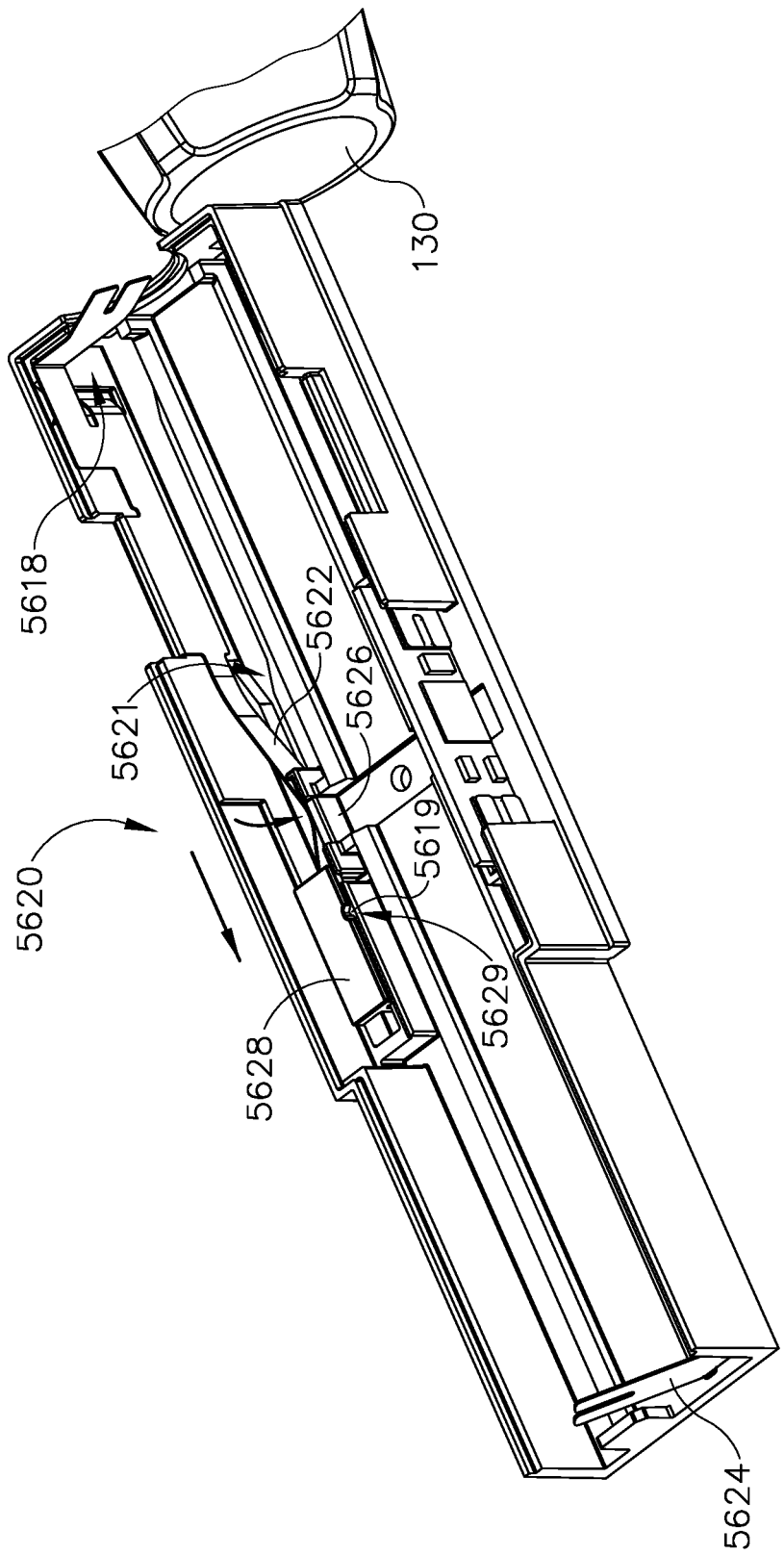
FIG. 55 depicts a perspective view of the handle assembly of FIG. 42, with a casing removed from the handle assembly, with the lower battery housing of FIG. 46 removed from the handle assembly such that the drain activation rail of FIG. 50 is removed from the lower battery housing, and with the battery drain sled of FIG. 47 remaining in the second position of FIG. 53 such that a drain contact of the battery pack of FIG. 52 is biased toward a positive contact of the battery pack.
Figure 56:
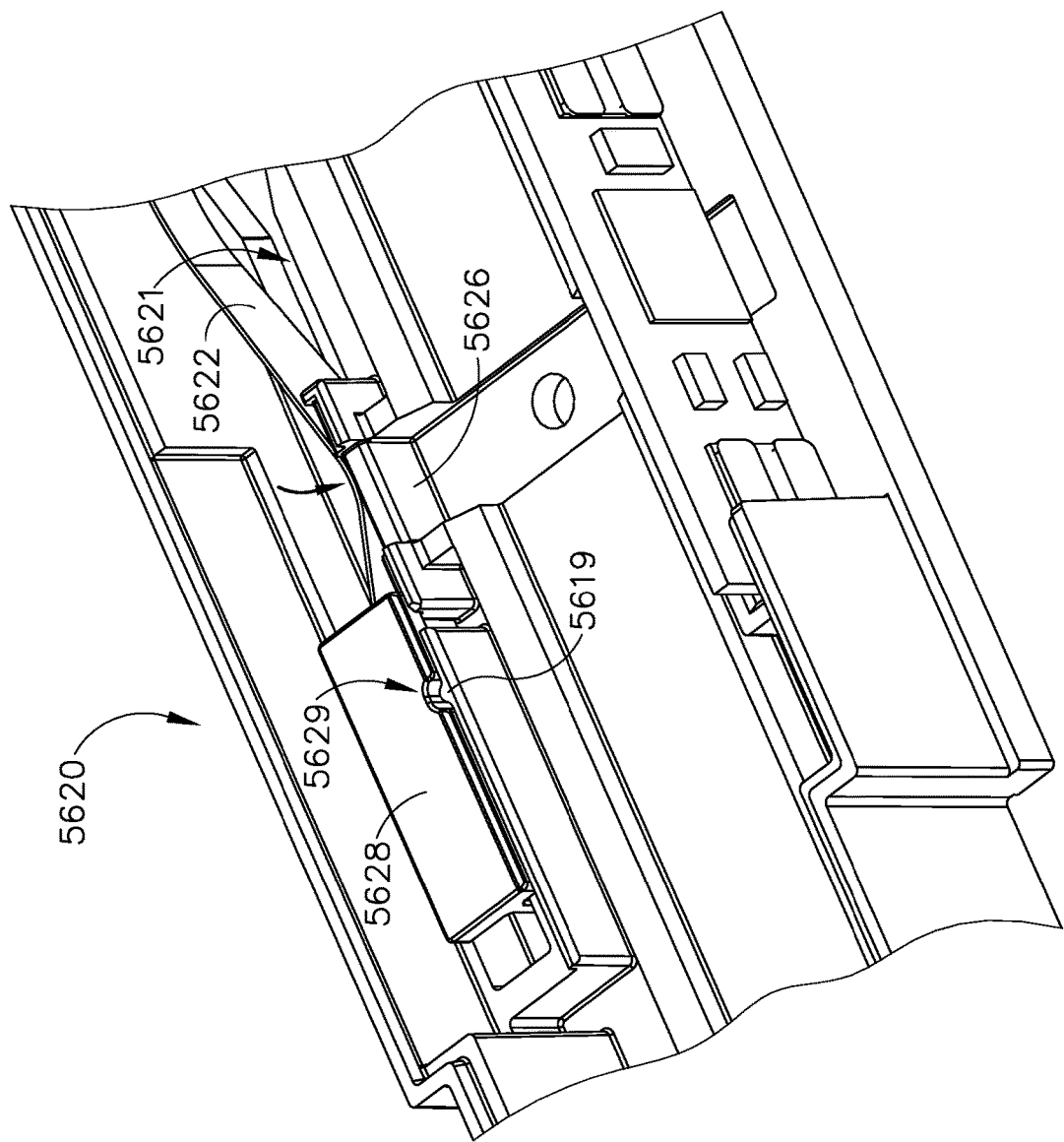
FIG. 56 depicts a detailed perspective view of the handle assembly of FIG. 42, with the lower battery housing of FIG. 46 removed from the handle assembly, and with the battery drain sled of FIG. 47 remaining in the second position of FIG. 53 such that the drain contact of FIG. 55 is biased toward the positive contact of FIG. 55.
Figure 57:
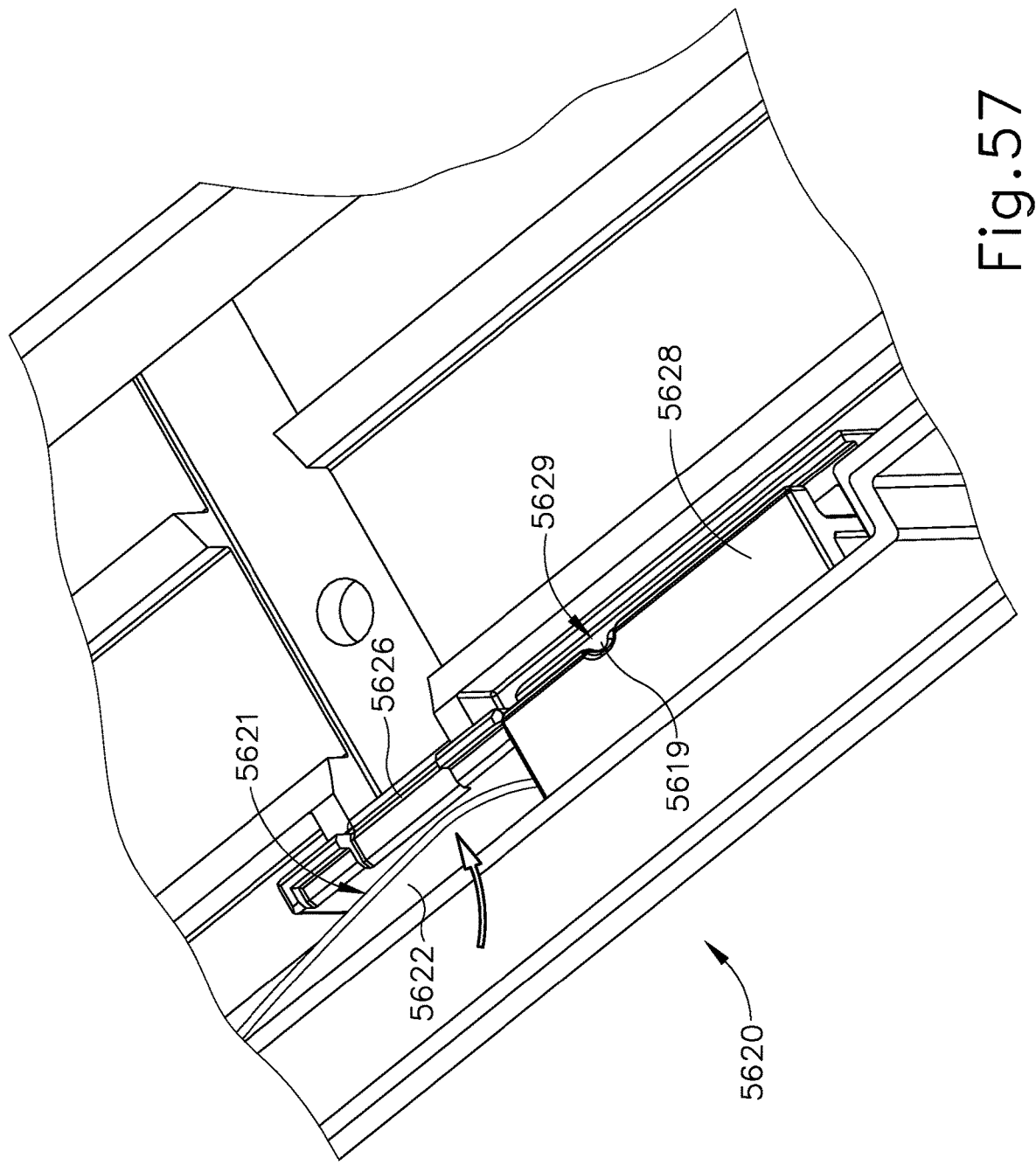
FIG. 57 depicts a detailed perspective view of the handle assembly of FIG. 42, with the lower battery housing of FIG. 46 removed from the handle assembly, and with the battery drain sled of FIG. 47 remaining in the second position of FIG. 53 such that the drain contact of FIG. 55 is biased toward the positive contact of FIG. 55.

As best seen in FIG. 54, as battery drain sled (5628) is driven proximally, a detent (5629) of battery drain sled (5628) engages a detent (5619) formed in a sidewall of channel (5621) so as to "lock" battery drain sled (5628) in the proximal position. As shown in FIGS. 55-57, as battery pack (5600) is removed, flange (111) is removed from lower battery housing (5620) such that flange (111) is no longer between positive battery contact (5622) and drain contact (5626). Thus, with battery drain sled (5628) in the proximal position, the proximal end of positive battery contact (5622) contacts drain contact (5626) so as to drain batteries (5630) of power. Thus, it should be understood that insertion and removal of battery pack (5600) from casing (110) will ultimately drain batteries (5630). In other words, battery pack (5600) will be drained of power after a single use. Such power drainage will further eliminate potential energy available from battery contacts (5622, 5624) so as to limit the chances of battery pack (5600) igniting combustible materials upon disposal.

Figure 58:
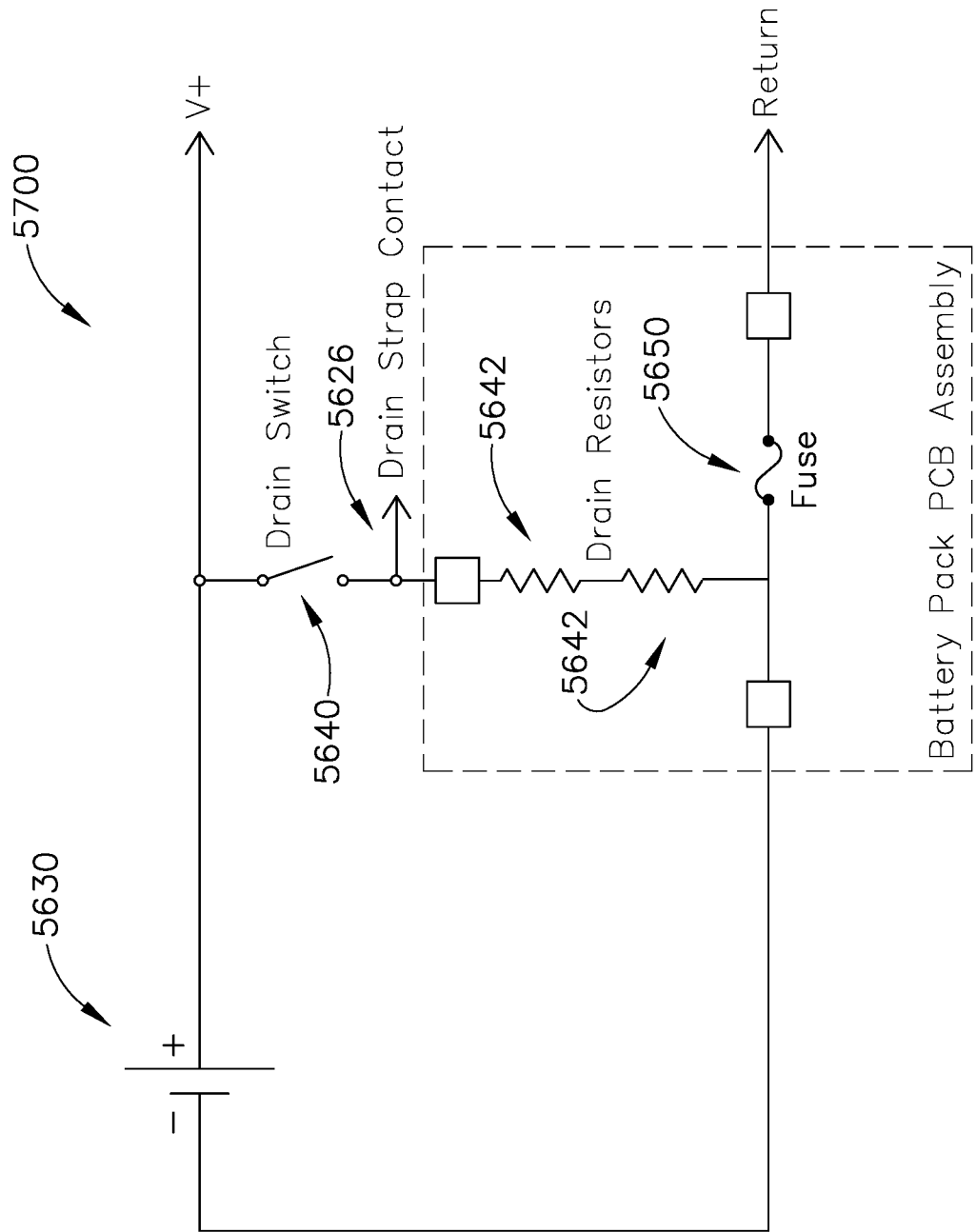
FIG. 58 depicts a schematic view of an exemplary battery drain circuit that may be incorporated into the circular stapler of FIG. 1.

FIG. 58 shows an exemplary battery drain circuit (5700) that may be used to drain batteries (5630) as described above. As shown, circuit (5700) of this example includes a drain switch (5640) that is closed when battery pack (5600) is inserted into casing (110). In this example, drain switch (5640) remains open before battery pack (5600) is initially inserted into casing (110); and remains closed even after battery pack (5600) is removed from casing (110). When drain switch (5640) is closed, batteries (5630) are placed in communication with a pair of drain resistors (5642). Drain resistors (5642) are placed in series with each other and in parallel with the remaining circuit (2700) of instrument (10). Drain resistors (5642) will continuously drain power from batteries (5630) upon closure of drain switch (5640). In some other variations, drain switch (5640) remains open until battery pack (5600) is removed from casing (110). In other words, battery drain circuit (5700) may be configured such that drain switch (5640) is only closed upon removal of battery pack (5600) from casing (110).

As also shown in FIG. 58, battery drain circuit (5700) of the present example also includes a fuse (5650). By way of example only, fuse (5650) may comprise a positive temperature coefficient (PTC) current limiting device. Fuse (5650) may thus control current during discharge of batteries (5630) so as to minimize any temperature rise in battery pack (5600) and/or its components. For instance, fuse (5650) may be configured to limit the temperature of battery pack (5600) and/or its components to below a flash point of common materials encountered during use or upon disposal. Various suitable materials and configurations that may be used to form fuse (5650) will be apparent to those of ordinary skill in the art in view of the teachings herein.

VIII. Exemplary Activation Circuit

Firing trigger (150) is operable to activate motor (161) to thereby actuate stapling head assembly (300). Safety trigger (140) is operable to selectively block actuation of firing trigger (150) based on the longitudinal position of anvil (400) in relation to stapling head assembly (300). Firing trigger (150) may thus not be actuated until after safety trigger (140) has been actuated. Handle assembly (100) also includes components that are operable to selectively lock out both triggers (140, 150) based on the position of anvil (400) relative to stapling head assembly (300). When triggers (140, 150) are locked out, safety trigger (140) is prevented from moving to permit actuation of firing trigger (150), and firing trigger (150) is prevented from initiating actuation of stapling head assembly (300). Thus, firing trigger (150) is only operable to initiate actuation of stapling head assembly (300) when the position of anvil (400) relative to stapling head assembly (300) is within a predefined range. By way of example only, such lockout features may be constructed and operable in accordance with at least some of the teachings of U.S. Pat. No. 10,307,157, entitled "Surgical Stapler with Anvil Seating Detection," issued Jun. 4, 2019, the disclosure of which is incorporated by reference herein.

Figure 59A:
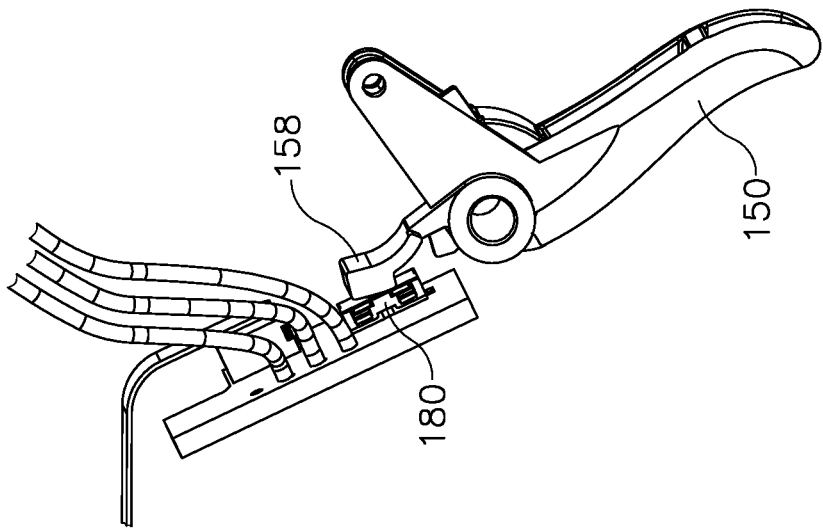
FIG. 59A depicts a perspective view of a firing trigger and motor activation module of the handle assembly of FIG. 18, with the firing trigger in a non-actuated position.
Figure 59B:
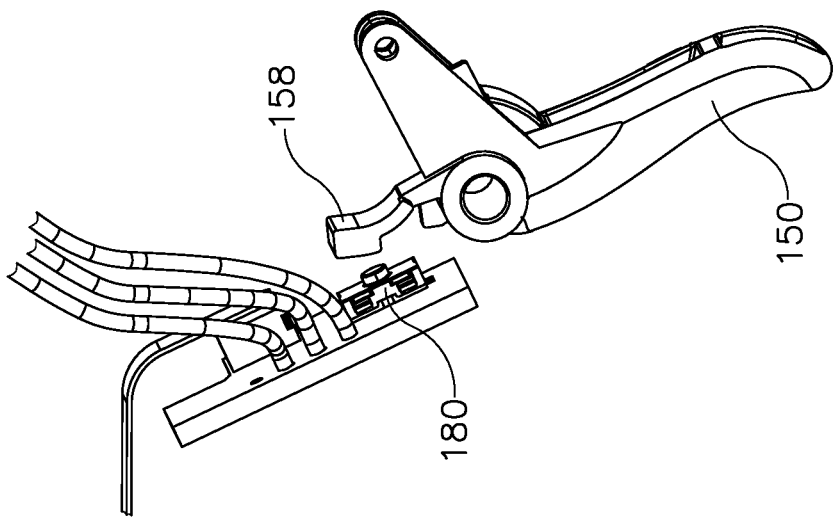
FIG. 59B depicts a perspective view of the firing trigger and motor activation module of FIG. 59A, with the firing trigger in an actuated position.

As best seen in FIGS. 59A-59B, firing trigger (150) of the present example includes an integral actuation paddle (158). In scenarios when safety trigger (140) has been actuated to permit actuation of firing trigger (150), paddle (158) pivots forwardly as firing trigger (150) pivots from the position shown in FIG. 59A to the position shown in FIG. 59B. Paddle (158) is configured to actuate a switch (182) (see FIG. 60) of a motor activation module (180) when firing trigger (150) pivots from the position shown in FIG. 59A to the position shown in FIG. 59B. Switch (182) of motor activation module (180) is in communication with battery pack (120) and motor (161), such that motor activation module (180) is configured to provide activation of motor (161) with electrical power from battery pack (120) in response to paddle (158) actuating switch (182) of motor activation module (180). Thus, motor (161) will be activated when firing trigger (150) is pivoted from the position shown in FIG. 59A to the position shown in FIG. 59B. This activation of motor (161) will actuate stapling head assembly (300) as described herein. By way of example only, this actuation may be carried out in accordance with at least some of the teachings of U.S. Pub. No. 2016/0374666, entitled "Surgical Stapler with Reversible Motor," published Dec. 29, 2016, issued as U.S. Pat. No. 10,456,134 on Oct. 29, 2019, the disclosure of which is incorporated by reference herein. An exemplary way in which motor activation module (180) may be integrated into a control circuit (2700) will be described in greater detail below with reference to FIG. 60. Other examples will be apparent to those of ordinary skill in the art in view of the teachings herein.

As noted above, paddle (806) is configured to actuate switch buttons (192) of motor stop module (190) at the end of an actuation stroke of stapling head assembly (300). In the present example, motor stop module (190) reverses the polarity of electrical power provided to motor (161) when switch buttons (192) are actuated. This results in dynamic braking of motor (161) once an actuation stroke of stapling head assembly (300) has been completed. By way of example only, motor stop module (190) may be configured and operable in accordance with at least some of the teachings of U.S. Pat. No. 9,907,552, issued Mar. 6, 2018, the disclosure of which is incorporated by reference herein. Other suitable configurations will be apparent to those of ordinary skill in the art in view of the teachings herein.

Those of ordinary skill in the art will recognize that, during normal use of instrument (10), at least certain portions of instrument (10) may be exposed to various fluids, including but not limited to patient bodily fluids, saline, etc. By way of example only, the regions of instrument (10) that may be most susceptible to liquid ingress may include stapling head assembly (300) and features at or near the underside of handle assembly (100), where liquid may tend to gather after running down shaft assembly (200). Those of ordinary skill in the art will also recognize that some electrical circuit components may experience compromised performance when such electrical circuit components are exposed to liquids. For instance, liquids may compromise the functioning of some electrical circuits and circuit components. In the context of a surgical instrument like instrument (10), a compromised circuit may cause a feature (e.g., motor (161) and thus stapling head assembly (300)) to activate prematurely, which may provide an undesirable outcome. It may therefore be desirable to provide a version of instrument (10) where ingress of liquid onto certain electrical circuit components will not compromise the performance of such electrical circuits and circuit components by causing premature activation or other undesirable effects.

While the following examples are provided in the context of a variation of instrument (10), the same teachings may be readily incorporated into various other kinds of surgical instruments. Other kinds of instruments to which the below teachings may be applied will be apparent to those of ordinary skill in the art.

Figure 60:
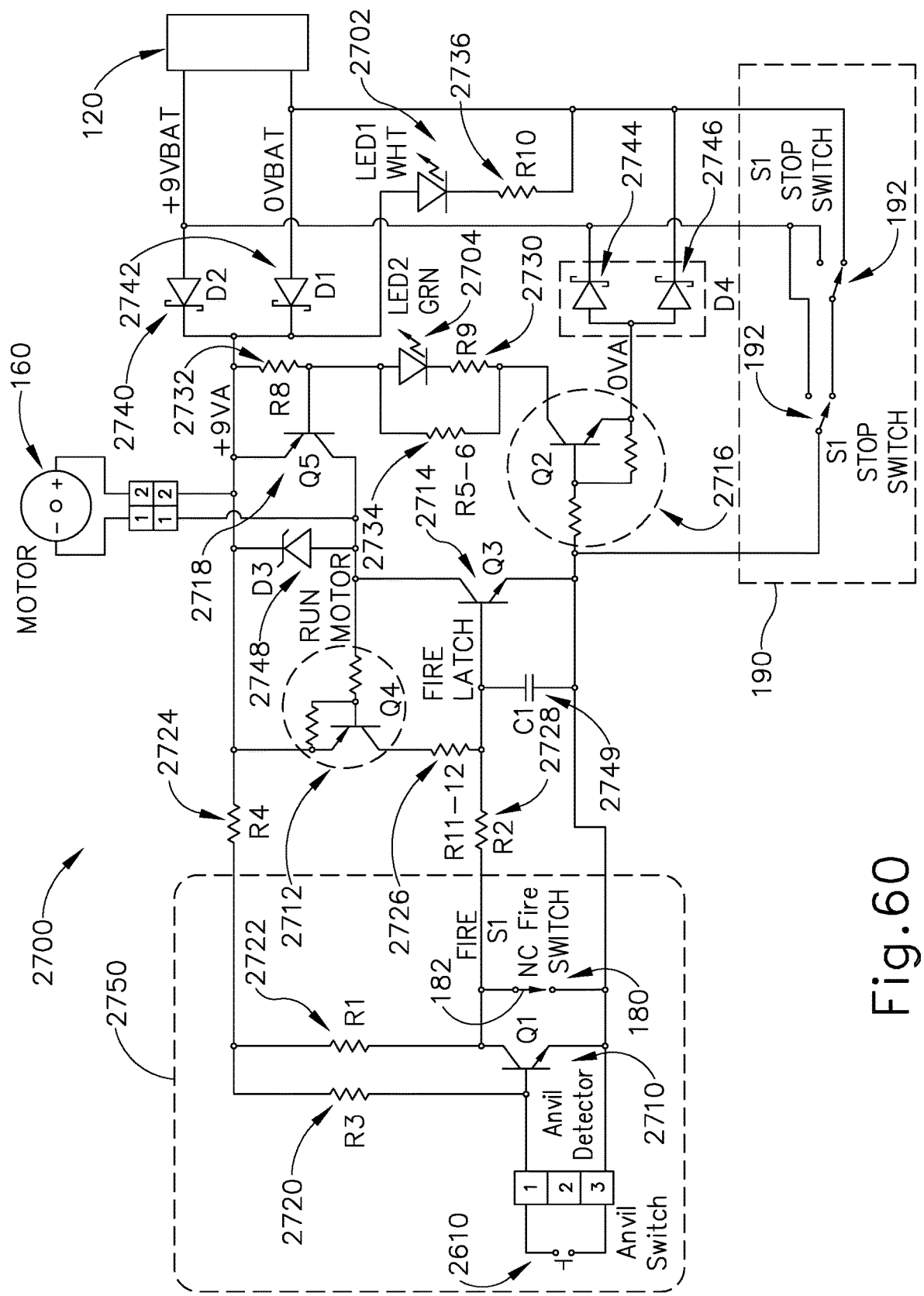
FIG. 60 depicts a schematic view of an exemplary control circuit that may be incorporated into the instrument of FIG. 1.

FIG. 60 shows an exemplary control circuit (2700) that may be incorporated into instrument (10). Circuit (2700) is configured such that ingress of liquid onto dome switch (2610) and motor activation module (180) will not compromise the performance of dome switch (2610), motor activation module (180), or motor stop module (190). Dome switch (2610) and motor activation module (180) are thus within a liquid-immune region (750) of circuit (2700). As shown, circuit (2700) of this example includes several transistors (2710, 2712, 2714, 2716, 2718), several resistors (2720, 2722, 2724, 2726, 2728, 2730, 2732, 2734, 2736), several schottky diodes (2740, 2742, 2744, 2746), a zener diode (2748), and a capacitor (2749). As also shown, battery pack (120), motor (161), motor activation module (180), switch buttons (192), dome switch (2610), and LEDs (2702, 2704) are also incorporated into circuit (2700). In the present example, control circuit (2700) is configured such that the electrical current flow to dome switch (2610) is less than the current flow to motor (161).

In the present example, transistor (2710), motor activation module (180), and resistors (2720, 2722) are all located within liquid-immune region (2750) of circuit (2700). Transistor (2710) of the present example has a relatively low voltage threshold and is in communication with dome switch (2610), motor activation module (180), and other components that are ultimately coupled with motor (161). In the present example, switch (182) of motor activation module (180) is configured such that switch (182) is held in a closed state by default. Thus, when paddle (158) engages motor activation module (180) in response to the operator pivoting firing trigger (150), paddle (158) transitions switch (182) of motor activation module (180) from a closed state to an open state.

Transistor (2710) and the associated components of circuit (2700) are configured to provide activation of motor (161) only when the switch of motor activation module (180) is in the open state (which would indicate that firing trigger (150) has been fully actuated) and when dome switch (2610) is in the closed state (which would indicate that anvil (400) is properly coupled with trocar (330)). Thus, motor (161) will not be activated when the switch of motor activation module (180) is in the closed state (which would indicate that firing trigger (150) has not been fully actuated), even if dome switch (2610) is in a closed state. Similarly, motor (161) will not be activated when dome switch (2610) is in an open state (which would indicate that anvil (400) is not properly coupled with trocar (330)), even if the switch of motor activation module (180) is in the open state.

Those of ordinary skill in the art will recognize that a switch that is flooded with liquid may tend to be compromised, which may prematurely produce the effect of a closed switch. Thus, in alternative versions of circuit (2700) where motor (161) is activated upon the transition of the switch of motor activation module (180) from an open state to a closed state, liquid ingress may compromise the switch to thereby effectively provide a closed state before firing trigger (150) is actuated. In other words, in alternative versions of circuit (2700) where motor (161) is activated upon the transition of the switch of motor activation module (180) from an open state to a closed state, liquid ingress may result in premature activation of motor (161) and thus stapling head assembly (300). However, by requiring the switch of motor activation module (180) to be in an open state to provide activation of motor (161), circuit (2700) of the present example prevents motor (161) and thus stapling head assembly (300) from being activated prematurely by liquid ingress.

When dome switch (2610) is in an open state (i.e., when anvil (400) has not actuated dome switch (2610) as described above), transistor (2710) acts as a closed switch ("on"). When dome switch (2610) is in a closed state (i.e., when anvil (400) has actuated dome switch (2610) as described above), transistor (2710) will behave as an open switch ("off"). Those of ordinary skill in the art will recognize that the voltage threshold of transistor (2714) is equal to or greater than 0.7V because the emitter (the point at which transistors (2714, 2716) are connected) is connected to 0V of the battery. When the point at which capacitor (2749), resistors (2728, 726), and transistor (2714) connect exceeds this threshold, transistor (2714) will act a closed switch ("on"), thereby allowing motor (161) to activate.

Transistor (2714) has a relatively low voltage threshold in the present example. Transistor (2714) is thus capable of recognizing an open state of switch (182) of motor activation module (180), even if motor activation module (180) is flooded with electrically conductive liquid, due to the fact that the liquid provides enough resistivity that it does not create an equivalency to a closed switch. The liquid's resistivity will lower the voltage but not to a level below the low voltage threshold of transistor (2710), thus allowing the transistor (2710) to recognize that switch (182) has been opened.

In addition to, or as an alternative to, providing the configuration of circuit (2700) described above, various electrical components may be coated with a liquid-impermeable coating to provide at least some degree of immunity to liquid ingress. For instance, in some versions, one or more printed circuit boards of circuit (2700) (e.g., a circuit board to which LEDs (2702, 2704) are mounted) may be coated with a liquid-impermeable coating. In addition, or in the alternative, either or both of LEDs (2702, 2704) may be coated with a liquid-impermeable coating. Other features of circuit (2700) that may be coated with a liquid-impermeable coating will be apparent to those of ordinary skill in the art in view of the teachings herein.

In some versions where a liquid-impermeable coating is used on one or more components of circuit (2700), the liquid-impermeable coating may comprise an ultraviolet-cured urethane coating. In some versions, the liquid-impermeable coating is transparent. By making the coating transparent, this may preserve legibility of coated features that are intended to be viewed (e.g., either or both of LEDs (2702, 2704)). Moreover, in versions where one or both of LEDs (2702, 2704) is/are coated, use of a transparent coating may prevent the light emitted from the coated LED (2702, 2704) from being transmitted along the coating (i.e., "bleeding"). Other various suitable materials that may be used to provide such coatings, and various methods that may be used to apply such coatings, will be apparent to those of ordinary skill in the art in view of the teachings herein.

IX. Exemplary Conical Coil Springs

As described above, instrument (10) may include a body (e.g. handle assembly (100)), a shaft (e.g. shaft assembly (200)), a stapling head assembly (e.g. stapling head assembly (300)), and an anvil (e.g. anvil (400)). Shaft assembly (200) extends distally from handle assembly (100), and stapling head assembly (300) is positioned at distal end of shaft assembly (200). Handle assembly (100) includes a chassis (e.g. chassis (3690) that may include left and right chassis portions (3691, 3693)), bracket (3650), and a coupling (e.g. nut (160)).

Figure 61:
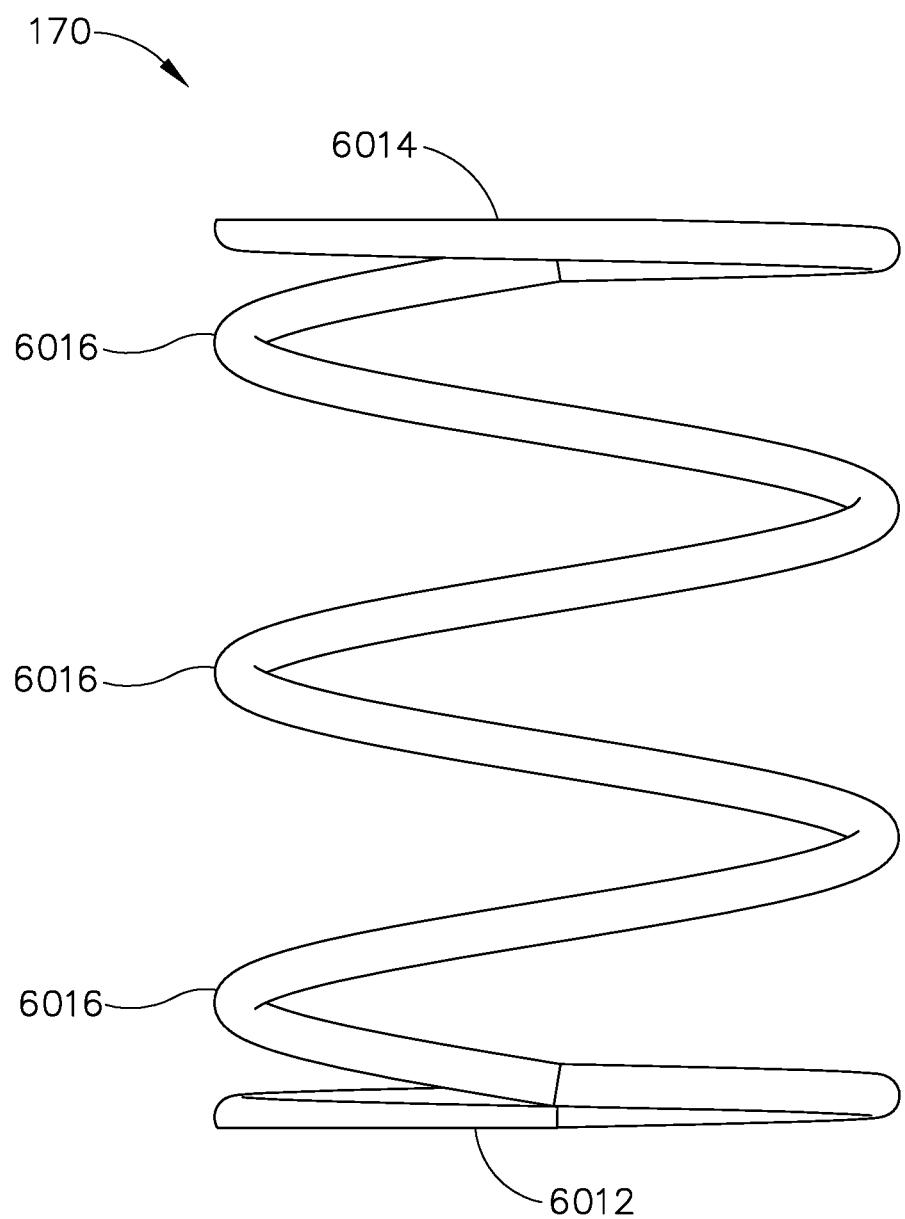
FIG. 61 depicts a detailed view of the coil spring of FIG. 18.

FIG. 61 shows a detailed view of coil spring (170) of FIG. 18. As shown, coil spring (170) includes a proximal end (6012), a distal end (6014), and helical coils (6016) disposed between proximal and distal ends (6012, 6014). Proximal and distal ends (6012, 6014) may be ground to have flat ends.

It would be desirable to prevent distal end (6014) of coil spring (170) from potentially being inadvertently caught (e.g. pinched) between bracket (3650) and chassis (3690), as coil spring (170) moves between first and second positions as safety trigger (140) is actuated. Additionally, it would be beneficial to ensure that coil spring (170) is correctly installed within the instrument (e.g. instrument (10)). As such, coil spring (170) of FIG. 61 may be interchanged with first, second, and third exemplary conical coil springs (6110, 6210, 6310) as shown and described below with reference to FIGS. 62-65. In other words, conical coil spring (6110, 6210, 6310) may be used in place of coil spring (170) and be suitably incorporated into instrument (10) without additional modifications.

A. First Exemplary Conical Coil Spring

Figure 62:
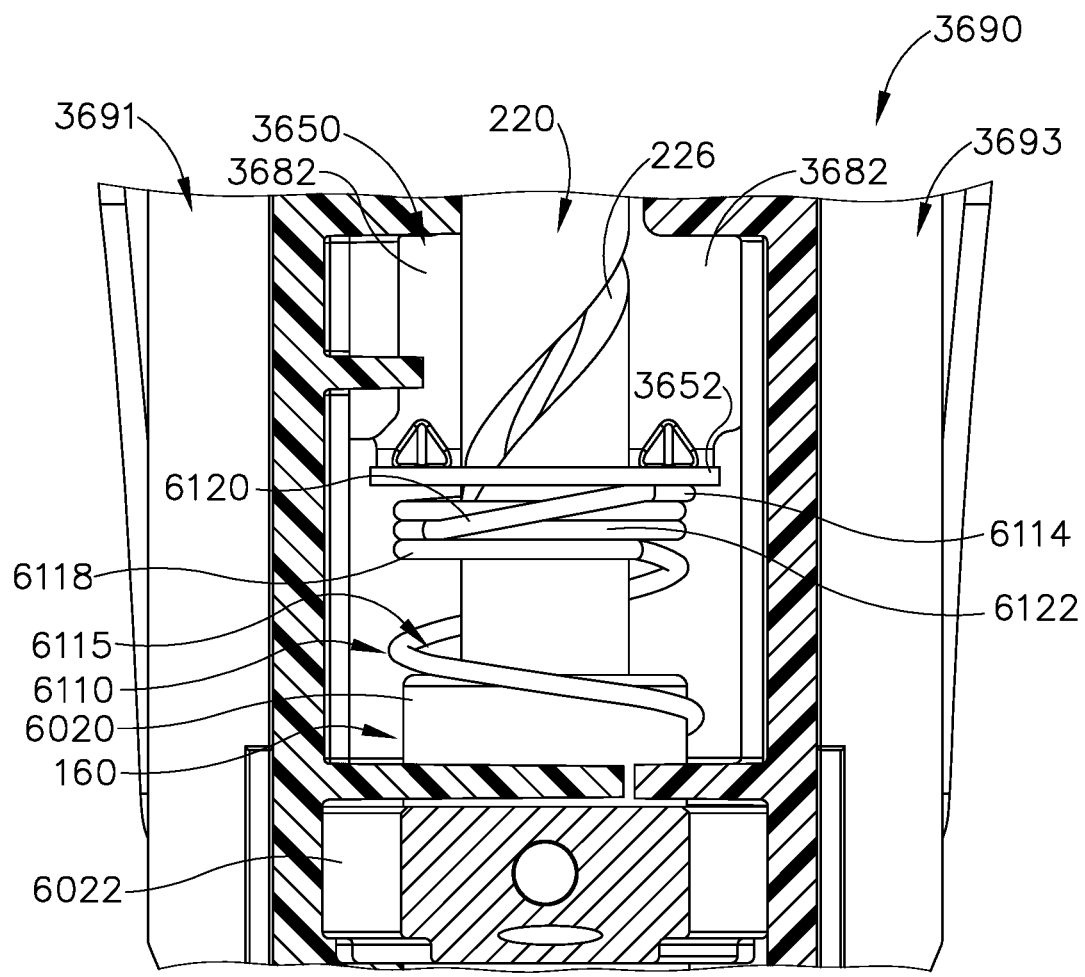
FIG. 62 depicts a bottom view of the trocar actuation rod of FIG. 17, the right chassis portion and the nut of FIG. 18, the bracket of FIG. 35, the left chassis portion of FIG. 37, and a first exemplary alternative coil spring.
Figure 63:
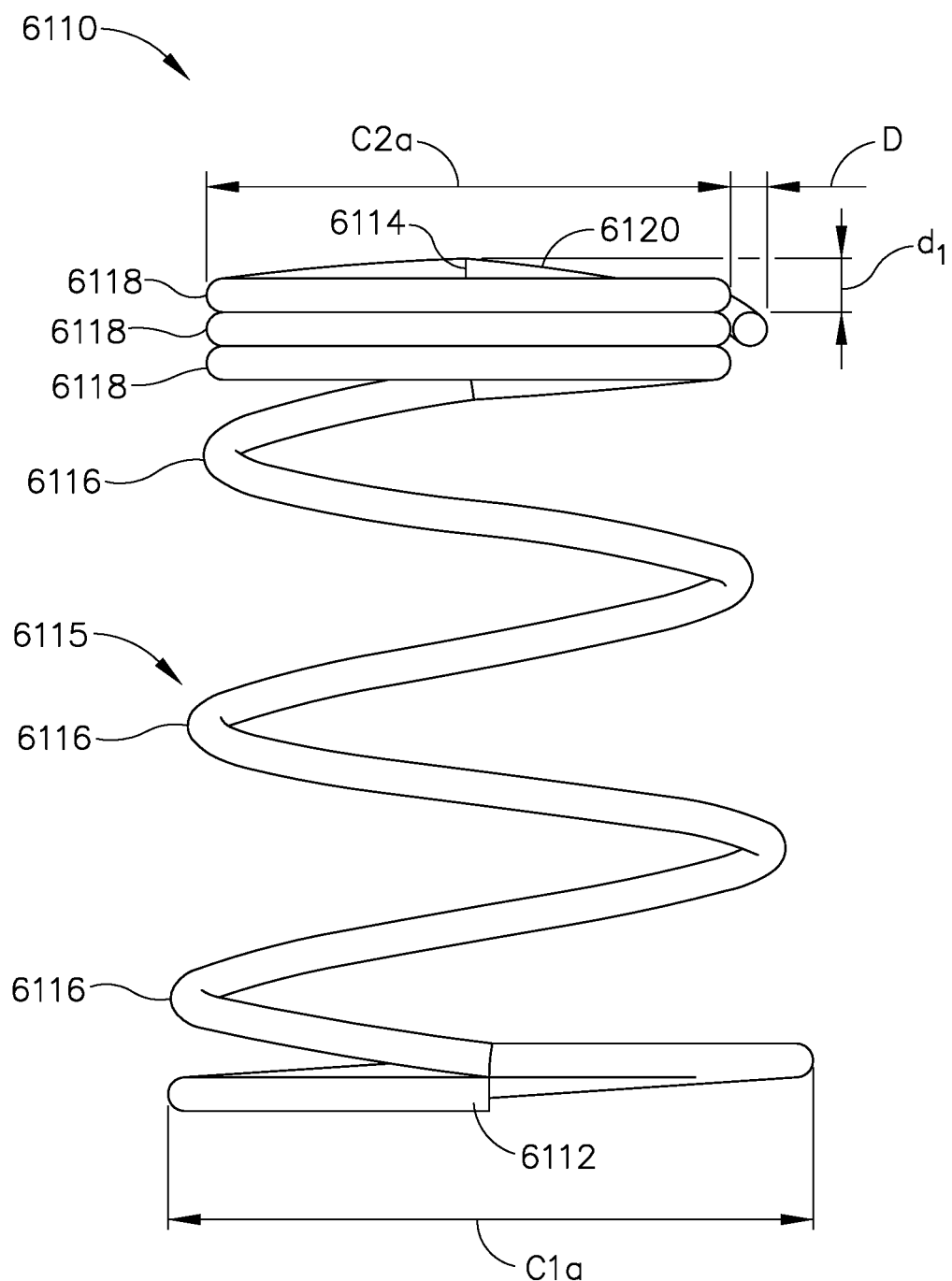
FIG. 63 depicts a detailed view of the coil spring of FIG. 62.

FIGS. 62-63 show a first exemplary conical coil spring (6110). FIG. 62 shows a bottom view of trocar actuation rod (220) of FIG. 17, right chassis portion (3693) of chassis (3690) and nut (160) of FIG. 18, bracket (3650) of FIG. 35, left chassis portion (3691) of FIG. 37, and conical coil spring (6110). As previously described, bracket (3650), also referred to a safety release plate, is configured to move relative to left and right chassis portions (3691, 3693) of chassis (3690) between first and second positions when selectively activated by a user. As described above, it is also envisioned at bracket (1500) may be used in place of bracket (3650). As shown, conical coil spring (6110) is disposed between bracket (3650) and nut (160).

As shown in FIGS. 62-63, conical coil spring (6110) includes a proximal end (6112), a distal end (6114), and a conical helical body (6115) disposed between proximal and distal ends (6112, 6114). Conical helical body (6115) includes a plurality of conical helical coils (6116). Conical coil spring (6110) includes at least one dead coil (6118) disposed at distal end (6114) of conical coil spring (6110). An active coil is a coil that stores and releases energy (e.g. conical helical coils (6116)). Conversely, a dead coil (i.e. an inactive coil) is a coil that does not store and release energy, such that the dead coil does not contribute to the motive force of the coil spring. FIG. 63 shows three dead coils (6118), however, more or fewer dead coils (6118) are envisioned. Dead coils (6118) may prevent distal end (6114) of conical coil spring (6110) from being inadvertently caught (e.g. pinched) between bracket (3650) and chassis (3690). Dead coils (6118) are also configured to prevent conical coil spring (6110) from catching on fine helical threading (226) of trocar actuation rod (220). Dead coils (6118) may also assist in identifying the orientation of conical coil spring (6110) to ensure correct installation of conical coil spring (6110) within an instrument (e.g. instrument (10)).

As shown in FIGS. 62-63, a bent-back portion (6120) generally disposed at distal end (6114) is bent back a distance (dl) toward proximal end (6112). Bent-back portion (6120) also ensures that conical coil spring (6110) is correctly installed within the instrument (e.g. instrument (10)), and that the instrument cannot be assembled incorrectly (while proximal end (6112) or distal end (6114) are disposed between bracket (3650) and left chassis portion (3691) of chassis (3690)). FIG. 63 shows a detailed view of conical coil spring (6110) of FIG. 62. Proximal end (6112) of conical coil spring (6110) has a first circumference (C1a). Likewise, distal end (6114) of conical coil spring (6110) has a second circumference (C2a) that is smaller than first circumference (C1a). Second circumference (C2a) being is smaller than first circumference (C1a) enables distal end (6114) of conical coil spring (6110), having a diameter (D), to include bent-back portion (6120) that is bent adjacent an outside (6122) of conical helical body (6115) without protruding past first circumference (C1a) of proximal end (6112) of conical coil spring (6110). As a result of the conical shape, conical coil spring (6110) may fit in the same space as coil spring (170), even with conical coil spring (6110) including bent-back portion (6120).

As shown in FIG. 62, nut (160) includes a proximal flange (6020) that is smaller than the first circumference (C1a) of conical coil spring (6110). Additionally, as shown in FIG. 62, nut (160) includes a body portion (6022) that is larger than first circumference (C1a) of conical coil spring (6110). Body portion (6022) includes an opening (shown in FIG. 18) that extends through proximal flange (6020) of nut (160) and body portion (6022) of nut (160), such that the opening is configured to receive trocar actuation rod (220) therethrough. Proximal end of trocar actuation rod (220) extends through opening (7204) in upright member (3652) of bracket (3650) and through conical coil spring (6110).

Instead of or in addition to incorporating conical coil springs (6110, 6210, 6310) in place of coil spring (170), a weld (not shown) may fixably couple distal end (6014) of coil spring (170) or distal end (6114, 6214, 6314) of conical coil spring (6110, 6210, 6310) to bracket (3650). Similarly, while not shown, adjacent coils of proximal end (6012) of coil spring (170) or proximal end (6112, 6212, 6312) of conical coil spring (6110, 6210, 6310) and/or adjacent coils of distal end (6014) of coil spring (170) or distal end (6114, 6214, 6314) of conical coil spring (6110, 6210, 6310) may be welded together. Instead of or in addition to incorporating conical coil springs (6110, 6210, 6310) in place of coil spring (170), alternative spring terminal ends may also be incorporated.

B. Second Exemplary Conical Coil Spring

Figure 64:
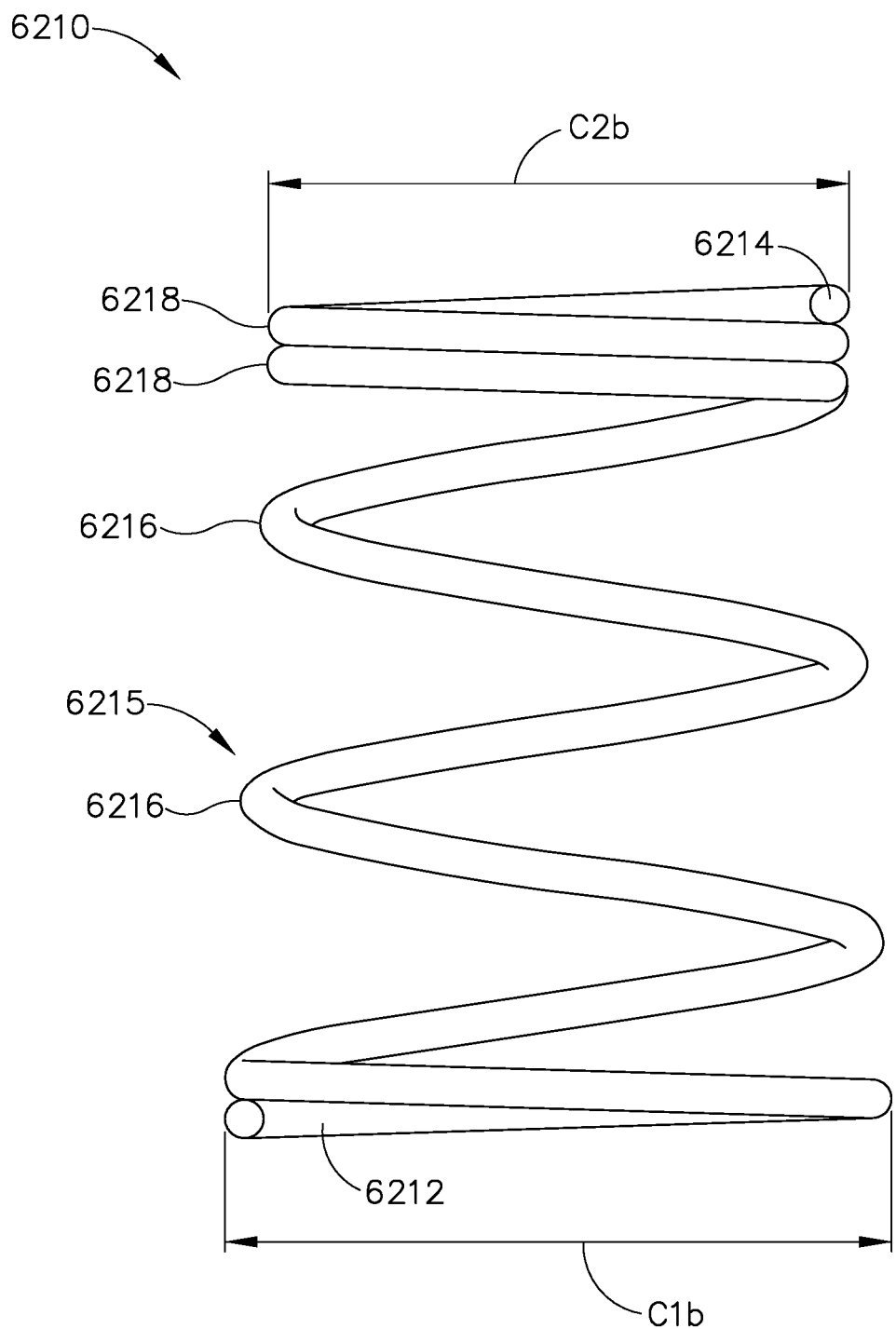
FIG. 64 depicts a detailed view of a second exemplary alternative coil spring.

FIG. 64 shows a detailed view of a second exemplary conical coil spring (6210). As described above, conical coil spring (6210) may be used in place of coil spring (170) or conical coil spring (6110). As shown, conical coil spring (6210) includes a proximal end (6212), a distal end (6214), and a conical helical body (6215) disposed between proximal and distal ends (6212, 6214). Conical helical body (6215) includes conical helical coils (6216). Conical coil spring (6210) includes at least one dead coil (6218) disposed at distal end (6214) of conical coil spring (6210). FIG. 64 shows two dead coils (6218), however, more or fewer dead coils (6218) are envisioned. Dead coils (6218) may prevent distal end (6214) of conical coil spring (6210) from being inadvertently pinched between bracket (3650) and chassis (3690). Dead coils (6218) are also configured to prevent conical coil spring (6210) from catching on fine helical threading (226) of trocar actuation rod (220). Dead coils (6218) may assist in identifying the orientation of conical coil spring (6210) to ensure correct installation of conical coil spring (6210). Proximal end (6212) of conical coil spring (6210) has a first circumference (C1b). Likewise, distal end (6214) of conical coil spring (6210) has a second circumference (C2b) that is smaller than first circumference (C1b). Second circumference (C2b) being is smaller than first circumference (C1b) ensures correct installation of conical coil spring (6210).

C. Third Exemplary Conical Coil Spring

Figure 65:
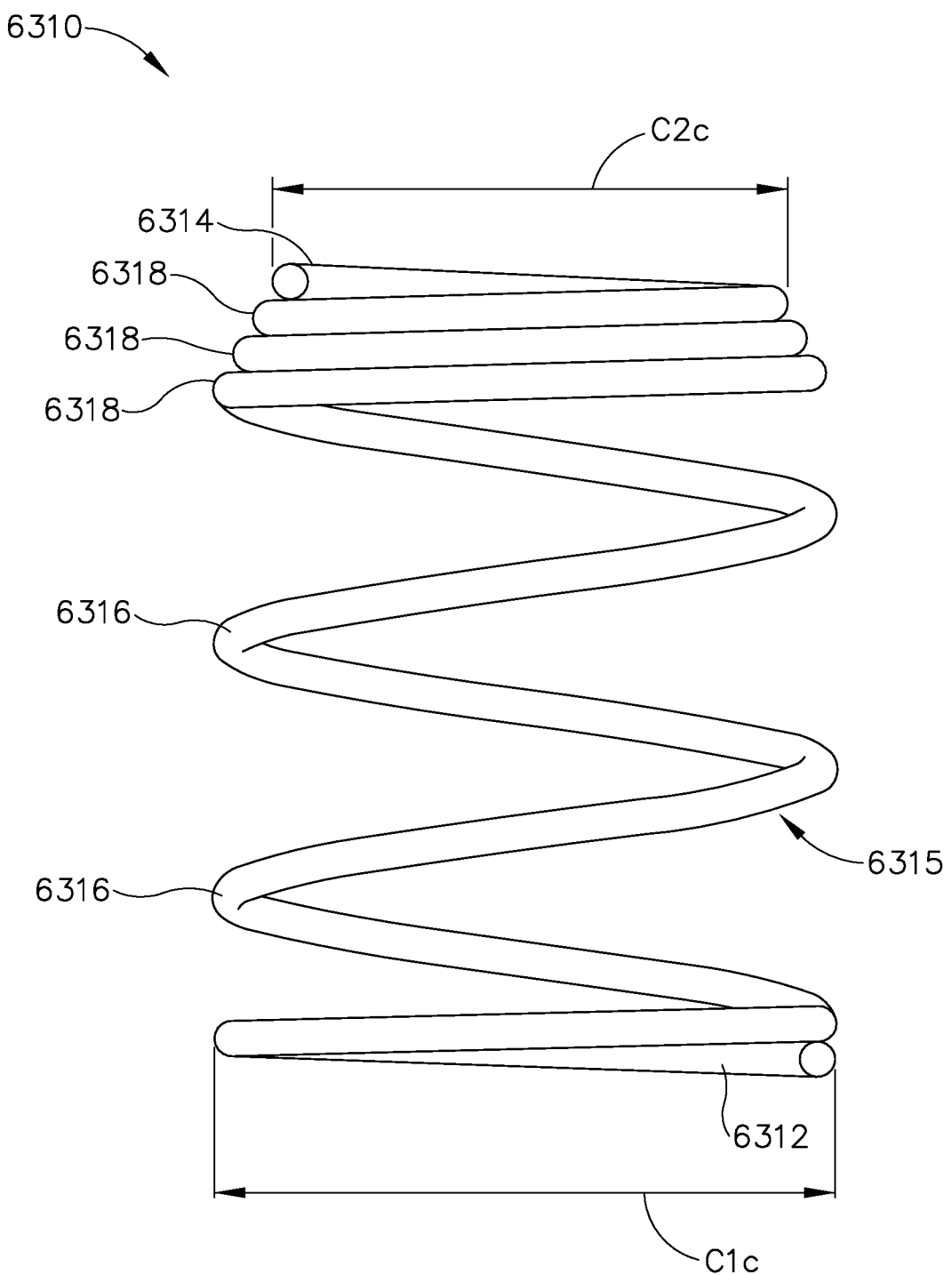
FIG. 65 depicts a detailed view of a third exemplary alternative coil spring.

FIG. 65 shows a detailed view of a third exemplary conical coil spring (6310). As described above, conical coil spring (6310) may be used in place of coil spring (170) or conical coil springs (6110, 6210). As shown, conical coil spring (6310) includes a proximal end (6312), a distal end (6314), and a conical helical body (6315) disposed between proximal and distal ends (6312, 6214). Conical helical body (6315) includes conical helical coils (6316). Conical coil spring (6310) includes at least one dead coil (6318) disposed at distal end (6314) of conical coil spring (6310). FIG. 65 shows three dead coils (6318), however, more or fewer dead coils (6318) are envisioned. Dead coils (6318) may prevent distal end (6314) of conical coil spring (6310) from being inadvertently pinched between bracket (3650) and chassis (3690). Dead coils (6318) are also configured to prevent conical coil spring (6310) from catching on fine helical threading (226) of trocar actuation rod (220). Dead coils (6318) may assist in identifying the orientation of conical coil spring (6310) to ensure correct installation of conical coil spring (6310). Proximal end (6312) of conical coil spring (6310) has a first circumference (C1c). Likewise, distal end (6314) of conical coil spring (6310) has a second circumference (C2c) that is smaller than first circumference (C1c). Second circumference (C2c) being is smaller than first circumference (C1c) ensures correct installation of conical coil spring (6310).

X. Additional Modifications

Alternatively, or in addition to incorporating conical coil spring (6110, 6210, 6310) in place of coil spring (170), additional modifications may be incorporated into instrument (10). As will be described below with reference to FIGS. 66-74, these additional modifications may include an exemplary slidable coupling (6410), an exemplary guide bushing (6510), an exemplary centering feature (6612) on an exemplary bracket (6610), and/or an exemplary sleeve (6710). Other modifications are also envisioned. For example, while not shown, left chassis portion (3691) may also include a cutout configured to prevent distal end (6014) of coil spring (170) or distal end (6114, 6214, 6314) of conical coil spring (6110, 6210, 6310) from being pinched.

As shown in FIG. 35 and below in FIG. 66, bracket (3650) is configured to move along a longitudinal axis between first and second positions when selectively activated by a user. Bracket (3650) includes proximal and distal portions (3678, 3680). Proximal portion (3678) includes flared-out portions (3682) disposed along the longitudinal axis. Proximal portion (3678) also includes upright member (3652) disposed perpendicular to flared-out portions (3682). Upright member (3652) of bracket (3650) includes inner and outer surfaces (3686, 3688) (see FIG. 68).

A. Exemplary Slidable Coupling

Figure 66:
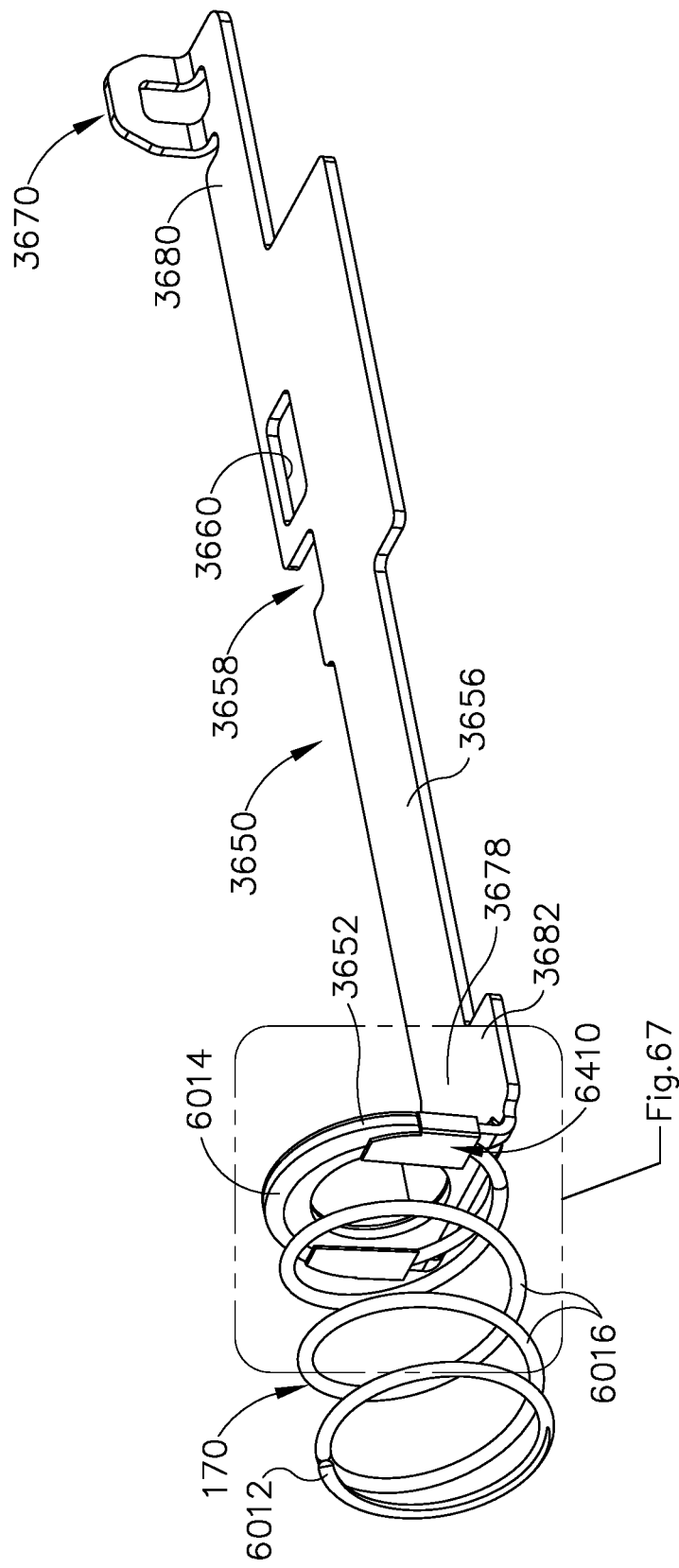
FIG. 66 depicts a perspective view of the bracket of FIG. 35 coupled with the coil spring of FIG. 61 using an exemplary slidable coupling.
Figure 67:
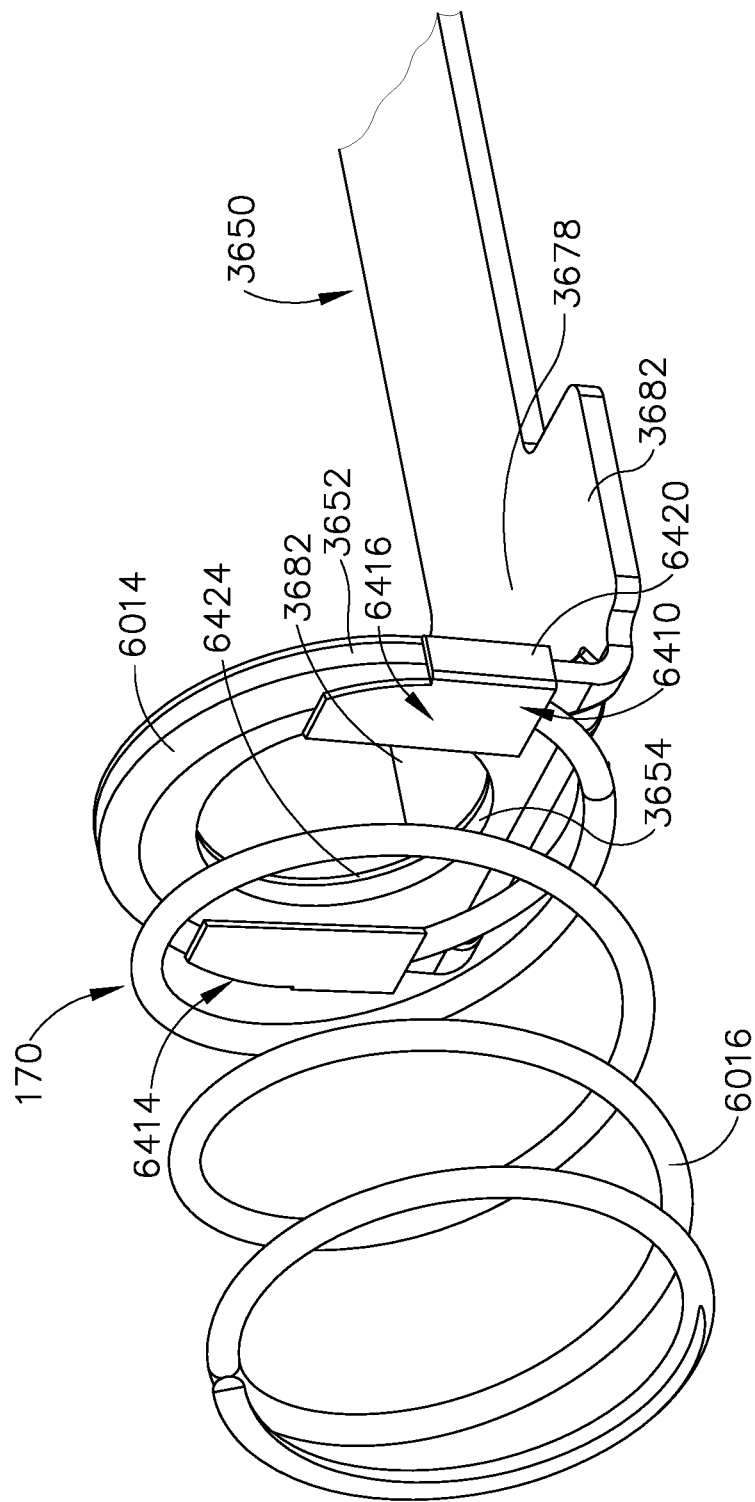
FIG. 67 depicts a detailed perspective portion of the bracket, the coil spring, and the slidable coupling of FIG. 66.
Figure 68:
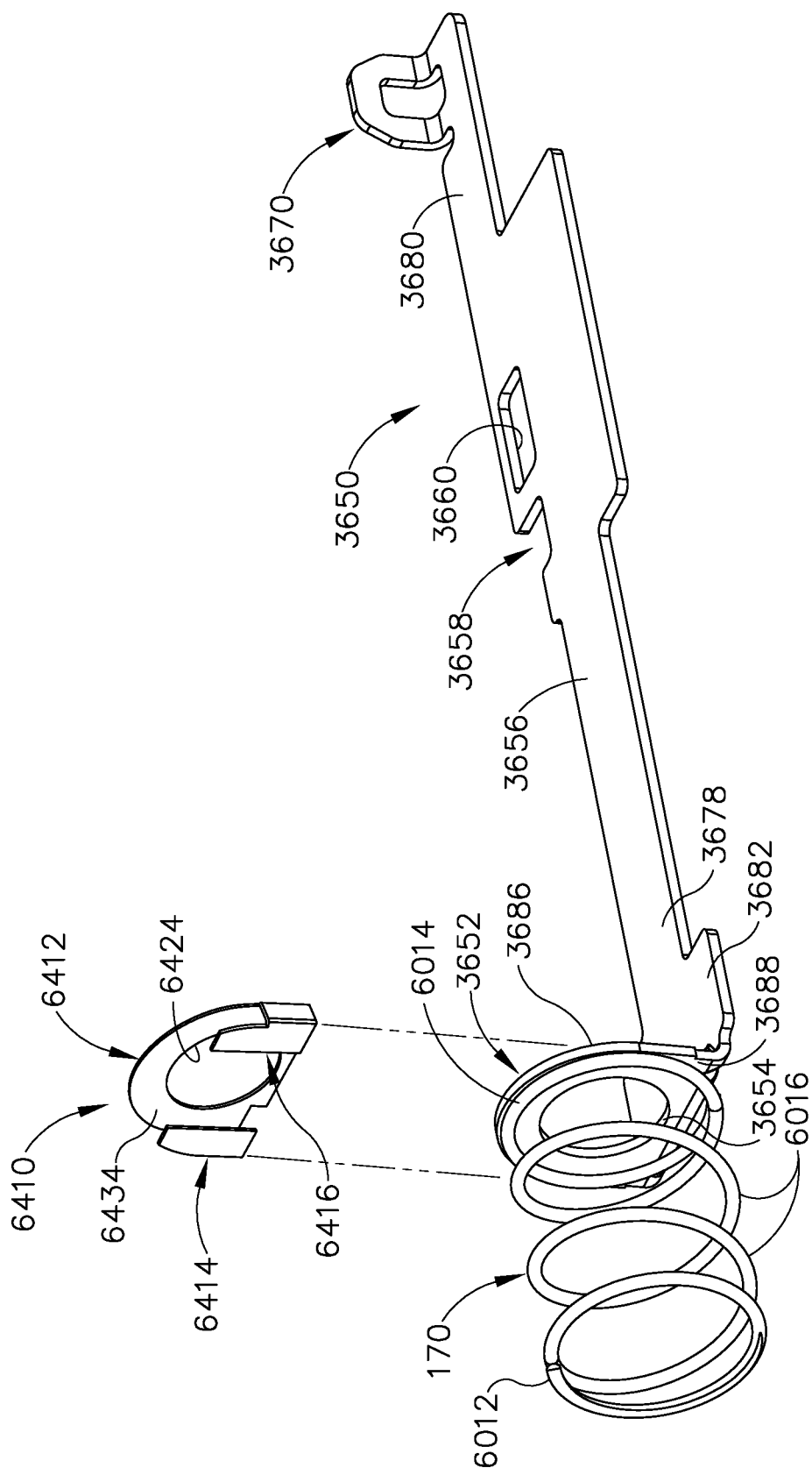
FIG. 68 depicts an exploded perspective view of the slidable coupling separated from the bracket and the coil spring of FIG. 66.
Figure 69:
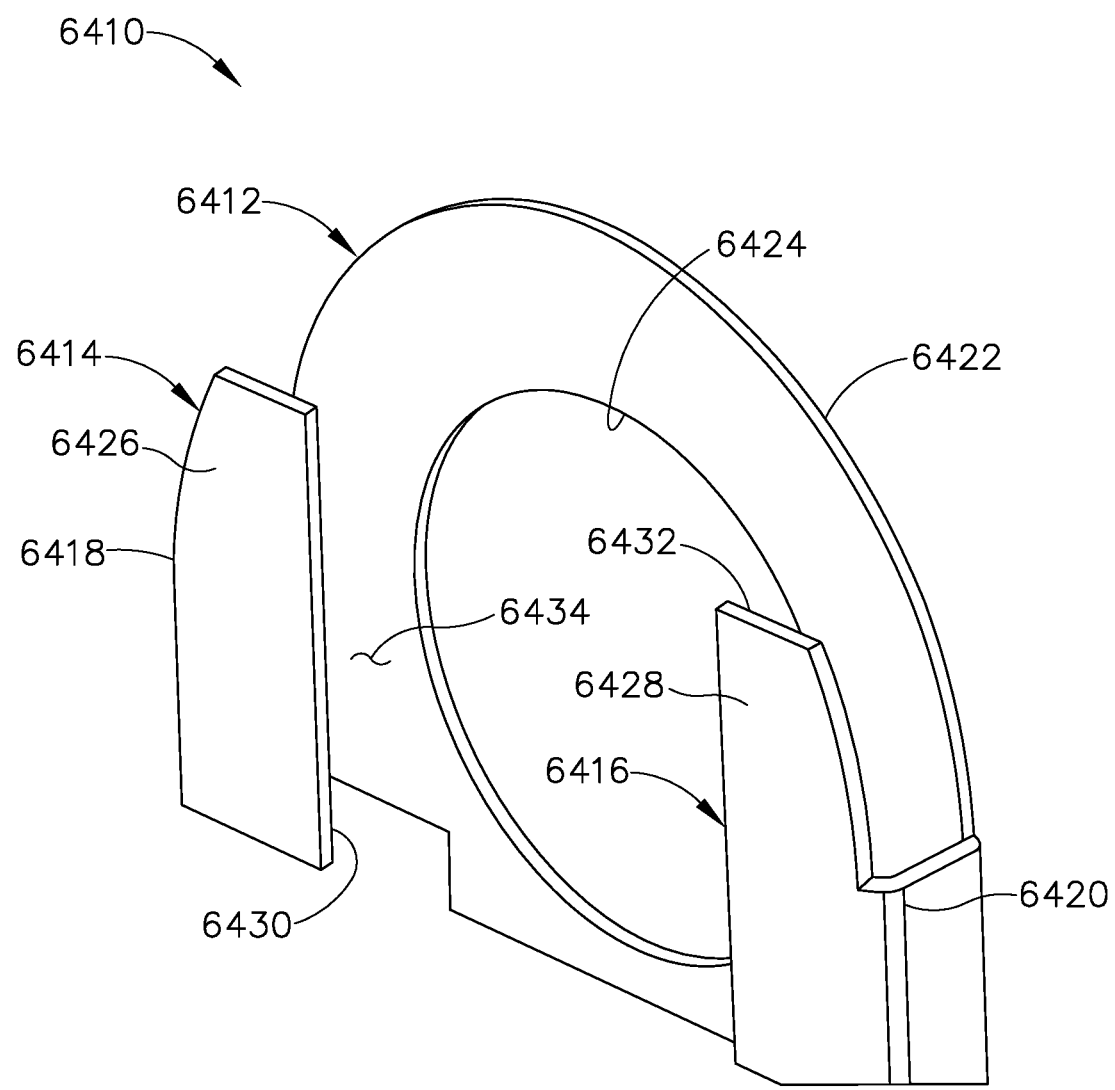
FIG. 69 depicts a detailed perspective view of the slidable coupling of FIG. 68.

FIG. 66-69 show various perspective views of slidable coupling (6410). Particularly, FIG. 66 shows a perspective view of bracket (3650) of FIG. 35 coupled with coil spring (170) of FIG. 61 using slidable coupling (6410). FIG. 67 shows a detailed perspective portion of FIG. 66, and FIG. 68 shows an exploded perspective view of FIG. 66. Slidable coupling (6410) is configured to retain distal end (6114) of coil spring (170) and upright member (3652). As shown in FIGS. 68-69, slidable coupling (6410) includes a body portion (6412) that may be shaped to generally correspond to the profile of upright member (3652). Slidable coupling (6410) includes first and second arms (6414, 6416) spaced longitudinally from body portion (6412). As shown, slidable coupling (6410) is integrally formed together as a unitary piece. For example, slidable coupling (6410) may be formed from one or more stamping operations (e.g. from a thin plate of metal).

As shown in FIG. 69, first arm (6414) is connected with body portion (6412) by a first lateral portion (6418), and second arm (6416) is connected with body portion (6412) by a second lateral portion (6420). Body portion (6412) includes an arcuate upper portion (6422) that includes an arcuate opening (6424) configured to receive a proximal end of trocar actuation rod (220). As previously described, arcuate upper portion (6422) may be shaped to generally correspond to the profile of upright member (3652). First and second arms (6414, 6416) respectively include first and second upwardly extending portions (6426, 6428) and first and second inner surfaces (6430, 6432). As shown, first and second inner surfaces (6430, 6432) of first and second arms (6414, 6416) along with an inner surface (6434) of body portion (6412) are configured to longitudinally retain distal end (6014) of coil spring (170) and upright member (3652) of bracket (3650). Particularly, inner surface (6434) of body portion (6412) is disposed against inner surface (3686) of upright member (3652). Additionally, outer surface (3688) of upright member (3652) is disposed against distal end (6014) of coil spring (170), and distal end (6014) of coil spring (170) is also disposed against first and second inner surfaces (6430, 6432) of first and second arms (6414, 6416). Additionally, first and second lateral portions (6418, 6420) center coil spring (170) by bounding coil spring (170) in the direction perpendicular to the longitudinal direction.

First lateral portion (6418) is partially obstructed from view in FIG. 69 but is a mirror image of second lateral portion (6420). This may prevent lateral movement of coil spring (170). As such, slidable coupling (6410) may prevent distal end (6014) of coil spring (170) or distal end (6114, 6214, 6314) of conical coil spring (6110, 6210, 6310) from being pinched. Slidable coupling (6410) may be incorporated into instrument (10) alternatively, or in addition to, incorporating conical coil spring (6110, 6210, 6310) in place of coil spring (170).

B. Exemplary Guide Bushing

Figure 70:
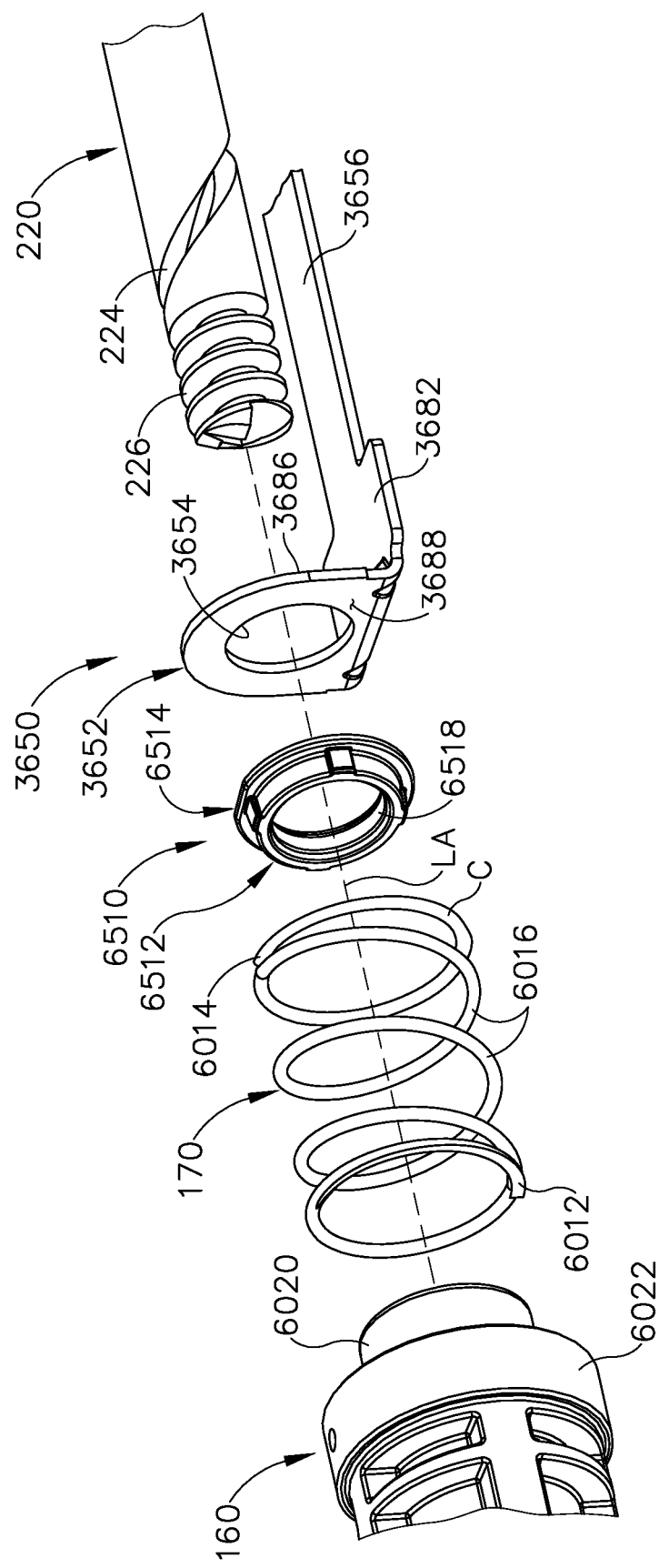
FIG. 70 depicts an exploded perspective view of the trocar actuation rod of FIG. 17, the nut and coil spring of FIG. 18, the bracket of FIG. 35, and an exemplary guide bushing.
Figure 71:
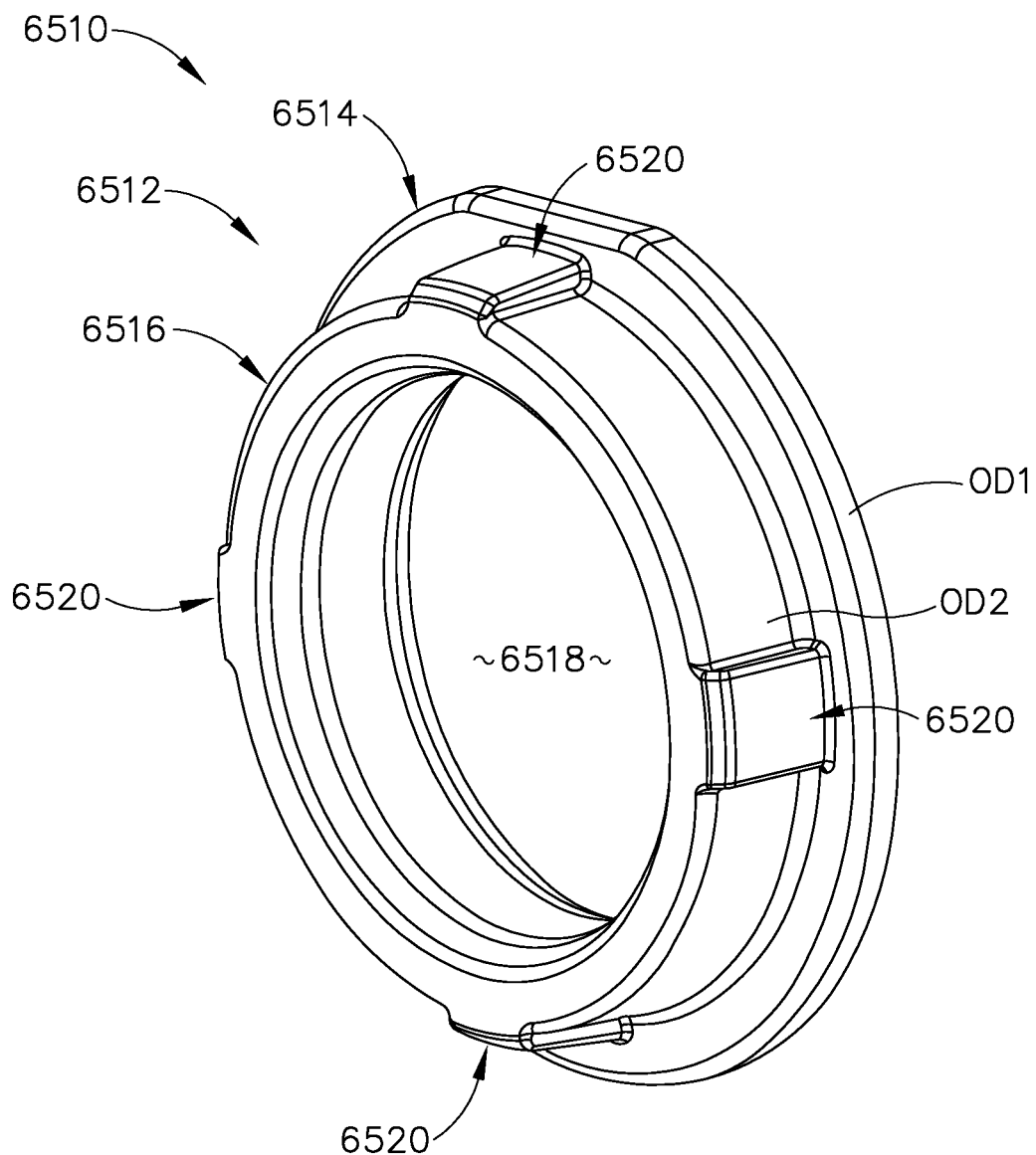
FIG. 71 depicts a detailed perspective view of the guide bushing of FIG. 70.

FIGS. 70-71 show an exemplary guide bushing (6510). FIG. 70 shows an exploded perspective view of trocar actuation rod (220) of FIG. 17, nut (160) and coil spring (170) of FIG. 18, as well as bracket (3650) of FIG. 35, and guide bushing (6510). FIG. 71 shows a detailed perspective view of guide bushing (6510) of FIG. 70. As shown in FIG. 70, guide bushing (6510) is configured to be coupled between upright member (3652) and coil spring (170). Guide bushing (6510) includes a generally annular body (6512). If desired, guide bushing (6510) may be fixably coupled with upright member (3652) using a variety of methods (e.g. adhesive or welding). Body (6512) includes a first portion (6514) having a first outer diameter (OD1) and a second portion (6516) (e.g. a receiving portion) having a second outer diameter (OD2). First outer circumference (OD1) is greater than the circumference (C) of distal end (6014) of coil spring (170), while second outer circumference (OD2) is less than the circumference (C) of distal end (6014) of coil spring (170). Trocar actuation rod (220) is configured to pass through an opening (6518) of guide bushing (6510). As shown, second portion (6516) includes projections (6018) that are configured to retain distal end (6014) of coil spring (170). As shown, projections 6018) include an arcuate surface (6522) that increases outer diameter of second portion (5614) moving toward first portion (6514). As such, guide bushing (6510) may prevent distal end (6014) of coil spring (170) or distal end (6114, 6214, 6314) of conical coil spring (6110, 6210, 6310) from being pinched. Guide bushing (6510) may be incorporated into instrument (10) alternatively, or in addition to, incorporating conical coil spring (6110, 6210, 6310) in place of coil spring (170).

C. Exemplary Centering Feature

Figure 72:
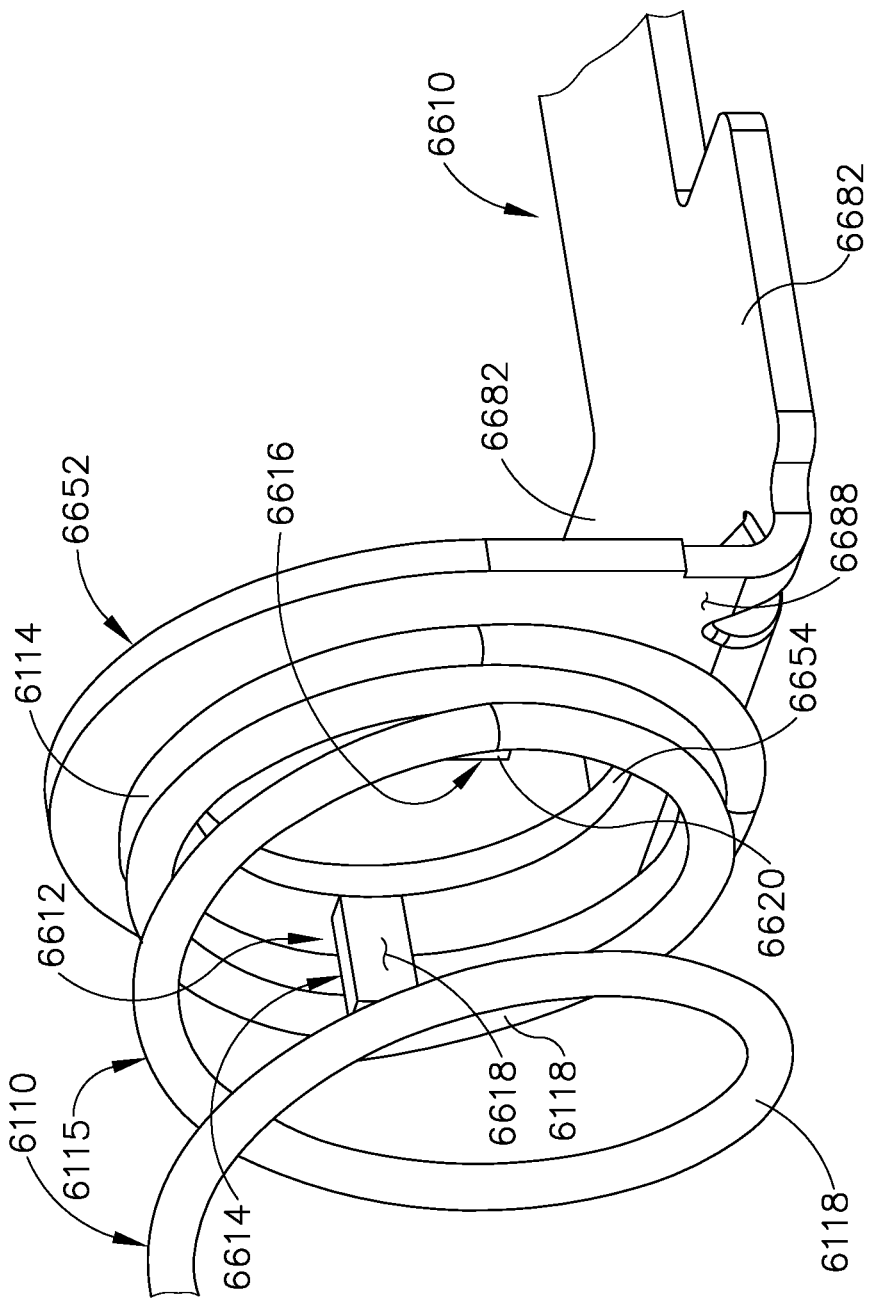
FIG. 72 depicts a perspective view of the bracket and the coil spring of FIG. 62, but with the bracket including a centering feature.

FIG. 72 shows a perspective view of conical coil spring (6110) of FIG. 62 and an exemplary alternative bracket (6610) that includes an exemplary centering feature (6612). Bracket (6610) is similar to bracket (3650), but with bracket (6610) additionally including centering feature (6612). Similar to bracket (3650), bracket (6610) is shown as including upright member (6652) similar to upright member (3652), opening (6654) similar to opening (7204), flared out portions (6682), similar to flared-out portions (3682), and outer surface (6688) similar to outer surface (3688). Other features of bracket (6610) are not shown, which may be the similar or the same as bracket (3650).

As shown, centering feature (6612) is disposed on outer surface (6688) of bracket (6610). Centering feature (6612) is configured to retain distal end (6114) of conical coil spring (6110). Centering feature includes first and second projections (6614, 6616). As shown, first and second projections (6614, 6616) are separated by opening (6654). First projection (6614) includes a first inner surface (6618) and second projection (6616) includes a second inner surface (6620). First and second inner surfaces (6618, 6620) allow trocar actuation rod (220) to pass through unimpeded. While centering feature (6612) is shaped as a cuboid, it is envisioned that centering feature (6612) may have a variety of shapes and sizes. First and second projections (6614, 6616) may be integrally formed as a unitary piece with bracket (6610), or alternatively, first and second projections (6614, 6616) may be subsequently fixably coupled with bracket (6610) using a variety of methods (e.g. adhesive or welding). Centering feature (6612) may prevent distal end (6114) of conical coil spring (6110) from moving laterally (i.e. in a direction perpendicular to the longitudinal axis). As such, centering feature (6612) may prevent distal end (6014) of coil spring (170) or distal end (6114, 6214, 6314) of conical coil spring (6110, 6210, 6310) from being pinched. Centering feature (6612) may be incorporated into instrument (10) alternatively, or in addition to, incorporating conical coil spring (6110, 6210, 6310) in place of coil spring (170).

D. Exemplary Sleeve

Figure 73:
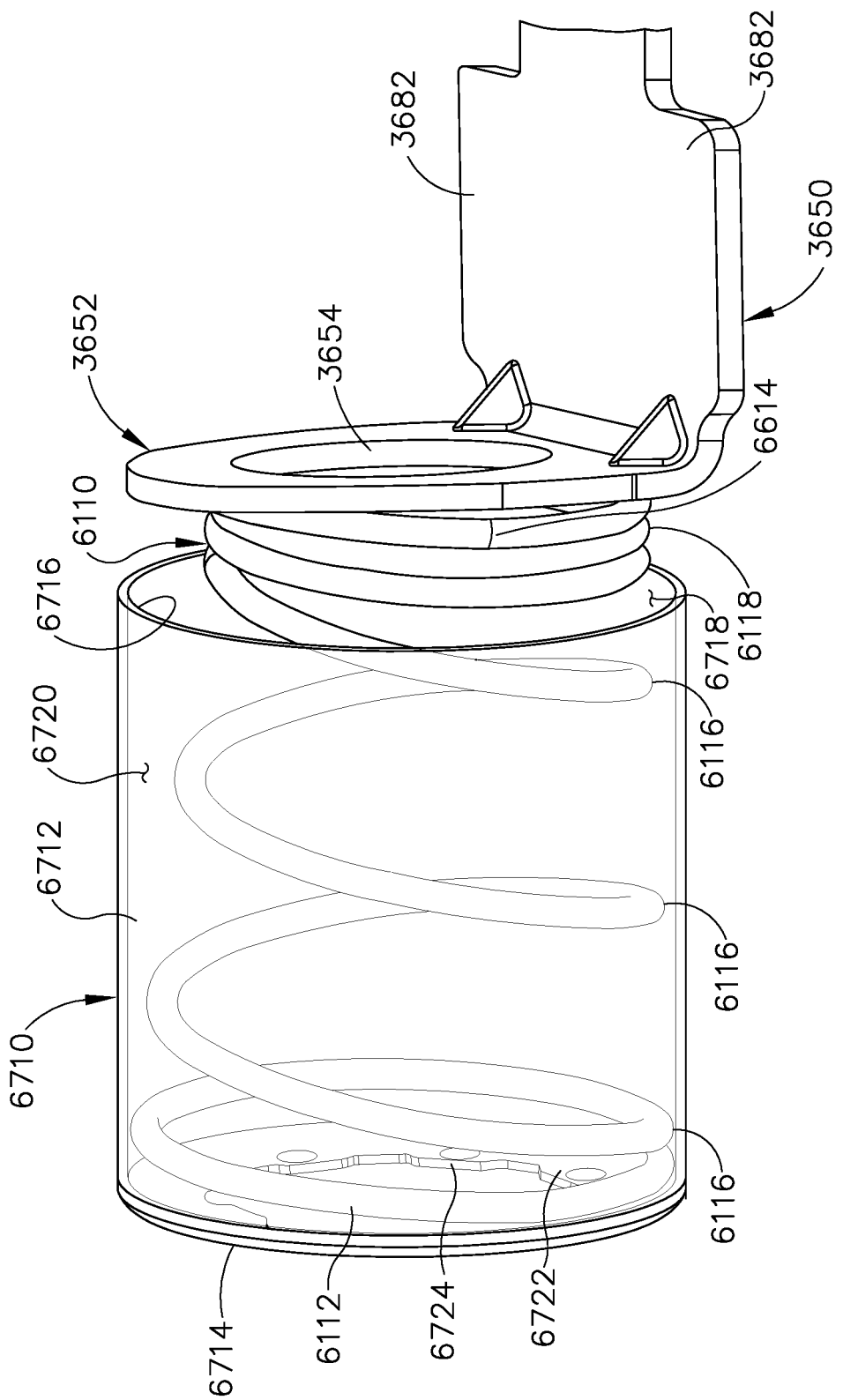
FIG. 73 depicts a perspective view of the bracket and the coil spring of FIG. 62, but with the coil spring disposed in a sleeve.
Figure 74:
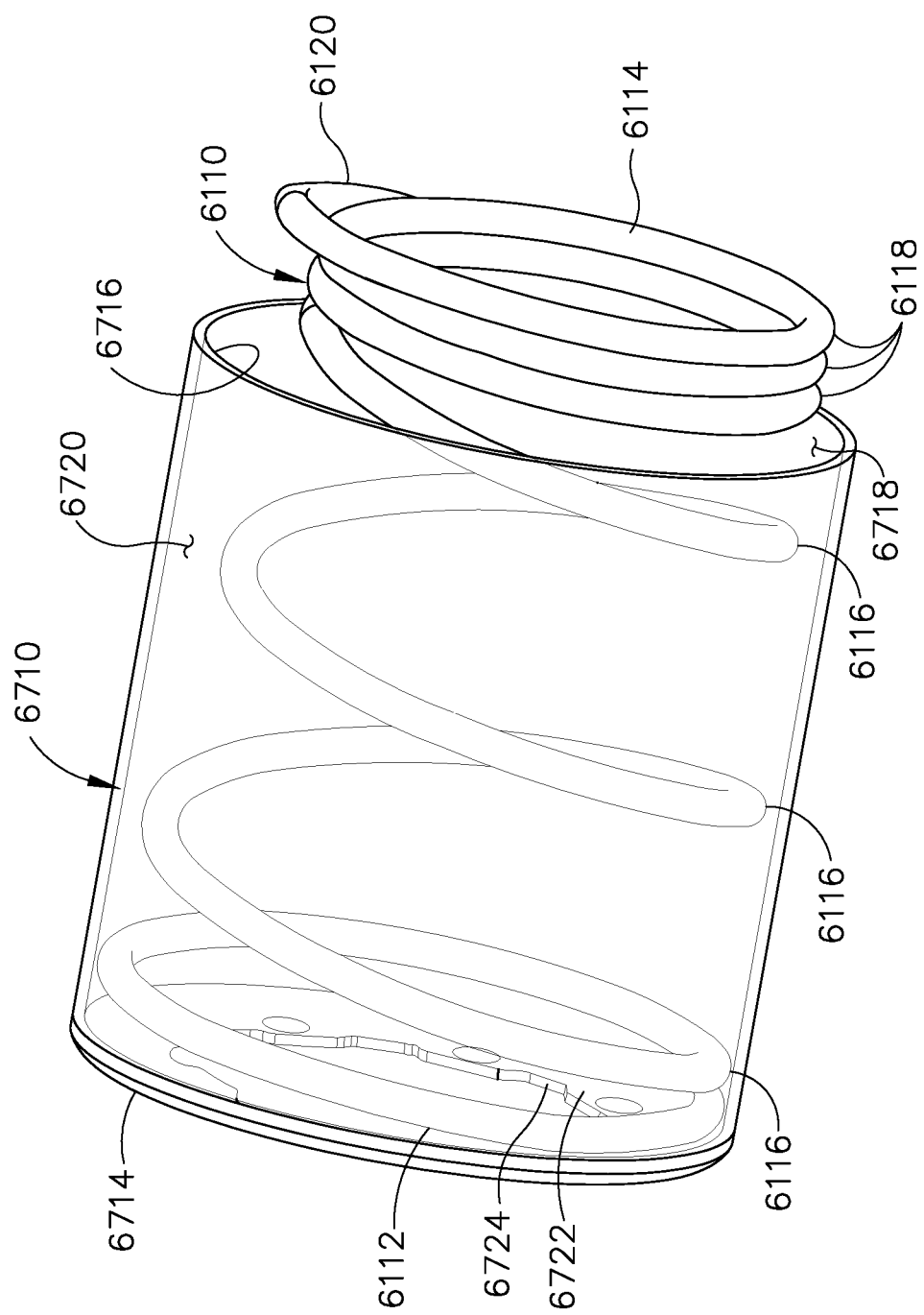
FIG. 74 depicts a detailed perspective view of the coil spring and the sleeve of FIG. 73.

FIGS. 73-74 show an exemplary sleeve (6710). FIG. 73 shows a perspective view of bracket (3650) and conical coil spring (6110) of FIG. 62, but with conical coil spring (6110) partially disposed within sleeve (6710). FIG. 74 shows a detailed perspective view of conical coil spring (6110) and sleeve (6710) of FIG. 73. Sleeve (6710) includes a body (6712) having proximal and distal ends (6714, 6716). Body (6712) includes inner and outer surfaces (6718, 6720). Sleeve (6710) includes a proximal wall (6722) and an inner opening (6724) configured to allow trocar actuation rod (220) to extend therethrough. Sleeve (6710) circumferentially surrounds proximal end (6112) of conical coil spring (6110) and is configured to prevent proximal end (6112), i.e. the tail, from being inadvertently pinched. Sleeve (6710) may be incorporated into instrument (10) alternatively, or in addition to, incorporating conical coil spring (6110, 6210, 6310) in place of coil spring (170).

XI. Exemplary Chassis

A. Left Chassis Portion without Longitudinal Rib

Figure 75:
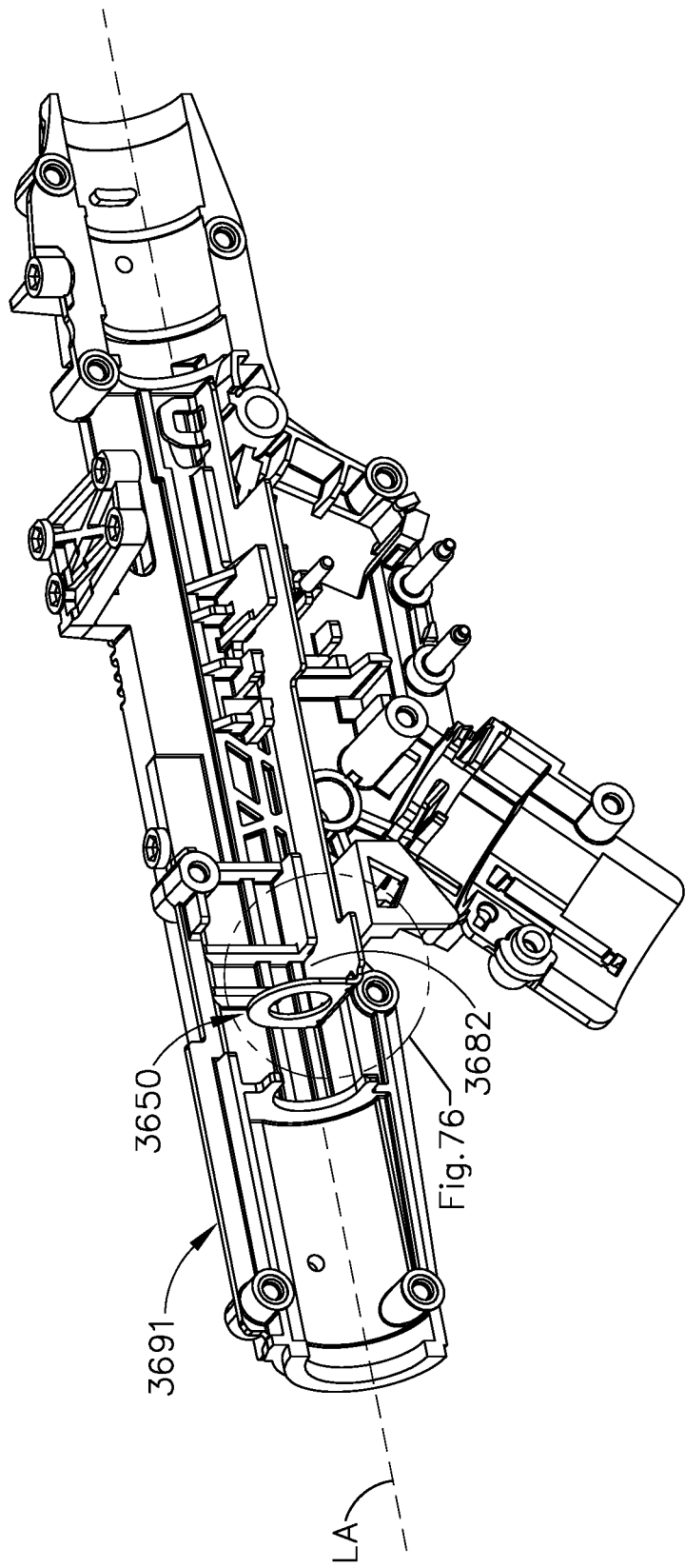
FIG. 75 depicts a perspective view of the bracket of FIG. 35 disposed within the left chassis portion.
Figure 76:
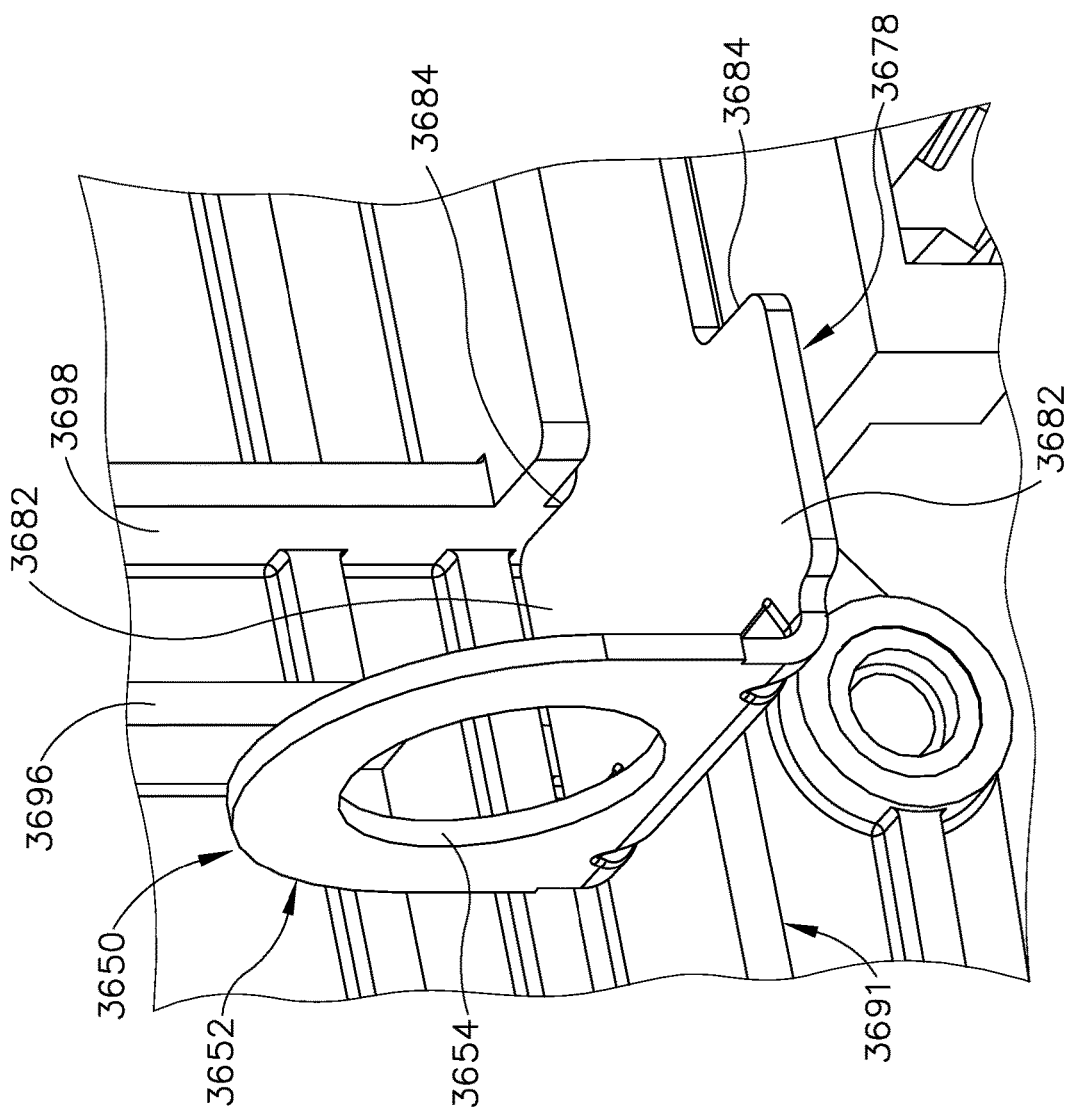
FIG. 76 depicts a detailed perspective view of the bracket and the left chassis portion of FIG. 75.
Figure 77:
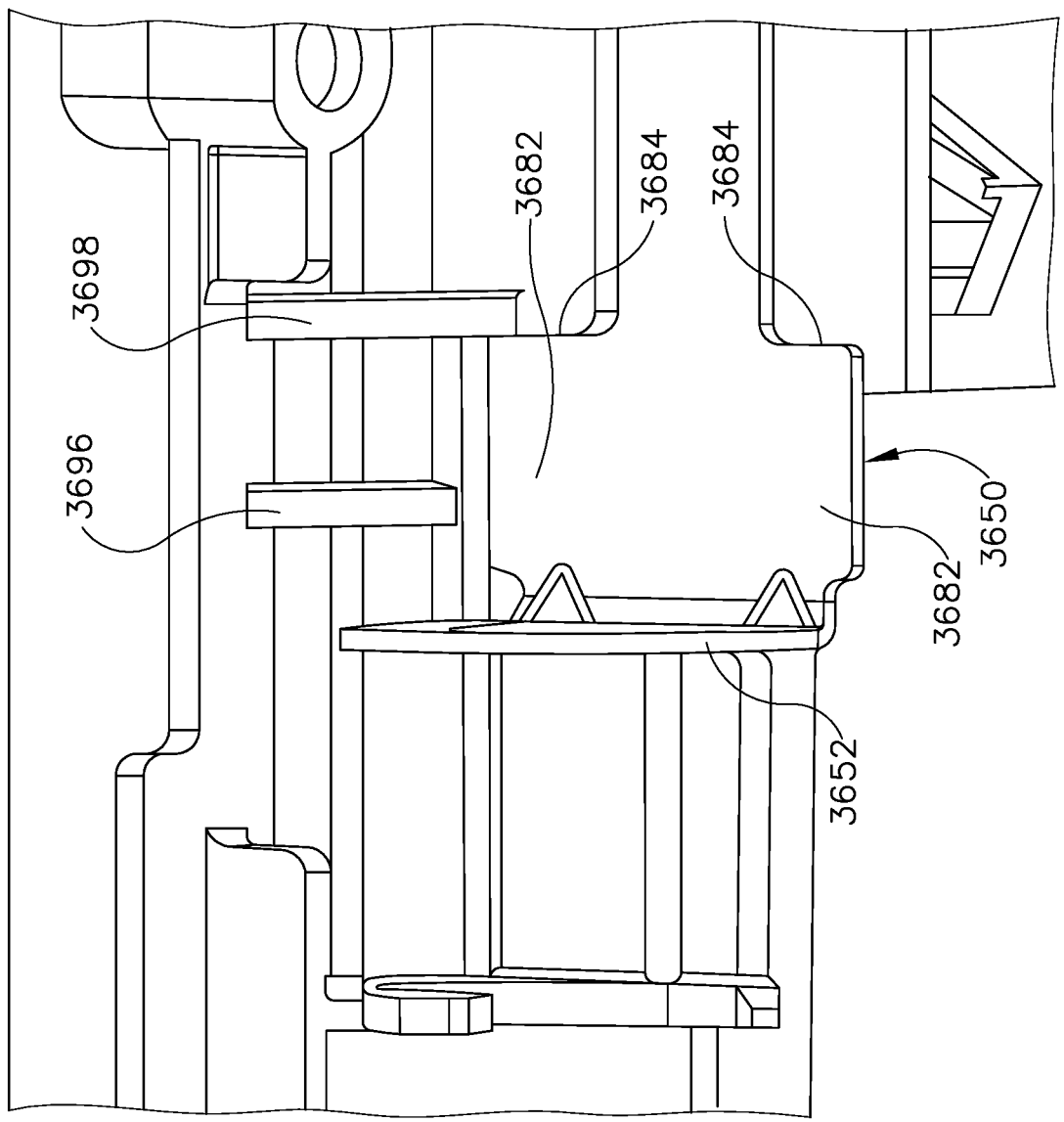
FIG. 77 depicts a perspective view of the bracket and the left chassis portion of FIG. 76 but from another angle.

FIGS. 75-77 show various views of bracket (3650) of FIG. 35 disposed within left chassis portion (3691). FIG. 76 shows a detailed perspective view of bracket (3650) and left chassis portion (3691) of FIG. 75. FIG. 77 shows a perspective view of bracket (3650) and left chassis portion (3691) of FIG. 76 from another angle. As shown, left chassis portion (3691) includes first and second vertically extending ribs (3696, 3698) that extend generally perpendicular to longitudinal axis (LA).

B. Exemplary Left Chassis Portion with Longitudinal Rib

Figure 78:
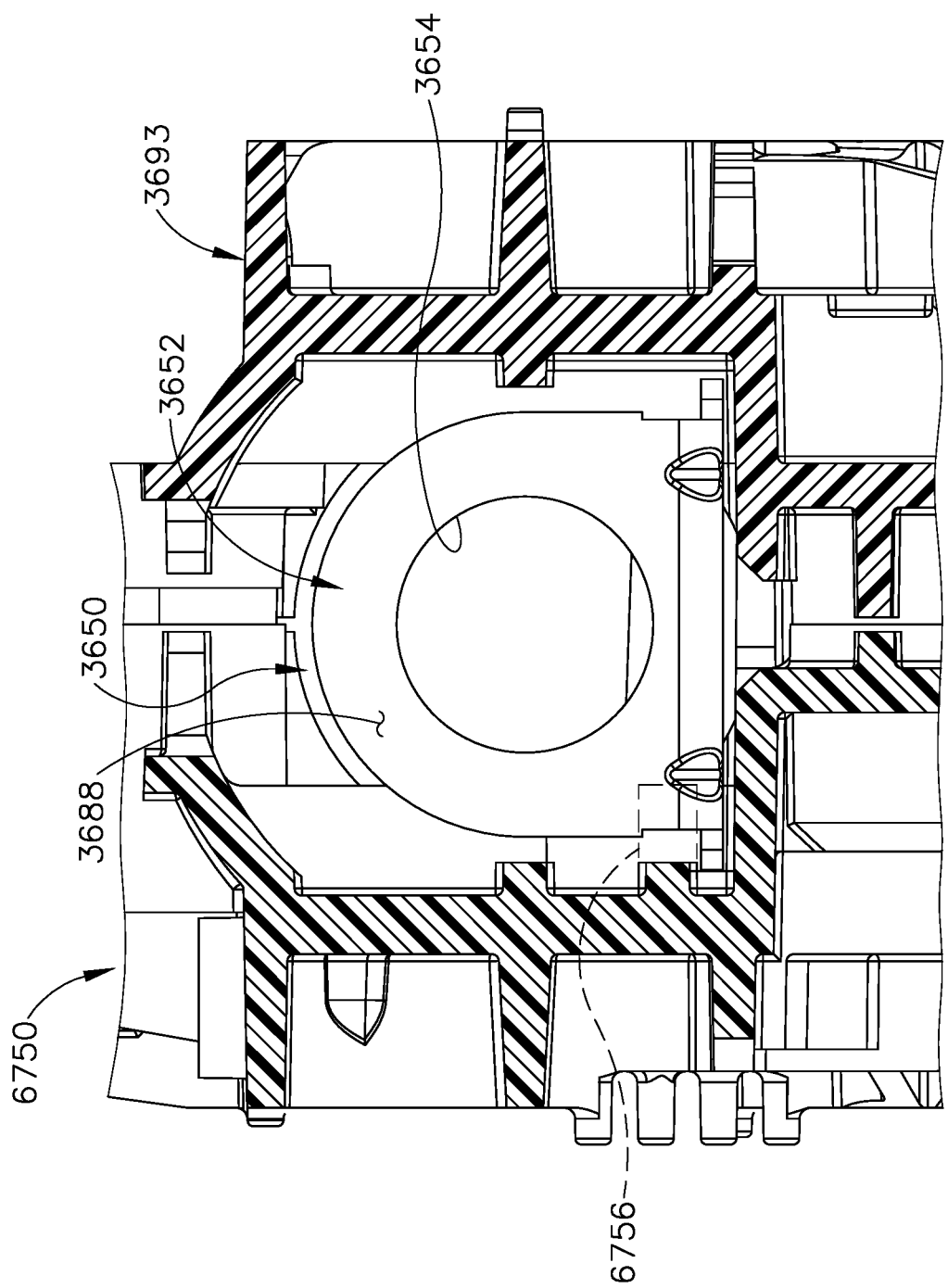
FIG. 78 depicts a rear elevational view of the bracket and left chassis portion of FIG. 75, but with the left chassis portion including a longitudinal rib.
Figure 79:
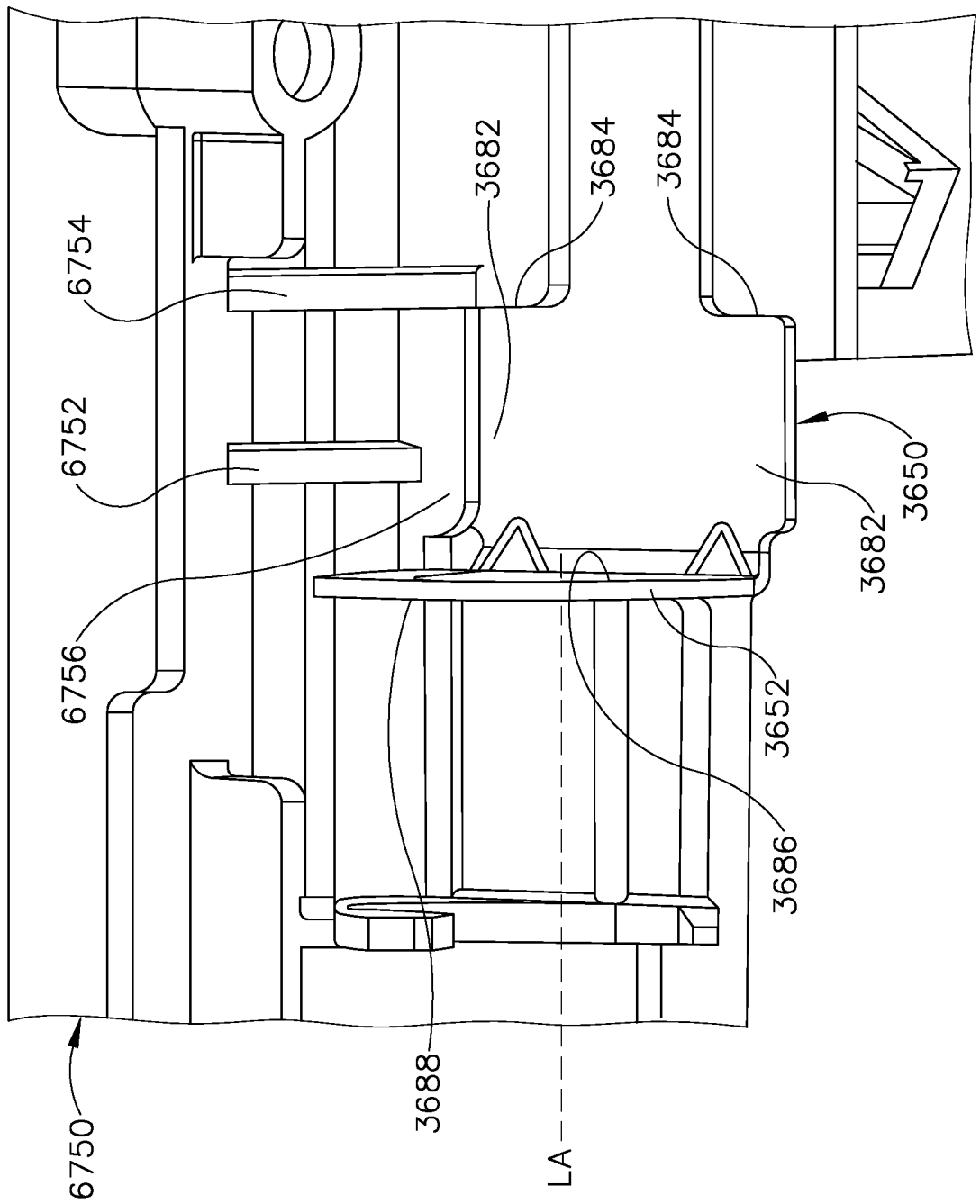
FIG. 79 depicts a right perspective view of the bracket and the left chassis portion of FIG. 78.

FIGS. 78-79 depict an exemplary alternative left chassis portion (6750) that is similar to left chassis portion (3691), but with left chassis portion (6750) including a longitudinal rib (6756). FIG. 78 shows a rear elevational view of bracket (3650) of FIG. 35 disposed within left chassis portion (6750)

of longitudinal rib (6756). FIG. 79 shows a right perspective view of bracket (3650) and left chassis portion (6750) of FIG. 78.

Proximal portion (3678) of bracket (3650) includes flared-out portions (3682) disposed along longitudinal axis (LA). Proximal portion (3678) also includes upright member (3652) disposed perpendicular to flared-out portion (3682). Flared-out portions (3682) include a flared-out distal surface (3684). Upright member (3652) of bracket (3650) includes inner and outer surfaces (3686, 3688). Left chassis portion (6750) includes first and second vertically extending ribs (6752, 6754) that extend generally perpendicular to longitudinal axis (LA). Longitudinally extending rib (6756) extends generally parallel to longitudinal axis (LA) and abuts first vertically extending rib (6752). Longitudinally extending rib (6756) is configured to prevent bracket (3650) from contacting first vertically extending rib (6752). As a result, longitudinal rib (6756) may prevent bracket (3650) from become fixed (e.g. stuck). Second vertically extending rib (6754) abuts longitudinally extending rib (6756). Coil spring (170) or conical coil spring (6110, 6210, 6310) is configured to be disposed between upright member (3652) of bracket (3650) and nut (160).

XII. Exemplary Guidance Track

A. Guidance Track without Raised Portion

Figure 80:
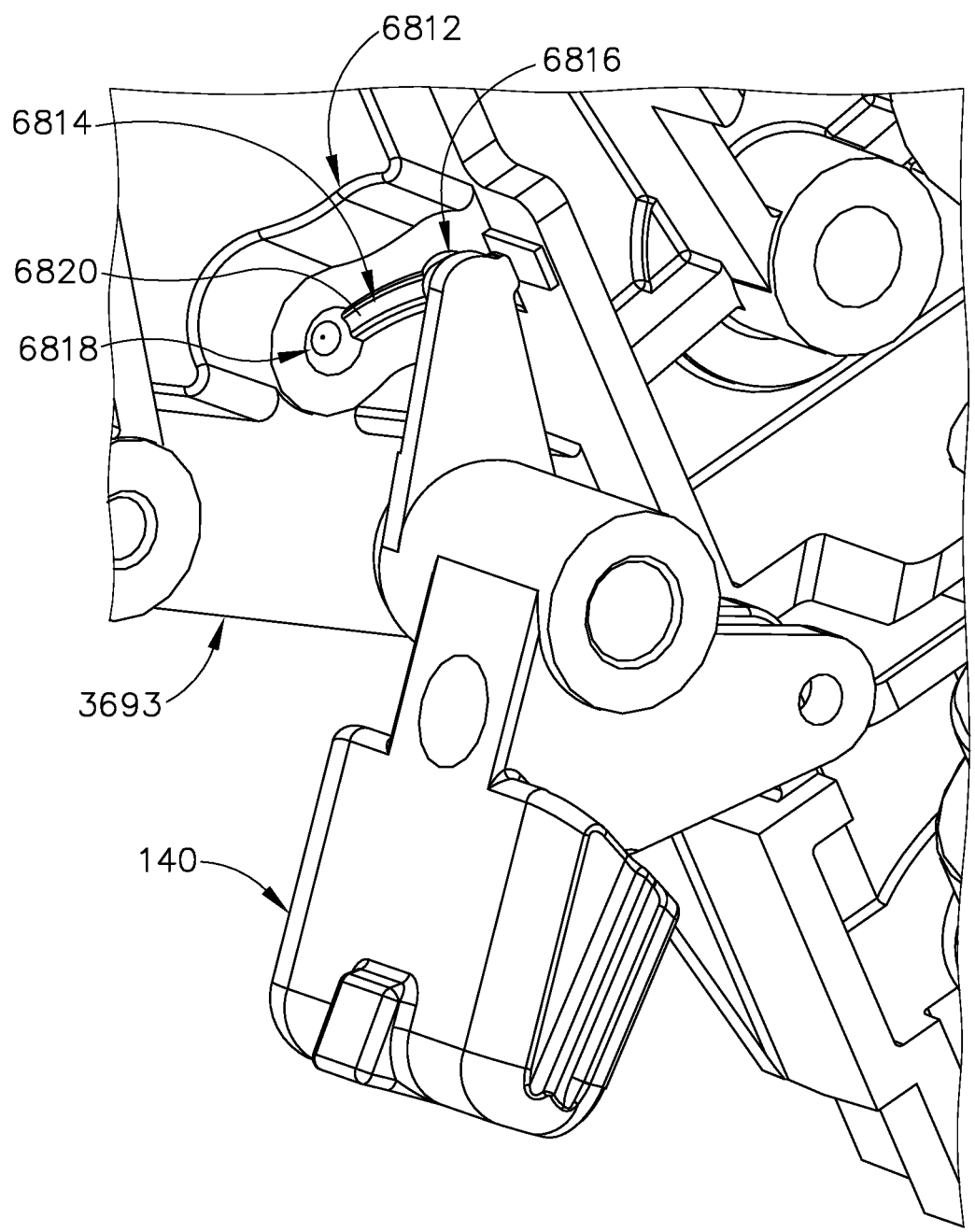
FIG. 80 depicts a perspective view of a protrusion of a safety trigger interacting with a track bounded by first and second detents of right chassis portion of FIG. 18.

FIG. 80 shows a perspective view of protrusion (141) of safety trigger (140) of FIG. 31 interacting with right chassis portion (3693) of FIG. 18 taken from another angle. As shown, right chassis portion (3693) includes a projecting portion (6812). Projecting portion (6812) includes a guidance track (6814). Guidance track (6814) includes first and second detents (6816, 6818) separated by a channel (6820). First detent (6816) is configured to receive protrusion (141) of safety trigger (140) in the safety engaged position (i.e. locked out position). Second detent (6818) is configured to receive protrusion (141) of safety trigger (140) in the safety disengaged position (i.e. ready to be fired position). Channel (6820) is configured to receive protrusion (141) of safety trigger (140) when safety trigger (140) is moved between the safety engaged and the safety disengaged positions. Safety trigger (140) is configured to transition when selectively activated by the user from the engaged position that prevents actuation of instrument (10) to the disengaged position that enables actuation of instrument (10).

In other words, protrusion (141) is configured to cooperate with first detent (6816) of right chassis portion (3693), to selectively retain safety trigger (140) in the flipped-up position shown in FIGS. 30D-30E. Protrusion (141) is configured to prevent inadvertent movement of safety trigger (140) from the flipped-up position (FIGS. 30D-30E) to the flipped-down position (FIGS. 30A-30C).

B. Exemplary Guidance Track with Raised Portion

As previously described with reference to FIG. 80, safety trigger (140) is configured to transition when selectively activated by the user from the engaged position that prevents actuation of the instrument (e.g. instrument (10)) to the disengaged position that enables actuation of the instrument. It is desirable to allow safety trigger (140) to only be actuated within the desired tissue gap range. When safety trigger (140) is left in an intermediate position (not within first and second detents (6816, 6818) of guidance track (6814)), it may be possible to fire instrument (10). As such, it would desirable to prevent safety trigger (140) from being able to rest in the intermediate position, which may be outside of the indicated desired tissue gap range. Preventing safety trigger (140) from remaining in the intermediate position may be obtained by forcing safety trigger (140) to one of only the two following acceptable positions: (1) the safety engaged position (i.e. locked out), or (2) the safety disengaged position (i.e. ready to be fired).

Figure 81:
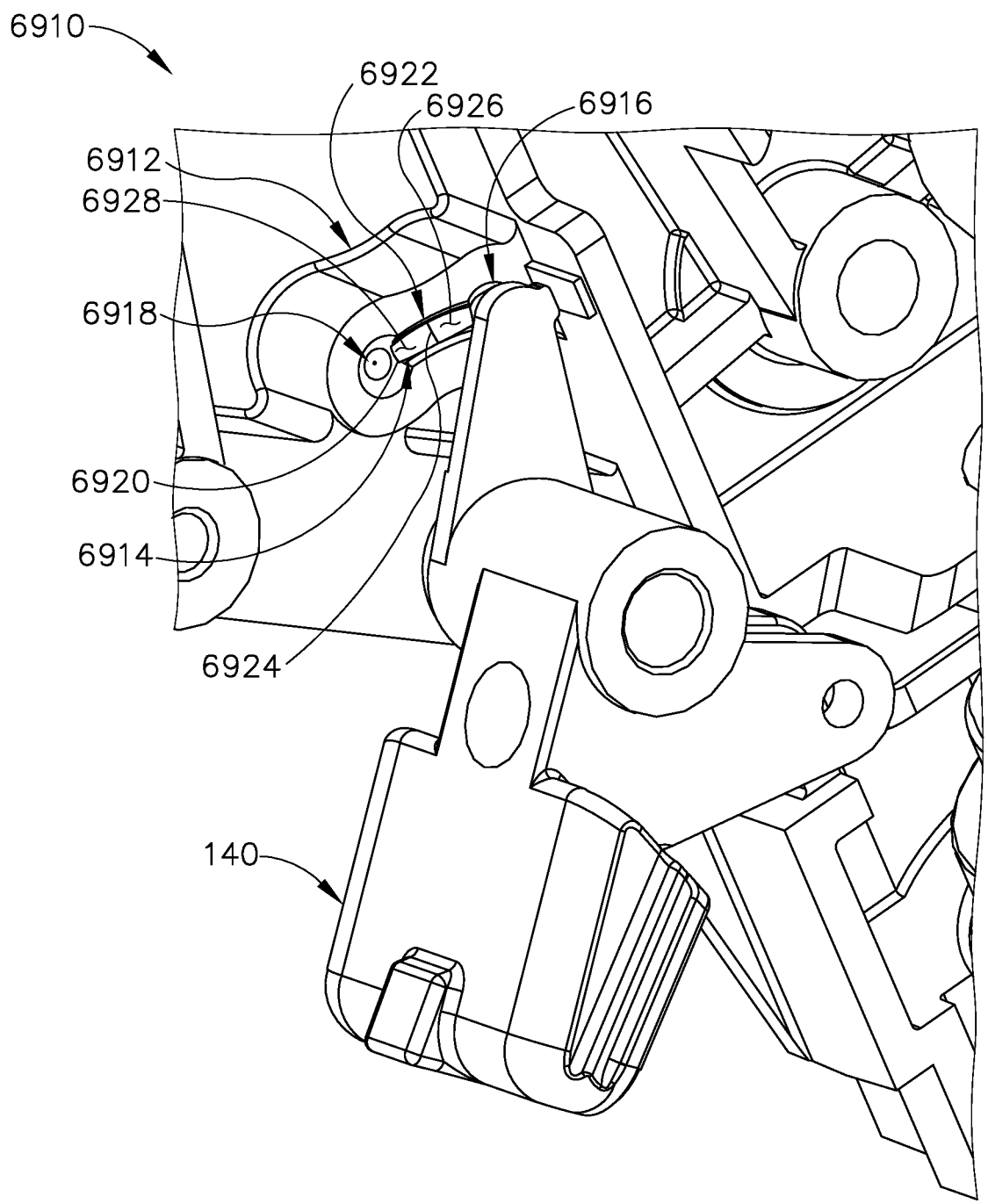
FIG. 81 depicts a perspective view of the protrusion of the safety trigger of FIG. 80 interacting with another exemplary right chassis portion that includes a raised portion between the first and second detents.

FIG. 81 shows a perspective view of protrusion (141) of safety trigger (140) interacting with an exemplary alternative right chassis portion (6910). Right chassis portion (6910) includes a projecting portion (6912). Projecting portion (6912) includes a guidance track (6914). Guidance track (6914) includes a first detent (6916), a second detent (6918), a channel (6920), and a raised portion (6922). Unlike FIG. 80 that does not include raised portion (6922), guidance track (6914) of FIG. 81 includes raised portion (6922) that protrudes outwardly (e.g. upwardly) from channel (6920). Raised portion (6922) is configured to force safety trigger (140) to either the engaged position or the disengaged position, and not allow safety trigger (140) in remain in an intermediate position. In other words, raised portion (6922) of guidance track (6914) forces one of two discrete positions that force binary on/off of safety trigger (140) that may prevent firing outside the desired tissue gap range.

As shown in FIG. 81, raised portion (6922) includes a peak (6924) that defines a furthermost point that raised portion (6922) is disposed away from the surface of channel (6920). As shown, peak (6924) is disposed centrally (i.e. in the middle between) between first and second detents (6916, 6918). Raised portion (6922) includes a first downwardly sloping surface (6926) that slopes downwardly from peak (6924) to first detent (6916). Similarly, raised portion (6922) includes a second downwardly sloping surface (6928) that slopes downwardly from peak (6924) to second detent (6918). As shown, first downwardly sloping surface (6926) slopes downwardly the entire distance between peak (6924) and first detent (6916), and second downwardly sloping surface (6928) slopes downwardly the entire distance between peak (6924) and second detent (6918). First and second downwardly sloping surfaces (6926, 6928) maintain the safety trigger (140) in either the safety engaged position or the safety disengaged position. As such, raised portion (6922) forces safety trigger (140) into one of only two acceptable positions—either (1) the safety engaged position (i.e. locked out), or (2) the safety disengaged position (i.e. ready to be fired). This may reduce the possibility that safety trigger (140) may be left in the intermediate position between engaged and disengaged positions, which would be undesirable.

First detent (6916) is configured to receive protrusion (141) of safety trigger (140) in the safety engaged position (i.e. locked out position). Second detent (6918) is configured to receive protrusion (141) of safety trigger (140) in the safety disengaged position (i.e. ready to be fired position). Raised portion (6922) is configured to receive protrusion (141) of safety trigger (140) when safety trigger (140) is moved between the engaged and disengaged positions. As shown, guidance track (6914) is integrally formed together as a unitary piece together with right chassis portion (6910).

XIII. Illumination of User Feedback Feature by Main Circuit Board Assembly

A. Overview of User Feedback Feature and Main Circuit Board Assembly

Figure 82:
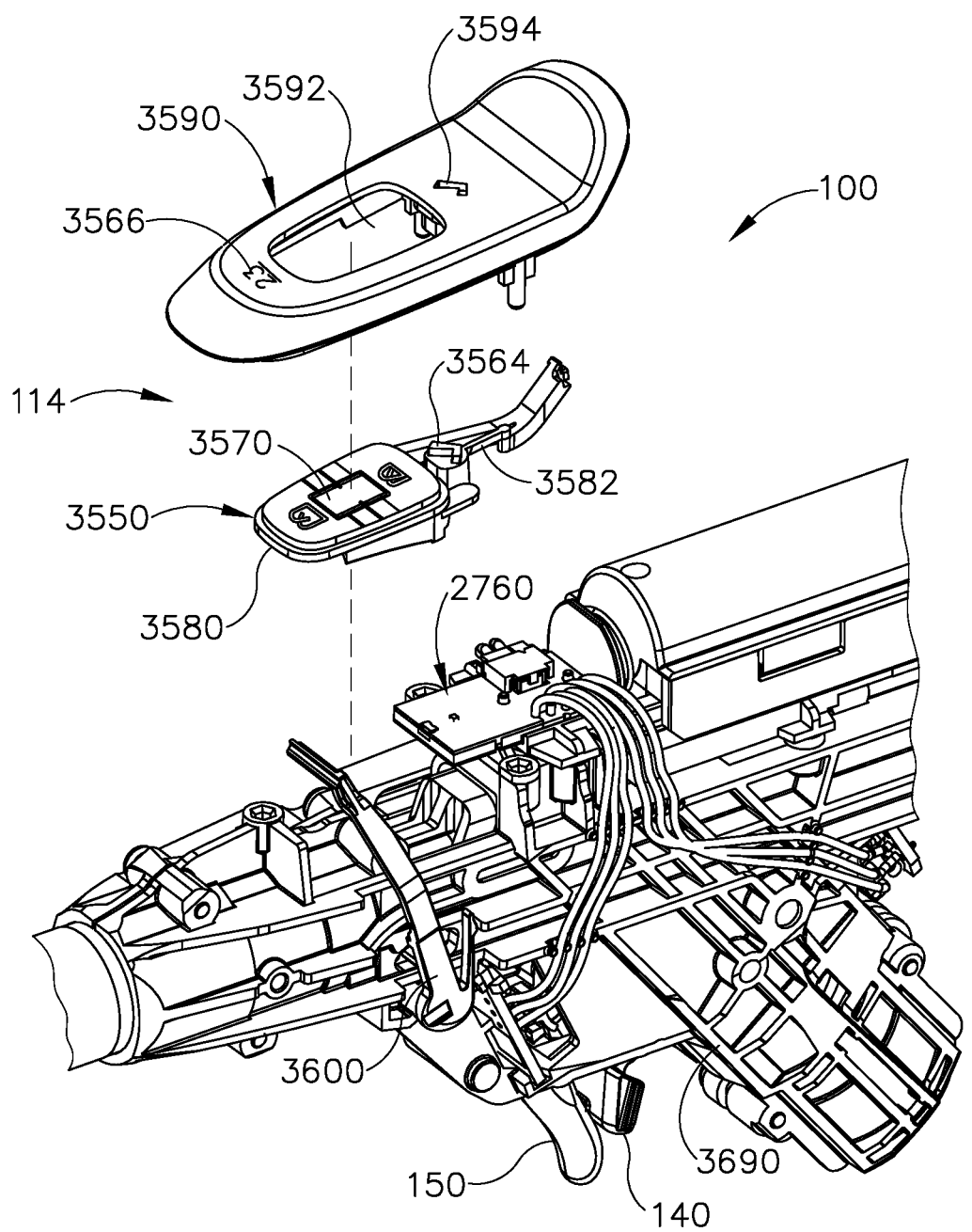
FIG. 82 depicts a partially exploded perspective view of a portion of the handle assembly of the surgical stapler of FIG. 1, with a housing portion of the handle assembly omitted, and showing a lens member and a cover plate of the user feedback feature of FIG. 32 separated from the handle assembly.
Figure 83:
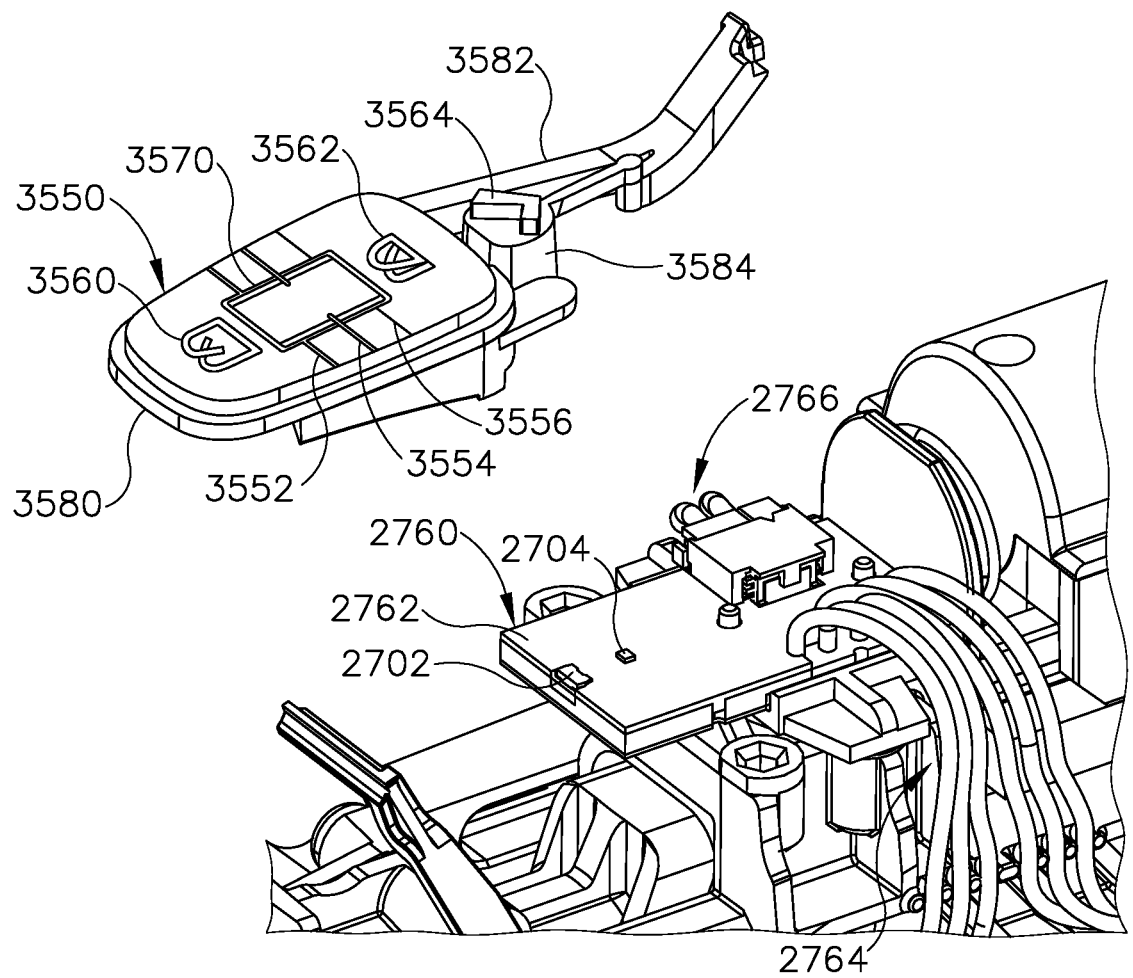
FIG. 83 depicts an enlarged perspective view of the lens member and a main circuit board assembly of the handle assembly of FIG. 82.

FIGS. 82 and 83 show additional details of user feedback feature (114) of handle assembly (100) and a main circuit board assembly (2760) of control circuit (2700) over which user feedback feature (114) is positioned. As described above in connection with FIG. 32, user feedback feature (114) includes several feedback elements configured to enable a user to monitor certain conditions of instrument (10). One such condition is a closure position of anvil (400)

relative to deck member (320) of stapling head assembly (300), and a resulting height of staples to be formed in the tissue, indicated via a longitudinal position of indicator needle (1526) within window (3570) of lens member (3550). Another such condition is whether the actuation stroke (or "firing stroke") of stapling head assembly (300) has been completed, indicated via illumination of checkmark feature (3564) of lens member (3550). As also described above, window (3570) is illuminated by a first LED (2702) and checkmark feature (3564) is illuminated by a second LED (2704), both LEDs (2702, 2704) being components of main circuit board assembly (2760). In the present version, window (3570) and first LED (2702) are arranged distally, and checkmark feature (3564) and second LED (2704) are arranged proximally.

As shown in FIGS. 82 and 83, a cover plate (3590) of user feedback feature (114) is positioned over lens member (3550), which in turn is positioned over main circuit board assembly (2760). Cover plate (3590) includes a central opening (3592) configured to receive a primary body portion (3580) of lens member (3550). Proximally of central opening (3592), cover plate (3590) further includes a checkmark-shaped opening (3594) configured to receive a secondary body portion (3582) of lens member (3550) that defines checkmark feature (3564). Distally of central opening (3592), cover plate (3590) of further includes indicia field (3566), which indicates a size of stapling head assembly (300) in the present version. As shown best in FIG. 82, lens member (3550) of the present example is formed as a unitary structure having primary body portion (3580) and secondary body portion (3582) extending proximally from primary body portion (3580). Primary body portion (3580) defines window (3570) and includes fixed linear indicia (3552, 3554, 3556) and staple graphics (3560, 3562). Secondary body portion (3582) includes a cap feature (3584) having a closed upper end that defines checkmark feature (3564).

As shown best in FIG. 83, main circuit board assembly (2760) of control circuit (2700) is supported by handle assembly chassis (3690) at a location beneath user feedback feature (114). Main circuit board assembly (2760) of the present version includes a circuit board (2762) that is electrically coupled with motor activation module (180) and motor stop module (190) via a first plurality of wires (2764) on a first lateral side of circuit board (2762); and is electrically coupled with motor (161) via a second plurality of wires (2766) on a second lateral side of circuit board (2762). In the present example, circuit board (2762) is electrically coupled with anvil dome switch (2610) via motor activation module (180).

B. Exemplary Alternative Main Circuit Board Assembly Having Light Directing Features In some instances, it may be desirable to configure main circuit board assembly (2760) with features that control the illumination effects of each LED (2702, 2704). For instance, it may be desirable to provide features that inhibit window backlighting LED (2702) from illuminating checkmark feature (3564), thereby preventing false indications of firing stroke completion to the user. Such features may thus enable a user to ensure that the distal end of surgical instrument (10) remains stabilized within the patient during a surgical procedure until the firing stroke is indeed complete. Such features may thus enhance user confidence in safe and precise operation of instrument (10) during a surgical procedure.

Figure 84:
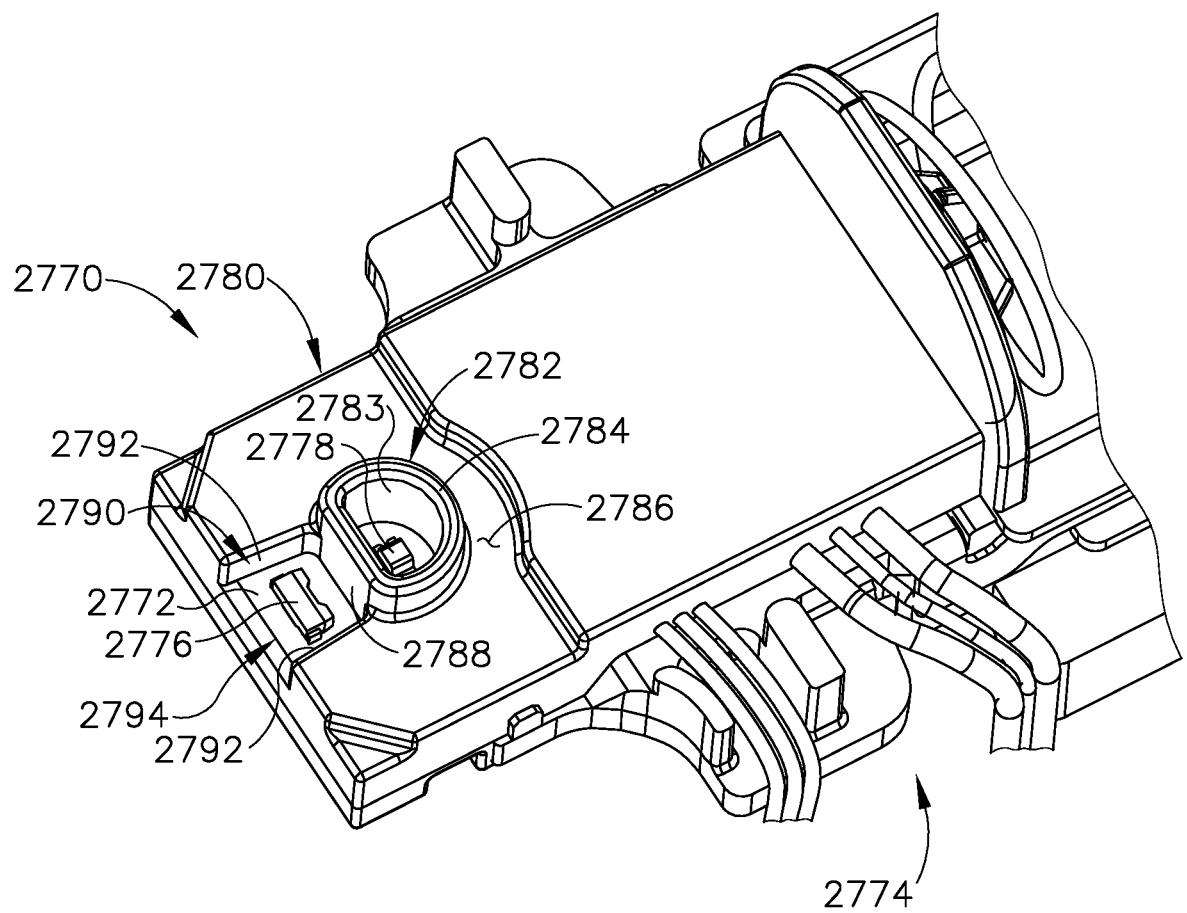
FIG. 84 depicts a perspective view of an exemplary alternative main circuit board assembly configured for use with the handle assembly of FIG. 82.
Figure 85:
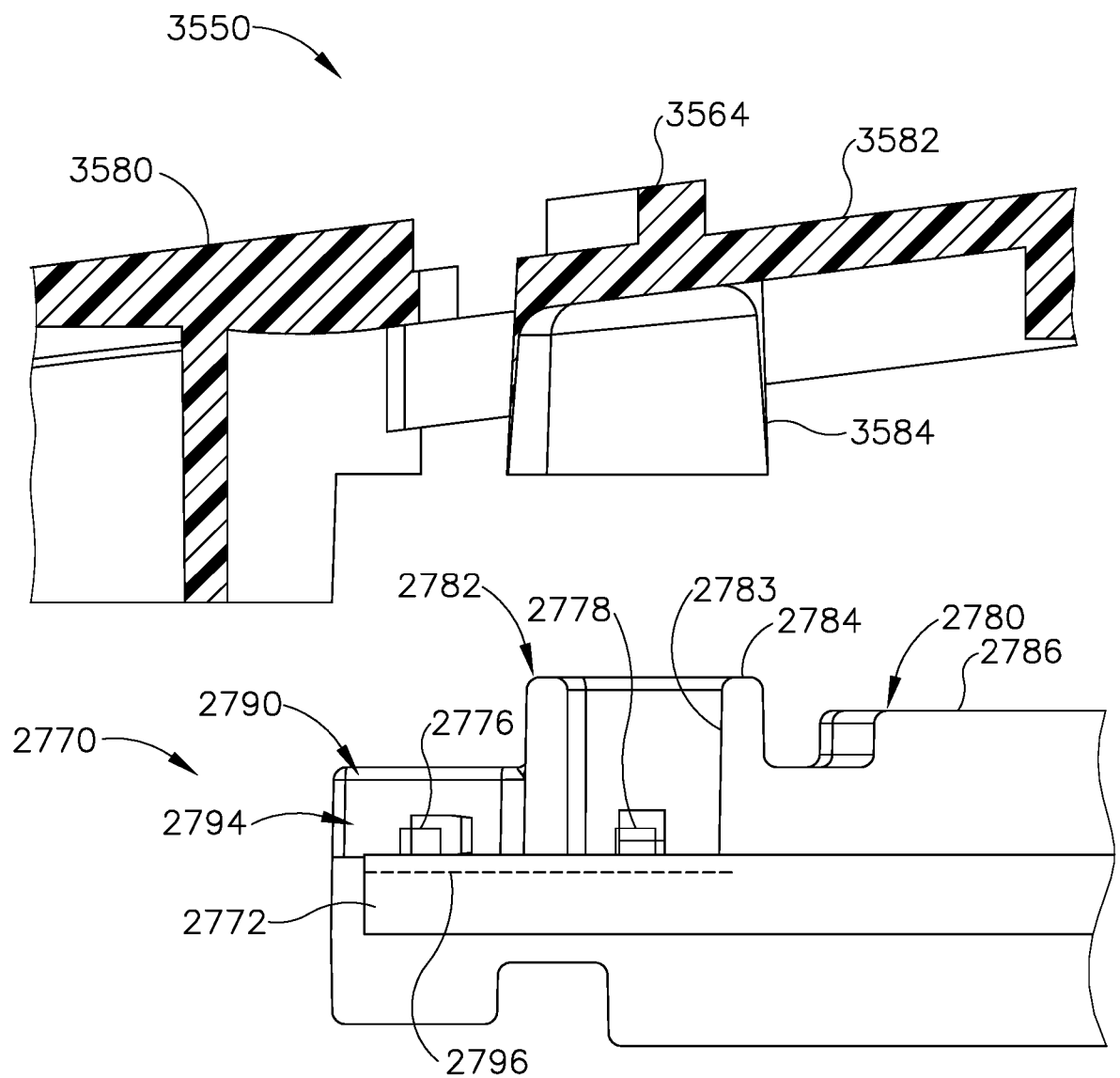
FIG. 85 depicts a side cross-sectional view of a distal portion of the main circuit board assembly of FIG. 84 and a proximal portion of the lens member of the user feedback feature of FIG. 82, showing a proximal light guide feature of the lens member positioned to receive a distal light guide feature of the main circuit board assembly.

FIGS. 84 and 85 show another exemplary main circuit board assembly (2770) configured for use with control circuit (2700) of surgical instrument (10), and which is similar to main circuit board assembly (2760) described above except as otherwise described below. Like main circuit board assembly (2760), main circuit board assembly (2770) is configured to be supported by handle assembly chassis (3690) at a location beneath user feedback feature (114). Main circuit board assembly (2770) includes a circuit board (2772) that is electrically coupled with motor activation module (180), motor stop module (190), and motor (161) via wires (2774). A first LED (2776) is arranged at a distal end of an upper side of circuit board (2772), and a second LED (2778) is arranged proximal to first LED (2776) on the upper side of circuit board (2772). LEDs (2776, 2778) may be similar in structure and function to LEDS (2702, 2704) of circuit board assembly (2760) described above, and are configured to illuminate the undersides of window (3570) and checkmark feature (3564), respectively, of user feedback feature (114).

Main circuit board assembly (2770) of the present example further includes an opaque conformal coating (2780) that encapsulates circuit board (2772) while leaving LEDs (2776, 2778) exposed. Opaque coating (2780) is formed of an opaque, liquid-impermeable material configured to inhibit liquid ingress and also directionally limit the illumination provided by LEDs. In some versions, opaque coating (2780) may be formed of a black material, such as a carbon-infused material. Opaque coating (2780) of the present example defines a first light guide feature in the form of a generally cylindrical projection (2782) that encircles second LED (2778) and extends upwardly from circuit board (2772) to define an upper edge (2784) that is raised above an upper surface (2786) of coating (2780) that spans laterally across circuit board (2772). A distal side of cylindrical projection (2782) includes a flat wall (2788) that confronts first LED (2776). Opaque coating (2780) further defines a second light guide feature in the form of a generally rectangular recess (2790) arranged distally of cylindrical projection (2782) and in which first LED (2776) is centrally positioned. Recess (2790) is defined by flat wall (2788) and a pair of laterally opposed side walls (2792) that extend distally from flat wall (2788) to a distal opening (2794) at a distal edge of circuit board.

As seen in FIGS. 84 and 85, an inner surface (2783) of cylindrical projection (2782) is spaced outwardly away from second LED (2778), and walls (2788, 2792) are spaced outwardly away from first LED (2776). Accordingly, light guide features (2782, 2790) of opaque conformal coating (2780) are configured to direct light emitted by LEDs (2776, 2778) without obstructing LEDs (2776, 2778) themselves, while simultaneously inhibiting fluid ingress. It will be appreciated that LEDs (2776, 2778) and the corresponding exposed portions of circuit board (2772) to which LEDS (2776, 2778) are mounted may be coated with a translucent liquid-impermeable coating that inhibits liquid ingress while permitting light transmission therethrough.

As shown in FIG. 85, cap feature (3584) of secondary body portion (3582) of lens member (3550) is sized to receive therein and thereby mate with an upper portion of cylindrical projection (2782) of opaque conformal coating (2780). Cap feature (3584) and cylindrical projection (2782) cooperate to guide light emitted by second LED (2778) directly toward checkmark feature (3564), such that cap feature (3584) and cylindrical projection (2782) function as a "light pipe" structure. Simultaneously, cylindrical projection (2782) and optionally also cap feature (3584) block light emitted by first LED (2776) from reaching checkmark feature (3564). In that regard, the cylindrical sidewall of cap feature (3584) may be formed of an opaque material that inhibits light transmission therethrough, similar to cylindrical projection (2782).

In addition to inhibiting light emitted by first LED (2776) from reaching and illuminating checkmark feature (3564), distal wall (2788) of cylindrical projection (2782) may be configured to deflect the light emitted by first LED (2776) distally toward window (3570) of user feedback feature (114). Additionally, lateral sidewalls (2792) of recess (2790) may laterally constrain the light emitted by first LED (2776) so that the emitted light is focused directly upwardly and distally toward window (3570). In this manner, light guide features (2782, 2790) defined by opaque conformal coating (2780) of main circuit board assembly (2770) advantageously focus the light emitted by LEDs (2776, 2778) in the direction of their intended target zones for illumination, with minimal or no illumination of unintended zones.

As shown schematically in FIG. 85, main circuit board assembly (2770) of the present version further includes a light blocking layer (2796) operable to inhibit light emitted by either LED (2776, 2778) from bleeding longitudinally through circuit board (2772) toward the opposing LED (2776, 2778). Light blocking layer (2796) of the present example is embedded within circuit board (2772) at a distal end thereof such that light blocking layer (2796) underlies first and second LEDs (2776, 2778). In other versions, light blocking layer (2796) may be formed on a top surface of circuit board (2772). Light blocking layer (2796) may be formed of any opaque material suitably configured to inhibit light passage therethrough. In some versions, light blocking layer (2796) may be formed of copper, such as the same copper that defines the electrically conductive traces of circuit board (2772), or any other metallic material (electrically conductive or otherwise). In other versions, light blocking layer (2796) may be formed of a polymeric material, such as a material suitable to simultaneously function as a solder mask over conductive traces of circuit board (2772).

XIV. Exemplary Additional Conformal Coatings for Electrical Components

As described above, opaque conformal coating (2780) is configured to inhibit light transmission as well as protect circuit board (2772) against fluid ingress. In some instances, it may be desirable to provide conformal coatings at additional locations of control circuit (2700) to protect against fluid ingress and also to strengthen mechanical connections between wires and the circuit board(s) to which they are connected.

Figure 86:
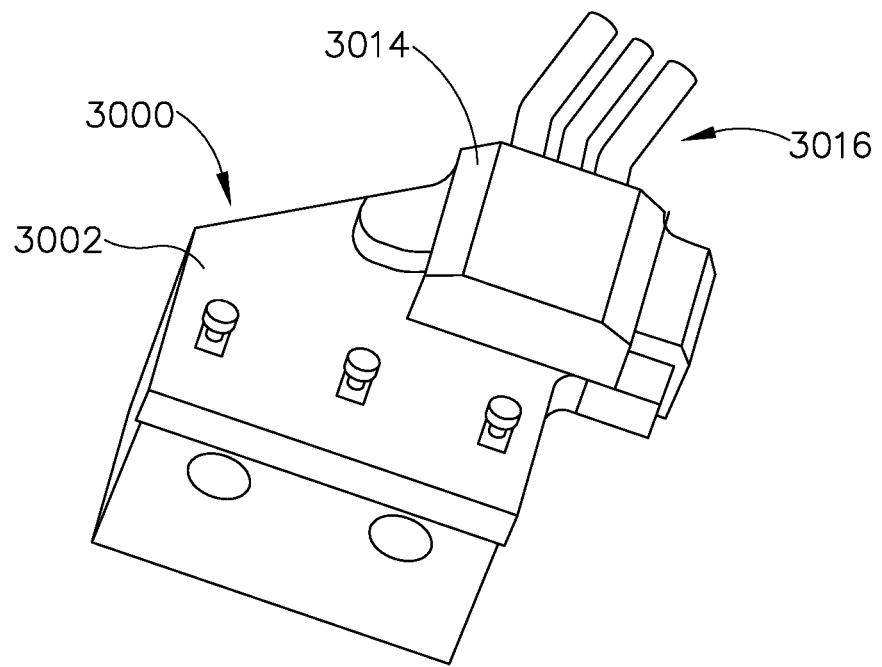
FIG. 86 depicts a perspective view of an exemplary circuit board assembly configured for use with the handle assembly of FIG. 82 and having a conformal coating.
Figure 87:
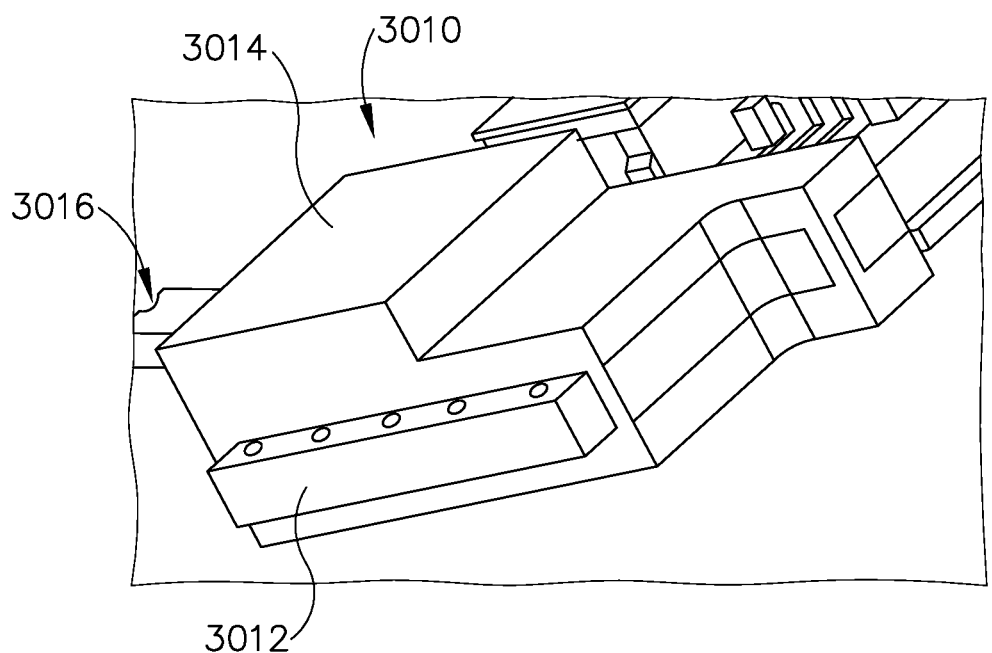
FIG. 87 depicts a perspective view of another exemplary circuit board assembly configured for use with the handle assembly of FIG. 82 and having a conformal coating.

FIG. 86 shows an exemplary circuit board assembly (3000) configured for use with handle assembly (100) and having a circuit board (3002) with a conformal coating (3004) of liquid-impermeable material formed about the junction between wires (3006) and circuit board (3002). FIG. 87 shows another exemplary circuit board assembly (3010) configured for use with handle assembly (100) and having a circuit board (3012) with a conformal coating (3014) of liquid-impermeable material formed about the junction between wires (3016) and circuit board (3012). As noted above, conformal coatings (3004, 3014) protect circuit boards (3002, 3012) against liquid ingress while also strengthening the mechanical connections between circuit boards (3002, 3012) and wires (3006, 3016), respectively. It will be appreciated that circuit board assemblies (3000, 3010) may be otherwise similar in structure and function to any of the exemplary circuit boards assemblies of control circuit (2700) described above.

XV. Exemplary Features for Calibrating Tissue Gap Green Zone of User Feedback Feature As described above in connection with FIG. 32, fixed linear indicia (3552, 3556) of user feedback feature (114) indicate respective ends of a "green zone" of axial spacing (or "tissue gap") between anvil (400) and stapling head assembly (300) that enables successful formation of staples fired into tissue by stapling head assembly (300). The longitudinal position of indicator needle (1526) relative to linear indicia (3552, 3556) may be observed by the operator through window (3570) of lens member (3550) to monitor the longitudinal position of anvil (400) relative to the boundaries of the green zone. In particular, a position of indicator needle (1526) closer to distal linear indicia (3552) indicates a larger tissue gap and a resulting taller height of the formed staples, as indicated by tall formed-staple graphic (3560) at the distal end of window (3570). Conversely, a position of indicator needle (1526) closer to proximal linear indicia (3556) indicates a smaller tissue gap and a resulting shorter height of the formed staples, as indicated by short formed-staple graphic (3562) at the proximal end of window (3570).

During manufacture of stapler instrument (10), instrument (10) may be calibrated such that indicator needle (1526) aligns with distal linear indicia (3552) to define the distal end of the green zone. The longitudinal position at which proximal linear indicia (3556) is fixed may then be calculated based on the position of distal linear indicia (3552) to define the proximal end of the green zone. In some instances, however, it may be desirable to calibrate user feedback feature (114) after manufacture and before or during use of instrument (10) so that proximal linear indicia (3554), and thus the proximal end of the green zone, aligns accurately with indicator needle (1526) when anvil (400) is in the fully closed state relative to stapling head assembly (300). The exemplary configurations described below in connection with FIGS. 88-94 enable such calibration.

A. Exemplary User Feedback Feature Having Sliding Shutter

Figure 88:
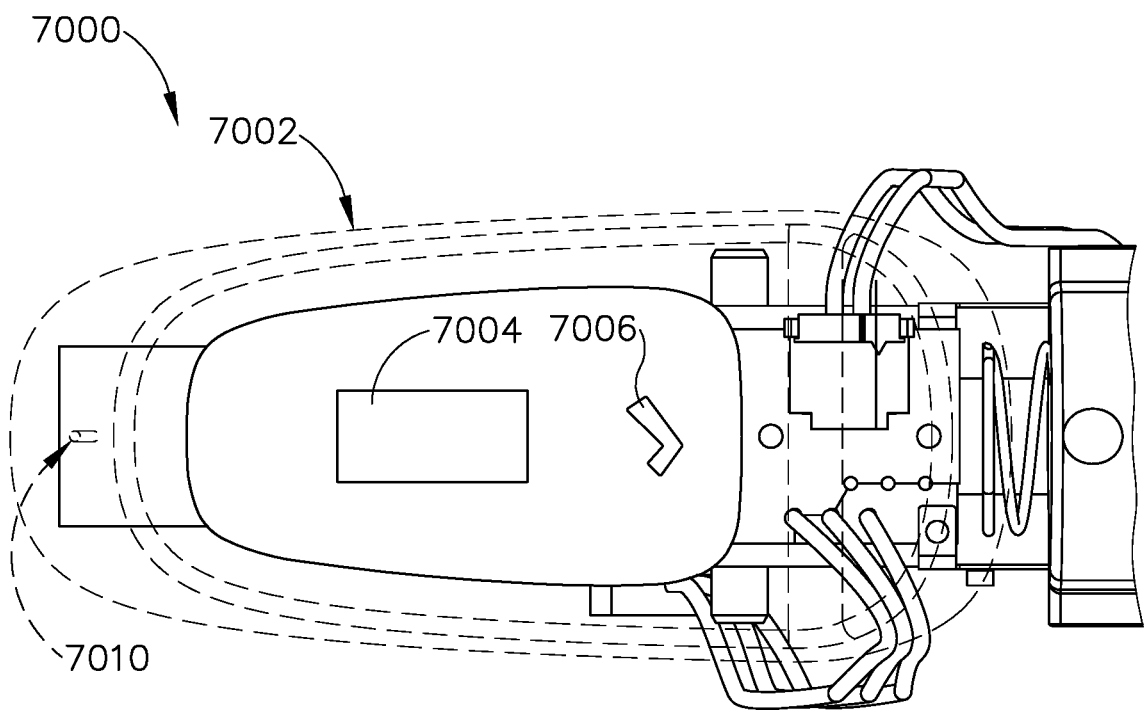
FIG. 88 depicts a top plan view of a portion of another exemplary user feedback feature configured for use with the handle assembly of FIG. 82 and having a cover plate and a slidable shutter configured to adjust a "green zone" visible through a window of the cover plate.
Figure 89:
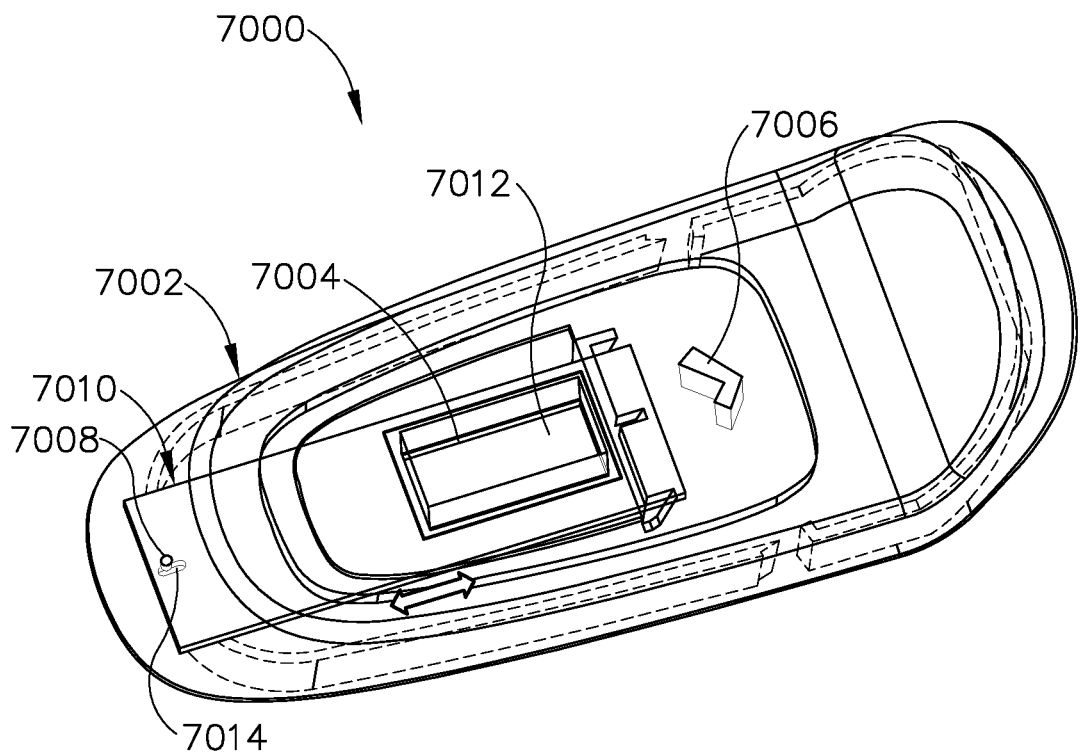
FIG. 89 depicts a perspective view of the cover plate and the slidable shutter of FIG. 88, with a portion of the cover plate shown transparently to reveal features of the slidable shutter.
Figure 90:
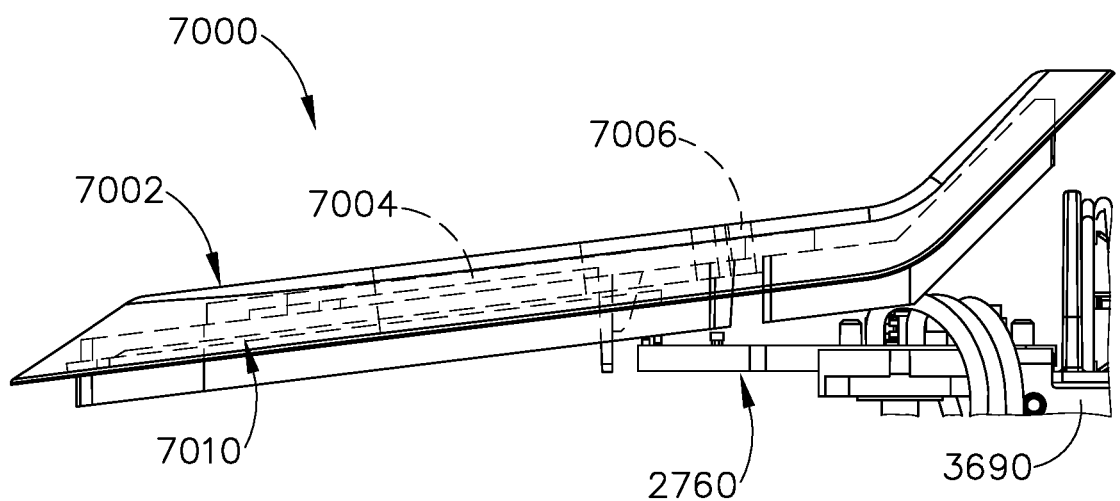
FIG. 90 depicts a side elevational view of the cover plate and the slidable shutter of FIG. 88, positioned atop a distal end of a main circuit board assembly of the surgical stapler of FIG. 1.

FIGS. 88-90 show another exemplary user feedback feature (7000) configured for use with handle assembly (100) of instrument (10), and which is similar to user feedback feature (114) described above except as otherwise described below. User feedback feature (7000) includes a cover plate (7002) configured to be positioned atop lens member (3550) at the distal end of handle assembly (100). Cover plate (7002) includes a centrally positioned rectangular opening (7004) through which linear indicia (3552, 3554, 3556), the corresponding green zone, and window (3570) of lens member (3550) are visible. Cover plate (7002) further includes a checkmark-shaped opening (7006) positioned proximal to rectangular opening (7004) and which is configured to provide visualization of checkmark feature (3564) of lens member (3550).

User feedback feature (7000) further includes a shutter (7010) slidably coupled to an underside of cover plate (7002). Shutter (7010) has a generally elongate rectangular body with a rectangular opening (7012) formed at a proximal end thereof such that opening (7012) is configured to align with rectangular opening (7004) of cover plate (7002). A distal end of shutter (7010) includes an elongate groove (7014) configured to receive the tip of an adjustable set screw (7008) that extends downwardly from cover plate (7002). Shutter (7010) is selectively adjustable in longitudinal position relative to cover plate (7002) to thereby locate shutter opening (7012) in a desired longitudinal position relative to cover plate opening (7004). In this manner, the user may selectively obscure or reveal a desired portion of the green zone of lens member (3550) to thereby adjust the proximal end of the green zone relative to indicator needle (1526) when anvil (400) is in a fully closed position, thereby calibrating user feedback feature (7000). Once calibrated, the longitudinal position of shutter (7010) may be fixed relative to cover plate (7002) via tightening of set screw (7008).

B. Exemplary User Feedback Feature Having Ratcheting Shutter

Figure 91:
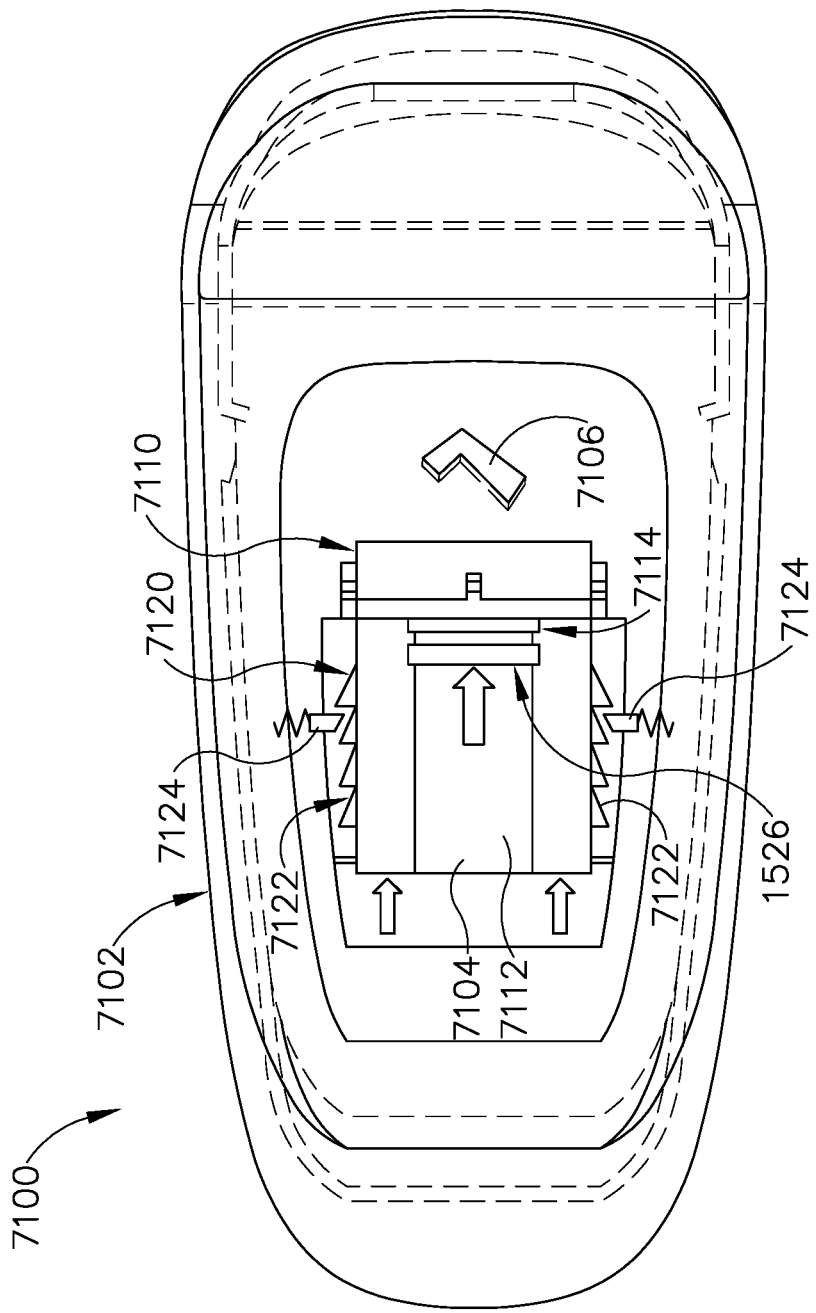
FIG. 91 depicts a top plan view of a portion of another exemplary user feedback feature configured for use with the handle assembly of FIG. 82 and having a cover plate and a ratcheting shutter configured to adjust a "green zone" visible through a window of the cover plate.

FIG. 91 shows another exemplary user feedback feature (7100) configured for use with handle assembly (100) and which is similar to user feedback features (114, 7000) described above except as otherwise described above. User feedback feature (7100) includes a cover plate (7102) configured to be positioned atop lens member (3550) at the distal end of handle assembly (100). Cover plate (7102) includes has a rectangular central opening (7104) through which linear indicia (3552, 3554, 3556), the corresponding green zone, and window (3570) of lens member (3550) are visible. Cover plate (7102) further includes a checkmark-shaped opening (7106) positioned proximal to rectangular opening (7104) and which is configured to provide visualization of checkmark feature (3564) of lens member (3550).

User feedback feature (7100) further includes a shutter (7110) movably coupled to an underside of cover plate (7102). Shutter (7110) has a generally U-shaped body defining an opening (7112) configured to align with rectangular opening (7112) of cover plate (7102) to reveal features of lens member (3550). A laterally extending rib (7114) is secured at a proximal end of opening (7112) and is configured to directly contact indicator needle (1526), as described below. Shutter (7110) is slidable longitudinally relative to cover plate (7102) and is biased distally in the present example by a resilient member shown in the formed of a compression spring (7116) disposed at the proximal end of shutter (7110).

A ratchet mechanism (7120) of user feedback feature (7100) is configured to releasably maintain a longitudinal position of shutter (7110) relative to cover plate (7102). Ratchet mechanism (7120) includes a pair of ratchet racks (7122), each secured to a respective lateral side of shutter (7110) and having a plurality of ratchet teeth, and a pair of spring biased pawl plungers (7124), each configured to releasably engage a respective one of the ratchet racks (7122). Pawl plungers (7124) may be anchored to cover plate (7102) or to a portion of handle assembly (100) positioned beneath cover plate (7102). As anvil (400) is retracted proximally toward stapling head assembly (300), indicator needle (1526) advances proximally within shutter opening (7112) and drives against shutter rib (7114), thereby driving shutter (7110) proximally against compression spring (7116) while ratchet mechanism (7120) prevents shutter (7110) from reverting distally. As shutter (7110) advances proximally, progressively more of the green zone of lens member (3550) is visually revealed through shutter opening (7112). Indicator needle (1526) remains in contact with shutter rib (7114) during proximal advancement such that upon anvil (400) reaching its fully closed position, indicator needle (1526) is positioned in alignment with the proximal end of the visible portion of the green zone. In this manner, user feedback feature (7100) automatically assumes a calibrated state throughout its use, without need for manual adjustment by the user.

C. Exemplary User Feedback Feature Having Display Screen

FIGS. 88-91 described above illustrate exemplary mechanical features that provide calibration of a user feedback feature (114, 7000, 7100). In some instances, it may be desirable to incorporate non-mechanical features that provide such calibration. FIG. 91A-92B show an exemplary user feedback feature (7200) configured for use with handle assembly (100) and which is similar to user feedback feature (114) described above except as otherwise described below. User feedback feature (7200) includes a cover plate (7202) having a central opening (7204) and a lens member (7210) received within and visible through central opening (7204).

Lens member (7210) is similar to lens member (3550) described above except that lens member (7210) includes a digital display (7212), such as a liquid crystal display (LCD) screen, configured to digitally display linear indicia (7214, 7216, 7218) and the corresponding green zone. Digital display (7212) is controlled by control circuit (2700), which may be configured to monitor proximal retraction of anvil (400) and automatically adjust the longitudinal position of proximal linear indicia (7218) (i.e., the proximal end of the green zone) displayed by digital display (7212) in real time during retraction. In this manner, control circuit (2700) may ensure that proximal linear indicia (7218) aligns with indicator needle (1526) visible through window (7220) when anvil (400) is in the fully closed position. It will be appreciated that digital display (7212) may be further configured to display various other types of information pertaining to surgical instrument (10) and/or use thereof.

Figures 92A, 92B:
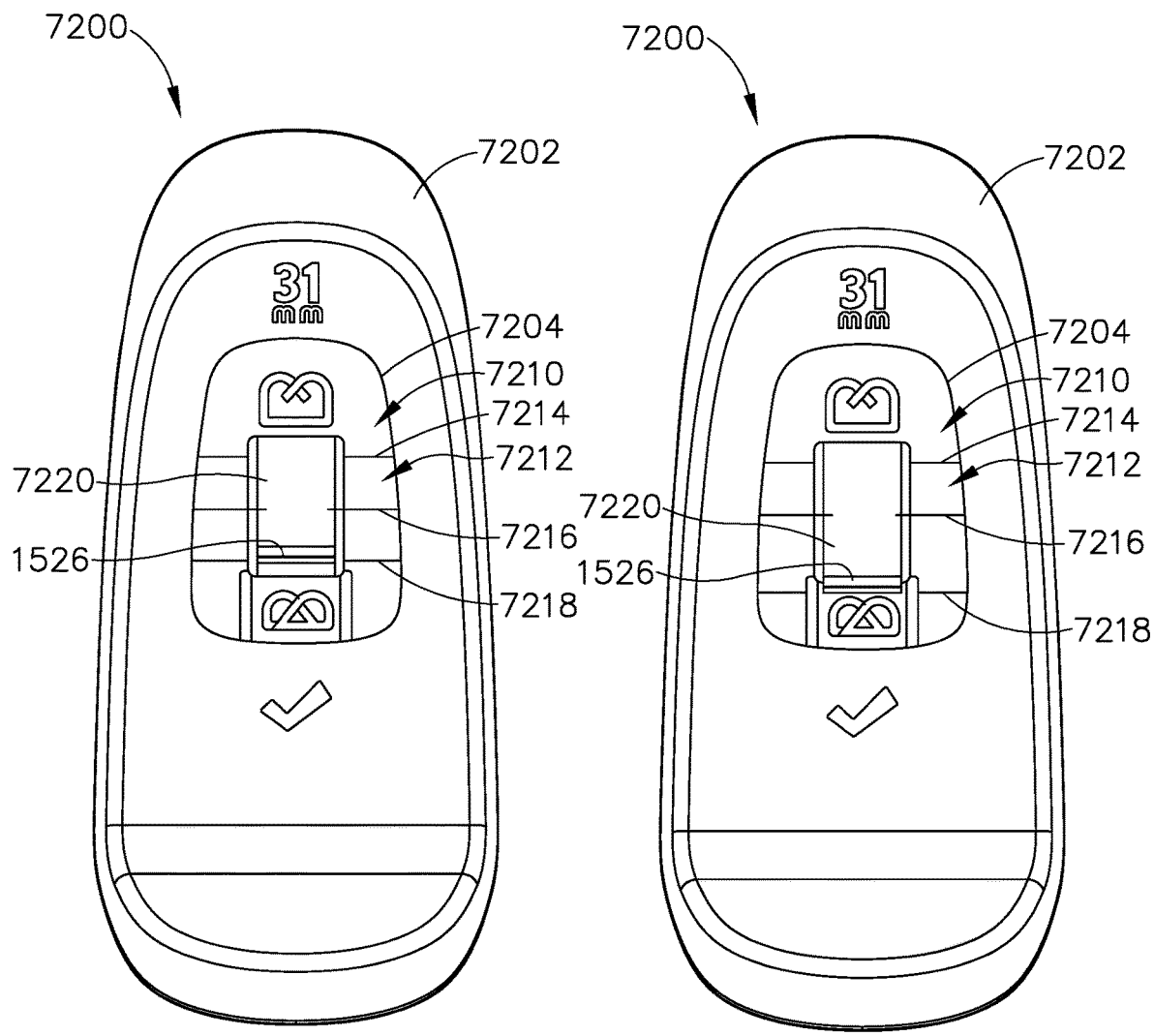
FIG. 92A depicts a top elevational view of an exemplary user feedback feature configured for use with the surgical stapler of FIG. 1, showing the user feedback feature in a first state in which a proximal end of the visible "green zone" is at a first longitudinal location before being adjusted.
FIG. 92B depicts a top elevational view of the user feedback feature of FIG. 90A, showing the user feedback feature in a second state in which the proximal end of the visible "green zone" has been adjusted proximally to a second longitudinal location to align with an indicator needle.

FIG. 92A shows user feedback feature (7200) in a first exemplary state in which indicator needle (1526) assumes a first longitudinal position within window (7220) when anvil (400) is fully closed. Digital display (7212) displays proximal linear indicia (7218) in alignment with indicator needle (1526). FIG. 92B shows user feedback feature (7200) in a second exemplary state in which indicator needle (1526) assumes a second, more-proximal longitudinal position within window (7220) when anvil (400) is fully closed. Digital display (7212) displays proximal linear indicia (7218) in alignment with indicator needle (1526) and thus expands the green zone proximally.

D. Exemplary Indicator Member Having Adjustable Calibration Screw

FIGS. 88-92 described above illustrate exemplary features and methods of calibrating a user feedback feature (114, 7000, 7100, 7200) via adjustment of the longitudinal position of a proximal end of the displayed green zone to align with indicator needle (1526) when anvil (400) is in a fully closed position. In some instances, it may be desirable to calibrate a user feedback feature via adjustment of the longitudinal position of indicator needle (1526) to align with the existing proximal end of the green zone.

Figure 93:
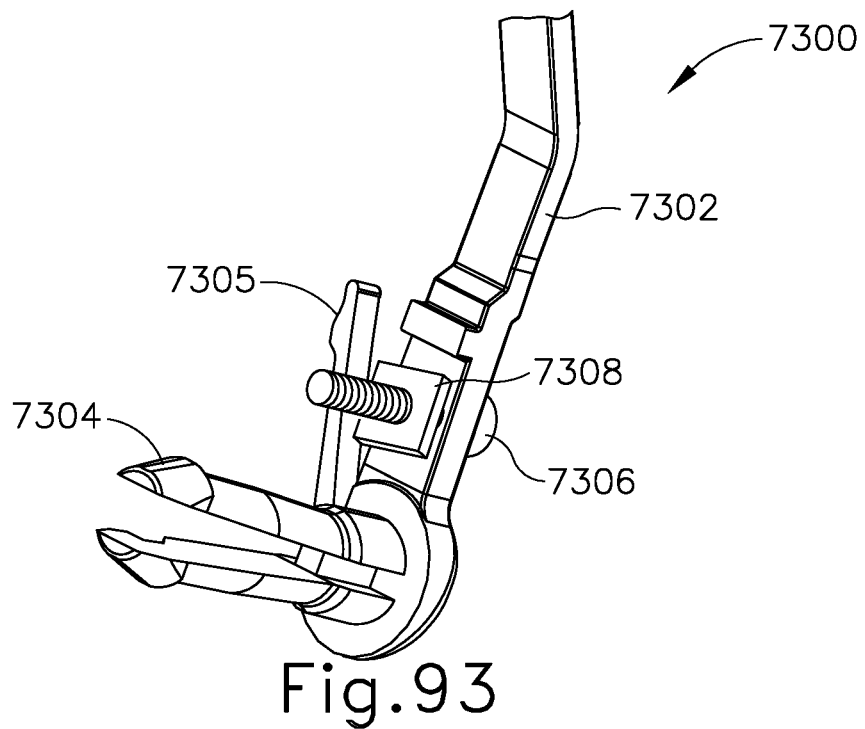
FIG. 93 depicts a perspective view of an exemplary alternative indicator member having a screw and a nut configured to enable adjustment of an angular position of the indicator member relative to a translatable bracket of the handle assembly of FIG. 82.
Figure 94:
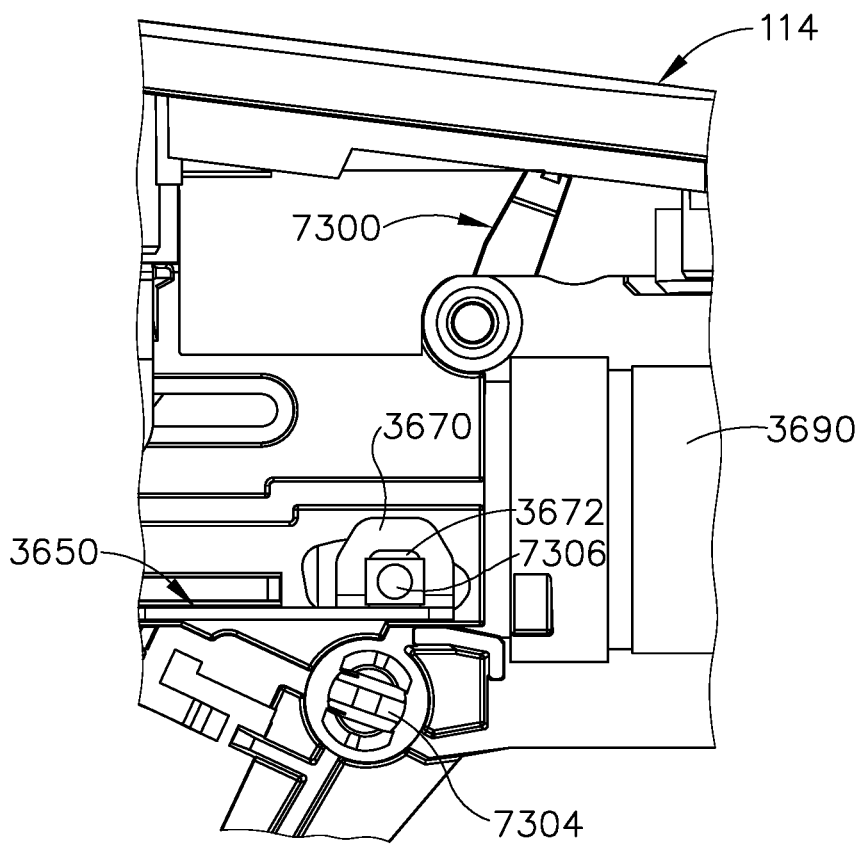
FIG. 94 depicts a side elevational view of a portion of the handle assembly of the surgical stapler of FIG. 1, with various components omitted from view, showing the indicator member of FIG. 93 in combination with a translatable bracket.

FIGS. 93 and 94 show an exemplary alternative indicator member (7300) configured for use with instrument (10) in place of indicator members (1520, 3600), and which is similar to indicator member (3600) described above except as otherwise described below. As shown best in FIG. 93, indicator member (7300) includes an upright arm (7302), a snap pin (7304) projecting laterally from a lower end of arm (7302), an indicator needle (not shown) projecting laterally from an upper end of arm (7302), and a resilient arm (7305) projecting upwardly and obliquely from the lower end of arm (7302). An angle adjustment screw (7306) projects laterally through an opening in arm (7302) above snap pin (7304), and a nut (7308) is threadedly coupled to adjustment screw (7306).

As shown best in FIG. 94, adjustment screw (7306) is configured to extend laterally through flange opening (3672) of bracket (3650), described in greater detail above in connection with FIG. 35. Nut (7308) is configured to be tightened on the threaded shaft of adjustment screw (7306)

to clamp bracket flange (3670) against arm (7302) of indicator member (7300). The threaded shaft of adjustment screw (7306) is smaller in diameter than a longitudinal dimension of flange opening (3672) such that screw (7306) is longitudinally movable within flange opening (3672) when screw (7306) is loosened relative to nut (7308). Accordingly, an angular orientation of indicator member (7300) relative to bracket (3650) may be adjusted by loosening adjustment screw relative to nut (7308), sliding adjustment screw (7306) proximally or distally within flange opening (3672), and then re-tightening adjustment screw (7306) relative to nut (7308). In this manner, a longitudinal position of the indicator needle (not shown) of indicator member (7300) within window (3570) may be adjusted to align the indicator needle with proximal linear indicia (3556) of lens member (3550), thereby calibrating user feedback feature (114).

XVI. Exemplary Alternative Firing Trigger Having Resiliently Deflectable Activation Paddle As described above in connection with FIGS. 30D-30E and 59A-59B, depression of firing trigger (150) by a user causes trigger paddle (158) to pivot into contact with a switch of motor actuation module (180), thereby activating motor (161) to initiate a firing sequence. Chassis (3690) of handle assembly (100) may include one or more mechanical stop features configured to prevent over-rotation of firing trigger (150) and resultant damage to motor activation module (180) by compression forces exerted by paddle (158). Nevertheless, in some instances it may be desirable to provide paddle (158) with a resiliently deflectable configuration to provide an addition degree of protection against transmission of excessive compression force from paddle (158) to motor activation module (180) during actuation of firing trigger (150).

FIG. 95 shows an exemplary alternative firing trigger (7400) configured for use with handle assembly (100) of instrument (10) in place of firing trigger (150). Firing trigger (7400) is similar to firing trigger (150) except that firing trigger (7400) includes an upwardly extending activation paddle (7402) having an elongated and thinned configuration relative to that of paddle (158). Paddle (7402) is configured to resiliently deflect relative to its neutral position shown in FIG. 95 in response to a threshold compression force exerted between paddle (7402) and motor activation module (180) when firing trigger (7400) is actuated by the user. Such resilient deflection of paddle (7402) protects motor activation module (180) from undesirable damage. Similar to firing trigger (150), firing trigger (7400) additionally includes a mechanical stop feature (7404) configured to contact a corresponding feature of chassis (3690) to prevent over-rotation of trigger (7400).

XVII. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body assembly; (b) a shaft assembly extending distally from the body assembly; (c) a stapling assembly at a distal end of the shaft assembly, wherein the stapling assembly is actuatable between an open state and a closed state for clamping tissue, wherein the stapling assembly in the closed state is configured to staple and cut the clamped tissue; (d) a first user feedback element configured to visually inform a user of a first condition of the stapling assembly; (e) a second user feedback element configured to visually inform the user of a second condition of the stapling assembly; and (f) a circuit board assembly including: (i) a circuit board, (ii) a first light source coupled to the circuit board, wherein the first light source is configured to illuminate the first user feedback element, (iii) a second light source coupled to the circuit board, wherein the second light source is configured to illuminate the second user feedback element, and (iv) a light guide feature, wherein the light guide feature is configured to direct light from the second light source toward the second user feedback element and simultaneously inhibit light emitted by the first light source from illuminating the second user feedback element.

Example 2

The surgical instrument of Example 1, wherein the first user feedback element and the second user feedback element are positioned on the body assembly.

Example 3

The surgical instrument of any of the preceding Examples, further comprising a movable indicator member, wherein the first user feedback element includes a window configured to provide visualization of the movable indicator member.

Example 4

The surgical instrument of Example 3, wherein the second user feedback element includes a checkmark feature.

Example 5

The surgical instrument of any of the preceding Examples, wherein the second user feedback feature is positioned proximal to the first user feedback feature, wherein the second light source is positioned proximal to the first light source.

Example 6

The surgical instrument of any of the preceding Examples, wherein the first condition comprises a closed state of the stapling assembly, wherein the second condition comprises a fired state of the stapling assembly.

Example 7

The surgical instrument of any of the preceding Examples, wherein the first light source includes a first light emitting diode, wherein the second light source includes a second light emitting diode.

Example 8

The surgical instrument of any of the preceding Examples, wherein the light guide feature projects outwardly from the circuit board in a direction toward the second user feedback element.

Example 9

The surgical instrument of Example 8, wherein the light guide feature encircles the second light source.

Example 10

The surgical instrument of Example 9, wherein an interior surface of the light guide feature is spaced away from the second light source.

Example 11

The surgical instrument of any of the preceding Examples, wherein the handle assembly includes a structure that provides the first and second user feedback elements, wherein the structure is configured to mate with the light guide feature.

Example 12

The surgical instrument of any of the preceding Examples, wherein the circuit board assembly includes a conformal coating that at least partially encapsulates the circuit board, wherein the conformal coating defines the light guide feature.

Example 13

The surgical instrument of Example 12, wherein the conformal coating comprises an opaque material.

Example 14

The surgical instrument of any of the preceding Examples, wherein the circuit board includes a light blocking layer configured to inhibit light emitted by the first light source from transmitting through the circuit board toward the second light source.

Example 15

The surgical instrument of Example 14, wherein the light blocking layer comprises a metallic material.

Example 16

A surgical instrument comprising: A surgical instrument comprising: (a) a body assembly; (b) a shaft assembly extending distally from the body assembly; (c) a stapling assembly at a distal end of the shaft assembly, wherein the stapling assembly is actuatable between an open state and a closed state for clamping tissue, wherein the stapling assembly in the closed state is configured to staple and cut the clamped tissue; (d) a first user feedback element configured to visually inform a user of a first condition of the stapling assembly; (e) a second user feedback element configured to visually inform the user of a second condition of the stapling assembly; and (f) a circuit board assembly including: (i) a circuit board, (ii) a first light source coupled to the circuit board, wherein the first light source is configured to illuminate the first user feedback element, (iii) a second light source coupled to the circuit board, wherein the second light source is configured to illuminate the second user feedback element, and (iv) a conformal coating that at least partially encapsulates the circuit board, wherein the conformal coating is configured to inhibit light emitted by the first light source from illuminating the second user feedback element.

Example 17

The surgical instrument of Example 16, wherein the conformal coating comprises an opaque material configured to inhibit transmission of light therethrough.

Example 18

The surgical instrument of any of Examples 16 through 17, wherein the conformal coating defines a cylindrical projection configured to guide light emitted by the second light source toward the second user feedback element.

Example 19

A surgical instrument comprising: (a) a body assembly; (b) a shaft assembly extending distally from the body assembly; (c) a stapling assembly at a distal end of the shaft assembly, wherein the stapling assembly is actuatable between an open state and a closed state for clamping tissue, wherein the stapling assembly in the closed state is configured to staple and cut the clamped tissue; (d) a first user feedback element configured to visually inform a user of a first condition of the stapling assembly; (e) a second user feedback element configured to visually inform the user of a second condition of the stapling assembly; and (f) a circuit board assembly including: (i) a circuit board having a light blocking layer, (ii) a first light source coupled to the circuit board, wherein the first light source is configured to illuminate the first user feedback element, and (iii) a second light source coupled to the circuit board, wherein the second light source is configured to illuminate the second user feedback element, wherein the light blocking layer is configured to inhibit light emitted by the first light source from transmitting through the circuit board toward the second light source.

Example 20

The surgical instrument of Example 19, wherein the light blocking layer comprises copper.

XVIII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in and/or U.S. Pat. App. No. 16/583,690, entitled "Circular Surgical Stapler," filed on Sep. 26, 2019, published as U.S. Pub. No. 2020/0281596 on Sep. 10, 2020, U.S. Pat. App. No. 16/583,376, entitled "Timer Circuit to Control Firing of Powered Surgical Stapler," filed on Sep. 26, 2019, published as U.S. Pub. No. 2020/0281592 on Sep. 10, 2020; U.S. Pat. App. No. 16/583,381, entitled "Power Control Circuit for Powered Surgical Stapler," filed on Sep. 26, 2019, published as U.S. Pub. No. 2020/0281593 on Sep. 10, 1010; and/or U.S. Pat. App. No. 16/583,386, entitled "Electrical Potential Shifting Circuit for Powered Surgical Stapler," filed on Sep. 26, 2019, published as U.S. Pub. No. 2020/0281594 on Sep. 10, 2020. The disclosure of each of these U.S. patent applications is incorporated by reference herein.

At least some of the teachings herein may also be readily combined with one or more teachings of U.S. Pub. No. 2015/0083772, entitled "Surgical Stapler with Rotary Cam Drive and Return," published Mar. 26, 2015, now abandoned, the disclosure of which is incorporated by reference herein; U.S. Pat. No. 9,936,949, entitled "Surgical Stapling Instrument with Drive Assembly Having Toggle Features," issued Apr. 10, 2018, the disclosure of which is incorporated by reference herein; U.S. Pat. No. 9,907,552, entitled "Control Features for Motorized Surgical Stapling Instrument," issued Mar. 6, 2018, the disclosure of which is incorporated by reference herein; U.S. Pat. No. 9,713,469, entitled "Surgical Stapler with Rotary Cam Drive," issued Jul. 25, 2017, the disclosure of which is incorporated by reference herein; U.S. Pub. No. 2016/0374665, entitled "Surgical Stapler with Electromechanical Lockout," published Dec. 29, 2016, issued as U.S. Pat. No. 10,905,415 on Feb. 2, 2021, the disclosure of which is incorporated by reference herein; U.S. Pub. No. 2016/0374666, entitled "Surgical Stapler with Reversible Motor," published Dec. 29, 2016, issued as U.S. Pat. No. 10,456,134 on Oct. 29, 2019, the disclosure of which is incorporated by reference herein; U.S. Pat. No. 10,307,157, entitled "Surgical Stapler with Anvil Seating Detection," issued Jun. 4, 2019, the disclosure of which is incorporated by reference herein; U.S. Pub. No. 2016/0374673, entitled "Firing Circuit for Surgical Stapler," published Dec. 29, 2016, issued as U.S. Pat. No. 10,405,855 on Sep. 10, 2019, the disclosure of which is incorporated by reference herein; U.S. Pat. No. 10,194,911, entitled "Surgical Stapler with Ready State Indicator," issued Feb. 5, 2019, the disclosure of which is incorporated by reference herein; U.S. Pat. No. 10,188,386, entitled "Surgical Stapler with Anvil State Indicator," issued Jan. 29, 2019, the disclosure of which is incorporated by reference herein; U.S. Pat. No. 10,265,066, entitled "Surgical Stapler with Incomplete Firing Indicator," issued Apr. 23, 2019, the disclosure of which is incorporated by reference herein; U.S. Pat. No. 10,271,841, entitled "Bailout Assembly for Surgical Stapler," issued Apr. 30, 2019, the disclosure of which is incorporated by reference herein; U.S. Pat. No. 10,226,253, entitled "Firing Assembly for Circular Stapler," issued Mar. 12, 2019, the disclosure of which is incorporated by reference herein; U.S. Pat. No. 10,271,842, entitled "Anvil Stabilization Features for Surgical Stapler," issued Apr. 30, 2019, the disclosure of which is incorporated by reference herein; U.S. Pub. No. U.S. Pub. No. 2016/0374672, entitled "Method of Applying an Annular Array of Staples to Tissue," published Dec. 29, 2017, issued as U.S. Pat. No. 10,478,189 on Nov. 19, 2019, the disclosure of which is incorporated by reference herein; U.S. Pub. No. 2018/0132853, entitled "Circular Stapler with Recessed Deck," published May 17, 2018, issued as U.S. Pat. No. 10,980,542 on Apr. 20, 2021, the disclosure of which is incorporated by reference herein; U.S. Pub. No. 2018/0132848, entitled "Atraumatic Stapling Head Features for Circular Surgical Stapler," published May 17, 2018, issued as U.S. Pat. No. 10,542,981 on Jan. 28, 2020, the disclosure of which is incorporated by reference herein; U.S. Pub. No. 2018/0132849, entitled "Staple Forming Pocket Configurations for Circular Surgical Stapler," published May 17, 2018, the disclosure of which is incorporated by reference herein; U.S. Pub. No. 2018/0132854, entitled "Circular Surgical Stapler with Angularly Asymmetric Deck Features," published May 17, 2018, issued as U.S. Pat. No. 10,603,041 on Mar. 31, 2020, the disclosure of which is incorporated by reference herein; U.S. Pub. No. 2018/0310938, entitled "Hysteresis Removal Feature in Surgical Stapling Instrument," published Nov. 1, 2018, issued as U.S. Pat. No. 10,695,068 on Jun. 30, 2020, the disclosure of which is incorporated by reference herein; and/or U.S. Pub. No. 2018/0310939, entitled "Liquid-Immune Trigger Circuit for Surgical Instrument," published Nov. 1, 2018, issued as U.S. Pat. No. 10,729,444 on Aug. 4, 2020, the disclosure of which is incorporated by reference herein. Various suitable ways in which the teachings herein may be combined with the teachings of the above-referenced patents, publications, and patent applications will be apparent to those of ordinary skill in the art.

At least some of the teachings herein may also be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pat. No. 9,572,573, entitled "Trans-Oral Circular Anvil Introduction System with Dilation Feature," issued Feb. 21, 2017, the disclosure of which is incorporated by reference herein; U.S. Pat. No. 9,289,207, entitled "Surgical Staple with Integral Pledget for Tip Deflection," issued Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pat. No. 9,498,222, entitled "Pivoting Anvil for Surgical Circular Stapler," issued Nov. 22, 2016, the disclosure of which is incorporated by reference herein; U.S. Pat. No. 9,724,100, entitled "Circular Anvil Introduction System with Alignment Feature," issued Aug. 8, 2017, the disclosure of which is incorporated by reference herein; U.S. Pat. No. 9,532,783, entitled "Circular Stapler with Selectable Motorized and Manual Control, Including a Control Ring," issued Jan. 3, 2017, the disclosure of which is incorporated by reference herein; U.S. Pat. No. 9,597,081, entitled "Motor Driven Rotary Input Circular Stapler with Modular End Effector," issued Mar. 21, 2017, the disclosure of which is incorporated by reference herein; and/or U.S. Pat. No. 9,463,022, entitled "Motor Driven Rotary Input Circular Stapler with Lockable Flexible Shaft," issued Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pat. No. 8,453,914, entitled "Motor-Driven Surgical Cutting Instrument with Electric Actuator Directional Control Assembly," issued Jun. 4, 2013, the disclosure of which is incorporated by reference herein, and/or U.S. Pat. No. 8,408,439, entitled "Surgical Stapling Instrument with An Articulatable End Effector," issued Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pat. No. 9,161,803, entitled "Motor Driven Electrosurgical Device with Mechanical and Electrical Feedback," issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body assembly;
   (b) a shaft assembly extending distally from the body assembly;
   (c) a stapling assembly at a distal end of the shaft assembly, wherein the stapling assembly is actuatable between an open state and a closed state for clamping tissue, wherein the stapling assembly in the closed state is configured to staple and cut the clamped tissue;
   (d) a first user feedback element configured to visually inform a user of a first condition of the stapling assembly;
   (e) a second user feedback element configured to visually inform the user of a second condition of the stapling assembly; and
   (f) a circuit board assembly including:
      (i) a circuit board,
      (ii) a first light source coupled to the circuit board, wherein the first light source is configured to illuminate the first user feedback element,
      (iii) a second light source coupled to the circuit board, wherein the second light source is configured to illuminate the second user feedback element, and
      (iv) a light guide feature, wherein the light guide feature is configured to direct light from the second light source toward the second user feedback element and simultaneously inhibit light emitted by the first light source from illuminating the second user feedback element.

2. The surgical instrument of claim 1, wherein the first user feedback element and the second user feedback element are positioned on the body assembly.

3. The surgical instrument of claim 1, further comprising a movable indicator member, wherein the first user feedback element includes a window configured to provide visualization of the movable indicator member.

4. The surgical instrument of claim 3, wherein the second user feedback element includes a checkmark feature.

5. The surgical instrument of claim 1, wherein the second user feedback feature is positioned proximal to the first user feedback feature, wherein the second light source is positioned proximal to the first light source.

6. The surgical instrument of claim 1, wherein the first condition comprises a closed state of the stapling assembly, wherein the second condition comprises a fired state of the stapling assembly.

7. The surgical instrument of claim 1, wherein the first light source includes a first light emitting diode, wherein the second light source includes a second light emitting diode.

8. The surgical instrument of claim 1, wherein the light guide feature projects outwardly from the circuit board in a direction toward the second user feedback element.

9. The surgical instrument of claim 8, wherein the light guide feature encircles the second light source.

10. The surgical instrument of claim 9, wherein an interior surface of the light guide feature is spaced away from the second light source.

11. The surgical instrument of claim 1, wherein the handle assembly includes a structure that provides the first and second user feedback elements, wherein the structure is configured to mate with the light guide feature.

12. The surgical instrument of claim 1, wherein the circuit board assembly includes a conformal coating that at least partially encapsulates the circuit board, wherein the conformal coating defines the light guide feature.

13. The surgical instrument of claim 12, wherein the conformal coating comprises an opaque material.

14. The surgical instrument of claim 1, wherein the circuit board includes a light blocking layer configured to inhibit light emitted by the first light source from transmitting through the circuit board toward the second light source.

15. The surgical instrument of claim 14, wherein the light blocking layer comprises a metallic material.

16. A surgical instrument comprising:
(a) a body assembly;
(b) a shaft assembly extending distally from the body assembly;
(c) a stapling assembly at a distal end of the shaft assembly, wherein the stapling assembly is actuatable between an open state and a closed state for clamping tissue, wherein the stapling assembly in the closed state is configured to staple and cut the clamped tissue;
(d) a first user feedback element configured to visually inform a user of a first condition of the stapling assembly;
(e) a second user feedback element configured to visually inform the user of a second condition of the stapling assembly; and
(f) a circuit board assembly including:
  (i) a circuit board,
  (ii) a first light source coupled to the circuit board, wherein the first light source is configured to illuminate the first user feedback element,
  (iii) a second light source coupled to the circuit board, wherein the second light source is configured to illuminate the second user feedback element, and
  (iv) a conformal coating that at least partially encapsulates the circuit board, wherein the conformal coating is configured to inhibit light emitted by the first light source from illuminating the second user feedback element.

17. The surgical instrument of claim 16, wherein the conformal coating comprises an opaque material configured to inhibit transmission of light therethrough.

18. The surgical instrument of claim 16, wherein the conformal coating defines a cylindrical projection configured to guide light emitted by the second light source toward the second user feedback element.

19. A surgical instrument comprising:
(a) a body assembly;
(b) a shaft assembly extending distally from the body assembly;
(c) a stapling assembly at a distal end of the shaft assembly, wherein the stapling assembly is actuatable between an open state and a closed state for clamping tissue, wherein the stapling assembly in the closed state is configured to staple and cut the clamped tissue;
(d) a first user feedback element configured to visually inform a user of a first condition of the stapling assembly;
(e) a second user feedback element configured to visually inform the user of a second condition of the stapling assembly; and
(f) a circuit board assembly including:
  (i) a circuit board having a light blocking layer,
  (ii) a first light source coupled to the circuit board, wherein the first light source is configured to illuminate the first user feedback element, and
  (iii) a second light source coupled to the circuit board, wherein the second light source is configured to illuminate the second user feedback element,
  wherein the light blocking layer is configured to inhibit light emitted by the first light source from transmitting through the circuit board toward the second light source.

20. The surgical instrument of claim 19, wherein the light blocking layer comprises copper.

* * * * *